(12) United States Patent
Serizawa et al.

(10) Patent No.: US 9,045,403 B2
(45) Date of Patent: Jun. 2, 2015

(54) GERANYL GERANYL ACETONE (GGA) DERIVATIVES AND COMPOSITIONS THEREOF

(71) Applicant: Coyote Pharmaceuticals, Inc., Menlo Park, CA (US)

(72) Inventors: Hiroaki Serizawa, Palo Alto, CA (US); Ankush B. Argade, Menlo Park, CA (US); Akash Datwani, Menlo Park, CA (US); Natalie Spencer, Menlo Park, CA (US); Yonghua Pan, San Francisco, CA (US); Florian Ermini, Santa Cruz, CA (US)

(73) Assignee: Coyote Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 13/779,568

(22) Filed: Feb. 27, 2013

(65) Prior Publication Data

US 2013/0296323 A1    Nov. 7, 2013

Related U.S. Application Data

(60) Provisional application No. 61/605,115, filed on Feb. 29, 2012, provisional application No. 61/605,089, filed on Feb. 29, 2012, provisional application No. 61/605,094, filed on Feb. 29, 2012, provisional application No. 61/741,793, filed on May 21, 2012, provisional application No. 61/649,875, filed on May 21, 2012, provisional application No. 61/674,127, filed on Jul. 20, 2012, provisional application No. 61/674,203, filed on Jul. 20, 2012, provisional application No. 61/694,696, filed on Aug. 29, 2012, provisional application No. 61/708,569, filed on Oct. 1, 2012.

(51) Int. Cl.
| | | |
|---|---|---|
| *C07C 49/203* | (2006.01) | |
| *C07C 69/145* | (2006.01) | |
| *C07C 69/02* | (2006.01) | |
| *C07C 69/24* | (2006.01) | |
| *C07C 69/743* | (2006.01) | |
| *C07C 69/74* | (2006.01) | |
| *C07C 69/75* | (2006.01) | |
| *C07C 309/66* | (2006.01) | |
| *C07C 309/73* | (2006.01) | |
| *C07C 333/04* | (2006.01) | |
| *C07C 333/06* | (2006.01) | |
| *C07C 333/08* | (2006.01) | |
| *C07D 211/26* | (2006.01) | |
| *C07D 295/13* | (2006.01) | |
| *A61K 31/185* | (2006.01) | |

(Continued)

(52) U.S. Cl.
CPC ............ *C07C 49/203* (2013.01); *C07C 69/608* (2013.01); *C07C 2101/02* (2013.01); *C07C 69/587* (2013.01); *C07C 211/08* (2013.01); *C07C 33/02* (2013.01); *C07C 271/22* (2013.01); *C07C 2103/74* (2013.01); *C07C 271/30* (2013.01); *C07C 69/92* (2013.01); *C07C 69/007* (2013.01); *C07C 49/21* (2013.01); *C07D 263/38* (2013.01); *C07C 333/08* (2013.01); *C07C 47/21* (2013.01); *C07C 49/647* (2013.01); *C07C 33/14* (2013.01); *C07C 271/12* (2013.01); *C07C 69/738* (2013.01); *C07C 69/75* (2013.01); *C07C 69/76* (2013.01); *C07C 69/02* (2013.01); *C07D 295/13* (2013.01); *C07C 2103/18* (2013.01); *C07C 69/743* (2013.01); *C07C 2101/14* (2013.01); *C07C 57/66* (2013.01); *C07C 69/757* (2013.01); *C07C 57/03* (2013.01); *C07C 49/557* (2013.01); *C07D 307/46* (2013.01); *C07C 2101/08* (2013.01); *C07C 333/10* (2013.01); *C07C 205/57* (2013.01); *C07C 2101/18* (2013.01); *C07C 211/35* (2013.01); *C07C 309/66* (2013.01); *C07C 69/145* (2013.01); *C07C 211/38* (2013.01); *C07C 69/24* (2013.01); *C07C 217/08* (2013.01); *C07C 309/73* (2013.01); *C07C 69/74* (2013.01); *C07D 271/10* (2013.01); *C07D 413/04* (2013.01); *C07C 271/28* (2013.01); *C07C 333/06* (2013.01); *C07D 213/75* (2013.01); *C07D 307/52* (2013.01); *C07C 2102/42* (2013.01); *C07D 263/32* (2013.01); *C07C 49/255* (2013.01); *C07D 211/26* (2013.01); *C07C 251/60* (2013.01); *C07C 333/04* (2013.01); *C07C 251/40* (2013.01); *C07C 271/24* (2013.01)

(58) Field of Classification Search
USPC ............. 514/675, 237.8, 315, 517, 529, 530, 514/531, 535, 544, 546; 568/417; 560/1, 560/122, 124, 22, 249, 64, 129, 261; 558/55, 44, 56; 544/160; 546/247
See application file for complete search history.

(56) References Cited

U.S. PATENT DOCUMENTS

| | | | |
|---|---|---|---|
| 3,939,202 A | 2/1976 | Matsui et al. | |
| 4,059,641 A | 11/1977 | Mishima et al. | |

(Continued)

FOREIGN PATENT DOCUMENTS

| | | |
|---|---|---|
| EP | 1 447 083 A1 | 8/2004 |
| EP | 1717315 | 11/2006 |

(Continued)

OTHER PUBLICATIONS

Chemical Abstract Service (CAS) STN Registry Database No. 1350042-87-3 [entered STN: Dec. 7, 2011].*

(Continued)

*Primary Examiner* — Samantha Shterengarts
*Assistant Examiner* — Amanda L Aguirre
(74) *Attorney, Agent, or Firm* — Foley & Lardner LLP

(57) ABSTRACT

This invention relates to geranylgeranyl acetone (GGA) derivatives and the use of GGA, its isomers, and GGA derivatives in methods for inhibiting neural death, increasing neural activity, increasing axon growth and cell viability, and increasing the survival rate of subjects administered the GGA or GGA derivatives.

8 Claims, 7 Drawing Sheets

(51) Int. Cl.

| | | |
|---|---|---|
| A61K 31/13 | (2006.01) | |
| C07C 69/608 | (2006.01) | |
| C07C 69/587 | (2006.01) | |
| C07C 211/08 | (2006.01) | |
| C07C 33/02 | (2006.01) | |
| C07C 271/22 | (2006.01) | |
| C07C 271/30 | (2006.01) | |
| C07C 69/92 | (2006.01) | |
| C07C 69/007 | (2006.01) | |
| C07C 49/21 | (2006.01) | |
| C07D 263/38 | (2006.01) | |
| C07C 47/21 | (2006.01) | |
| C07C 49/647 | (2006.01) | |
| C07C 33/14 | (2006.01) | |
| C07C 271/12 | (2006.01) | |
| C07C 69/738 | (2006.01) | |
| C07C 69/76 | (2006.01) | |
| C07C 57/66 | (2006.01) | |
| C07C 69/757 | (2006.01) | |
| C07C 57/03 | (2006.01) | |
| C07C 49/557 | (2006.01) | |
| C07D 307/46 | (2006.01) | |
| C07C 333/10 | (2006.01) | |
| C07C 205/57 | (2006.01) | |
| C07C 211/35 | (2006.01) | |
| C07C 211/38 | (2006.01) | |
| C07C 217/08 | (2006.01) | |
| C07D 271/10 | (2006.01) | |
| C07D 413/04 | (2006.01) | |
| C07C 271/28 | (2006.01) | |
| C07D 213/75 | (2006.01) | |
| C07D 307/52 | (2006.01) | |
| C07D 263/32 | (2006.01) | |
| C07C 49/255 | (2006.01) | |
| C07C 251/60 | (2006.01) | |
| C07C 251/40 | (2006.01) | |
| C07C 271/24 | (2006.01) | |
| A01N 37/00 | (2006.01) | |

(56) References Cited

U.S. PATENT DOCUMENTS

| | | | |
|---|---|---|---|
| 4,169,157 | A | 9/1979 | Kijima et al. |
| 4,281,019 | A | 7/1981 | Shepherd |
| 4,900,749 | A | 2/1990 | Matsumoto et al. |
| 4,977,170 | A | 12/1990 | Matsumoto et al. |
| 5,344,850 | A | 9/1994 | Hata et al. |
| 5,427,775 | A | 6/1995 | Sakai et al. |
| 5,453,524 | A | 9/1995 | Tagami et al. |
| 5,560,907 | A | 10/1996 | Sakai et al. |
| 5,574,025 | A | 11/1996 | Anthony et al. |
| 5,851,783 | A | 12/1998 | Appel et al. |
| 6,080,779 | A | 6/2000 | Gasper et al. |
| 6,090,407 | A | 7/2000 | Knight et al. |
| 6,130,048 | A | 10/2000 | Nixon |
| 6,391,553 | B1 | 5/2002 | Chartier-Harlin et al. |
| 6,846,845 | B2 | 1/2005 | Takahashi et al. |
| 7,087,649 | B2 | 8/2006 | Barth et al. |
| 7,268,124 | B2 | 9/2007 | Wiemer et al. |
| 7,341,988 | B2 | 3/2008 | Nishizono et al. |
| 7,356,521 | B2 | 4/2008 | Wang et al. |
| 7,563,244 | B2 | 7/2009 | Kent et al. |
| 7,678,078 | B1 | 3/2010 | Peyman et al. |
| 2002/0082244 | A1 | 6/2002 | Reszka et al. |
| 2004/0022869 | A1 | 2/2004 | Chen et al. |
| 2004/0249219 | A1 | 12/2004 | Saucy |
| 2006/0078604 | A1 | 4/2006 | Kanios et al. |
| 2007/0154534 | A1 | 7/2007 | Sheitman et al. |
| 2008/0113919 | A1 | 5/2008 | Rose et al. |
| 2009/0054623 | A1 | 2/2009 | DeFrees |
| 2009/0214607 | A1 | 8/2009 | Lintner et al. |
| 2010/0038141 | A1 | 2/2010 | Johnson et al. |
| 2010/0068141 | A1 | 3/2010 | Kaushal et al. |
| 2011/0158983 | A1 | 6/2011 | Bascomb et al. |
| 2011/0286993 | A1 | 11/2011 | Jensen et al. |
| 2012/0009125 | A1 | 1/2012 | Lombard |
| 2012/0172453 | A1 | 7/2012 | Barres et al. |
| 2013/0085283 | A1 | 4/2013 | Serizawa et al. |
| 2013/0245126 | A1 | 9/2013 | Serizawa |

FOREIGN PATENT DOCUMENTS

| | | |
|---|---|---|
| JP | 55-020713 | 2/1980 |
| JP | 55-022632 | 2/1980 |
| JP | 06-192073 | 7/1994 |
| JP | 2001-172171 | 6/2001 |
| JP | 2001-322929 | 11/2001 |
| JP | 2004-010574 | 1/2004 |
| JP | 2005-060303 | 3/2005 |
| JP | 2006-063012 | 3/2006 |
| JP | 2007-075071 | 3/2007 |
| JP | 2008-127296 | 6/2008 |
| WO | WO-99/66929 | 12/1999 |
| WO | WO-99/67809 | 12/1999 |
| WO | WO-02/03981 | 1/2002 |
| WO | WO-02/080926 | 10/2002 |
| WO | WO-03/035052 A1 | 5/2003 |
| WO | WO-2005/112915 | 12/2005 |
| WO | WO-2010/042841 | 4/2010 |
| WO | WO-2012/026813 | 8/2010 |
| WO | WO-2012/031028 | 3/2012 |
| WO | WO-2013/023274 | 2/2013 |
| WO | WO-2013/052148 | 4/2013 |

OTHER PUBLICATIONS

Ichikawa et al. J. Chem. Soc. Perkin Trans. 1 1993, 20, 2429-2432.*
Ito et al. Cancer Science 2003, 94, 3-8.*
U.S. Appl. No. 13/815,740, filed Mar. 15, 2013, Serizawa et al.
U.S. Appl. No. 13/815,741, filed Mar. 15, 2013, Serizawa et al.
U.S. Appl. No. 13/815,792, filed Mar. 15, 2013, Boyle et al.
U.S. Appl. No. 13/815,805, filed Mar. 15, 2013, Abril-Hörpel et al.
U.S. Appl. No. 13/815,831, filed Mar. 15, 2013, Boyle et al.
U.S. Appl. No. 13/815,852, filed Mar. 15, 2013, Serizawa.
U.S. Appl. No. 13/815,870, filed Mar. 15, 2013, Serizawa et al.
U.S. Appl. No. 13/943,606, filed Jul. 16, 2013, Serizawa.
Barrero, et al., "Regio- and Enantioselective Functionalization of Acyclic Polyprenoide," J. Mex. Chem. Soc., (2006), 50(4):149-156.
Bestmann et al., "All-trans Geranylgeranyl Acetate and Geranylgeraniol, Recruitment Pheromone Components in the Dufour Gland of the Ponerine Ant Ectatomma ruidum," Naturwissenschaften, (1995), p. 334, Fig 2 and its legend, 82(12):334-336.
Boyle et al., "Osteoclast differentiation and activation", Nature (2003), 423(6937):337-342.
Bruestle et al., "Decline in Daily Running Distance Presages Disease Onset in a Mouse Model of ALS," Neuromolecular Med. (2009), 11(2):58-62.
Bruijn, "Aggregation and Motor Neuron Toxicity of an ALS-Linked SOD1 Mutant Independent from Wild-Type SOD1," Science (1998), 281:1851-1854.
Bucciantini et al., "Inherent toxicity of aggregates implies a common mechanism for protein misfolding diseases," Nature (2002), 416:507-510.
Burgess et al., "The Ligand for Osteoprotegerin (OPGL) Directly Activates Mature Osteoclasts", J. Cell Biol. (1999), 145(3):527-538.
Casez et al., "Dual-energy X-ray absorptionmetry for measuring total bone mineral content in the rat: Study of accuracy and precision", Bone and Mineral (1994), 26:61-68.
Cereda et al, "The Acetate of (Z)-4-Chloro-2-Methyl-2-Buten-A-Ol Stereoselective Wittig Synthesis of a New Hemiterpenoid Synthon", Tetrahedron Lett. (1982), 23(21):2219-2222.
Chapelat, et al., "Biomimetic Chromanol Cyclisation: A common route to α-Tocotrienol and á-Tocopherol," Eur. J. Org. Chem., (2009), 2069-2076.

(56) References Cited

OTHER PUBLICATIONS

Eisai Co., Ltd., "Patent Registration Completed for SELBEX Gastritis Use Treatment", News Release (1998).

Ernest et al, "Synthesis of the 7-CIS Isomer of the Natural Leukotriene D4," Tetrahedron Lett. (1982), 23(2):167-170.

Ferretti, "Perspectives of pQCT Technology Associated to Biomechanical Studies in Skeletal Research Employing Rat Models", Bone (1995), 17(4):353S-364S.

Fujiki et al., "Role of Protein Kinase C in Neuroprotective Effect of Geranylgeranylacetone, a Noninvasive Inducing Agent of Heat Shock Protein, on Delayed Neuronal Death Caused by Transient Ischemia in Rats," J Neurotrauma (2006), 23(7):1164-78.

Gracias et al., "Synthesis of Fused Bicyclic Imidazoles by Sequential Van Leusen/Ring-Closing Metathesis Reactions", Org. Lett. (2005), 7(15):3183-3186.

Grinco et al. (2007) "Superacid-Catalyzed Cyclization of Methyl (6Z)-Geranylfarnesoates," Helv. Chim. Acta. 90:1223-1229.

Heller et al., "1,3-Diketones from Acid Chlorides and Ketones: A Rapid and General One-Pot Synthesis of Pyrazoles", Org Lett (2006), 8(13):2675-2678.

Henderson et al., "Purified embryonic motoneurons," J Cohen and G P Wilkin (ed.), Neural Cell Culture (1995), 69-81.

Holmes et al., "Strategies for Combinatorial Organic Synthesis: Solution and Polymer Supported Synthesis of 4-Thiazolidinones and 4-Metathiazanones Derived from Amino Acids", J Org Chem (1995), 60:7328-7333.

Iguchi et al., "TDP-43 Depletion Induces Neuronal Cell Damage through Dysregulation of Rho Family GTPases," J. Bio Chem. (2009), 284(33):22059-22066.

International Search Report and Written Opinion dated Apr. 30, 2013 in related PCT Patent Appl. No. PCT/US13/28073.

International Search Report and Written Opinion dated Apr. 30, 2013 in related PCT Patent Appl. No. PCT/US13/28075.

International Search Report and Written Opinion dated Jun. 18, 2013 in related PCT Patent Appl. No. PCT/US13/28081.

International Search Report dated Jan. 6, 2014 in related PCT Appl. No. PCT/US2013/062708.

International Search Report dated Jun. 2, 2013 in related PCT Patent Appl. No. PCT/US2013/025427.

International Search Report dated Sep. 28, 2012 in related PCT Appl. No. PCT/US2012/027147.

Irvine et al., "Protein Aggregation in the Brain: The Molecular Basis for Alzheimer's and Parkinson's Diseases," Mol Med. (2008), 14(7-8):451-464.

Ishii et al., "Retinal Ganglion Cell Protection with Geranylgeranylacetone, a Heat Shock Protein Inducer, in a Rat Glaucoma Model," Invest Ophthalmol Vis Sci (2003), 44(5):1982-92.

Iuchi et al., "Oligomeric and polymeric aggregates formed by proteins containing expanded polyglutamine", PNAS (2003), 100(5):2409-2414.

Kato et al., "Synthesis and Pheromone Activities of Optically Active Neocembrenes and Their Geometrical Isomers, (E,Z,E)- and (E,E,Z)-Neocembrenes," J. Org. Chem. (1980), 45:1126-1130.

Katsuno et al., "Pharmacological induction of heat-shock proteins alleviates polyglutamine-mediated motor neuron disease", Proc. Natl. Acad. Sci. USA (2005), 102(46):16801-16806.

Kimmel et al., "The Effect of Recombinant Human (1-84) or Synthetic Human (1-34) Parathyroid Hormone on the Skeleton of Adult Osteopenic Ovariectomized Rats", Endocrinology (1993), 132(4):1577-1584.

Lacey et al., "Osteoprotegerin Ligand Is a Cytokine that Regulates Osteoclast Differentiation and Activation", Cell (1998), 93:165-176.

Laval-Jeantet et al., "Dual-Energy X-Ray Absorptiometry of the Calcaneus: Comparison with Vertebral Dual-Energy X-Ray Absorptiometry and Quantitative Computed Tomography ", Calcif Tissue Intl (1995), 56:14-18.

Liu et al., "Influence of geranylgeranylacetone on the expression of HSP70 in retina of rats with chronic IOP elevation," Int. J. Ophthalmol., (2010), 3(1):28-31.

Liu, G.T., "Bicyclol: A novel drug for treating chronic viral hepatitis B and C," Medicinal Chemistry, (2009), 5:29-43.

Martin-Murphy et al., "The role of damage associated molecular pattern molecules in acetaminophen-induced liver injury in mice," Toxicology Letters, (2010), 192:387-394.

Masuda et al., "Geranylgeranylacetone attenuates septic diaphragm dysfunction by induction of heat shock protein 70*," Crit. Care Med., (2003), 31(11):2585-2591.

Nagai, et al., "Neuroprotective effect of geranylgeranylacetone, a noninvasive heat shock protein inducer, on cerebral infarction in rats," Neuroscience Letters, (2005), 374:183-188.

Ooie et al., "Single Oral Dose of Geranylgeranylacetone Induces Heat-Shock Protein 72 and Renders Protection Against Ischemia/Reperfusion Injury in Rat Heart," Circulation (2001), 104:1837-43.

Pezron et al., "Prodrug strategies in nasal drug delivery", Expert Opinion on Therapeutic Patents, (2002), 12(3):331-340.

Pfitzner et al., "The Synthesis of Nucleoside-5' Aldehydes", J. Am. Chem. Soc. (1963), 85:3027.

Physician's Desk Reference for Ophthalmology 1982 Edition, published by Medical Economics Company, Inc., 112-114.

PubChem AC1NSMQO. Compound Summary (CID 5366012). (2E;6E,10E)-3,7,11,15-Tetramethyl-2,6,10,14-hexadecatetraenyl acetate. Mar. 27, 2005. [online]; [Retrieved from the Internet Jun. 6, 2013: <http://pubchem.ncbi.nlm.nih.gov/summary/summary.cgi?cid=5366012&loc=ec_rcs>].

Racine, "Modification of Seizure Activity by Electrical Stimulation: II. Motor Seizure," Electroenceph. Clin. Neurophysiol., (1972), 32:281-294.

Ross & Poirier, "Protein aggregation and neurodegenerative disease," Nat Med. (2004), S10-S17.

Schenk et al., "Quantitative Morphometric Evaluation of the Inhibitory Activity of New Aminobisphosphonates on Bone Resorption in the Rat", Calcif.Tissues Int (1986), 38:342-349.

Simonet et al., "Osteoprotegerin: A Novel Secreted Protein Involved in the Regulation of Bone Density", Cell (1997), 89:308-319.

Sorrell et al., "A Regiospecific Synthesis of 1,4-Disubstituted Imidazoles", J Org Chem (1994), 59:1589-1590.

Sreekumar et al, "A Direct Synthesis of 2-Trisubstituted Allylic Alcohols via the Wittig Reaction", J. Org. Chem. (1980), 45:4260-4262.

Stotter et al., "$\alpha$-Halocarbonyl Compounds. II. A Position-Specific Preparation of $\alpha$-Bromo Ketones by Bromination of Lithium Enolates. A Position- Specific Introduction of $\alpha,\beta$-Unsaturation into Unsymmetrical Ketones", J Org Chem (1973), 38(14):2576-2578.

Suzuki et al., "Geranylgeranylacetone ameliorates ischemic acute renal failure via induction of Hsp70," Kidney Int (2005), 67:2210-20.

Tanaka et al., "Protective role of HSF 1 and HSP 70 against gastrointestinal diseases," Int. J. Hyperthermia, (2009), 25(8):668-676.

Tanito et al., "Cytoprotective Effects of Geranylgeranylacetone against Retinal Photooxidative Damage," J Neurosci (2005), 25(9):2396-404.

Tokumasu et al. "Synthesis of rac-hippospongic acid A and revision of the structure", JCS Perkin Trans. (1999), 1(4):489-496.

Van Leusen et al., "Base-Induced Cycloaddition of Sulfonylmethyl Isocyanides to C,N. Double Bonds. Synthesis of 1,5-Disubstituted and 1,4,5-Trisubstituted Imidazoles from Aldimines and Imidoyl Chlorides", J. Org. Chem. (1977), 42(7):1153-1159.

Vig., et al., Stereospecific synthesis of (+)-2,3-Dihydro-6(E)-farnesol. Indian J. Chem., Section B: Org. Incl. Med. Chem., (1979), 18B:31-38.

Vik et al., "Screening of Terpenes and Derivatives for Antimycobacterial Activity; Identification of Geranylgeraniol and Geranylgeranyl Acetate as Potent Inhibitors of Mycobacterium tuberculosis in vitro," Planta Med., (2007), p. 1411, Fig. 1, compound 1, 73(13):1410-1412.

Wang et al., "Protein Aggregation and Protein Instability Govern Familial Amyotrophic Lateral Sclerosis Patient Survival", PLoS Biology (2008), 6(7):1508-1526.

Wasserman et al., "Mechanism of the Robinson-Gabriel synthesis of oxazoles", J Org Chem (1973), 38(13):2407-2408.

(56) References Cited

OTHER PUBLICATIONS

Yasuda et al., "Neuroprotective effect of a heat shock protein inducer, geranylgeranylacetone in permanent focal cerebral ischemia," Brain Res (2005), 1032:176-82.

Yu et al., "Synthesis of Farnesol Isomers via a Modified Wittig Procedure", Organc Letters (2005), 7(22):4803-4806.

International Search Report and Written Opinion dated Mar. 27, 2014 in related PCT Patent Application No. PCT/US2013/035333.

Pfitzner et al., "A New and Selective Oxidation of Alcohols," J. Am. Chem. Soc., 1963, 85 (19), pp. 3027-3028.

U.S. Appl. No. 13/779,564, filed Feb. 27, 2013, Serizawa.

U.S. Appl. No. 13/819,681, filed Feb. 8, 2013, Serizawa.

U.S. Appl. No. 14/045,219, filed Oct. 3, 2013, Serizawa.

Harada et al., "Neuroprotective Effect of Geranylgeranylacetone against Ischemia-Induced Retinal Injury", Molecular Vision, 2007, 13:1601-1607.

Kikuchi et al., "Effect of Geranylgeranylaceton on Cellular Damage Induced by Proteasome Inhibition in Cultured Spinal Neurons," J. Neuro Res., (2002), 69:373-381.

Namba et al., "Suppression of Expression of Heat Shock Protein 70 by Gefitinib and Its Contribution to Pulmonary Fibrosis," PLoS One, (2011), 6(11):e27296.

PCT International Search Report and Written Opinion for PCT/US2014/010385, dated Jun. 3, 2014.

PCT International Search Report and Written Opinion for PCT/US2014/026277, dated Jun. 27, 2014.

Gittens et al., "Designing proteins for bone targeting," Adv Drug Deliv Rev., (2005), 57(7):1011-1036.

PCT International Preliminary Report on Patentability in PCT Patent Application No. PCT/US2013/028073, dated Sep. 12, 2014.

PCT International Preliminary Report on Patentability in PCT Patent Application No. PCT/US2013/028081, dated Sep. 12, 2014.

PCT International Search Report and Written Opinion in PCT Patent Application No. PCT/US2014/026263, dated Aug. 7, 2014.

PCT International Search Report and Written Opinion in PCT Patent Application No. PCT/US2014/026307, dated Aug. 28, 2014.

PubChem Submission CID 5282199 titled "Geranylgeranylacetone" (Mar. 25, 2005) retrieved from internet http://pubchem.ncbi.nlm.nih.gov/summary/summary.cgi?cid=5282199.

Wang et al., "Bisphosphonate-decorated lipid nanoparticles designed as drug carriers for bone diseases," J Biomed Mater Res. A., (2012), 100(3):684-693.

* cited by examiner

GERANYL GERANYL ACETONE (GGA) DERIVATIVES AND COMPOSITIONS THEREOF

CROSS REFERENCE TO RELATED APPLICATIONS

This application claims priority under 35 U.S.C. section 119(e) to U.S. provisional application Ser. Nos. 61/605,089, filed on Feb. 29, 2012; 61/605,094, filed on Feb. 29, 2012; 61/605,115, filed on Feb. 29, 2012; 61/649,875, filed on May 21, 2012; 61/674,127, filed on Jul. 20, 2012; 61/674,203, filed on Jul. 20, 2012; 61/694,696, filed on Aug. 29, 2012; 61/708,569, filed on Oct. 1, 2012; and 61/741,793, filed on May 21, 2012. All of which are incorporated herein by reference in their entirety.

FIELD OF THE INVENTION

This invention relates generally to GGA derivatives, methods for inhibiting neural death and increasing neural activity with the compound geranylgeranyl acetone (GGA) or a GGA derivative, and compositions used for these indications. The invention also relates to cis and trans isomers of geranylgeranyl acetone, and mixtures of various GGA isomers and their therapeutic uses.

STATE OF THE ART

Geranylgeranyl acetone is an acyclic isoprenoid compound with a retinoid skeleton that has been shown to induce expression of heat shock proteins in various tissue types. GGA is a known anti-ulcer drug used commercially and in clinical situations.

GGA has also been shown to exert cytoprotective effects on a variety of organs, such as the eye, brain, and heart (See for example Ishii Y., et al., Invest Ophthalmol Vis Sci 2003; 44:1982-92; Tanito M, et al., J Neurosci 2005; 25:2396-404; Fujiki M, et al., J Neurotrauma 2006; 23:1164-78; Yasuda H, et al., Brain Res 2005; 1032:176-82; Ooie T, et al., Circulation 2001; 104:1837-43; and Suzuki S, et al., Kidney Int 2005; 67:2210-20). The effects and cytoprotective benefits of GGA in these settings is less understood as is the relationship of isomers of GGA to these cytoprotective benefits. Of particular interest, is the effect of GGA on extranuclear neurodegeneration both on an intracellular or extracellular basis.

Neurodegeneration is often the result of increased age, sporadic mutations, disease, and/or protein aggregation in neural cells. Neurodegenerative diseases are often characterized by a progressive neurodegeneration of tissues of the nervous system and a loss of functionality of the neurons themselves. One commonality seen in most neurodegenerative diseases is the accumulation of protein aggregates intracellularly or in the extracellular space between neurons.

Protein aggregation is facilitated by partial unfolding or denaturation of cellular proteins. This may be due to mutations in the sequence of the DNA, transcriptional misincorporation, modifications to the RNA, and modifications or oxidative stress to the protein. There is an increasing amount of evidence to suggest that protein aggregates contribute to disease progression. In one study, aggregates of two non-disease proteins were formed in vitro and added to the medium of cultured cells. Addition of granular-structured, protein aggregates significantly reduced the cell viability of both the fibroblastic cell line (NIH-3T3) and neural cell line (PC12). However, addition of more organized fibrillar protein aggregates did not compromise the cell viability. (Bucciantini et al. (2002) Nature 14:507-510.)

Protein aggregates can be extracellular (i.e. in the space between neural cells), intracellular such as intranuclear (i.e. in the nucleus of the cell), or in the cytoplasm. Extracellular and/or cytoplasm protein aggregates are a pathological characteristic of Alzheimer's disease (AD) and amyotrophic lateral sclerosis (ALS). AD is a progressive brain disease that destroys memory and cognitive function. AD has been linked to the aggregation of the β-amyloid peptide. The β-amyloid peptide is derived from the amyloid precursor protein (APP) that has been processed by two aspartyl proteases called β and γ secretases. Similar to AD, ALS is also a progressive neurodegenerative disease and is characterized by loss of functionality of motor neurons. The progressive degeneration of motor neurons results in loss of ability of the brain to initiate and control muscle movement. ALS is a devastating disease, in which the last stage is complete paralysis. The complete molecular mechanism of disease progression in ALS is not yet clear, but mutations in the Cu/Zn superoxide dismutase (Sod) gene, Sod1, have been linked to the degeneration of motor neurons. The disease symptoms of ALS and AD may differ, but the presence of cytotoxic aggregate proteins in both diseases suggests a common mechanism in pathogenicity. (Ross & Poirier. (2004) Nat Med. ppS10-S17; Irvine et al. (2008) Mol Med. 14(7-8):451-464; Wang et al. (2008) PLoS One Vol. 6, Issue 7, pp 1508-1526. Iguchi et al. (2009) J. Bio Chem. Vol. 284 no. 33 pp. 22059-22066; Bruijn (1998) Science Vol. 281: 1851-1854.)

Recently, it was also found that depletion of the TDP-43 protein (TAR DNA binding protein or TARDBP) in Neuro-2a cells causes protein aggregation similar to what is observed in ALS. In fact, point mutations in TARDBP have been linked to familial and sporadic ALS. TDP-43 depletion by TARDBP siRNA in Neuro-2a cells also causes inhibition of the biological activity of the Rho family of small G proteins. Therefore, TDP-43 and Rho family proteins negatively affect protein aggregate formation in neural cells. The Rho family proteins are responsible for regulating cell movement, cell survival, cell growth, transcription, and motility of cells (Iguchi et al. (2009) J. Bio Chem. Vol. 284 no. 33 pp. 22059-22066). Therapies that prevent reduction in the amount and/or activity of TDP-43 or Rho family proteins may have a neuroprotective effect on cells.

There is a need for more effective therapies for neurodegenerative diseases such as AD and ALS. Research suggests that therapies targeting cellular mechanisms that control protein aggregation are likely to reduce the loss of functionality and viability of neurons in these diseases, thus, alleviating the symptoms. Therapies that enhance a small G protein activity may also be useful in inhibiting neural death and increasing neural activity in ALS. This application relates to the use of geranylgeranyl acetone (GGA) to inhibit or alter the formation of protein aggregates and modulate the activity of small G proteins in neural cells.

SUMMARY OF THE INVENTION

In various aspects, provided herein are GGA derivatives, such as those of Formulas (I)-(V) and sub-formulas thereof, compositions, preferably pharmaceutical formulations, thereof, processes of their syntheses, and their use in improving neural disorders or reducing the negative effects of neural disorders.

This invention also arises, in part, out of the surprising result that low doses of 5-trans GGA were efficacious in vivo. This invention also arises, in part, out of the discovery that 5-trans GGA was substantially and suitably distributed to the brain when administered in vivo.

In one aspect, this invention provides a pharmaceutical composition comprising an effective amount of 5E, 9E, 13E geranylgeranyl acetone or a GGA derivative, and optionally at least one pharmaceutical excipient, wherein the effective amount is from about 1 mg/kg/day to about 12 mg/kg/day. In another embodiment the effective amount is from about 1 mg/kg/day to about 5 mg/kg/day or from about 6 mg/kg/day to about 12 mg/kg/day. Preferably, the effective amount is about 3 mg/kg/day, about 6 mg/kg/day, or about 12 mg/kg/day.

In another aspect, this invention provides a method for modulating the expression of a heat shock protein or mRNA in a cell comprising contacting the cell with a compound or a composition provided and/or utilized herein. In one embodiment, this invention provides a method for increasing the expression of a heat shock protein or mRNA in a cell comprising contacting the cell with a compound or a composition provided and/or utilized herein. In another embodiment, this invention provides a method for decreasing the expression of a heat shock protein or mRNA in a cell comprising contacting the cell with a compound or a composition provided and/or utilized herein. In another aspect, this invention provides a method for increasing the expression of a heat shock protein or mRNA in a subject in need thereof comprising administering to the subject an effective amount of a compound or a composition provided and/or utilized herein. In one embodiment, the heat shock protein is selected from the group consisting of HSP60, HSP70, HSP90 or HSP27. In another embodiment, the heat shock protein is HSP70. In another embodiment, the mRNA of HSP70 is increased by at least 4%. In another embodiment, the mRNA of HSP70 is increased by at least 15%. In another embodiment, the HSP or prererably the HSP 70 is upregulated in the brain, the spinal chord, or the eyeball.

In another aspect, this invention provides a method for modulating the prenylation of G-protein a cell comprising contacting the cell with a compound or a composition provided and/or utilized herein. This aspect comprises contacting a cell with a compound or a composition provided and/or utilized herein and determining the occurance of an increase or an inhibition of prenylation of G-protein a cell. In one embodiment, this invention provides a method for increasing the prenylation of G-protein a cell comprising contacting the cell with a compound or a composition provided and/or utilized herein. In another embodiment, this invention provides a method for decreasing the prenylation of G-protein a cell comprising contacting the cell with a compound or a composition provided and/or utilized herein.

In another aspect, this invention provides a method for assaying a compound suitable for any of the methods disclosed herein.

In certain aspects, this invention relates to pharmaceutical uses of geranylgeranyl acetone (GGA) and GGA derivatives, pharmaceutical compositions of isomers of geranylgeranyl acetone, preferably synthetic geranylgeranyl acetone, and GGA derivatives, and methods of using such compounds and pharmaceutical compositions. In certain aspects, this invention relates to a 5-trans isomer compound of formula VI:

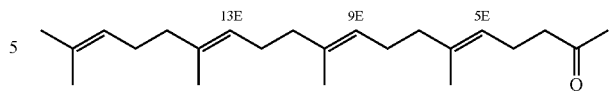

wherein VI is at least 80% in the 5E, 9E, 13E configuration. In one embodiment, this invention provides a compound, which is synthetic 5E, 9E, 13E geranylgeranyl acetone. In another embodiment, the synthetic 5E, 9E, 13E geranylgeranyl acetone is free of 5Z, 9E, 13E geranylgeranyl acetone. In another aspect, this invention provides a pharmaceutical composition comprising synthetic GGA or synthetic 5E, 9E, 13E GGA, and at least one pharmaceutical excipient.

Another aspect of this invention relates to a synthetic 5-cis isomer compound of formula VII:

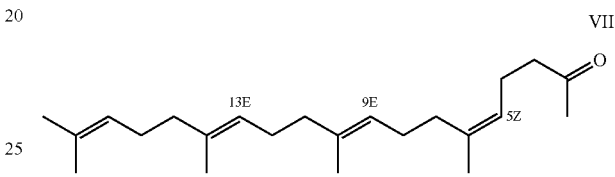

wherein VII is at least 80% in the 5Z, 9E, 13E configuration, or a ketal thereof of formula XII:

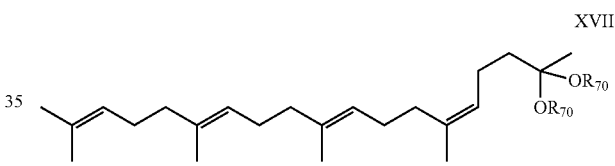

wherein each $R_{70}$ independently is $C_1$-$C_6$ alkyl, or two $R_{70}$ groups together with the oxygen atoms they are attached to form a 5 or 6 membered ring, which ring is optionally substituted with 1-3, preferably 1-2, $C_1$-$C_6$ alkyl groups. Preferably, the two $R_{70}$ groups are the same. In one embodiment, $R_{70}$ is, methyl, ethyl, or propyl. In another embodiment, the cyclic ring is:

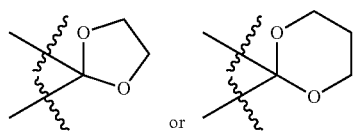

In another aspect, this invention provides a composition for increasing the expression and/or release of one or more neurotransmitters from a neuron at risk of developing pathogenic protein aggregates associated with AD or ALS, said composition comprising a protein aggregate inhibiting amount of GGA, a GGA derivative, or an isomer or a mixture of isomers thereof.

In another aspect, this invention provides a composition for increasing the expression and/or release of one or more neurotransmitters from a neuron at risk of developing extracellular pathogenic protein aggregates, said composition comprising an extracellular protein aggregate inhibiting amount of GGA, a GGA derivative, or an isomer or a mixture of isomers thereof.

In another of its method aspects, there is provided a method for increasing the axon growth of neurons by contacting said neurons with an effective amount of GGA or a GGA derivative.

In another aspect, this invention relates to a method for inhibiting or reducing the cell death of neurons susceptible to neuronal cell death, which method comprises contacting said neurons with an effective amount of GGA or a GGA derivative.

In yet another of its method aspects, there is provided a method for increasing the neurite growth of neurons by contacting said neurons with an effective amount of GGA a GGA derivative.

Other aspects of this invention relate to methods for neurostimulation by contacting neurons with an effecting amount of GGA or a GGA derivative. In one embodiment neurostimulation consists of increasing the expression and/or release of one or more neurotransmitters from a neuron. In another embodiment the neurostimulation consists of enhancing synapse formation of a neuron, or, alternatively, enhancing electrical excitability. In yet another embodiment, the neurostimulation includes modulating the activity of G proteins in neurons. In a related embodiment, the activation of G proteins is enhanced by GGA or a GGA derivative.

In another embodiment, this invention provides methods for neuroprotection of neurons at risk of neural damage or death by contacting said neurons with an effective amount of GGA. In one particular embodiment, neurons at risk of neural toxicity or death include those affected by, or those in the pathogenesis of, Alzheimer's Disease or ALS. In each case, neuroprotection is affected by contacting the neurons at risk of neural damage or death with an effective amount of GGA or a GGA derivative.

Yet another aspect of this invention relates to neuroprotective methods such as methods for protecting neurons at risk of neurotoxicity wherein the method comprises contacting cells comprising the neurons at risk of neurotoxicity with an effective amount of GGA or a GGA derivative. Without being limited to a particular theory, it is contemplated that GGA may be antagonistic to the neurotoxicity of the β-amyloid peptide or oligomers or polymers thereof.

Yet another neuroprotective aspect is a method for protecting neurons from neurodegeneration arising from ALS.

In another aspect, this invention relates to a method for inhibiting the death of neurons due to formation of or further formation of pathogenic protein aggregates either between, outside or inside neurons, wherein said method comprises contacting said neurons at risk of developing said pathogenic protein aggregates with a protein aggregate inhibiting amount of GGA or a GGA derivative provided that said pathogenic protein aggregates are not related to SBMA.

In yet another aspect, this invention relates to a method for inhibiting neural death and increasing neural activity in a mammal suffering from a neural disease, wherein the etiology of said neural disease comprises formation of protein aggregates which are pathogenic to neurons which method comprises administering to said mammal an amount of GGA or a GGA derivative which will inhibit further pathogenic protein aggregation provided that said pathogenic protein aggregation is not intranuclear.

Another aspect of this invention relates to a method for inhibiting neural death and increasing neural activity in a mammal suffering from a neural disease, wherein the etiology of said neural disease comprises formation of protein aggregates which are pathogenic to neurons which method comprises administering to said mammal an amount of GGA or a GGA derivative which will inhibit further pathogenic protein aggregation provided that said pathogenic protein aggregation is not related to SBMA.

Yet another aspect of this invention relates to methods for prolonging the survival of a subject with amyotrophic lateral sclerosis (ALS), including administering a therapeutically effective amount of GGA or a GGA derivative. Another aspect of this invention relates to methods for reducing mortality of a subject with amyotrophic lateral sclerosis (ALS), comprising administering a therapeutically effective amount of GGA or a GGA derivative. In some embodiments of the foregoing aspects, the GGA is a 5-trans isomer of GGA or a GGA derivative.

In one embodiment, the treatment of the neuron or the neural disease improves ambulatoty competence, motor performance, or partial paralysis of one or more limbs in a mammal. As used herein, partial paralysis refers to minimal or partial limb movement.

In another aspect, provided herein is a method of increasing ambulatory competence in a mammal exhibiting deficient ambulatory competence, the method comprising administering a therapeutically effective amount of GGA or a GGA derivative to the mammal in need thereof. As used herein, deficient ambulatory competence refers to a deficiency that is due at least in part to neural deficiency arising from a neural disease or injury. That is to say that deficient ambulatory competence is different from complete ambulatory competence or incompetence due to a broken leg, etc.

In another aspect, provided herein is a method of increasing motor performance in a mammal exhibiting deficient motor performance, the method comprising administering a therapeutically effective amount of GGA or a GGA derivative to the mammal in need thereof. As used herein, increasing motor performance refers to an increase in arm, leg and hand movement, where the decreased motor performance requiring improvement will be due at least in part to neural deficiency arising from disease or injury.

In another aspect, provided herein is a method of reducing the progressive degeneration of motor function, or improving motor function in a mammal in need thereof, comprising administering to the mammal a therapeutically effective amount of GGA or a GGA derivative, wherein the progressive degeneration of motor function or a worsening motor function requiring improvement is caused at least in part by oxidative neuronal damage.

In one embodiment, the GGA used according to this invention is 5-trans GGA or substantially pure 5-trans GGA which is optionally free of cis GGA or is essentially free of cis GGA.

In other embodiments the effective amount of GGA is from about 1 mg/kg/day to about 12 mg/kg/day, or from about 1 mg/kg/day to about 5 mg/kg/day, or from about 6 mg/kg/day to about 12 mg/kg/day, or preferably, about 3 mg/kg/day, about 6 mg/kg/day, or about 12 mg/kg/day.

DETAILED DESCRIPTION

Figure 1:
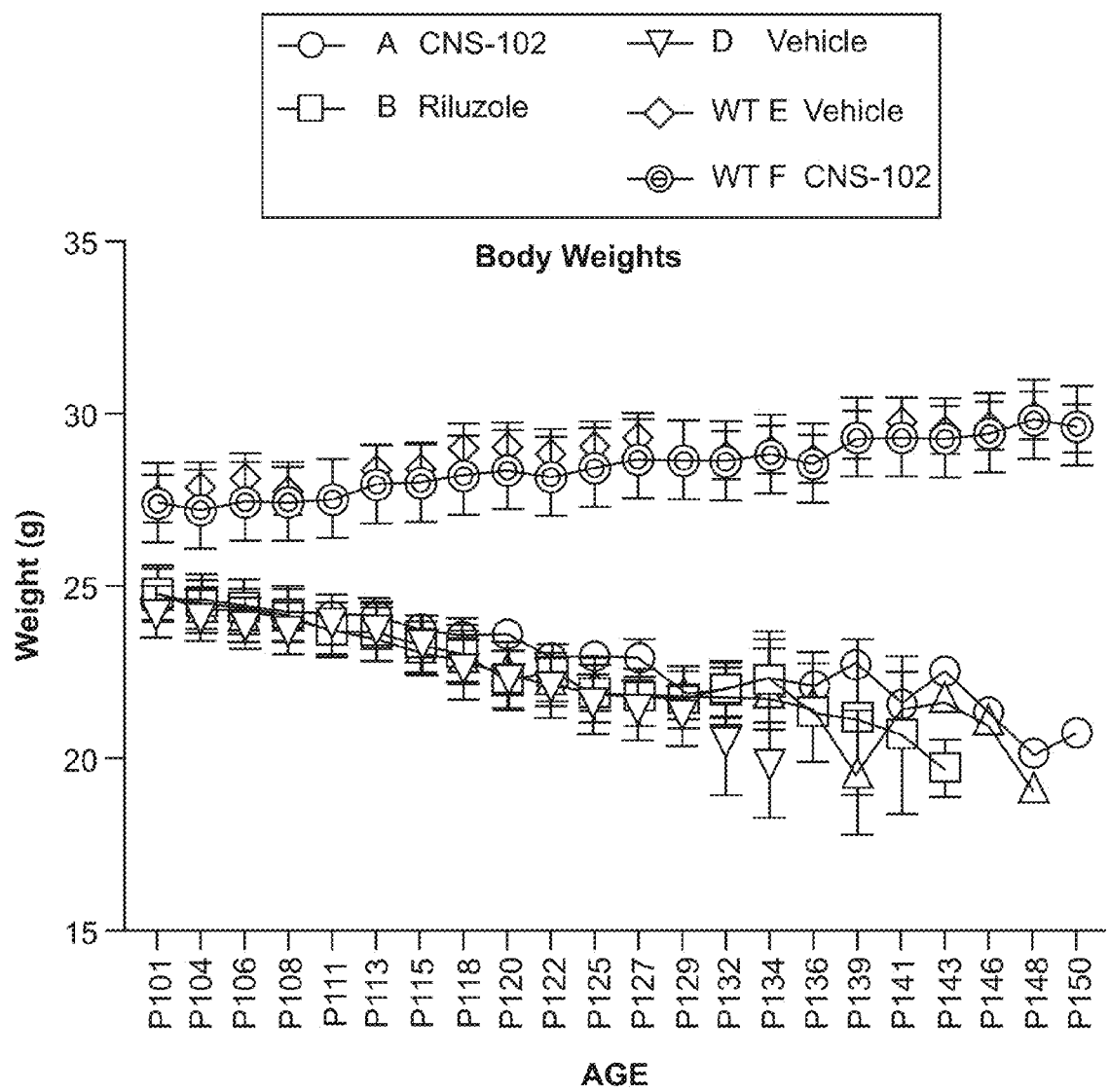
FIG. 1 shows the time course of body weights of test animals.

It is to be understood that this invention is not limited to particular embodiments described. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "an excipient" includes a plurality of excipients.

1. DEFINITIONS

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "neuroprotective" refers to reduced toxicity of neurons as measured in vitro in assays where neurons susceptible to degradation are protected against degradation as compared to control. Neuroprotective effects may also be evaluated in vivo by counting neurons in histology sections.

The term "neuron" or "neurons" refers to all electrically excitable cells that make up the central and peripheral nervous system. The neurons may be cells within the body of an animal or cells cultured outside the body of an animal. The term "neuron" or "neurons" also refers to established or primary tissue culture cell lines that are derived from neural cells from a mammal or tissue culture cell lines that are made to differentiate into neurons. "Neuron" or "neurons" also refers to any of the above types of cells that have also been modified to express a particular protein either extrachromosomally or intrachromosomally. "Neuron" or "neurons" also refers to transformed neurons such as neuroblastoma cells and support cells within the brain such as glia.

The term "protein aggregates" refers to a collection of proteins that may be partially or entirely mis-folded. The protein aggregates may be soluble or insoluble and may be inside the cell or outside the cell in the space between cells. Protein aggregates inside the cell can be intranuclear in which they are inside the nucleus or cytoplasm in which they are in the space outside of the nucleus but still within the cell membrane. The protein aggregates described in this invention are granular protein aggregates.

As used herein, the term "protein aggregate inhibiting amount" refers to an amount of GGA that inhibits the formation of protein aggregates at least partially or entirely. Unless specified, the inhibition could be directed to protein aggregates inside the cell or outside the cell.

As used herein, the term "intranuclear" or "intranuclearly" refers to the space inside the nuclear compartment of an animal cell.

The term "cytoplasm" refers to the space outside of the nucleus but within the outer cell wall of an animal cell.

As used herein, the term "pathogenic protein aggregate" refers to protein aggregates that are associated with disease conditions. These disease conditions include but are not limited to the death of a cell or the partial or complete loss of the neuronal signaling among two or more cells. Pathogenic protein aggregates can be located inside of a cell, for example, pathogenic intracellular protein aggregates or outside of a cell, for example, pathogenic extracellular protein aggregates.

As used herein, the term "SBMA" refers to the disease spinal and bulbar muscular atrophy. Spinal and bulbar muscular atrophy is a disease caused by pathogenic androgen receptor protein accumulation intranuclearly.

As used herein, the term "ALS" refers to amyotrophic lateral sclerosis disease.

As used herein, the term "AD" refers to Alzheimer's disease.

The term "neurotransmitter" refers to chemicals which transmit signals from a neuron to a target cell. Examples of neurotransmitters include but are not limited to: amino acids such as glutamate, aspartate, serine, γ-aminobutyric acid, and glycine; monoamines such as dopamine, norepinephrine, epinephrine, histamine, serotonin, and melatonin; and other molecules such as acetycholine, adenosine, anadamide, and nitric oxide.

The term "synapse" refers to junctions between neurons. These junctions allow for the passage of chemical signals from one cell to another.

The term "G protein" refers to a family of proteins involved in transmitting chemical signals outside the cell and causing changes inside of the cell. The Rho family of G proteins is small G protein, which are involved in regulating actin cytoskeletal dynamics, cell movement, motility, transcription, cell survival, and cell growth. RHOA, RAC1, and CDC42 are the most studied proteins of the Rho family. Active G proteins are localized to the cellular membrane where they exert their maximal biological effectiveness.

As used herein, the term "treatment" or "treating" means any treatment of a disease or condition in a patient, including one or more of:

preventing or protecting against the disease or condition, that is, causing the clinical symptoms not to develop, for example, in a subject at risk of suffering from such a disease or condition, thereby substantially averting onset of the disease or condition;

inhibiting the disease or condition, that is, arresting or suppressing the development of clinical symptoms; and/or relieving the disease or condition that is, causing the regression of clinical symptoms.

The term "axon" refers to projections of neurons that conduct signals to other cells through synapses. The term "axon growth" refers to the extension of the axon projection via the growth cone at the tip of the axon.

The term "neural disease" refers to diseases that compromise the cell viability of neurons. Neural diseases in which the etiology of said neural disease comprises formation of protein aggregates which are pathogenic to neurons provided that the protein aggregates are not related to the disease SBMA and are not intranuclear, include but are not limited to ALS, AD, Parkinson's Disease, multiple sclerosis, and prion diseases such as Kuru, Creutzfeltdt-Jakob disease, Fatal familial insomnia, and Gerstmann-Straussler-Scheinker syndrome. These neural diseases are also different from SBMA in that they do not contain polyglutamine repeats. Neural diseases can be recapitulated in vitro in tissue culture cells. For example, AD can be modeled in vitro by adding pre-aggregated β-amyloid peptide to the cells. ALS can be modeled by depleting an ALS disease-related protein, TDP-43. Neural disease can also be modeled in vitro by creating protein aggregates through providing toxic stress to the cell. One way this can be achieved is by mixing dopamine with neurons such as neuroblastoma cells. These neural diseases can also be recapitulated in vivo in mouse models. A transgenic mouse that expresses a mutant Sod1 protein has similar pathology to humans with ALS. Similarly, a transgenic mouse that over-expresses APP has similar pathology to humans with AD.

An effective amount of GGA is the amount of GGA required to produce a protective effect in vitro or in vivo. In some embodiments the effective amount in vitro is about from 0.1 nM to about 1 mM. In some embodiments the effective amount in vitro is from about 0.1 nM to about 0.5 nM or from about 0.5 nM to about 1.0 nM or from about 1.0 nM to about 5.0 nM or from about 5.0 nM to about 10 nM or from about 10 nM to about 50 nM or from about 50 nM to about 100 nM or from about 100 nM to about 500 nM or from about 500 nM to about 1 mM. In some embodiments, the effective amount for an effect in vivo is about 0.1 mg to about 100 mg, or preferably, from about 1 mg to about 50 mg, or more preferably, from about 1 mg to about 25 mg per kg/day. In some other embodiments, the effective amount in vivo is from about 10 mg/kg/day to about 100 mg/kg/day, about 20 mg/kg/day to about 90 mg/kg/day, about 30 mg/kg/day to about 80 mg/kg/day, about 40 mg/kg/day to about 70 mg/kg/day, or about 50 mg/kg/day to about 60 mg/kg/day. In some embodiments, the effective amount in vivo is from about 1 mg/kg/day to about 5 mg/kg/day, In some embodiments, the effective amount in vivo is from about 6 mg/kg/day to about 12 mg/kg/day, In one embodiment, the effective amount in vivo is about 3 mg/kg/day. In another embodiment, the effective amount in vivo is about 6 mg/kg/day. In another embodiment, the effective amount in vivo is about 12 mg/kg/day. In still some other embodiments, the effective amount in vivo is from about 100 mg/kg/day to about 1000 mg/kg/day.

Routes of administration refers to the method for administering GGA to a mammal. Administration can be achieved by a variety of methods. These include but are not limited to subcutaneous, intravenous, transdermal, sublingual, or intraperitoneal injection or oral administration.

The term "about" when used before a numerical designation, e.g., temperature, time, amount, and concentration, including range, indicates approximations which may vary by (+) or (−) 10%, 5%, or 1%.

The term "halogenating" is defined as converting a hydroxy group to a halo group. The term "halo" or "halo group" refers to fluoro, chloro, bromo and iodo.

The term "stereoselectively" is defined as providing over 90% of the E isomer for the newly formed double bond.

"Geometrical isomer" or "geometrical isomers" refer to compounds that differ in the geometry of one or more olefinic centers. "E" or "(E)" refers to the trans orientation and "Z" or "(Z)" refers to the cis orientation.

Geranylgeranyl acetone (GGA) refers to a compound of the formula:

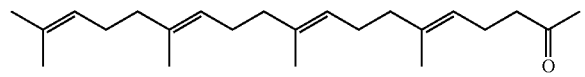 [SMILES: CC(=O)CC/C=C(\C)CC/C=C(\C)CC/C=C(\C)CCC=C(C)C]

wherein compositions comprising the compound are mixtures of geometrical isomers of the compound.

The 5-trans isomer of geranylgeranyl acetone refers to a compound of the formula VI:

VI

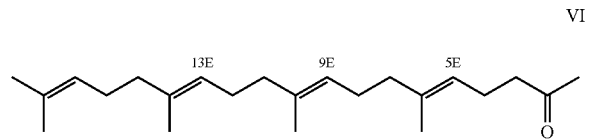 [SMILES: CC(=O)CC/C=C(\C)CC/C=C(\C)CC/C=C(\C)CCC=C(C)C]

wherein the number 5 carbon atom is in the 5-trans (5E) configuration.

The 5-cis isomer of geranylgeranyl acetone refers to a compound of the formula VII:

VII

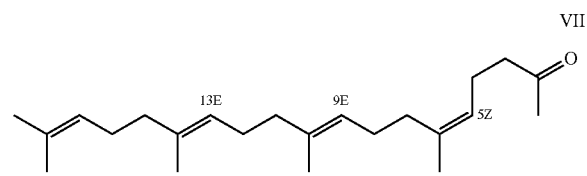 [SMILES: CC(=O)CC/C=C(/C)CC/C=C(\C)CC/C=C(\C)CCC=C(C)C]

wherein the number 5 carbon atom is in the 5-cis (5Z) configuration.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques.

As used herein, $C_m$-$C_n$, such as $C_1$-$C_{10}$, $C_1$-$C_6$, or $C_1$-$C_4$ when used before a group refers to that group containing m to n carbon atoms.

The term "about" when used before a numerical designation, e.g., temperature, time, amount, and concentration, including range, indicates approximations which may vary by (+) or (−) 10%, 5% or 1%.

The term "alkoxy" refers to —O-alkyl.

The term "alkyl" refers to monovalent saturated aliphatic hydrocarbyl groups having from 1 to 10 carbon atoms (i.e., $C_1$-$C_{10}$ alkyl) or 1 to 6 carbon atoms (i.e., $C_1$-$C_6$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)(CH$_3$CH$_2$)CH—), t-butyl (($CH_3$)$_3$C—), n-pentyl ($CH_3CH_2CH_2CH_2CH_2$—), and neopentyl (($CH_3$)$_3$CCH$_2$—). In some embodiments, the term "alkyl" refers to substituted or unsubstituted, straight chain or branched alkyl groups with $C_1$-$C_{12}$, $C_1$-$C_6$ and preferably $C_1$-$C_4$ carbon atoms.

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom. For example, and without limitation, the following is an aryl group:

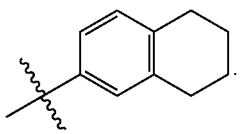 [SMILES: *c1ccc2c(c1)CCCC2]

In some embodiments, the term "aryl" refers to a 6 to 10 membered, preferably 6 membered aryl group. An aryl group may be substituted with 1-5, preferably 1-3, halo, alkyl, and/ or —O-alkyl groups.

The term "—$CO_2H$ ester" refers to an ester formed between the —$CO_2H$ group and an alcohol, preferably an aliphatic alcohol. A preferred example included —$CO_2R^E$, wherein $R^E$ is alkyl or aryl group optionally substituted with an amino group.

"Co-crystal," or as sometimes referred to herein "co-precipitate" refers to a solid, preferably a crystalline solid, comprising GGA or a GGA derivative, and urea or thiourea, more preferably, where, the GGA or the GGA derivative reside within the urea or thiourea lattice, such as in channels formed by urea or thiourea.

"Complexed" refers to GGA or a GGA derivative bound by certain quantifiable intermolecular forces, non-limiting examples of which include hydrogen bonding and Van-Der Waals' interactions, and also by entropic effects.

The term "chiral moiety" refers to a moiety that is chiral. Such a moiety can possess one or more asymmetric centers. Preferably, the chiral moiety is enantiomerically enriched, and more preferably a single enantiomer. Non limiting examples of chiral moieties include chiral carboxylic acids, chiral amines, chiral amino acids, such as the naturally occurring amino acids, chiral alcohols including chiral steroids, and the likes.

The term "cycloalkyl" refers to a monovalent, preferably saturated, hydrocarbyl mono-, bi-, or tricyclic ring having 3-12 ring carbon atoms. While cycloalkyl, refers preferably to saturated hydrocarbyl rings, as used herein, it also includes rings containing 1-2 carbon-carbon double bonds. Nonlimiting examples of cycloalkyl include cyclopropyl, cyclobutyl, cyclopentyl, cyclohexyl, cycloheptyl, adamantyl, and the like. The condensed rings may or may not be non-aromatic hydrocarbyl rings provided that the point of attachment is at a cycloalkyl carbon atom. For example, and without limitation, the following is a cycloalkyl group:

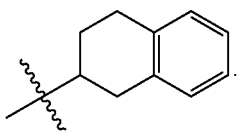 [SMILES: *C1CCc2ccccc2C1]

The term "halo" refers to F, Cl, Br, and/or I.

The term "heteroaryl" refers to a monovalent, aromatic mono-, bi-, or tricyclic ring having 2-14 ring carbon atoms and 1-6 ring heteroatoms selected preferably from N, O, S, and P and oxidized forms of N, S, and P, provided that the ring contains at least 5 ring atoms. Nonlimiting examples of heteroaryl include furan, imidazole, oxadiazole, oxazole, pyridine, quinoline, and the like. The condensed rings may or may not be a heteroatom containing aromatic ring provided that the point of attachment is a heteroaryl atom. For example, and without limitation, the following is a heteroaryl group:

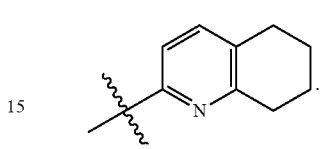

The term "heterocyclyl" or heterocycle refers to a non-aromatic, mono-, bi-, or tricyclic ring containing 2-10 ring carbon atoms and 1-6 ring heteroatoms selected preferably from N, O, S, and P and oxidized forms of N, S, and P, provided that the ring contains at least 3 ring atoms. While heterocyclyl preferably refers to saturated ring systems, it also includes ring systems containing 1-3 double bonds, provided that they ring is non-aromatic. Nonlimiting examples of heterocyclyl include, azalactones, oxazoline, piperidinyl, piperazinyl, pyrrolidinyl, tetrahydrofuranyl, and tetrahydropyranyl. The condensed rings may or may not contain a non-aromatic heteroatom containing ring provided that the point of attachment is a heterocyclyl group. For example, and without limitation, the following is a heterocyclyl group:

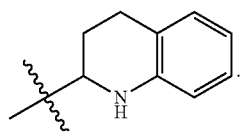

The term "hydrolyzing" refers to breaking an $R^H$—O—CO—, $R^H$—O—CS—, or an $R^H$—O—$SO_2$— moiety to an $R^H$—OH, preferably by adding water across the broken bond. A hydrolyzing is performed using various methods well known to the skilled artisan, non limiting examples of which include acidic and basic hydrolysis.

The term "oxo" refers to a C=O group, and to a substitution of 2 geminal hydrogen atoms with a C=O group.

The term "pharmaceutically acceptable" refers to safe and non-toxic for in vivo, preferably, human administration.

The term "pharmaceutically acceptable salt" refers to a salt that is pharmaceutically acceptable.

The term "salt" refers to an ionic compound formed between an acid and a base. When the compound provided herein contains an acidic functionality, such salts include, without limitation, alkai metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, $NH_4$, Ca, Ba, imidazolium, and ammonium cations based on naturally occurring amino acids. When the compounds provided and/or utilized herein contain basic functinaly, such salts include, without limitation, salts of organic acids, such as caroboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisalfate, mono-, di-, and tribasic phosphate, mesylate, tosylate, and the likes.

The term "substantially pure trans isomer" refers to a trans isomer that is by molar amount 95%, preferably 96%, more preferably 99%, and still more preferably 99.5% or more a trans isomer with the rest being the corresponding cis isomer.

"Trans" in the context of GGA and GGA derivatives refer to the GGA scaffold as illustrated below:

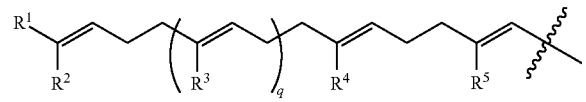

wherein $R^1$-$R^5$ is defined herein and q is 0-2. As shown, each double bond is in a trans or E configuration. In contrast, a cis form of GGA or a GGA derivative will contain one or more of these bonds in a cis or Z configuration.

2. COMPOUNDS

GGA

This invention relates to compounds and pharmaceutical compositions of isomers of geranylgeranyl acetone. In certain aspects, this invention relates to a synthetic 5-trans isomer compound of formula VI:

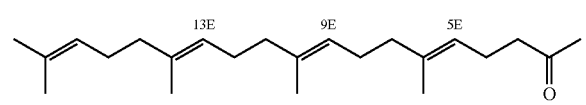

wherein VI is at least 80% in the 5E, 9E, 13E configuration. In some embodiments, the invention provides for a compound of formula VI wherein VI is at least 85%, or at least 90%, or at least 95%, or at least 96%, or at least 97%, or at least 98%, or at least 99%, or at least 99.5%, or at least 99.9% in the 5E, 9E, 13E configuration. In some embodiments the invention for the compound of formula VI does not contain any of the cis-isomer of GGA.

Another aspect of this invention relates to a synthetic 5-cis isomer compound of formula VII:

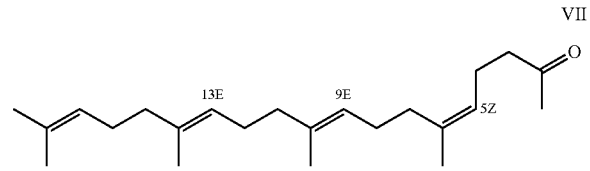 [SMILES: CC(=O)CC/C=C(/C)CC/C=C(\C)CC/C=C(\C)CCC=C(C)C]

wherein VII is at least 75% in the 5Z, 9E, 13E configuration. In certain embodiments, the invention provides for a compound of formula VII wherein VII is at least 80% in the 5E, 9E, 13E configuration, or alternatively, at least 85%, or at least 90%, or at least 95%, or at least 96%, or at least 97%, or at least 98%, or at least 99%, or at least 99.5%, or at least 99.9% in the 5E, 9E, 13E configuration. In some embodiments of the invention, the compound of formula VII does not contain any of the trans-isomer of GGA.

The configuration of compounds can be determined by methods known to those skilled in the art such as chiroptical spectroscopy and nuclear magnetic resonance spectroscopy.

The data contained in the examples herewith demonstrate at low concentrations the trans-isomer of GGA is pharmacologically active and shows a dose-dependent relationship. In contrast, the cis-isomer of GGA does not demonstrate a dose dependent relationship and is deemed to be at best of minimal activity.

GGA Derivatives

GGA derivatives useful in this invention include those described in PCT publication no. WO 2012/031028 and PCT application no. PCT/US2012/027147, each of which are incorporated herein by reference in its entirety. These and other GGA derivatives provided and/or utilized herein are structurally shown below.

In one aspect, the GGA derivative provided and/or utilized herein is of Formula I:

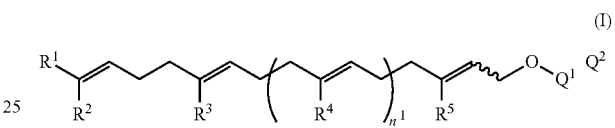

or a tautomer or pharmaceutically acceptable salt thereof, wherein $n^1$ is 1 or 2;

each $R^1$ and $R^2$ are independently $C_1$-$C_6$ alkyl, or $R^1$ and $R^2$ together with the carbon atom they are attached to form a $C_5$-$C_7$ cycloalkyl ring optionally substituted with 1-3 $C_1$-$C_6$ alkyl groups;

each of $R^3$, $R^4$, and $R^5$ independently are hydrogen or $C_1$-$C_6$ alkyl;

$Q^1$ is —(C=O)—, —(C=S)—, or —S($O_2$)—;

$Q_2$ is hydrogen, $R^6$, —O—$R^6$, —$NR^7R^8$, or is a chiral moiety;

$R^6$ is:

$C_1$-$C_6$ alkyl, optionally substituted with —$CO_2H$ or an ester thereof, $C_1$-$C_6$ alkoxy, oxo, OH, —CR=$CR_2$, —C≡CR, $C_3$-$C_{10}$ cycloalkyl, $C_3$-$C_8$ heterocyclyl, $C_6$-$C_{10}$ aryl, $C_2$-$C_{10}$ heteroaryl, wherein each R independently is hydrogen or $C_1$-$C_6$ alkyl;

CO—$C_1$-$C_6$ alkyl;

$C_3$-$C_{10}$ cycloalkyl;

$C_3$-$C_8$ heterocyclyl;

$C_6$-$C_{10}$ aryl; or $C_2$-$C_{10}$ heteroaryl;

wherein each cycloalkyl, heterocyclyl, aryl, or heteroaryl is optionally substituted with 1-3 alkyl groups; —$CF_3$, 1-3 halo, preferably, chloro or fluoro, groups; 1-3 nitro groups; 1-3 $C_1$-$C_6$ alkoxy groups; —CO-phenyl; or —$NR^{18}R^{19}$, each $R^{18}$ and $R^{19}$ independently is hydrogen; $C_1$-$C_6$ alkyl, optionally substituted with —$CO_2H$ or an ester thereof, $C_1$-$C_6$ alkoxy, oxo, —CR=$CR_2$, —CCR, $C_3$-$C_{10}$ preferably $C_3$-$C_8$ cycloalkyl, $C_3$-$C_8$ heterocyclyl, $C_6$-$C_{10}$ aryl, or $C_2$-$C_{10}$ heteroaryl, wherein each R independently is hydrogen or $C_1$-$C_6$ alkyl; $C_3$-$C_{10}$ cycloalkyl; $C_3$-$C_8$ heterocyclyl; $C_6$-$C_{10}$ aryl; or $C_2$-$C_{10}$ heteroaryl; wherein each cycloalkyl, heterocyclyl, aryl, or heteroaryl is optionally substituted with 1-3 alkyl groups, optionally substituted with 1-3 halo, preferably, fluoro, groups, where $R^{18}$ and $R^{19}$ together with the nitrogen atom they are attached to form a 5-7 membered heterocycle;

each $R^7$ and $R^8$ are independently hydrogen or defined as $R^6$; and

⤳ refers to a mixture of cis and trans isomers at the corresponding position wherein at least 80% and, preferably, no more than 95% of the compound of Formula (I) is present as a trans isomer.

In one embodiment, the GGA derivative provided and/or utilized is of Formula (I-A):

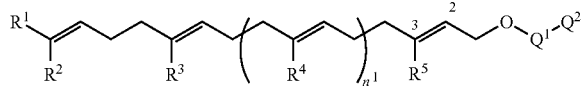
(I-A)

as a substantially pure trans isomer around the 2,3 double bond wherein, $n^1$, $R^1$-$R^5$, $Q^1$, and $Q^2$ are defined as in Formula (I) above.

In another embodiment, $n^1$ is 1. In another embodiment, $n^1$ is 2.

In another embodiment, the GGA derivative provided and/or utilized is of Formula (I-B):

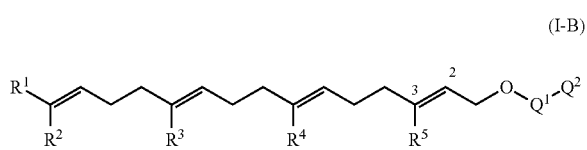
(I-B)

as a substantially pure trans isomer around the 2,3 double bond wherein, $R^1$-$R^5$, $Q^1$, and $Q^2$ are defined as in Formula (I) above.

In another embodiment, the GGA derivative provided and/or utilized is of Formula I-C:

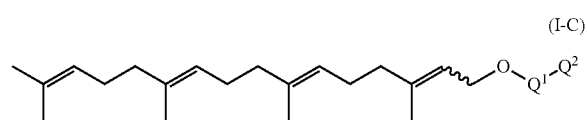
(I-C)

wherein $Q^1$ and $Q^2$ are defined as in Formula (I) above.

In another embodiment, the GGA derivative provided and/or utilized is of Formula (I-D), (I-E), or (I-F):

(I-D)

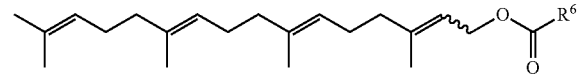
(I-E)

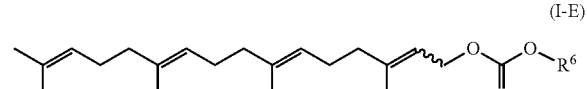
(I-F)

wherein $R^6$-$R^8$ are defined as in Formula (I) above.

In another embodiment, the GGA derivative provided and/or utilized is of Formula (I-G), (I-H), or (I-I):

(I-G)

(I-H)

(I-I)

as a substantially pure trans isomer around the 2,3 double bond wherein $R^6$-$R^8$ are defined as in Formula (I) above.

In a preferred embodiment, $R^6$ is $C_6$-$C_{10}$ aryl, such as naphthyl. In another preferred embodiment, $R^6$ is a heteroaryl, such as quinolinyl.

In another aspect, the GGA derivative provided and/or utilized in this invention is of Formula (II):

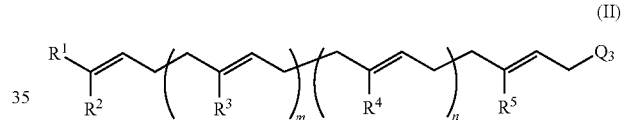
(II)

or a pharmaceutically acceptable salt thereof, wherein
m is 0 or 1;
n is 0, 1, or 2;
each $R^1$ and $R^2$ are independently $C_1$-$C_6$ alkyl, or $R^1$ and $R^2$ together with the carbon atom they are attached to form a $C_5$-$C_7$ cycloalkyl ring optionally substituted with 1-3 $C_1$-$C_6$ alkyl groups;
each of $R^3$, $R^4$, and $R^5$ independently are hydrogen or $C_1$-$C_6$ alkyl;
$Q_3$ is —OH, —$NR^{22}R^{23}$—X—CO—$NR^{24}R^{25}$, —X—CS—$NR^{24}R^{25}$, or —X—$SO_2$—$NR^{24}R^{25}$;
X is —O—, —S—, —$NR^{26}$—, or —$CR^{27}R^{28}$;
each $R^{22}$ and $R^{23}$ independently is hydrogen; $C_1$-$C_6$ alkyl, optionally substituted with $C_1$-$C_6$ alkoxy; and $C_3$-$C_{10}$ cycloalkyl;
each $R^{24}$ and $R^{25}$ independently is hydrogen, $C_1$-$C_6$ alkyl, optionally substituted with —$CO_2H$ or an ester thereof, $C_1$-$C_6$ alkoxy, oxo, —OH, —CR=$CR_2$, —C≡CR, $C_3$-$C_{10}$ cycloalkyl, $C_3$-$C_8$ heterocyclyl, $C_6$-$C_{10}$ aryl, $C_2$-$C_{10}$ heteroaryl, wherein each R independently is hydrogen or $C_1$-$C_6$ alkyl;
$C_3$-$C_{10}$ cycloalkyl;
$C_3$-$C_8$ heterocyclyl;
$C_6$-$C_{10}$ aryl; or
$C_2$-$C_{10}$ heteroaryl;
wherein each cycloalkyl, heterocyclyl, aryl, or heteroaryl is optionally substituted with 1-3 alkyl groups; —$CF_3$, 1-3 halo, preferably, chloro or fluoro, groups; 1-3 nitro groups; 1-3 $C_1$-$C_6$ alkoxy groups; —CO-phenyl; or —$NR^{18}R^{19}$;

each $R^{18}$ and $R^{19}$ independently is hydrogen; $C_1$-$C_6$ alkyl, optionally substituted with —$CO_2H$ or an ester thereof, $C_1$-$C_6$ alkoxy, oxo, —$CR$=$CR_2$, —CCR, $C_3$-$C_{10}$ preferably $C_3$-$C_8$ cycloalkyl, $C_3$-$C_8$ heterocyclyl, $C_6$-$C_{10}$ aryl, or $C_2$-$C_{10}$ heteroaryl, wherein each R independently is hydrogen or $C_1$-$C_6$ alkyl; $C_3$-$C_{10}$ cycloalkyl; $C_3$-$C_8$ heterocyclyl; $C_6$-$C_{10}$ aryl; or $C_2$-$C_{10}$ heteroaryl; wherein each cycloalkyl, heterocyclyl, aryl, or heteroaryl is optionally substituted with 1-3 alkyl groups, optionally substituted with 1-3 halo, preferably, fluoro, groups, where $R^{18}$ and $R^{19}$ together with the nitrogen atom they are attached to form a 5-7 membered heterocycle; $R^{26}$ is hydrogen or together with $R^{24}$ or $R^{25}$ and the intervening atoms form a 5-7 membered heterocyclic ring optionally substituted with 1-3 $C_1$-$C_6$ alkyl groups; and each $R^{27}$ and $R^{28}$ independently are hydrogen, $C_1$-$C_6$ alkyl, —$COR^{81}$ or —$CO_2R^{81}$, or $R^{27}$ together with $R^{24}$ or $R^{25}$ and the intervening atoms form a 5-7 membered heterocyclyl ring optionally substituted with 1-3 $C_1$-$C_6$ alkyl groups.

As used herein, the compound of Formula (II) includes optical isomers such as enantiomers and diastereomers. As also used herein, an ester refers preferably to a phenyl or a $C_1$-$C_6$ alkyl ester, which phenyl or alkyl group is optionally substituted with a amino group.

In one embodiment, $Q_3$ is —$NR^{22}R^{23}$—X—CO—$NR^{24}R^{25}$, —X—CS—$NR^{24}R^{25}$, or —X—$SO_2$—$NR^{24}R^{25}$. In another embodiment, $Q_3$ is —X—CO—$NR^{24}R^{25}$, —X—CS—$NR^{24}R^{25}$, or —X—$SO_2$—$NR^{24}R^{25}$. In another embodiment, $Q_3$ is —$NR^{22}R^{23}$. In another embodiment, $Q_3$ is —OH.

In one embodiment, the compound of Formula (II) is of formula:

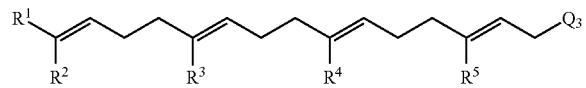

wherein $R^1$, $R^2$, $R^3$, $R^4$, $R^5$, and $Q_3$ are defined as in any aspect or embodiment herein.

In another embodiment, the GGA derivative provided and/or utilized is of formula:

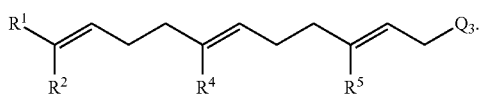

wherein $R^1$, $R^2$, $R^4$, $R^5$, and $Q_3$ are defined as in any aspect and embodiment here.

In one embodiment, the compound of Formula (II) is of formula:

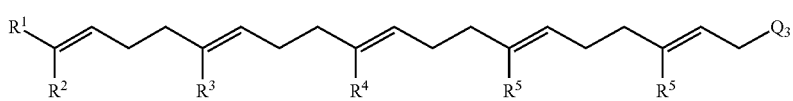

wherein $R^1$, $R^2$, $R^3$, $R^4$, $R^5$, and $Q_3$ are defined as in any aspect or embodiment herein.

In another embodiment, the GGA derivative provided and/or utilized is of formula:

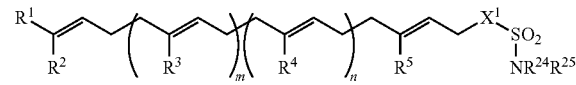

wherein $R^1$, $R^2$, $R^4$, $R^5$, m, n, X, $R^{24}$ and $R^{25}$ are defined as in any aspect and embodiment here.

In another embodiment, the GGA derivative provided and/or utilized is of formula:

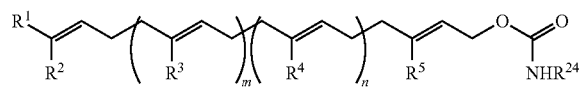

wherein $R^1$, $R^2$, $R^4$, $R^5$, m, n, and $R^{24}$ are defined as in any aspect and embodiment here.

In another embodiment, the GGA derivative provided and/or utilized is of formula:

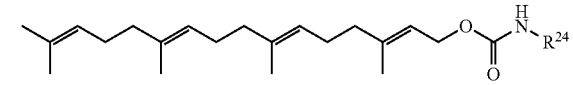

wherein $R^{24}$ is defined as in any aspect and embodiment here.

In another embodiment, the GGA derivative provided and/or utilized is of formula:

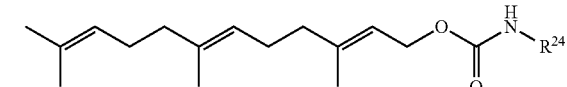

wherein $R^{24}$ is defined as in any aspect and embodiment here.

In another embodiment, the GGA derivative provided and/or utilized is of formula:

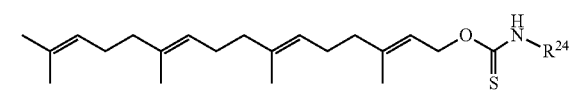

wherein $R^{24}$ is defined as in any aspect and embodiment here.

In another embodiment, the GGA derivative provided and/or utilized is of formula:

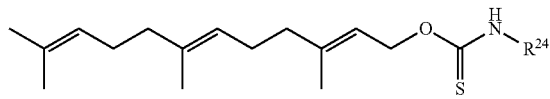

wherein $R^{24}$ is defined as in any aspect and embodiment here.

In another embodiment, the GGA derivative provided and/or utilized is of formula:

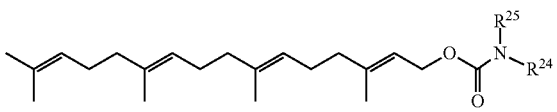

wherein $R^{24}$ and $R^{25}$ are defined as in any aspect and embodiment here.

In another embodiment, the GGA derivative provided and/or utilized is of formula:

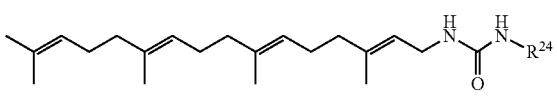

wherein $R^{24}$ is defined as in any aspect and embodiment here.

In another embodiment, the GGA derivative provided and/or utilized is of formula:

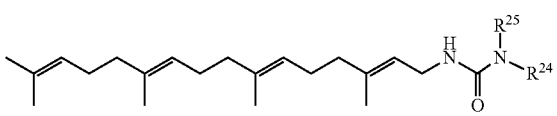

wherein $R^{24}$ and $R^{25}$ are defined as in any aspect and embodiment here.

In one embodiment, m is 0. In another embodiment, m is 1.
In another embodiment, n is 0. In another embodiment, n is 1. In another embodiment, n is 2.
In another embodiment, m+n is 1. In another embodiment, m+n is 2. In another embodiment, m+n is 3.
In another embodiment, $R^1$ and $R^2$ are independently $C_1$-$C_6$ alkyl. In another embodiment, $R^1$ and $R^2$ independently are methyl, ethyl, or isopropyl.
In another embodiment, $R^1$ and $R^2$ together with the carbon atom they are attached to form a $C_5$-$C_7$ cycloalkyl ring optionally substituted with 1-3 $C_1$-$C_6$ alkyl groups. In another embodiment, $R^1$ and $R^2$ together with the carbon atom they are attached to form a ring that is:

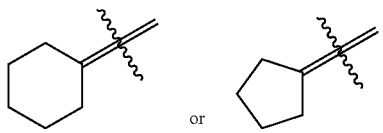

In another embodiment, $R^3$, $R^4$, and $R^5$ are independently $C_1$-$C_6$ alkyl. In another embodiment, one of $R^3$, $R^4$, and $R^5$ are alkyl, and the rest are hydrogen. In another embodiment, two of $R^3$, $R^4$, and $R^5$ are alkyl, and the rest are hydrogen. In another embodiment, $R^3$, $R^4$, and $R^5$ are hydrogen. In another embodiment, $R^3$, $R^4$, and $R^5$ are methyl.

In another embodiment, $Q_3$ is —X—CO—NR$^{24}$R$^{25}$. In another embodiment, $Q_3$ is —X—CS—NR$^{24}$R$^{25}$. In another embodiment, $Q_3$ is —X—SO$_2$—NR$^{24}$R$^{25}$. In another embodiment, $Q_3$ is —OCONHR$^{24}$, —OCONR$^{24}$R$^{25}$, —NHCONHR$^{24}$, —NHCONR$^{24}$R$^{25}$, —OCSNHR$^{24}$, —OCSNR$^{24}$R$^{25}$, —NHCSNHR$^{24}$ or —NHCSNR$^{24}$R$^{25}$.

In another embodiment, X is —O—. In another embodiment, X is —NR$^{26}$—. In another embodiment, X is or —CR$^{27}$R$^{28}$.

In another embodiment, one of $R^{24}$ and $R^{25}$ is hydrogen. In another embodiment, one or both of $R^{24}$ and $R^{25}$ are $C_1$-$C_6$ alkyl. In another embodiment, one or both of $R^{24}$ and $R^{25}$ are $C_1$-$C_6$ alkyl, optionally substituted with an $R^{20}$ group, wherein $R^{20}$ is —CO$_2$H or an ester thereof, $C_1$-$C_6$ alkyl, $C_3$-$C_{10}$ cycloalkyl, $C_3$-$C_8$ heterocyclyl, $C_6$-$C_{10}$ aryl, or $C_2$-$C_{10}$ heteroaryl. In another embodiment, one or both of $R^{24}$ and $R^{25}$ are $C_3$-$C_{10}$ cycloalkyl. In another embodiment, one or both of $R^{24}$ and $R^{25}$ are $C_3$-$C_{10}$ cycloalkyl substituted with 1-3 alkyl groups. In another embodiment, one or both of $R^{24}$ and $R^{25}$ are $C_3$-$C_8$ heterocyclyl. In another embodiment, one or both of $R^{24}$ and $R^{25}$ are $C_6$-$C_{10}$ aryl. In another embodiment, one or both of $R^{24}$ and $R^{25}$ are $C_2$-$C_{10}$ heteroaryl. In another embodiment, $R^{24}$ and $R^{25}$ together with the nitrogen atom they are attached to form a 5-7 membered heterocycle.

In another embodiment, $R^{20}$ is —CO$_2$H or an ester thereof. In another embodiment, $R^{20}$ is $C_1$-$C_6$ alkyl. In another embodiment, $R^{20}$ is $C_3$-$C_{10}$ cycloalkyl. In another embodiment, $R^{20}$ is $C_3$-$C_8$ heterocyclyl. In another embodiment, $R^{20}$ is $C_6$-$C_{10}$ aryl. In another embodiment, $R^{20}$ is or $C_2$-$C_{10}$ heteroaryl.

In another embodiment, the GGA derivative provided and/or utilized is of formula (II):

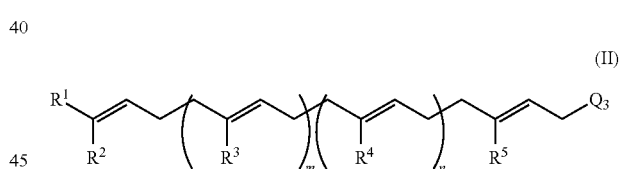

(II)

or a pharmaceutically acceptable salt thereof, wherein m is 0 or 1;

n is 0, 1, or 2;

each $R^1$ and $R^2$ are independently $C_1$-$C_6$ alkyl, or $R^1$ and $R^2$ together with the carbon atom they are attached to form a $C_5$-$C_7$ cycloalkyl ring optionally substituted with 1-3 $C_1$-$C_6$ alkyl groups;

each of $R^3$, $R^4$, and $R^5$ independently are hydrogen or $C_1$-$C_6$ alkyl;

$Q_3$ is —X—CO—NR$^{24}$R$^{25}$ or —X—SO$_2$—NR$^{24}$R$^{25}$;

X is —O—, —NR$^{26}$—, or —CR$^{27}$R$^{28}$;

$R^{26}$ is hydrogen or together with $R^{24}$ or $R^{25}$ and the intervening atoms form a 5-7 membered ring optionally substituted with 1-3 $C_1$-$C_6$ alkyl groups;

each $R^{27}$ and $R^{28}$ independently are hydrogen, $C_1$-$C_6$ alkyl, —COR$^{81}$ or —CO$_2$R$^{81}$, or $R^{27}$ together with $R^{24}$ or $R^{25}$ and the intervening atoms form a 5-7 membered cycloalkyl or heterocyclyl ring optionally substituted with 1-3 $C_1$-$C_6$ alkyl groups;

each $R^{24}$ and $R^{25}$ independently is hydrogen, $C_1$-$C_6$ alkyl, optionally substituted with —$CO_2H$ or an ester thereof, $C_3$-$C_{10}$ preferably $C_3$-$C_8$ cycloalkyl, $C_3$-$C_8$ heterocyclyl, $C_6$-$C_{10}$ aryl, or $C_2$-$C_{10}$ heteroaryl, $C_3$-$C_{10}$ cycloalkyl, $C_3$-$C_8$ heterocyclyl, $C_6$-$C_{10}$ aryl, or $C_2$-$C_{10}$ heteroaryl, wherein each cycloalkyl, heterocyclyl, aryl, or heteroaryl is optionally substituted with 1-3 $C_1$-$C_6$ alkyl groups, or $R^{24}$ and $R^{25}$ together with the nitrogen atom they are attached to form a 5-7 membered heterocycle.

In another embodiment, provided herein are compounds of formula:

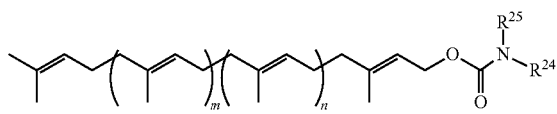

m = 0, n = 1, $R^{24}$ = cyclohexyl, and $R^{25}$ = methyl
m = 1, n = 1, $R^{24}$ = cyclohexyl, and $R^{25}$ = methyl
m = 1, n = 2, $R^{24}$ = cyclohexyl, and $R^{25}$ = methyl
m = 0, n = 1, $R^{24}$ = n-pentyl, and $R^{25}$ = methyl
m = 1, n = 1, $R^{24}$ = n-pentyl, and $R^{25}$ = methyl
m = 1, n = 2, $R^{24}$ = n-pentyl, and $R^{25}$ = methyl In another aspect, the GGA derivative provided and/or utilized herein is of Formula III:

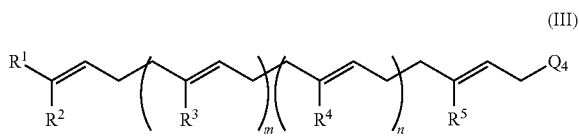

or a pharmaceutically acceptable salt of each thereof, wherein m is 0 or 1;

n is 0, 1, or 2;

each $R^1$ and $R^2$ are independently $C_1$-$C_6$ alkyl, or $R^1$ and $R^2$ together with the carbon atom they are attached to form a $C_5$-$C_7$ cycloalkyl ring optionally substituted with 1-3 $C_1$-$C_6$ alkyl groups;

each of $R^3$, $R^4$, and $R^5$ independently are hydrogen or $C_1$-$C_6$ alkyl;

$Q_4$ is selected from the group consisting of:

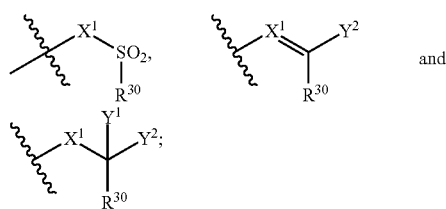

when $X^1$ is bonded via a single bond, $X^1$ is —O—, —$NR^{31}$—, or —$CR^{32}R^{33}$—, and when $X^1$ is bonded via a double bond, $X^1$ is —$CR^{32}$—;

$Y^1$ is hydrogen, —OH or —O—$R^{10}$, $Y^2$ is —OH, —$OR^{11}$ or —$NHR^{12}$, or $Y^1$ and $Y^2$ are joined to form an oxo group (=O), an imine group (=$NR^{13}$), a oxime group (=N—$OR^{14}$), or a substituted or unsubstituted vinylidene (=$CR^{16}R^{12}$);

$R^{30}$ is $C_1$-$C_6$ alkyl optionally substituted with 1-3 alkoxy or 1-5 halo group, $C_2$-$C_6$ alkenyl, $C_2$-$C_6$ alkynyl, $C_3$-$C_{10}$ cycloalkyl, $C_6$-$C_{10}$ aryl, $C_3$-$C_8$ heterocyclyl, or $C_2$-$C_{10}$ heteroaryl, wherein each cycloalkyl or heterocyclyl is optionally substituted with 1-3 $C_1$-$C_6$ alkyl groups, or wherein each aryl or heteroaryl is independently substituted with 1-3 $C_1$-$C_6$ alkyl or nitro groups, or $R^{30}$ is —$NR^{34}R^{35}$;

$R^{31}$ is hydrogen or together with $R^{30}$ and the intervening atoms form a 5-7 membered ring optionally substituted with 1-3 $C_1$-$C_6$ alkyl groups;

each $R^{32}$ and $R^{33}$ independently are hydrogen, $C_1$-$C_6$ alkyl, —$COR^{81}$ or —$CO_2R^{81}$, or $R^{32}$ together with $R^{30}$ and the intervening atoms form a 5-7 membered cycloalkyl or heterocyclyl ring optionally substituted with oxo or 1-3 $C_1$-$C_6$ alkyl groups;

$R^{10}$ is $C_1$-$C_6$ alkyl;

$R^{11}$ and $R^{12}$ are independently $C_1$-$C_6$ alkyl, $C_3$-$C_{10}$ cycloalkyl, —$CO_2R^{15}$, or —$CON(R^{15})_2$, or $R^{10}$ and $R^{11}$ together with the intervening carbon atom and oxygen atoms form a heterocycle optionally substituted with 1-3 $C_1$-$C_6$ alkyl groups;

$R^{13}$ is $C_1$-$C_6$ alkyl or $C_3$-$C_{10}$ cycloalkyl optionally substituted with 1-3 $C_1$-$C_6$ alkyl groups;

$R^{14}$ is hydrogen, $C_3$-$C_8$ heterocyclyl, or $C_1$-$C_6$ alkyl optionally substituted with a —$CO_2H$ or an ester thereof or a $C_6$-$C_{10}$ aryl, $C_2$-$C_6$ alkenyl, $C_2$-$C_6$ alkynyl, $C_3$-$C_{10}$ cycloalkyl, or a $C_3$-$C_8$ heterocyclyl, wherein each cycloalkyl, heterocyclyl, or aryl, is optionally substituted with 1-3 alkyl groups;

each $R^{15}$ independently are hydrogen, $C_3$-$C_{10}$ cycloalkyl, $C_1$-$C_6$ alkyl optionally substituted with 1-3 substituents selected from the group consisting of —$CO_2H$ or an ester thereof, aryl, or $C_3$-$C_8$ heterocyclyl, or two $R^{15}$ groups together with the nitrogen atom they are bonded to form a 5-7 membered heterocycle;

$R^{16}$ is hydrogen or $C_1$-$C_6$ alkyl;

$R^{17}$ is hydrogen, $C_1$-$C_6$ alkyl substituted with 1-3 hydroxy groups, —CHO, or is $CO_2H$ or an ester thereof;

each $R^{34}$ and $R^{35}$ independently is hydrogen, $C_1$-$C_6$ alkyl, optionally substituted with —$CO_2H$ or an ester thereof, $C_3$-$C_{10}$ cycloalkyl, $C_3$-$C_8$ heterocyclyl, $C_6$-$C_{10}$ aryl, or $C_2$-$C_{10}$ heteroaryl, or is $C_3$-$C_{10}$ cycloalkyl, $C_3$-$C_8$ heterocyclyl, $C_6$-$C_{10}$ aryl, or $C_2$-$C_{10}$ heteroaryl, wherein each cycloalkyl, heterocyclyl, aryl, or heteroaryl is optionally substituted with 1-3 alkyl groups, or $R^{34}$ and $R^{35}$ together with the nitrogen atom they are attached to form a 5-7 membered heterocycle; and each $R^{81}$ independently is $C_1$-$C_6$ alkyl.

In one embodiment, m is 0. In another embodiment, m is 1. In another embodiment, n is 0. In another embodiment, n is 1. In another embodiment, n is 2.

In one embodiment, the compound of Formula (III) is of formula:

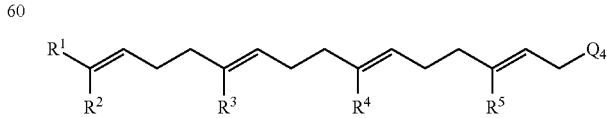

wherein $Q_4$, $R^1$, $R^2$, $R^3$, $R^4$, $R^5$, $R^{30}$, $X^1$, $Y^1$, and $Y^2$ are defined as in any aspect or embodiment herein.

In one embodiment, the GGA derivative provided and/or utilized is of formula:

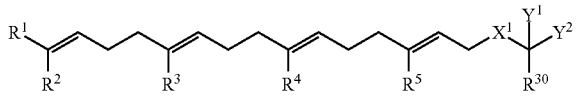

wherein $R^1$, $R^2$, $R^3$, $R^4$, $R^5$, $R^{30}$, $X^1$, $Y^1$, and $Y^2$ are defined as in any aspect and embodiment here.

In another embodiment, the GGA derivative provided and/or utilized is of formula:

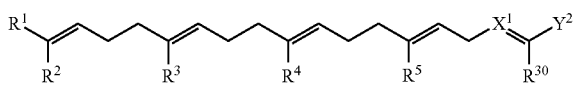

wherein $R^1$, $R^2$, $R^3$, $R^4$, $R^5$, $R^{30}$, $X^1$, and $Y^2$ are defined as in any aspect and embodiment herein.

In another embodiment, the GGA derivative provided and/or utilized is of formula:

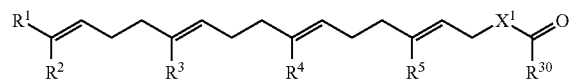

wherein $R^1$, $R^2$, $R^3$, $R^4$, $R^5$, $R^{30}$ and $X^1$ are defined as in any aspect and embodiment herein.

In another embodiment, the GGA derivative provided and/or utilized is of formula:

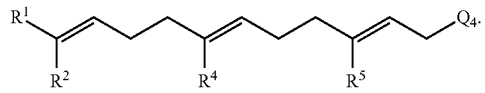

wherein $R^1$, $R^2$, $R^4$, $R^5$, and $Q_4$ are defined as in any aspect and embodiment herein.

In another embodiment, the GGA derivative provided and/or utilized is of formula:

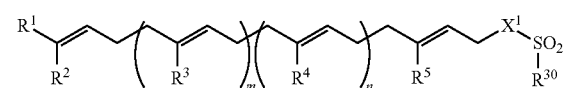

wherein $R^1$, $R^2$, $R^4$, $R^5$, m, n, $X^1$, and $R^{30}$ are defined as in any aspect and embodiment here.

In another embodiment, the GGA derivative provided and/or utilized is of formula:

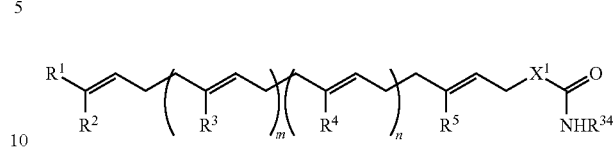

wherein $R^1$, $R^2$, $R^4$, $R^5$, m, n, and $R^{34}$ are defined as in any aspect and embodiment here.

In another embodiment, the GGA derivative provided and/or utilized is of formula:

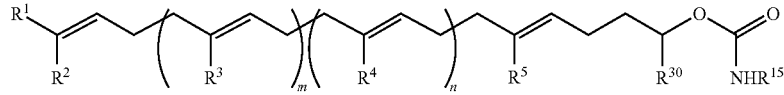

wherein $R^1$, $R^2$, $R^4$, $R^5$, $R^{30}$, m, n, and $R^{15}$ are defined as in any aspect and embodiment here.

In another embodiment, each $R^1$ and $R^2$ are $C_1$-$C_6$ alkyl. In another embodiment, each $R^1$ and $R^2$ are methyl, ethyl, or isopropyl. In another embodiment, $R^1$ and $R^2$ together with the carbon atom they are attached to form a 5-6 membered ring optionally substituted with 1-3 $C_1$-$C_6$ alkyl groups. In another embodiment, $R^1$ and $R^2$ together with the carbon atom they are attached to form a ring that is:

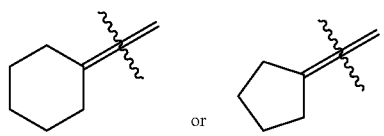

In another embodiment, $R^3$, $R^4$, and $R^5$ are $C_1$-$C_6$ alkyl. In another embodiment, one of $R^3$, $R^4$, and $R^5$ are alkyl, and the rest are hydrogen. In another embodiment, two of $R^3$, $R^4$, and $R^5$ are alkyl, and the rest are hydrogen. In another embodiment, $R^3$, $R^4$, and $R^5$ are hydrogen. In another embodiment, $R^3$, $R^4$, and $R^5$ are methyl.

In another embodiment, $X^1$ is O. In another embodiment, $X^1$ is —$NR^{31}$. In another embodiment, $R^{31}$ is hydrogen. In another embodiment, $R^{31}$ together with $R^{30}$ and the intervening atoms form a 5-7 membered ring optionally substituted with 1-3 $C_1$-$C_6$ alkyl groups. In another embodiment, $X^1$ is —$CR^{32}R^{33}$—. In another embodiment, $X^1$ is —$CR^{32}$—. In another embodiment, each $R^{32}$ and $R^{33}$ independently are hydrogen, $C_1$-$C_6$ alkyl, —$COR^{81}$, or —$CO_2R^{81}$. In another embodiment, $R^{32}$ is hydrogen, and $R^{33}$ is hydrogen, $C_1$-$C_6$ alkyl, —$COR^{81}$, or —$CO_2R^{81}$.

In another embodiment, $R^{33}$ is hydrogen. In another embodiment, $R^{33}$ $C_1$-$C_6$ alkyl. In another embodiment, $R^{33}$ is methyl. In another embodiment, $R^{33}$ is —$CO_2R^{81}$. In another embodiment, $R^{33}$ is —$COR^{81}$.

In another embodiment, $R^{32}$ together with $R^{30}$ and the intervening atoms form a 5-7 membered ring. In another embodiment, the moiety:

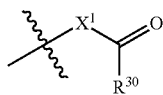

which is "$Q_4$," has the structure:

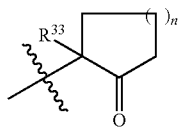

wherein $R^{33}$ is hydrogen, $C_1$-$C_6$ alkyl, or —$CO_2R^{81}$ and n is 1, 2, or 3. Within these embodiments, in certain embodiments, $R^{33}$ is hydrogen or $C_1$-$C_6$ alkyl. In one embodiment, $R^{33}$ is hydrogen. In another embodiment, $R^{33}$ is $C_1$-$C_6$ alkyl.

In another embodiment, $R^{30}$ is $C_1$-$C_6$ alkyl. In another embodiment, $R^{30}$ is methyl, ethyl, butyl, isopropyl, or tertiary butyl. In another embodiment, $R^{30}$ is $C_1$-$C_6$ alkyl substituted with 1-3 alkoxy or 1-5 halo group. In another embodiment, $R^{30}$ is alkyl substituted with an alkoxy group. In another embodiment, $R^{30}$ is alkyl substituted with 1-5, preferably, 1-3, halo, preferably fluoro, groups.

In another embodiment, $R^{30}$ is $NR^{34}R^{35}$. In a preferred embodiment, $R^{35}$ is H. In a preferred embodiment, $R^{34}$ is $C_1$-$C_6$ alkyl, optionally substituted with a group selected from the group consisting of —$CO_2H$ or an ester thereof, $C_3$-$C_{10}$ cycloalkyl, $C_3$-$C_8$ heterocyclyl, $C_6$-$C_{10}$ aryl, or $C_2$-$C_{10}$ heteroaryl. In another preferred embodiment, $R^{34}$ is $C_3$-$C_{10}$ cycloalkyl, $C_3$-$C_8$ heterocyclyl, $C_6$-$C_{10}$ aryl, or $C_2$-$C_{10}$ heteroaryl. In a more preferred embodiment, $R^{34}$ is $C_3$-$C_{10}$ cycloalkyl.

In another embodiment, $R^{30}$ is $C_2$-$C_6$ alkenyl or $C_2$-$C_6$ alkynyl. In another embodiment, $R^{30}$ is $C_3$-$C_{10}$ cycloalkyl. In another embodiment, $R^{30}$ is $C_3$-$C_{10}$ cycloalkyl substituted with 1-3 $C_1$-$C_6$ alkyl groups. In another embodiment, $R^{30}$ is cyclopropyl, cyclobutyl, cyclopentyl, cyclohexyl, or adamentyl. In another embodiment, $R^{30}$ is $C_6$-$C_{10}$ aryl or $C_2$-$C_{10}$ heteroaryl. In another embodiment, $R^{30}$ is a 5-7 membered heteroaryl containing at least 1 oxygen atom. In another embodiment, $R^{30}$ is $C_6$-$C_{10}$ aryl, $C_3$-$C_8$ heterocyclyl, or $C_2$-$C_{10}$ heteroaryl, wherein each aryl, heterocyclyl, or heteroaryl is optionally substituted with 1-3 $C_1$-$C_6$ alkyl groups.

In another embodiment, $Y^2$ is —O—$R^{11}$. In another embodiment, $Y^1$ and $Y^2$ are joined to form =$NR^{13}$. In another embodiment, $Y^1$ and $Y^2$ are joined to form =$NOR^{14}$. In another embodiment, $Y^1$ and $Y^2$ are joined to form (=O). In another embodiment, $Y^1$ and $Y^2$ are joined to form =$CR^{16}R^{17}$.

In another embodiment, $Q_4$ is —$CR^{33}COR^{30}$. In another embodiment, $R^{30}$ is $C_1$-$C_6$ alkyl optionally substituted with an alkoxy group. In another embodiment, $R^{30}$ is $C_3$-$C_8$ cycloalkyl. In another embodiment, $R^{33}$ is hydrogen. In another embodiment, $R^{33}$ is $C_1$-$C_6$ alkyl. In another embodiment, $R^{33}$ is $CO_2R^{81}$. In another embodiment, $R^{33}$ is $COR^{81}$.

In another embodiment, $Q_4$ is —$CH_2$—CH(O—CONHR$^{15}$)—$R^{30}$. In another embodiment, $R^{15}$ is $C_3$-$C_8$ cycloalkyl. In another embodiment, $R^{15}$ is $C_1$-$C_6$ alkyl optionally substituted with 1-3 substiteunts selected from the group consisting of —$CO_2H$ or an ester thereof, aryl, or $C_3$-$C_8$ heterocyclyl. In a preferred embodiment within these embodiments, $R^{30}$ is $C_1$-$C_6$ alkyl.

In another embodiment, $Q_4$ is —O—CO—$NHR^{34}$. within these embodiment, in another embodiment, $R^{34}$ is $C_1$-$C_6$ alkyl, optionally substituted with —$CO_2H$ or an ester thereof, $C_3$-$C_8$ cycloalkyl, $C_3$-$C_8$ heterocyclyl, $C_2$-$C_{10}$ aryl, or $C_2$-$C_{10}$ heteroaryl. In yet another embodiment, $R^{34}$ is $C_3$-$C_8$ cycloalkyl, $C_3$-$C_8$ heterocyclyl, $C_2$-$C_{10}$ aryl, or $C_2$-$C_{10}$ heteroaryl.

In another embodiment, $R^{14}$ is hydrogen. In another embodiment, $R^{14}$ is $C_1$-$C_6$ alkyl optionally substituted with a —$CO_2H$ or an ester thereof or a $C_6$-$C_{10}$ aryl optionally substituted with 1-3 alkyl groups. In another embodiment, $R^{14}$ is $C_2$-$C_6$ alkenyl. In another embodiment, $R^{14}$ is $C_2$-$C_6$ alkynyl In another embodiment, $R^{14}$ is $C_3$-$C_6$ cycloalkyl optionally substituted with 1-3 alkyl groups. In another embodiment, $R^{14}$ is $C_3$-$C_8$ heterocyclyl optionally substituted with 1-3 alkyl groups.

In another embodiment, preferably, $R^{16}$ is hydrogen. In another embodiment, $R^{12}$ is $CO_2H$ or an ester thereof. In another embodiment, $R^{12}$ is $C_1$-$C_6$ alkyl substituted with 1-3 hydroxy groups. In another embodiment, $R^{12}$ is $C_1$-$C_3$ alkyl substituted with 1 hydroxy group. In another embodiment, $R^{12}$ is —$CH_2OH$.

In another embodiment, $R^{10}$ and $R^{11}$ together with the intervening carbon atom and oxygen atoms form a heteroycle of formula:

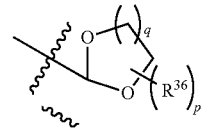

wherein q is 0 or 1, p is 0, 1, 2, or 3, and $R^{36}$ is $C_1$-$C_6$ alkyl.

In another embodiment, q is 1. In another embodiment, q is 2. In another embodiment, p is 0. In another embodiment, p is 1. In another embodiment, p is 2. In another embodiment, p is 3.

In one aspect, the GGA derivative provided and/or utilized herein is of Formula (IV):

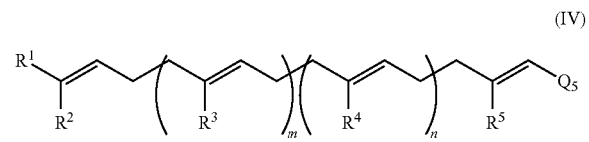

or a tautomer thereof, or a pharmaceutically acceptable salt of each thereof, wherein
m is 0 or 1;
n is 0, 1, or 2;
each $R^1$ and $R^2$ are independently $C_1$-$C_6$ alkyl, or $R^1$ and $R^2$ together with the carbon atom they are attached to form a $C_5$-$C_7$ cycloalkyl ring optionally substituted with 1-3 $C_1$-$C_6$ alkyl groups;
each of $R^3$, $R^4$, and $R^5$ independently are hydrogen or $C_1$-$C_6$ alkyl, or $R^5$ and $Q_5$ together with the intervening carbon atoms form a 6 membered aryl ring, or a 5-8 membered cycloalkenyl ring, or a 5-14 membered heteroaryl or heterocycle, wherein each aryl, cycloalkenyl, heteroaryl, or heterocycle, ring is optionally substituted with 1-2 substituents selected from the group consisting of halo, hydroxy, oxo, —N($R^{40}$)$_2$, and $C_1$-$C_6$ alkyl group;

$Q_5$ is —C(=O)H, —CO$_2$H or —CH=CHCO$_2$H, or a $C_1$-$C_6$ alkyl ester or acyl halide thereof, wherein the ester is optionally substituted with —CO-phenyl; a 6-10 membered aryl or a 5-14 membered heteroaryl or heterocycle containing up to 6 ring heteroatoms, wherein the heteroatom is selected from the group consisting of O, N, S, and oxidized forms of N and S, and further wherein the aryl, heteroaryl, or heterocyclyl ring is optionally substituted with 1-3 substituents selected from the group consisting of:

hydroxy, oxo, —N($R^{40}$)$_2$, $C_1$-$C_6$ alkoxy group, and $C_1$-$C_6$ alkyl group, wherein the alkyl group is optionally substituted with 1-3 substituents selected from hydroxy, NH$_2$, $C_6$-$C_{10}$ aryl, —CO$_2$H or an ester or an amide thereof, a 5-9 membered heteroaryl containing up to 3 ring heteroatoms, wherein the heteroaryl is optionally substituted with 1-3 hydroxy, —N($R^{40}$)$_2$, and $C_1$-$C_6$ alkyl group, benzyl, and phenyl optionally substituted with 1-3 substituents selected from the group consisting of $C_1$-$C_6$ alkyl, $C_1$-$C_6$ alkoxy, hydroxy, and halo groups; and wherein each $R^{40}$ independently is hydrogen or $C_1$-$C_6$ alkyl.

As used herein, the compound of Formula (IV) includes tautomers and optical isomers such as enantiomers and diastereomers. As also used herein, an ester refers preferably to a phenyl or a $C_1$-$C_6$ alkyl ester, which phenyl or alkyl group is optionally substituted with a amino group. As used herein, an amide refers preferably to a moiety of formula —CON($R^{40}$)$_2$, wherein $R^{40}$ is defined as above.

In some embodiment, $Q_6$ is selected from a group consisting of oxazole, oxadiazole, oxazoline, azalactone, imidazole, diazole, triazole, and thiazole, wherein each heteroaryl or heterocycle is optionally substituted as disclosed above.

In one embodiment, the GGA derivative provided and/or utilized is of formula IV-A:

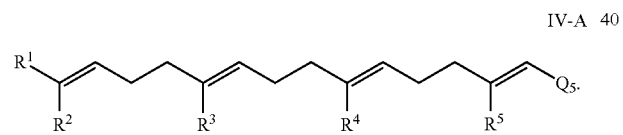

IV-A

In another embodiment, the GGA derivative provided and/or utilized is of formula IV-B:

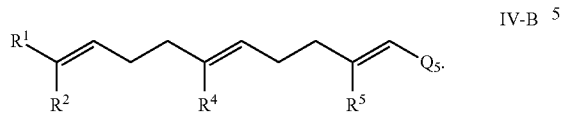

IV-B wherein $R^1$, $R^2$, $R^4$, $R^5$, and $Q_5$ are defined as in any aspect and embodiment here.

In another embodiment, $Q_5$ is selected from the group consisting of:

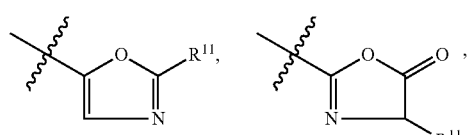

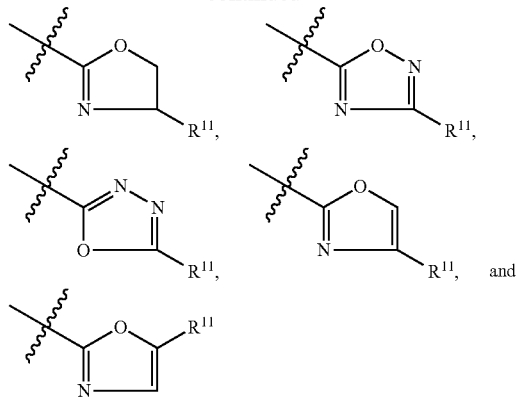

wherein $R^{11}$ is $C_1$-$C_6$ alkyl, $C_6$-$C_{10}$ aryl, $C_3$-$C_8$ heteroaryl, $C_3$-$C_8$ heteroaryl, $C_3$-$C_{10}$ cycloalkyl, and the alkyl group is optionally substituted with 1-3 $C_6$-$C_{10}$ aryl, $C_3$-$C_8$ heteroaryl, $C_3$-$C_8$ heteroaryl, $C_3$-$C_{10}$ cycloalkyl groups, and the aryl, heteroaryl, heteroaryl, cycloalkyl groups are optionally substituted with 1-3 $C_1$-$C_6$ alkyl, $C_1$-$C_6$ alkoxy, halo, preferably chloro or fluoro, $C_6$-$C_{10}$ aryl, $C_3$-$C_8$ heteroaryl, $C_3$-$C_8$ heteroaryl, $C_3$-$C_{10}$ cycloalkyl group.

In another embodiment, $Q_5$ is phenyl, optionally substituted as described herein. In another embodiment, $Q_5$ is benzimidazole, benzindazole, and such other 5-6 fused 9-membered bicyclic heteroaryl or heterocycle. In another embodiment, $Q_5$ is quinoline, isoquinoline, and such other 6-6 fused 10 membered heteroaryl or heterocycle. In another embodiment, $Q_5$ is benzodiazepine or a derivative thereof, such as, a benzodiazepinone. Various benzodiazepine and derivatives thereof are well known to the skilled artisan.

In another embodiment, m is 0. In another embodiment, m is 1.

In another embodiment, n is 0. In another embodiment, n is 1. In another embodiment, n is 2.

In another embodiment, m+n is 1. In another embodiment, m+n is 2. In another embodiment, m+n is 3.

In another embodiment, $R^1$ and $R^2$ are independently $C_1$-$C_6$ alkyl. In another embodiment, $R^1$ and $R^2$ independently are methyl, ethyl, or isopropyl.

In another embodiment, $R^1$ and $R^2$ together with the carbon atom they are attached to form a $C_5$-$C_7$ cycloalkyl ring optionally substituted with 1-3 $C_1$-$C_6$ alkyl groups. In another embodiment, $R^1$ and $R^2$ together with the carbon atom they are attached to form a ring that is:

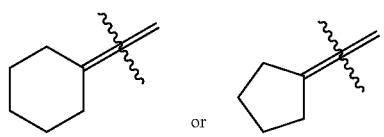

In another embodiment, $R^3$, $R^4$, and $R^5$ are independently $C_1$-$C_6$ alkyl. In another embodiment, one of $R^3$, $R^4$, and $R^5$ are alkyl, and the rest are hydrogen. In another embodiment, two of $R^3$, $R^4$, and $R^5$ are alkyl, and the rest are hydrogen. In another embodiment, $R^3$, $R^4$, and $R^5$ are hydrogen. In another embodiment, $R^3$, $R^4$, and $R^5$ are methyl.

In another embodiment, this invention provides a compound selected from the group consisting of:

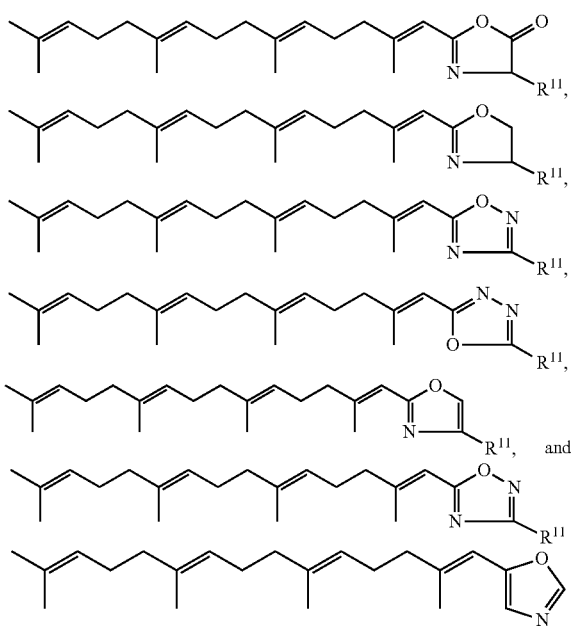

wherein $R^{11}$ is defined as above.

In another aspect, GGA derivatives provided and/or utilized herein are of formula (V):

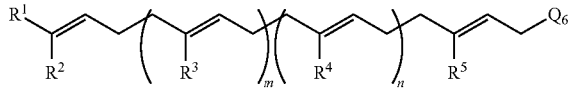

(V)

or a pharmaceutically acceptable salt thereof, wherein
m is 0 or 1;
n is 0, 1, or 2;
each $R^1$ and $R^2$ independently are $C_1$-$C_6$ alkyl, or $R^1$ and $R^2$ together with the carbon atom they are attached to form a $C_5$-$C_7$ cycloalkyl ring optionally substituted with 1-3 $C_1$-$C_6$ alkyl groups;
each of $R^3$, $R^4$, and $R^5$ independently is hydrogen or $C_1$-$C_6$ alkyl;
$Q_6$ is selected from the group consisting of:

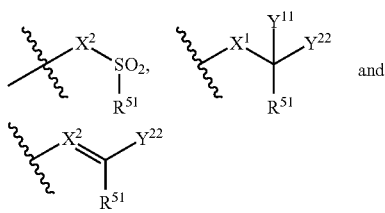

when $X^2$ is bonded via a single bond, $X^2$ is —O—, —$NR^{52}$—, or —$CR^{53}R^{54}$—, and when $X^2$ is bonded via a double bond, $X^2$ is —$CR^{53}$—;
$Y^{11}$ is hydrogen, —OH or —$OR^{55}$;
$Y^{22}$ is —OH, —$OR^{56}$, —$NHR^{57}$, or —O—CO—$NR^{58}R^{59}$, or $Y^{11}$ and $Y^{22}$ are joined to form an oxo group (=O), an imine group (=$NR^{60}$), a oxime group (=N—$OR^{61}$), or a substituted or unsubstituted vinylidene (=$CR^{63}R^{64}$);

$R^{51}$ is $C_1$-$C_6$ alkyl, $C_1$-$C_6$ alkyl substituted with 1-3 alkoxy or 1-5 halo groups, $C_2$-$C_6$ alkenyl, $C_2$-$C_6$ alkynyl, $C_3$-$C_{10}$ cycloalkyl, $C_3$-$C_8$ heterocyclyl, $C_6$-$C_{10}$ aryl, $C_2$-$C_{10}$ heteroaryl, or —$NR^{65}R^{66}$, wherein each cycloalkyl or heterocyclyl is optionally substituted with 1-3 $C_1$-$C_6$ alkyl groups, and wherein each aryl or heteroaryl is optionally substituted independently with 1-3 nitro and $C_1$-$C_6$ alkyl groups;
$R^{52}$ is hydrogen or together with $R^{51}$ and the intervening atoms form a 5-7 membered ring optionally substituted with 1-3 $C_1$-$C_6$ alkyl groups;
each $R^{53}$ and $R^{54}$ independently are hydrogen, $C_1$-$C_6$ alkyl, —$COR^{81}$, —$CO_2R^{81}$, or —$CONHR^{82}$, or $R^{53}$ together with $R^{51}$ and the intervening atoms form a 5-7 membered cycloalkyl or heterocyclyl ring optionally substituted with 1-3 $C_1$-$C_6$ alkyl groups;
$R^{55}$ is $C_1$-$C_6$ alkyl;
each $R^{56}$ and $R^{57}$ independently are $C_1$-$C_6$ alkyl, $C_3$-$C_{10}$ cycloalkyl, —$CO_2R^{62}$, or —$CON(R^{62})_2$, or $R^{55}$ and $R^{56}$ together with the intervening carbon atom and oxygen atoms form a heterocycle optionally substituted with 1-3 $C_1$-$C_6$ alkyl groups;
$R^{58}$ is: $C_3$-$C_{10}$ cycloalkyl, $C_1$-$C_6$ alkyl optionally substituted with —OH, $CO_2H$ or an ester thereof, or $C_3$-$C_{10}$ cycloalkyl,

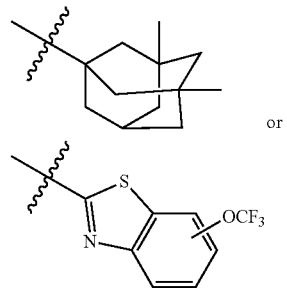

$R^{59}$ is hydrogen or $C_1$-$C_6$ alkyl;
$R^{60}$ is $C_1$-$C_6$ alkyl or $C_3$-$C_{10}$ cycloalkyl optionally substituted with 1-3 $C_1$-$C_6$ alkyl groups, or is:

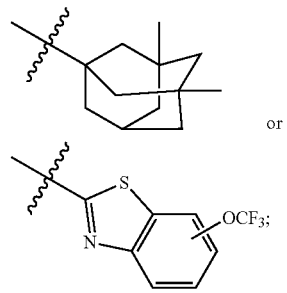

$R^{61}$ is hydrogen, $C_3$-$C_8$ heterocyclyl, or $C_1$-$C_6$ alkyl optionally substituted with a —$CO_2H$ or an ester thereof or a $C_6$-$C_{10}$ aryl, $C_2$-$C_6$ alkenyl, $C_2$-$C_6$ alkynyl, $C_3$-$C_{10}$ cycloalkyl, or a $C_3$-$C_8$ heterocyclyl, wherein each cycloalkyl, heterocyclyl, or aryl, is optionally substituted with 1-3 alkyl groups;
each $R^{62}$ independently are hydrogen, $C_3$-$C_{10}$ cycloalkyl, $C_1$-$C_6$ alkyl optionally substituted with 1-3 substituents selected from the group consisting of —$CO_2H$ or an ester thereof, aryl, $C_3$-$C_8$ heterocyclyl, or two $R^{62}$ groups together with the nitrogen atom they are bonded to form a 5-7 membered heterocycle;
$R^{63}$ is hydrogen or $C_1$-$C_6$ alkyl;
$R^{64}$ is hydrogen, $C_1$-$C_6$ alkyl substituted with 1-3 hydroxy groups, —CHO, or is $CO_2H$ or an ester thereof;
one or both of $R^{65}$ and $R^{66}$ independently are hydrogen, $C_1$-$C_6$ alkyl, optionally substituted with —$CO_2H$ or an ester thereof, $C_3$-$C_{10}$ cycloalkyl, $C_3$-$C_8$ heterocyclyl, $C_2$-$C_{10}$ aryl, or $C_2$-$C_{10}$ heteroaryl, or is $C_3$-$C_{10}$ cycloalkyl, $C_3$-$C_8$ heterocyclyl, $C_6$-$C_{10}$aryl, or $C_2$-$C_{10}$ heteroaryl, wherein each cycloalkyl, heterocyclyl, aryl, or heteroaryl is optionally substituted with 1-3 alkyl groups, or $R^{65}$ and $R^{66}$ gether with the nitrogen atom they are bonded to form a 5-7 membered heterocycle, and if only one of $R^{65}$ and $R^{66}$ are defined as above, then the other one is

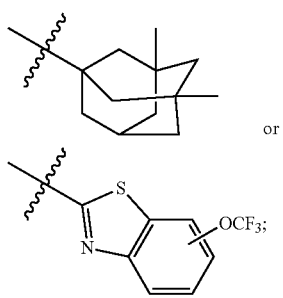

and
$R^{81}$ is $C_1$-$C_6$ alkyl; and
$R^{82}$ is:

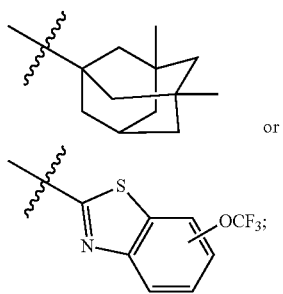

provided that, when $X^2$ is bonded via a single bond, and $R^{53}$ or $R^{54}$ is not —$CONHR^{82}$, $Y^{11}$ and $Y^{22}$ are joined to form an imine group (=$NR^{60}$), and $R^{60}$ is:

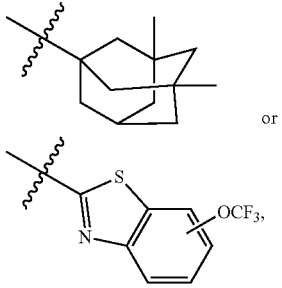

or $Y^{22}$ is —O—CO—$NR^{58}R^{59}$;
or provided that, when $Q_6$ is:

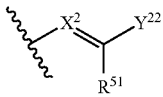

$Y^{22}$ and $R^{53}$ is not —$CONHR^{82}$, $Y^{22}$ is —O—CO—$NR^{58}R^{59}$;
or provided that, when $Q_6$ is —O—CO—$NR^{65}R^{66}$, then at least one of $R^{65}$ and $R^{66}$ is:

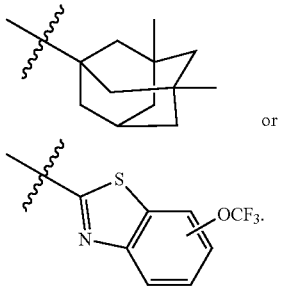

In one embodiment, the GGA derivative provided and/or utilized are of formula:

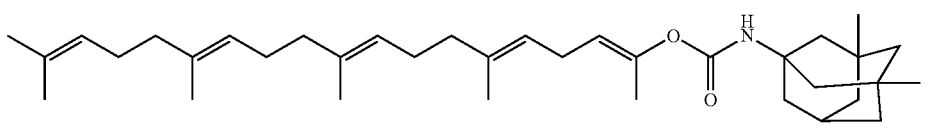

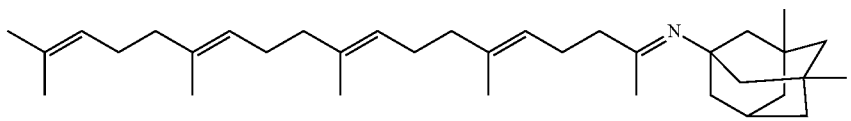

-continued

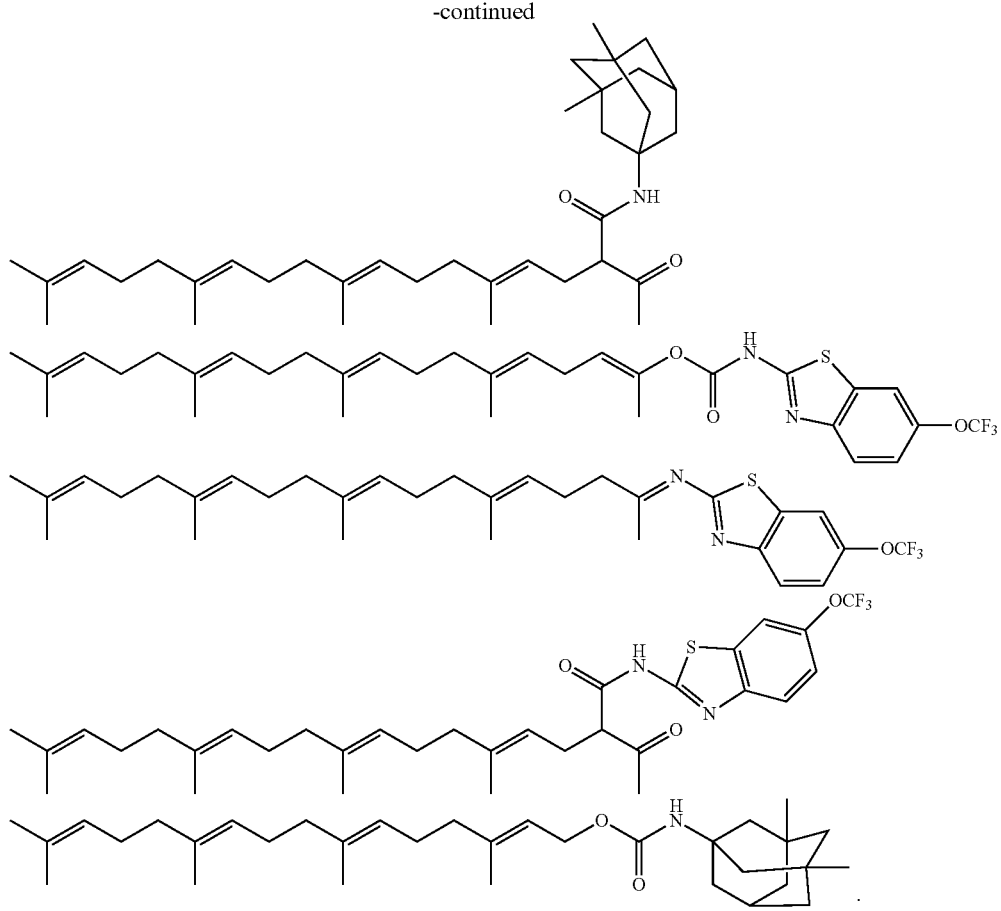

In another aspect, the GGA derivatives useful according to this invention is selected from:

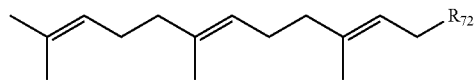

VIII: $R_{72} =$ —OH

IX: $R_{72} =$ Br

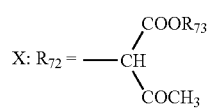

X: $R_{72} =$

XI: $R_{72} =$ CH$_2$COCH$_3$

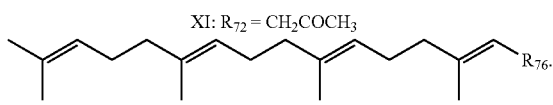

XIII: $R_{76} =$ —COOR$_{77}$

XIV: $R_{76} =$ —CH$_2$OH

XV: $R_{76} =$ —CH$_2$Br

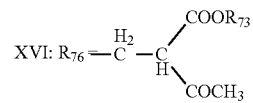

XVI: $R_{76} =$

VI: $R_{76} =$ —CH$_2$—CH$_2$—CO—CH$_3$

In one embodiment, the compounds provided herein excludes the compound of formula:

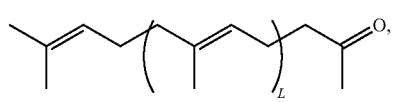

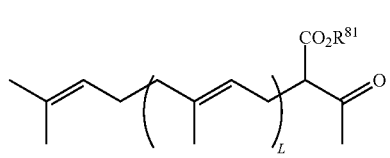

or

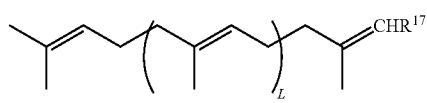

wherein L is 0, 1, 2, or 3, and $R^{17}$ is CO$_2$H or an ester thereof, or is —CH$_2$OH, or is a C$_1$-C$_6$ alkyl ester of —CH$_2$OH.

In another embodiment, examples of compounds provided and/or utilized by this invention include certain compounds tabulated below. Compound ID numbers in Table 1 refer to synthetic schemes in Example 7.

TABLE 1
| Compound ID (see Example 7) | Structure |
|---|---|
| 1 | 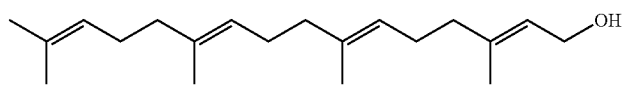 [SMILES: CC(C)=CCC/C(C)=C/CC/C(C)=C/CC/C(C)=C/CO] |
| 2a | 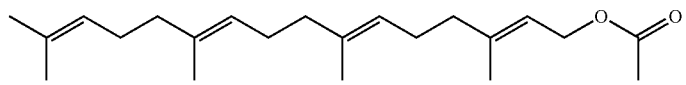 [SMILES: CC(=O)OC/C=C(\C)CC/C=C(\C)CC/C=C(\C)CCC=C(C)C] |
| 2b | 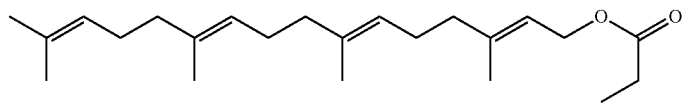 [SMILES: CCC(=O)OC/C=C(\C)CC/C=C(\C)CC/C=C(\C)CCC=C(C)C] |
| 2c | 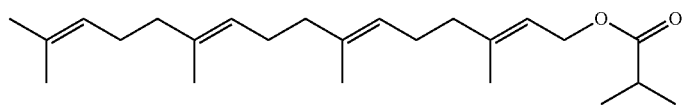 [SMILES: CC(C)=CCC/C(C)=C/CC/C(C)=C/CC/C(C)=C/COC(=O)C(C)C] |
| 2d | 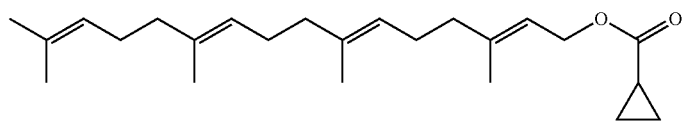 [SMILES: CC(C)=CCC/C(C)=C/CC/C(C)=C/CC/C(C)=C/COC(=O)C1CC1] |
| 2e | 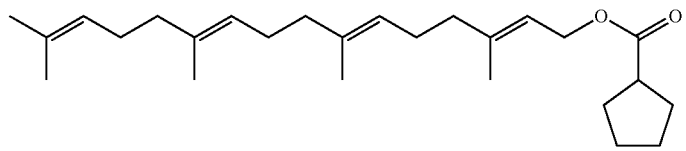 [SMILES: CC(C)=CCC/C(C)=C/CC/C(C)=C/CC/C(C)=C/COC(=O)C1CCCC1] |
| 2f | 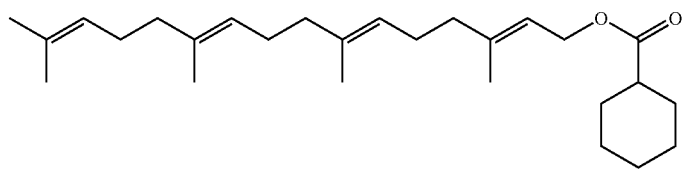 [SMILES: CC(C)=CCC/C(C)=C/CC/C(C)=C/CC/C(C)=C/COC(=O)C1CCCCC1] |
| 2g | 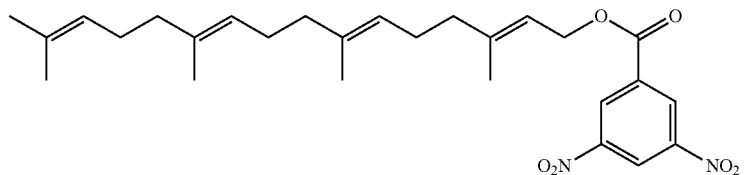 [SMILES: CC(C)=CCC/C(C)=C/CC/C(C)=C/CC/C(C)=C/COC(=O)c1cc([N+](=O)[O-])cc([N+](=O)[O-])c1] |
| 2h | 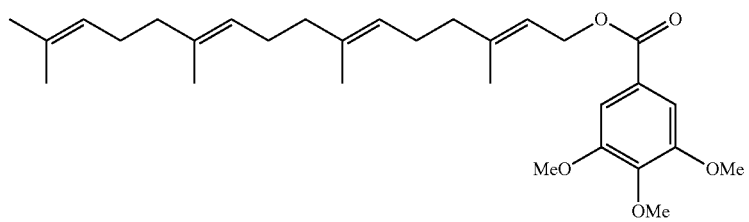 [SMILES: COc1cc(C(=O)OC/C=C(\C)CC/C=C(\C)CC/C=C(\C)CCC=C(C)C)cc(OC)c1OC] |
| 2i | 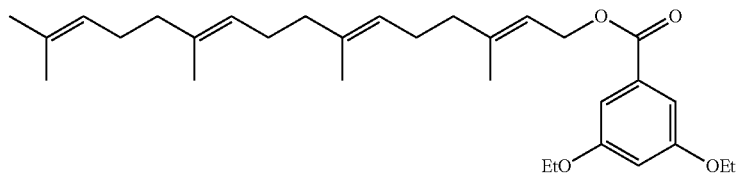 [SMILES: CCOc1cc(OCC)cc(C(=O)OC/C=C(\C)CC/C=C(\C)CC/C=C(\C)CCC=C(C)C)c1] |

TABLE 1-continued

| Compound ID (see Example 7) | Structure |
|---|---|
| 2j | Geranylgeranyl 2-ethoxybenzoate |
| 2k | Geranylgeranyl 2,4-dimethoxybenzoate |
| 2l | Geranylgeranyl 2,4,6-trimethylbenzoate |
| 4a | Geranylgeranyl methanesulfonate |
| 4b | Geranylgeranyl benzenesulfonate |
| 4c | Geranylgeranyl p-toluenesulfonate |
| 6a | Farnesyl benzenesulfonate |
| 6b | Farnesyl p-toluenesulfonate |
| 7a | Geranylgeranyl N-ethylcarbamate |
| 7b | Geranylgeranyl N-sec-butylcarbamate |

TABLE 1-continued
| Compound ID (see Example 7) | Structure |
|---|---|
| 7c | 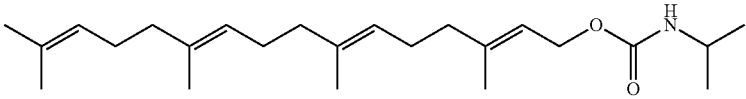 [SMILES: CC(C)=CCC/C(C)=C/CC/C(C)=C/CC/C(C)=C/COC(=O)NC(C)C] |
| 7d | 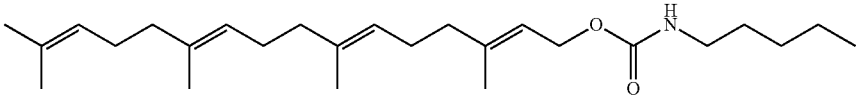 [SMILES: CCCCCNC(=O)OC/C=C(\C)CC/C=C(\C)CC/C=C(\C)CCC=C(C)C] |
| 7e | 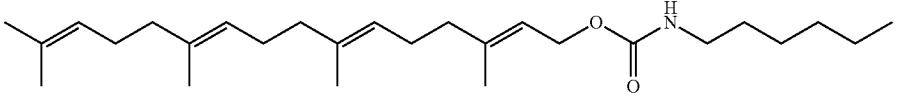 |
| 7f | 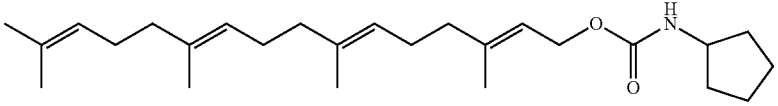 [SMILES: CC(C)=CCC/C(C)=C/CC/C(C)=C/CC/C(C)=C/COC(=O)NC1CCCC1] |
| 7g | 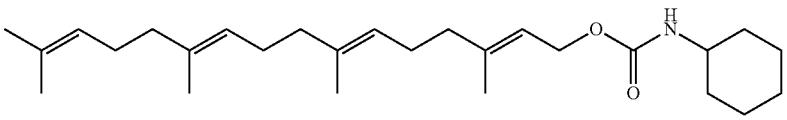 [SMILES: CC(C)=CCC/C(C)=C/CC/C(C)=C/CC/C(C)=C/COC(=O)NC1CCCCC1] |
| 7h | 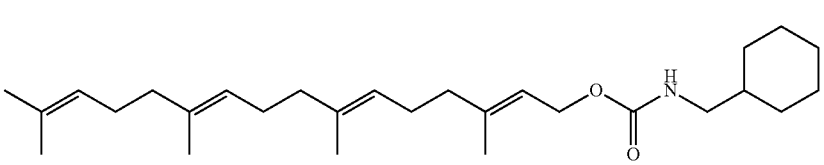 [SMILES: CC(C)=CCC/C(C)=C/CC/C(C)=C/CC/C(C)=C/COC(=O)NCC1CCCCC1] |
| 7i | 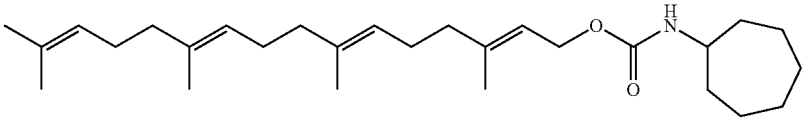 |
| 7j | 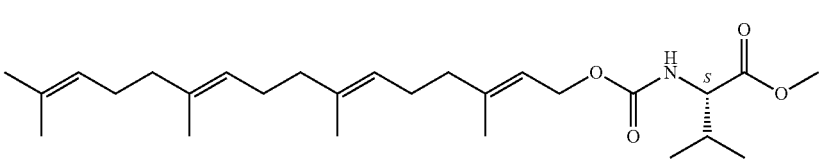 |
| 7k | 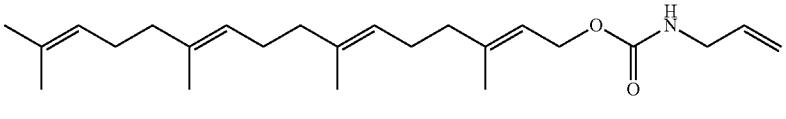 [SMILES: C=CCNC(=O)OC/C=C(\C)CC/C=C(\C)CC/C=C(\C)CCC=C(C)C] |
| 7l | 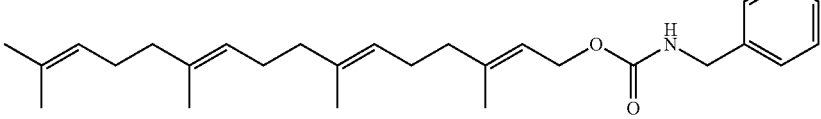 |
| 7m | 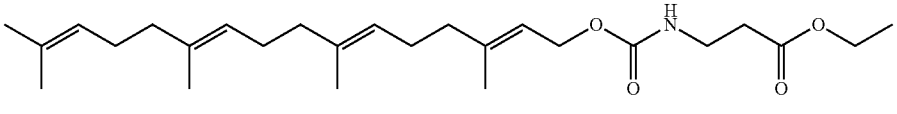 [SMILES: CCOC(=O)CCNC(=O)OC/C=C(\C)CC/C=C(\C)CC/C=C(\C)CCC=C(C)C] |
| 7n | 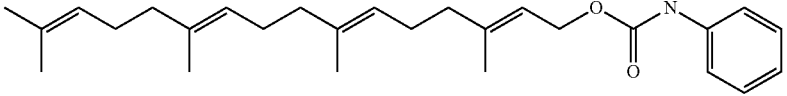 |

TABLE 1-continued

| Compound ID (see Example 7) | Structure |
|---|---|
| 7o | Geranylgeranyl-O-C(=O)-NH-(4-methylphenyl) |
| 7p | Geranylgeranyl-O-C(=O)-NH-CH2-C(=O)-O-ethyl |
| 7q | Geranylgeranyl-O-C(=O)-NH-(4-CF3-phenyl) |
| 7r | Geranylgeranyl-O-C(=O)-NH-(1-naphthyl) |
| 7s | Geranylgeranyl-O-C(=O)-NH-(2-naphthyl) |
| 7t | Geranylgeranyl-O-C(=O)-NH-(3,4-dimethoxyphenyl) |
| 7u | Geranylgeranyl-O-C(=O)-NH-(4-benzoylphenyl) |
| 7v | Geranylgeranyl-O-C(=O)-NH-(3,4,5-trimethoxyphenyl) |
| 7w | Geranylgeranyl-O-C(=O)-NH-(2,4-dimethoxyphenyl) |
| 7x | Geranylgeranyl-O-C(=O)-NH-(fluoren-2-yl) |

TABLE 1-continued

| Compound ID (see Example 7) | Structure |
|---|---|
| 7y | Geranylgeranyl O-C(=O)-NH-(3,4,5-trichlorophenyl) carbamate |
| 7z | Geranylgeranyl O-C(=O)-NH-(pyridin-3-yl) carbamate |
| 7aa | Geranylgeranyl O-C(=O)-NH-CH₂-(furan-2-yl) carbamate |
| 8a | Farnesyl O-C(=O)-NH-isopropyl carbamate |
| 8b | Farnesyl O-C(=O)-NH-pentyl carbamate |
| 8c | Farnesyl O-C(=O)-NH-cyclopentyl carbamate |
| 8d | Farnesyl O-C(=O)-NH-cycloheptyl carbamate |
| 8e | Farnesyl O-C(=O)-NH-adamantyl carbamate |
| 8f | Farnesyl O-C(=O)-NH-cyclohexyl carbamate |
| 8g | Farnesyl O-C(=O)-NH-sec-butyl carbamate |
| 8h | Farnesyl O-C(=O)-NH-ethyl carbamate |
| 8i | Farnesyl O-C(=O)-NH-hexyl carbamate |

TABLE 1-continued
| Compound ID (see Example 7) | Structure |
|---|---|
| 8j | 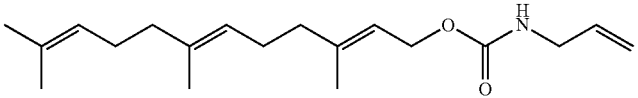 [SMILES: C=CCNC(=O)OC/C=C(\C)CC/C=C(\C)CCC=C(C)C] |
| 8k | 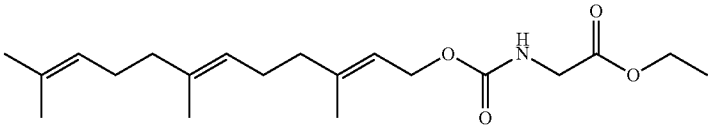 [SMILES: CCOC(=O)CNC(=O)OC/C=C(\C)CC/C=C(\C)CCC=C(C)C] |
| 8l | 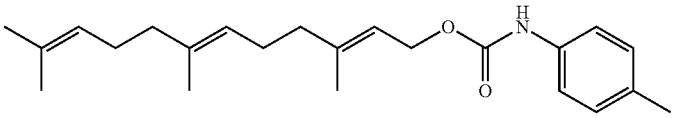 [SMILES: CC(C)=CCC/C(C)=C/CC/C(C)=C/COC(=O)Nc1ccc(C)cc1] |
| 8m | 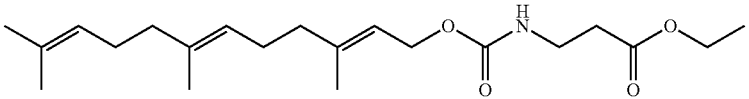 [SMILES: CCOC(=O)CCNC(=O)OC/C=C(\C)CC/C=C(\C)CCC=C(C)C] |
| 8n | 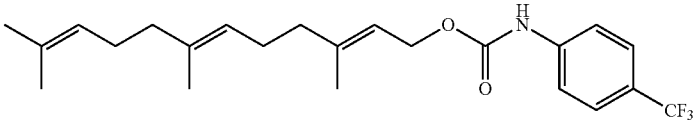 [SMILES: CC(C)=CCC/C(C)=C/CC/C(C)=C/COC(=O)Nc1ccc(C(F)(F)F)cc1] |
| 8o | 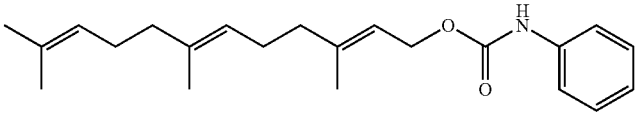 |
| 9a | 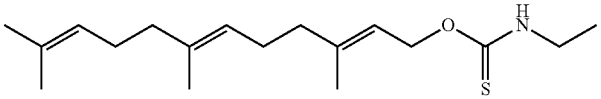 |
| 9b | 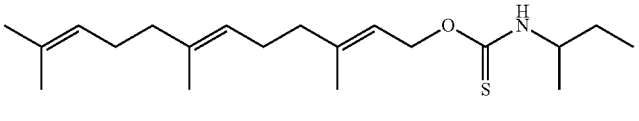 |
| 9c | 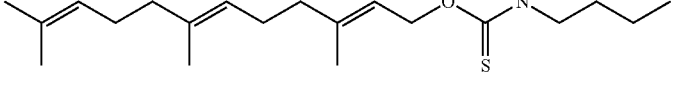 |
| 9d | 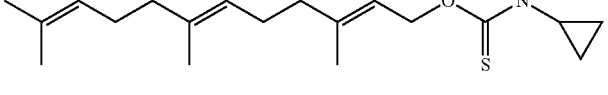 |
| 9e | 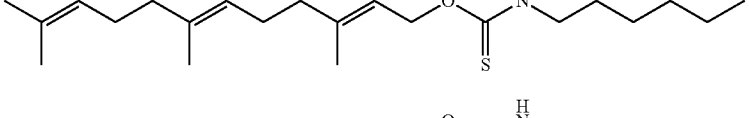 |
| 9f | 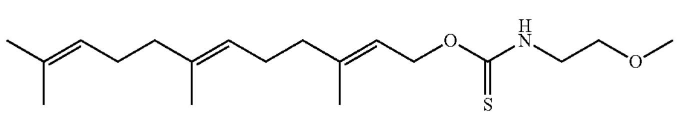 [SMILES: COCCNC(=S)OC/C=C(\C)CC/C=C(\C)CCC=C(C)C] |
| 9g | 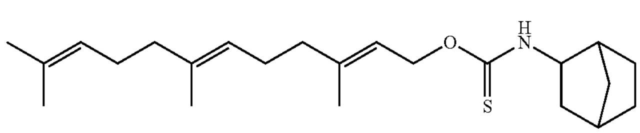 [SMILES: CC(C)=CCC/C(C)=C/CC/C(C)=C/COC(=S)NC1CC2CCC1C2] |

TABLE 1-continued
| Compound ID (see Example 7) | Structure |
|---|---|
| 9h | 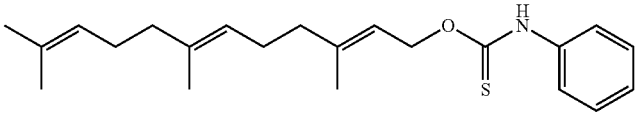 [SMILES: CC(C)=CCC/C(C)=C/CC/C(C)=C/COC(=S)Nc1ccccc1] |
| 9i | 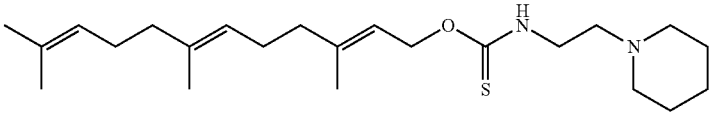 [SMILES: CC(C)=CCC/C(C)=C/CC/C(C)=C/COC(=S)NCCN1CCCCC1] |
| 9j | 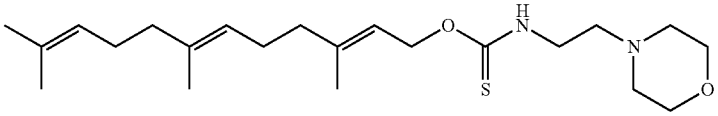 [SMILES: CC(C)=CCC/C(C)=C/CC/C(C)=C/COC(=S)NCCN1CCOCC1] |
| 9k | 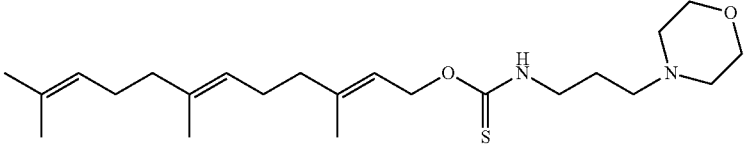 [SMILES: CC(C)=CCC/C(C)=C/CC/C(C)=C/COC(=S)NCCCN1CCOCC1] |
| 10a | 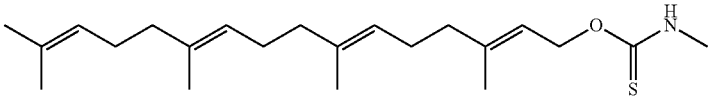 [SMILES: CNC(=S)OC/C=C(\C)CC/C=C(\C)CC/C=C(\C)CCC=C(C)C] |
| 10b | 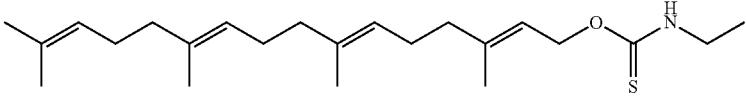 [SMILES: CCNC(=S)OC/C=C(\C)CC/C=C(\C)CC/C=C(\C)CCC=C(C)C] |
| 10c | 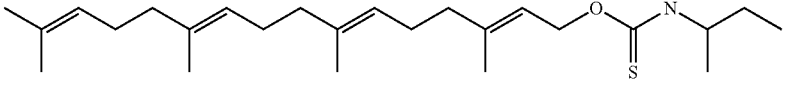 |
| 10d | 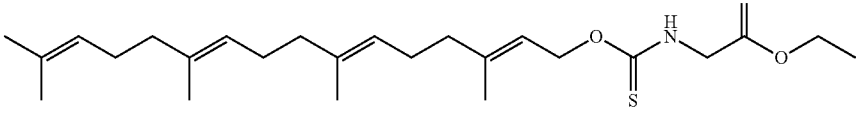 |
| 10e | 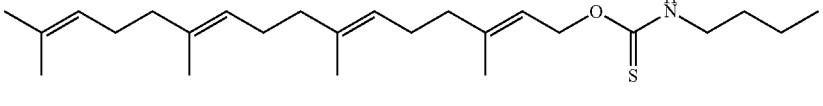 |
| 10f | 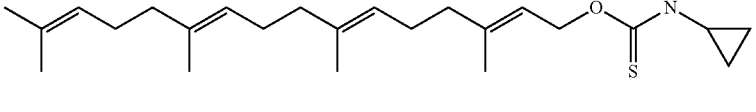 |
| 10g | 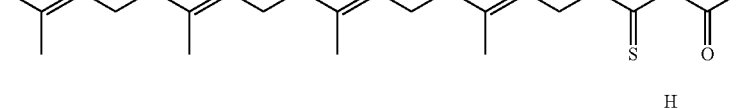 |
| 10h | 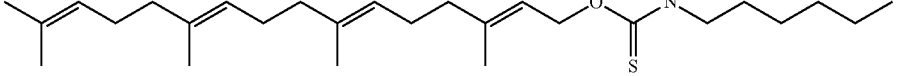 |

TABLE 1-continued

| Compound ID (see Example 7) | Structure |
|---|---|
| 10i | (geranylgeranyl)-O-C(=S)-NH-CH2CH2-OMe |
| 10j | (geranylgeranyl)-O-C(=S)-NH-(norbornyl) |
| 10k | (geranylgeranyl)-O-C(=S)-NH-Ph |
| 10l | (geranylgeranyl)-O-C(=S)-NH-CH2CH2-(piperidin-1-yl) |
| 10m | (geranylgeranyl)-O-C(=S)-NH-CH2CH2-(morpholin-4-yl) |
| 12 | (farnesyl)-(oxazol-5-yl) |
| 14 | (geranylgeranyl)-(oxazol-5-yl) |
| 15 | (farnesyl)-(5-methyloxazol-2-yl) |
| 16 | (geranylgeranyl)-(5-methyloxazol-2-yl) |
| 17a | (geranylgeranyl)-N(Me)-cyclohexyl |
| 17b | (geranylgeranyl)-N(Me)-pentyl |
| 17c | (geranylgeranyl)-N(Me)-heptyl |
| 17d | (geranylgeranyl)-NH-CH2CH2CH2-O-iPr |

TABLE 1-continued
| Compound ID (see Example 7) | Structure |
|---|---|
| 17e | 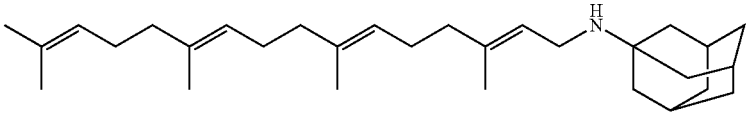 [SMILES: CC(C)=CCC/C(C)=C/CC/C(C)=C/CC/C(C)=C/CNC12CC3CC(CC(C3)C1)C2] |
| 19 | 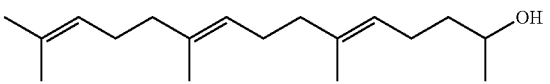 [SMILES: CC(C)=CCC/C(C)=C/CC/C(C)=C/CCC(C)O] |
| 20a | 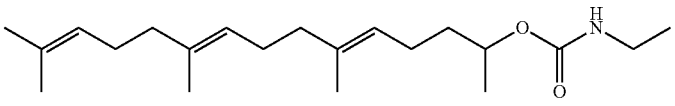 [SMILES: CCNC(=O)OC(C)CC/C=C(\C)CC/C=C(\C)CCC=C(C)C] |
| 20b | 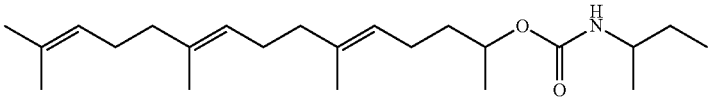 [SMILES: CCC(C)NC(=O)OC(C)CC/C=C(\C)CC/C=C(\C)CCC=C(C)C] |
| 20c | 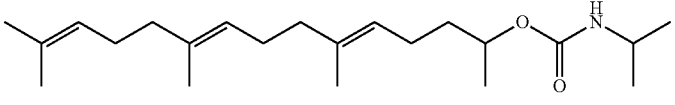 [SMILES: CC(C)=CCC/C(C)=C/CC/C(C)=C/CCC(C)OC(=O)NC(C)C] |
| 20d | 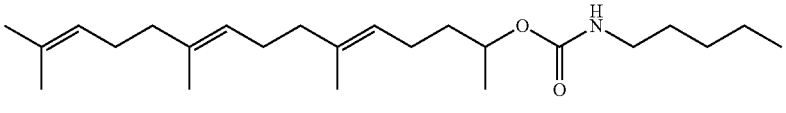 [SMILES: CCCCCNC(=O)OC(C)CC/C=C(\C)CC/C=C(\C)CCC=C(C)C] |
| 20e | 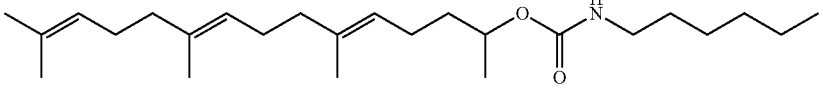 |
| 20f | 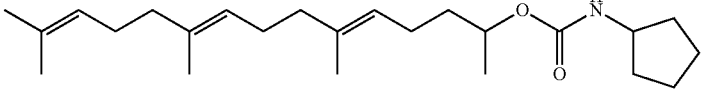 |
| 20g | 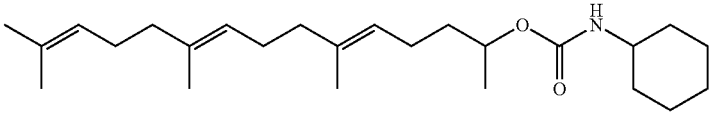 [SMILES: CC(C)=CCC/C(C)=C/CC/C(C)=C/CCC(C)OC(=O)NC1CCCCC1] |
| 20h | 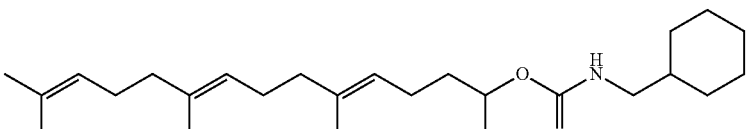 |
| 20i | 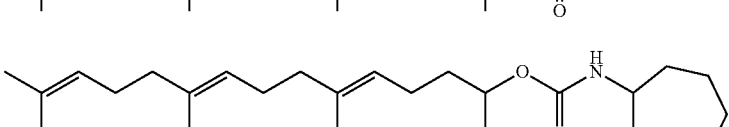 |
| 20j | 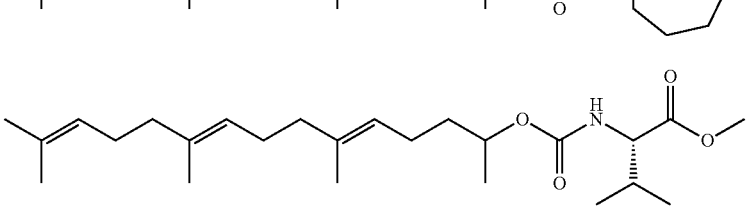 |

TABLE 1-continued

| Compound ID (see Example 7) | Structure |
|---|---|
| 22 | [structure: polyprenyl chain terminating in secondary alcohol (OH)] |
| 23a | [structure: polyprenyl chain with isopropyl carbamate] |
| 23b | [structure: polyprenyl chain with n-butyl carbamate] |
| 23c | [structure: polyprenyl chain with cyclopentyl carbamate] |
| 23d | [structure: polyprenyl chain with cyclohexylmethyl carbamate] |
| 23e | [structure: polyprenyl chain with cycloheptyl carbamate] |
| 23f | [structure: polyprenyl chain with n-hexyl carbamate] |
| 23g | [structure: polyprenyl chain with valine methyl ester carbamate] |
| 24 | [structure: polyprenyl carboxylic acid] |
| 25 | [structure: polyprenyl acyl chloride] |
| 27a | [structure: polyprenyl chain with 4-isopropyl oxazoline] |
| 27b | [structure: polyprenyl chain with 4-methyl oxazoline] |

TABLE 1-continued

| Compound ID (see Example 7) | Structure |
|---|---|
| 27c | (structure: geranylgeranyl-type tetraene chain attached to 4,5-dihydrooxazole with (S)-isobutyl substituent at C4) |
| 27d | (structure: geranylgeranyl-type tetraene chain attached to 4,5-dihydrooxazole with (S)-methyl substituent at C4) |
| 27e | (structure: geranylgeranyl-type tetraene chain attached to 4,5-dihydrooxazole with (S)-isopropyl substituent at C4) |
| 27f | (structure: geranylgeranyl-type tetraene chain attached to 4,5-dihydrooxazole with (R)-isobutyl substituent at C4) |
| 27g | (structure: geranylgeranyl-type tetraene chain attached to 4,5-dihydrooxazole with (S)-benzyl substituent at C4) |
| 29a | (structure: geranylgeranyl-type tetraene chain attached to 2,5-disubstituted-1,3,4-oxadiazole bearing a phenyl group) |
| 29b | (structure: geranylgeranyl-type tetraene chain attached to 2,5-disubstituted-1,3,4-oxadiazole bearing a 4-methylphenyl group) |

TABLE 1-continued

| Compound ID (see Example 7) | Structure |
|---|---|
| 29c | 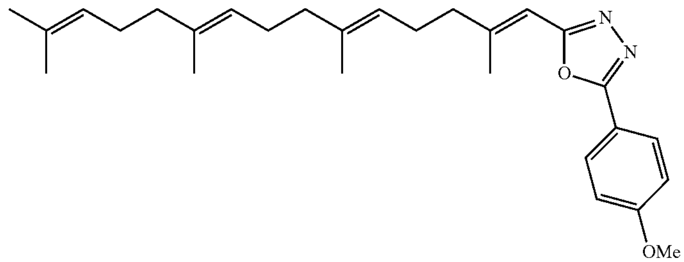 [SMILES: COc1ccc(-c2nnc(/C=C(\C)CC/C=C(\C)CC/C=C(\C)CCC=C(C)C)o2)cc1] |
| 29d | 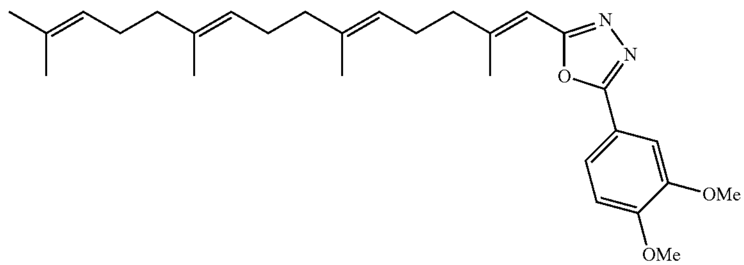 [SMILES: COc1ccc(-c2nnc(/C=C(\C)CC/C=C(\C)CC/C=C(\C)CCC=C(C)C)o2)cc1OC] |
| 29e | 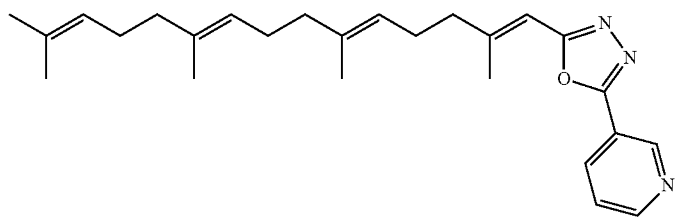 [SMILES: CC(C)=CCC/C(C)=C/CC/C(C)=C/CC/C(C)=C/c1nnc(-c2cccnc2)o1] |
| 29f | 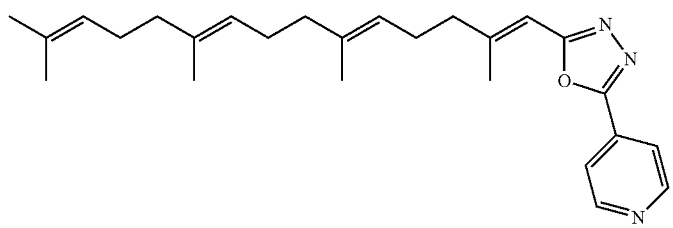 [SMILES: CC(C)=CCC/C(C)=C/CC/C(C)=C/CC/C(C)=C/c1nnc(-c2ccncc2)o1] |
| 31 | 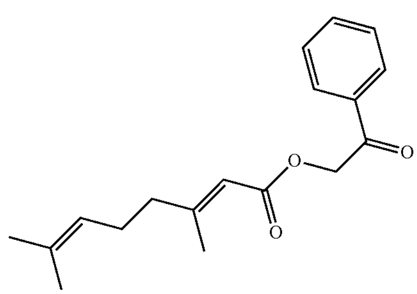 [SMILES: CC(C)=CCC/C(C)=C/C(=O)OCC(=O)c1ccccc1] |
| 32 | 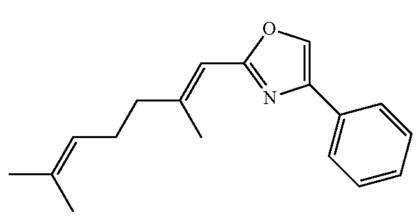 [SMILES: CC(C)=CCC/C(C)=C/c1nc(-c2ccccc2)co1] |

TABLE 1-continued
| Compound ID (see Example 7) | Structure |
|---|---|
| 35a | 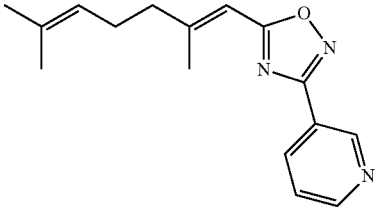 [SMILES: CC(C)=CCC/C(C)=C/c1nc(-c2cccnc2)no1] |
| 35b | 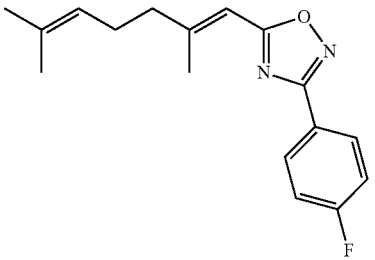 [SMILES: CC(C)=CCC/C(C)=C/c1nc(-c2ccc(F)cc2)no1] |
| 35c | 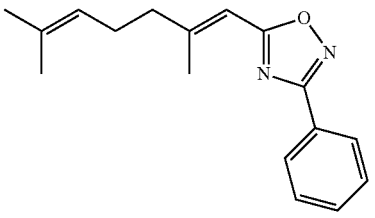 [SMILES: CC(C)=CCC/C(C)=C/c1nc(-c2ccccc2)no1] |
| 35d | 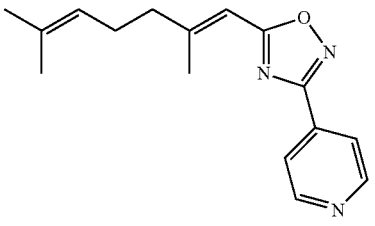 [SMILES: CC(C)=CCC/C(C)=C/c1nc(-c2ccncc2)no1] |
| 37a | 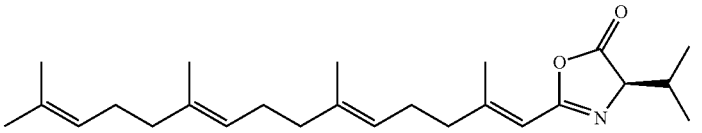 [SMILES: CC(C)=CCC/C(C)=C/CC/C(C)=C/CC/C(C)=C/C1=N[C@H](C(C)C)C(=O)O1] |
| 37b | 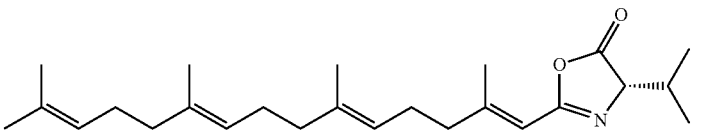 [SMILES: CC(C)=CCC/C(C)=C/CC/C(C)=C/CC/C(C)=C/C1=N[C@@H](C(C)C)C(=O)O1] |
| 37c | 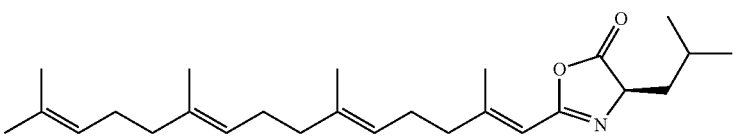 [SMILES: CC(C)=CCC/C(C)=C/CC/C(C)=C/CC/C(C)=C/C1=N[C@H](CC(C)C)C(=O)O1] |
| 37d | 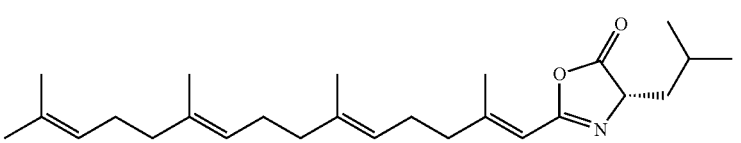 [SMILES: CC(C)=CCC/C(C)=C/CC/C(C)=C/CC/C(C)=C/C1=N[C@@H](CC(C)C)C(=O)O1] |

TABLE 1-continued

| Compound ID (see Example 7) | Structure |
|---|---|
| 38a | [structure: geranylgeranyl-O-C(=S)-NH-(pyridin-3-yl)] |
| 38b | [structure: geranylgeranyl-O-C(=S)-NH-CH2-(furan-2-yl)] |
| 39 | [structure: geranylgeranyl-O-C(=O)-NH-(pyridin-4-yl)] |
| 40a | [structure: geranylgeranyl-O-C(=O)-(4-methylpiperazin-1-yl)] |
| 40b | [structure: geranylgeranyl-O-C(=O)-NH-(pyridin-2-yl)] |
| 41 | [structure: geranylgeranyl-O-C(=O)-NH-(dimethyladamantyl)] |
| 42 | [structure: farnesyl-O-C(=O)-NH-CH3] |
| 43 | [structure: farnesyl-O-C(=S)-NH-CH3] |

In another embodiment, examples of compounds provided and/or utilized by this invention include certain compounds tabulated below.

TABLE 2

| Compound ID | Chemical Structure |
|---|---|
| 51 | [structure: farnesyl chain with CH(C(=O)OEt)(C(=O)CH3) terminus] |
| 52 | [structure: farnesyl methyl ketone] |

TABLE 2-continued

| Compound ID | Chemical Structure |
|---|---|
| 54 | 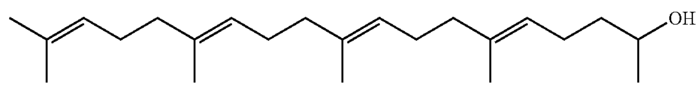 [SMILES: CC(C)=CCC/C(C)=C/CC/C(C)=C/CC/C(C)=C/CCC(C)O] |
| 55 | 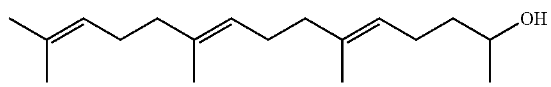 [SMILES: CC(C)=CCC/C(C)=C/CC/C(C)=C/CCC(C)O] |
| 56 | 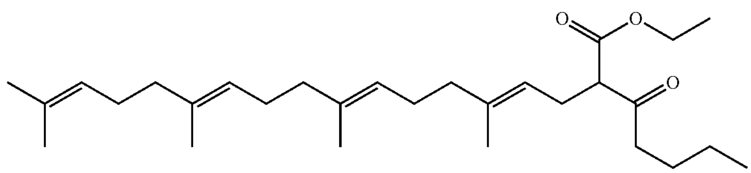 [SMILES: CCCCC(=O)C(C/C=C(\C)CC/C=C(\C)CC/C=C(\C)CCC=C(C)C)C(=O)OCC] |
| 57 | 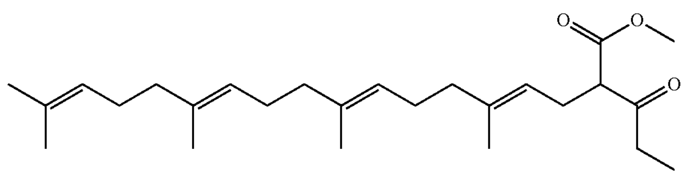 [SMILES: CCC(=O)C(C/C=C(\C)CC/C=C(\C)CC/C=C(\C)CCC=C(C)C)C(=O)OC] |
| 58 | 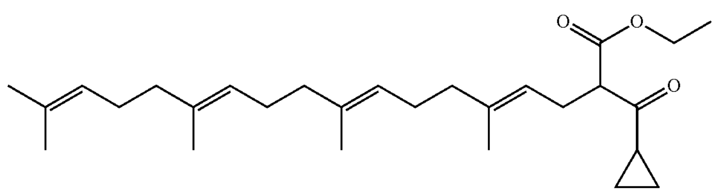 [SMILES: CCOC(=O)C(C/C=C(\C)CC/C=C(\C)CC/C=C(\C)CCC=C(C)C)C(=O)C1CC1] |
| 59 | 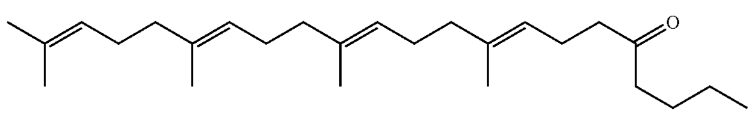 [SMILES: CCCCC(=O)CC/C=C(\C)CC/C=C(\C)CC/C=C(\C)CCC=C(C)C] |
| 60 | 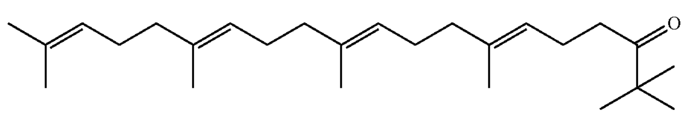 [SMILES: CC(C)=CCC/C(C)=C/CC/C(C)=C/CC/C(C)=C/CCC(=O)C(C)(C)C] |
| 61 | 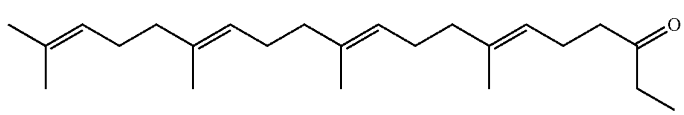 [SMILES: CCC(=O)CC/C=C(\C)CC/C=C(\C)CC/C=C(\C)CCC=C(C)C] |
| 62 | 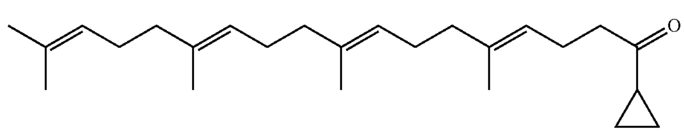 [SMILES: CC(C)=CCC/C(C)=C/CC/C(C)=C/CC/C(C)=C/CCC(=O)C1CC1] |
| 63 | 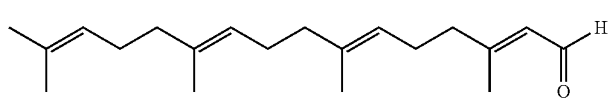 [SMILES: CC(C)=CCC/C(C)=C/CC/C(C)=C/CC/C(C)=C/C=O] |
| 64 | 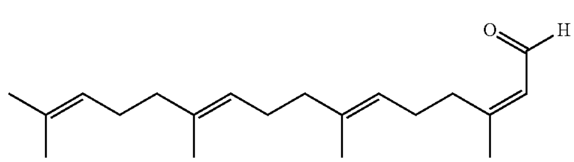 [SMILES: CC(C)=CCC/C(C)=C/CC/C(C)=C/CC/C(C)=C\C=O] |

TABLE 2-continued

| Compound ID | Chemical Structure |
|---|---|
| 65 | 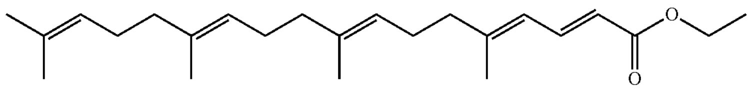 [SMILES: CCOC(=O)/C=C/C=C(\C)CC/C=C(\C)CC/C=C(\C)CCC=C(C)C] |
| 66 | 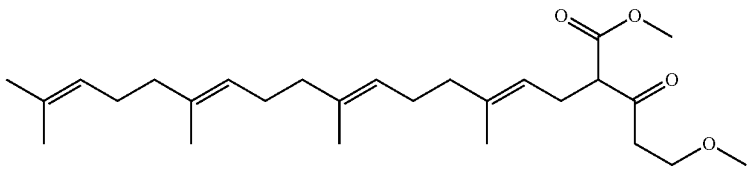 [SMILES: COCCC(=O)C(C/C=C(\C)CC/C=C(\C)CC/C=C(\C)CCC=C(C)C)C(=O)OC] |
| 67 | 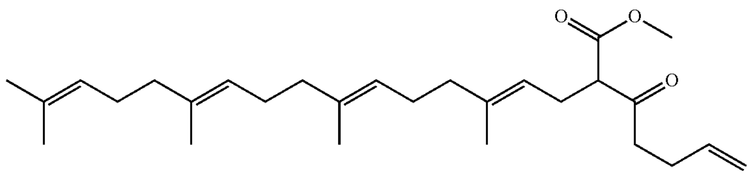 [SMILES: C=CCCC(=O)C(C/C=C(\C)CC/C=C(\C)CC/C=C(\C)CCC=C(C)C)C(=O)OC] |
| 68 | 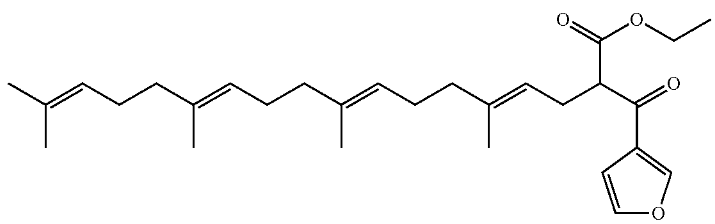 [SMILES: CCOC(=O)C(C/C=C(\C)CC/C=C(\C)CC/C=C(\C)CCC=C(C)C)C(=O)c1ccoc1] |
| 69 | 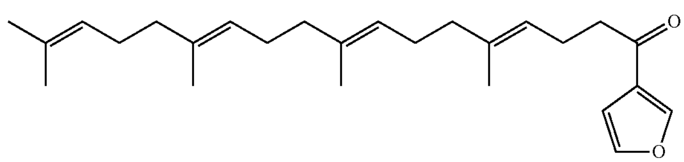 [SMILES: CC(C)=CCC/C(C)=C/CC/C(C)=C/CC/C(C)=C/CCC(=O)c1ccoc1] |
| 70 | 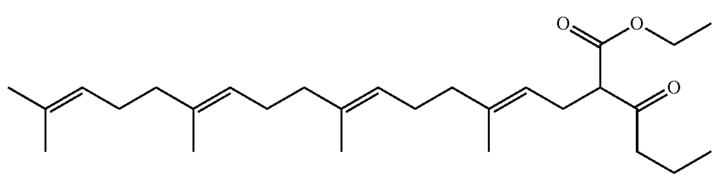 [SMILES: CCCC(=O)C(C/C=C(\C)CC/C=C(\C)CC/C=C(\C)CCC=C(C)C)C(=O)OCC] |
| 71 | 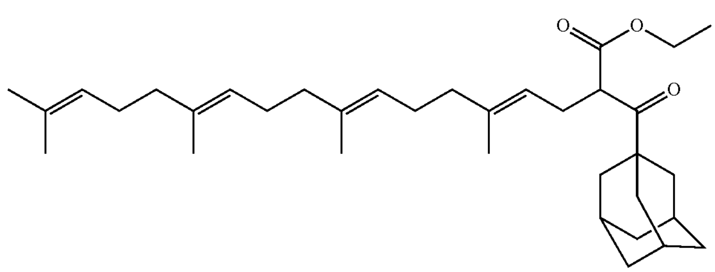 [SMILES: CCOC(=O)C(C/C=C(\C)CC/C=C(\C)CC/C=C(\C)CCC=C(C)C)C(=O)C12CC3CC(CC(C3)C1)C2] |
| 72 | 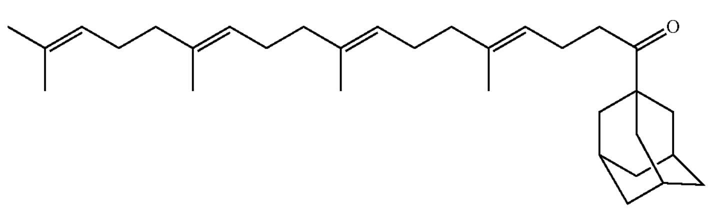 [SMILES: CC(C)=CCC/C(C)=C/CC/C(C)=C/CC/C(C)=C/CCC(=O)C12CC3CC(CC(C3)C1)C2] |

TABLE 2-continued

| Compound ID | Chemical Structure |
|---|---|
| 73 | 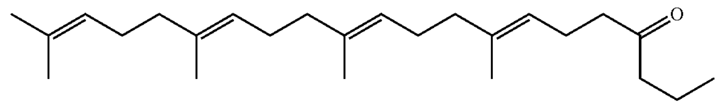 [SMILES: CCCC(=O)CC/C=C(\C)CC/C=C(\C)CC/C=C(\C)CCC=C(C)C] |
| 74 | 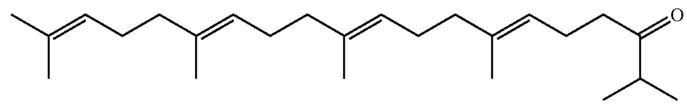 [SMILES: CC(C)=CCC/C(C)=C/CC/C(C)=C/CC/C(C)=C/CCC(=O)C(C)C] |
| 75 | 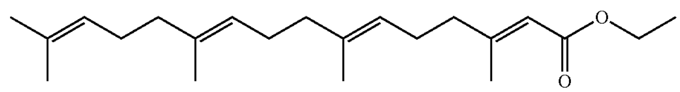 [SMILES: CCOC(=O)/C=C(\C)CC/C=C(\C)CC/C=C(\C)CCC=C(C)C] |
| 76 | 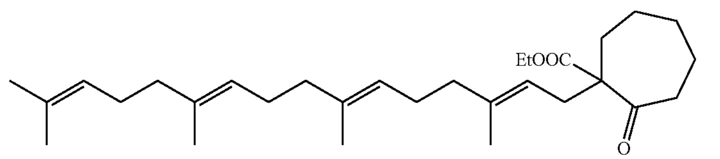 [SMILES: CCOC(=O)C1(C/C=C(\C)CC/C=C(\C)CC/C=C(\C)CCC=C(C)C)CCCCCC1=O] |
| 77 | 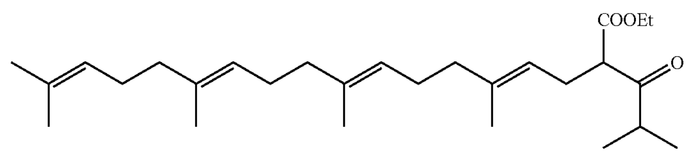 [SMILES: CCOC(=O)C(C/C=C(\C)CC/C=C(\C)CC/C=C(\C)CCC=C(C)C)C(=O)C(C)C] |
| 78 | 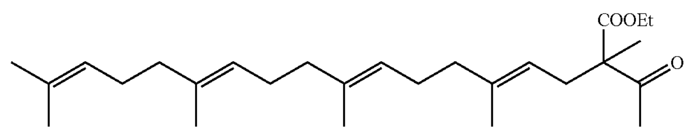 [SMILES: CCOC(=O)C(C)(C/C=C(\C)CC/C=C(\C)CC/C=C(\C)CCC=C(C)C)C(C)=O] |
| 79 | |
| 80 | 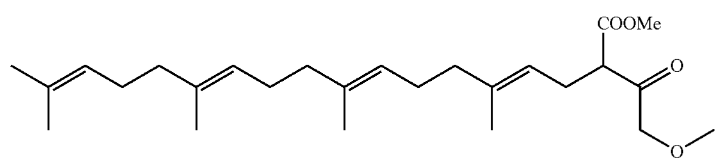 [SMILES: COCC(=O)C(C/C=C(\C)CC/C=C(\C)CC/C=C(\C)CCC=C(C)C)C(=O)OC] |
| 81 | 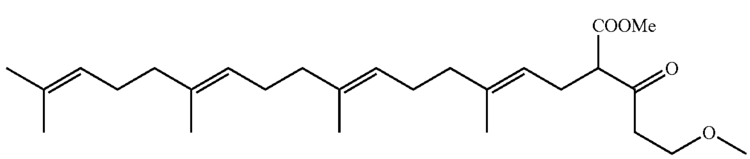 [SMILES: COCCC(=O)C(C/C=C(\C)CC/C=C(\C)CC/C=C(\C)CCC=C(C)C)C(=O)OC] |
| 82 | 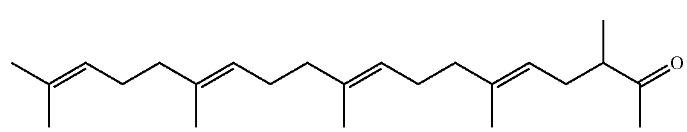 [SMILES: CC(=O)C(C)C/C=C(\C)CC/C=C(\C)CC/C=C(\C)CCC=C(C)C] |
| 83 | 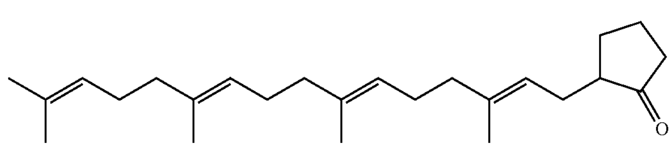 [SMILES: CC(C)=CCC/C(C)=C/CC/C(C)=C/CC/C(C)=C/CC1CCCC1=O] |

TABLE 2-continued
| Compound ID | Chemical Structure |
|---|---|
| 84 | 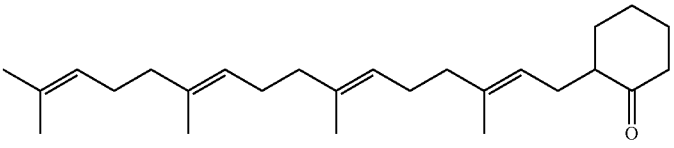 [SMILES: CC(C)=CCC/C(C)=C/CC/C(C)=C/CC/C(C)=C/CC1CCCCC1=O] |
| 85 | 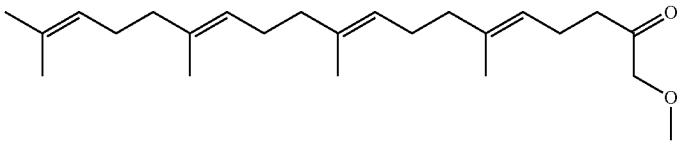 [SMILES: COCC(=O)CC/C=C(\C)CC/C=C(\C)CC/C=C(\C)CCC=C(C)C] |
| 86 | 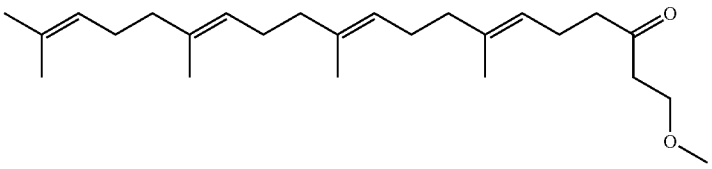 [SMILES: COCCC(=O)CC/C=C(\C)CC/C=C(\C)CC/C=C(\C)CCC=C(C)C] |
| 87 | 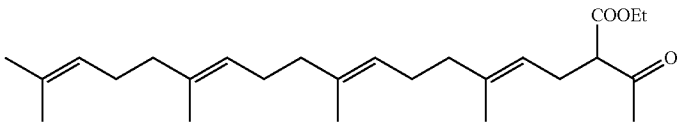 [SMILES: CCOC(=O)C(C/C=C(\C)CC/C=C(\C)CC/C=C(\C)CCC=C(C)C)C(C)=O] |
| 88 | 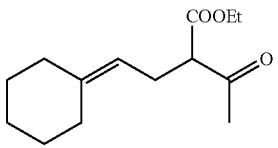 [SMILES: CCOC(=O)C(CC=C1CCCCC1)C(C)=O] |
| 89 | 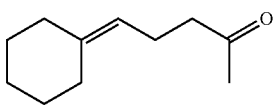 |
| 90 | 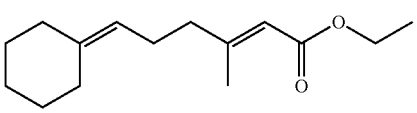 [SMILES: CCOC(=O)/C=C(\C)CCC=C1CCCCC1] |
| 91 | 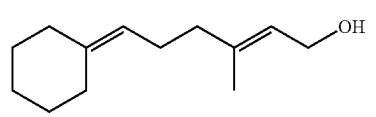 |
| 92 | 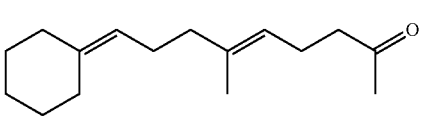 [SMILES: CC(=O)CC/C=C(\C)CCC=C1CCCCC1] |
| 93 | 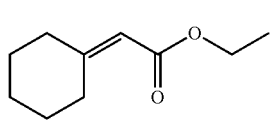 |
| 94 | 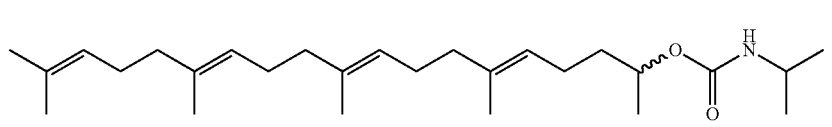 [SMILES: CC(C)=CCC/C(C)=C/CC/C(C)=C/CC/C(C)=C/CCC(C)OC(=O)NC(C)C] |

TABLE 2-continued
| Compound ID | Chemical Structure |
|---|---|
| 95 | 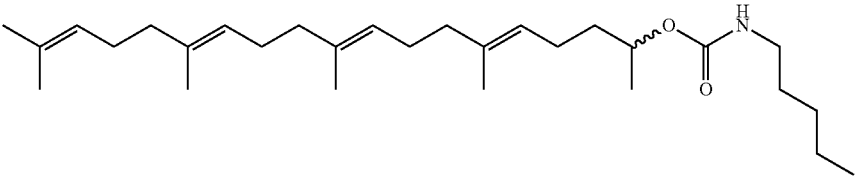 [SMILES: CCCCCNC(=O)OC(C)CC/C=C(\C)CC/C=C(\C)CC/C=C(\C)CCC=C(C)C] |
| 96 | 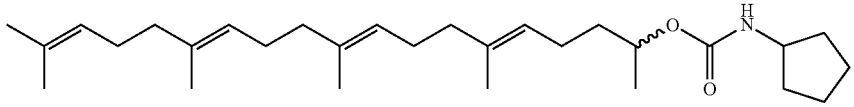 [SMILES: CC(C)=CCC/C(C)=C/CC/C(C)=C/CC/C(C)=C/CCC(C)OC(=O)NC1CCCC1] |
| 97 | 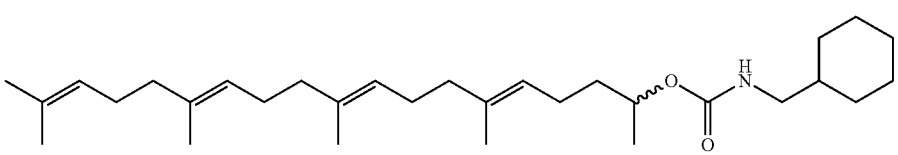 [SMILES: CC(C)=CCC/C(C)=C/CC/C(C)=C/CC/C(C)=C/CCC(C)OC(=O)NCC1CCCCC1] |
| 98 | 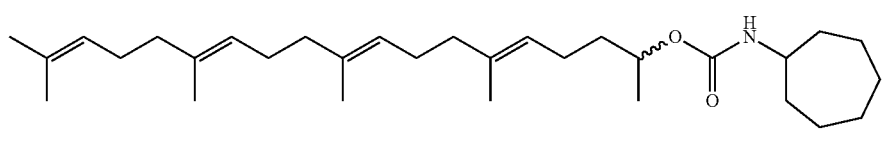 [SMILES: CC(C)=CCC/C(C)=C/CC/C(C)=C/CC/C(C)=C/CCC(C)OC(=O)NC1CCCCCC1] |
| 99 | 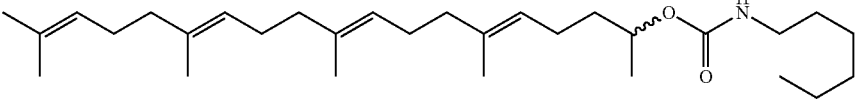 |
| 100 | 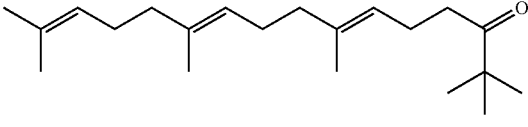 [SMILES: CC(C)=CCC/C(C)=C/CC/C(C)=C/CCC(=O)C(C)(C)C] |
| 101 | 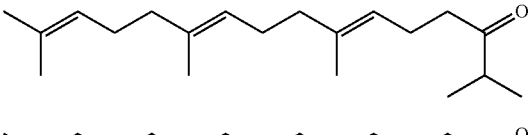 |
| 102 | 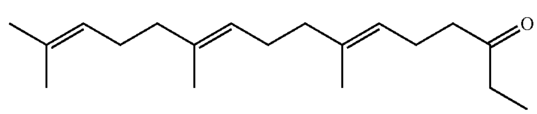 [SMILES: CCC(=O)CC/C=C(\C)CC/C=C(\C)CCC=C(C)C] |
| 103 | 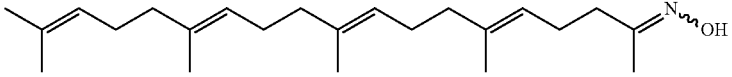 [SMILES: CC(C)=CCC/C(C)=C/CC/C(C)=C/CC/C(C)=C/CCC(C)=NO] |
| 104 | 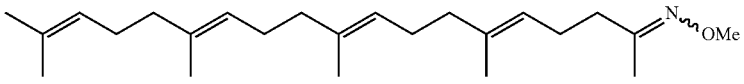 [SMILES: CON=C(C)CC/C=C(\C)CC/C=C(\C)CC/C=C(\C)CCC=C(C)C] |
| 105 | 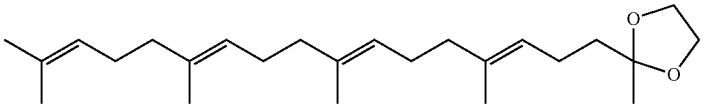 [SMILES: CC(C)=CCC/C(C)=C/CC/C(C)=C/CC/C(C)=C/CCC1(C)OCCO1] |
| 106 | 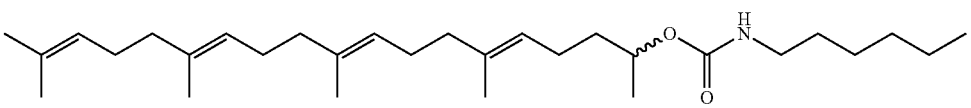 [SMILES: CCCCCCNC(=O)OC(C)CC/C=C(\C)CC/C=C(\C)CC/C=C(\C)CCC=C(C)C] |

TABLE 2-continued
| Compound ID | Chemical Structure |
|---|---|
| 107 | 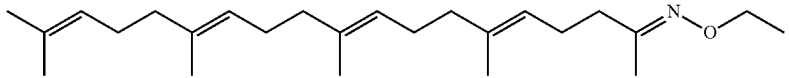 [SMILES: CCO/N=C(\C)CC/C=C(\C)CC/C=C(\C)CC/C=C(\C)CCC=C(C)C] |
| 108 | 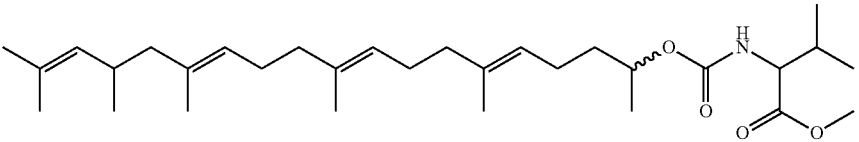 [SMILES: COC(=O)C(NC(=O)OC(C)CC/C=C(\C)CC/C=C(\C)CC/C=C(\C)CC(C)C=C(C)C)C(C)C] |
| 109 | 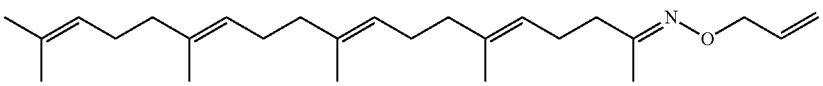 [SMILES: C=CCO/N=C(\C)CC/C=C(\C)CC/C=C(\C)CC/C=C(\C)CCC=C(C)C] |
| 110 | 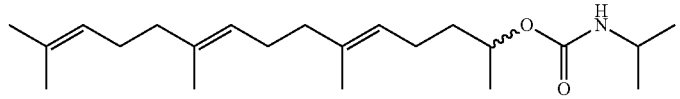 [SMILES: CC(C)=CCC/C(C)=C/CC/C(C)=C/CCC(C)OC(=O)NC(C)C] |
| 111 | 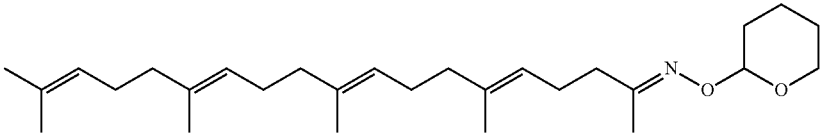 [SMILES: CC(C)=CCC/C(C)=C/CC/C(C)=C/CC/C(C)=C/CC/C(C)=N/OC1CCCCO1] |
| 112 | 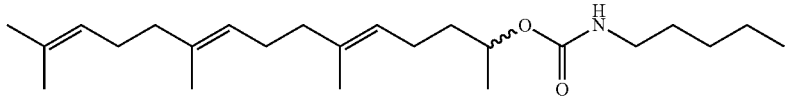 [SMILES: CCCCCNC(=O)OC(C)CC/C=C(\C)CC/C=C(\C)CCC=C(C)C] |
| 113 | 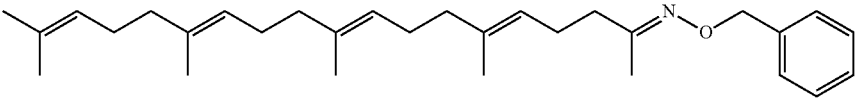 [SMILES: CC(C)=CCC/C(C)=C/CC/C(C)=C/CC/C(C)=C/CC/C(C)=N/OCc1ccccc1] |
| 114 | 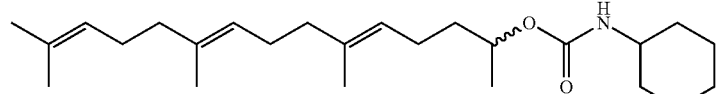 |
| 115 | 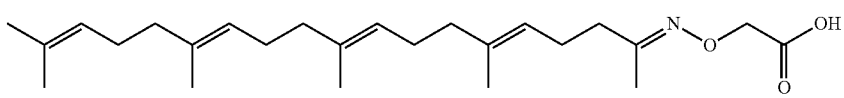 [SMILES: CC(C)=CCC/C(C)=C/CC/C(C)=C/CC/C(C)=C/CC/C(C)=N/OCC(=O)O] |
| 116 | 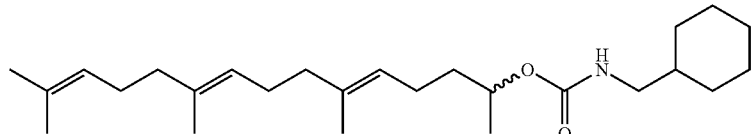 |
| 117 | 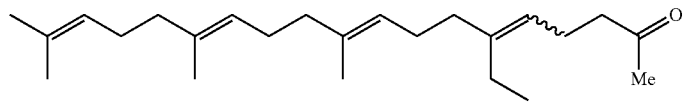 [SMILES: CCC(=CCCC(C)=O)CC/C=C(\C)CC/C=C(\C)CCC=C(C)C] |
| 118 | 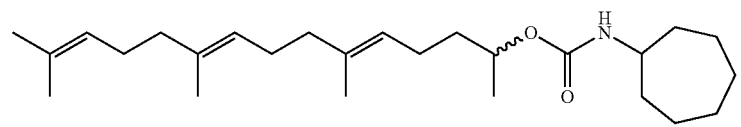 [SMILES: CC(C)=CCC/C(C)=C/CC/C(C)=C/CCC(C)OC(=O)NC1CCCCCC1] |

TABLE 2-continued

| Compound ID | Chemical Structure |
|---|---|
| 119 | 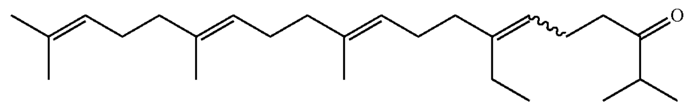 [SMILES: CCC(=CCCC(=O)C(C)C)CC/C=C(\C)CC/C=C(\C)CCC=C(C)C] |
| 120 | 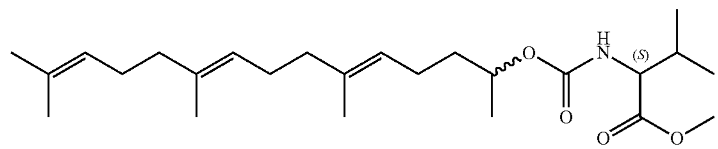 |
| 121 | 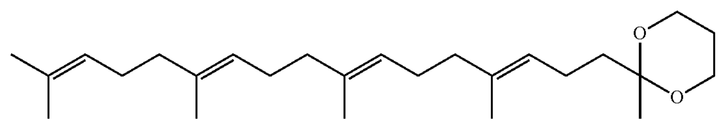 [SMILES: CC(C)=CCC/C(C)=C/CC/C(C)=C/CC/C(C)=C/CCC1(C)OCCCO1] |
| 122 | 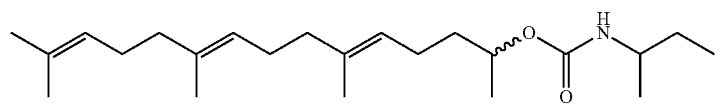 [SMILES: CCC(C)NC(=O)OC(C)CC/C=C(\C)CC/C=C(\C)CCC=C(C)C] |
| 123 | 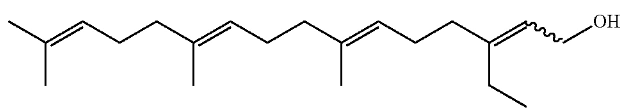 [SMILES: CCC(=CCO)CC/C=C(\C)CC/C=C(\C)CCC=C(C)C] |
| 124 | 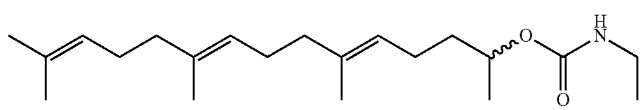 [SMILES: CCNC(=O)OC(C)CC/C=C(\C)CC/C=C(\C)CCC=C(C)C] |
| 125 | 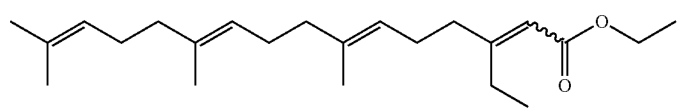 [SMILES: CCOC(=O)C=C(CC)CC/C=C(\C)CC/C=C(\C)CCC=C(C)C] |
| 126 | 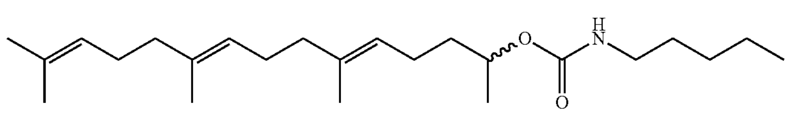 [SMILES: CCCCCNC(=O)OC(C)CC/C=C(\C)CC/C=C(\C)CCC=C(C)C] |
| 127 | 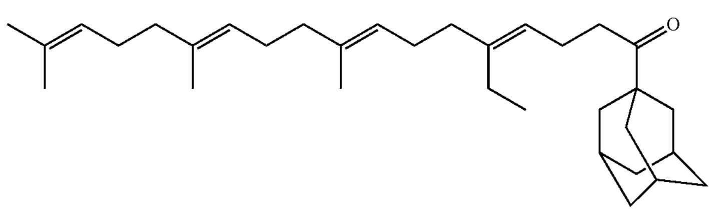 [SMILES: CC/C(=C\CCC(=O)C12CC3CC(CC(C3)C1)C2)CC/C=C(\C)CC/C=C(\C)CCC=C(C)C] |
| 128 | 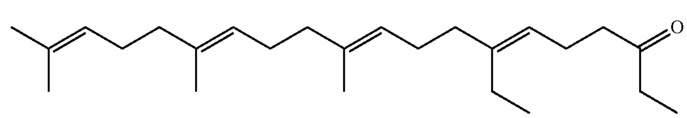 [SMILES: CCC(=O)CC/C=C(\CC)CC/C=C(\C)CC/C=C(\C)CCC=C(C)C] |
| 129 | 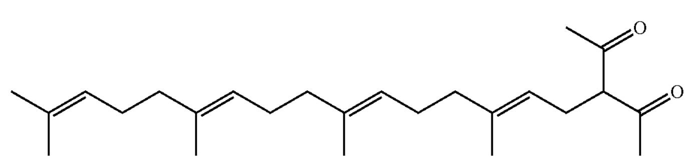 [SMILES: CC(=O)C(C/C=C(\C)CC/C=C(\C)CC/C=C(\C)CCC=C(C)C)C(C)=O] |
| 130 | 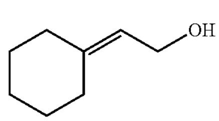 |

TABLE 2-continued
| Compound ID | Chemical Structure |
|---|---|
| 131 | 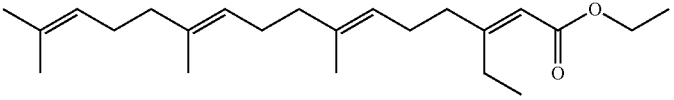 [SMILES: CCOC(=O)/C=C(\CC)CC/C=C(\C)CC/C=C(\C)CCC=C(C)C] |
| 132 | 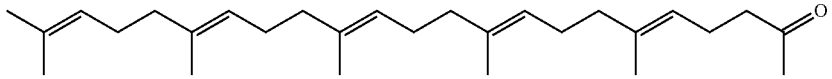 [SMILES: CC(=O)CC/C=C(\C)CC/C=C(\C)CC/C=C(\C)CC/C=C(\C)CCC=C(C)C] |
| 133 | 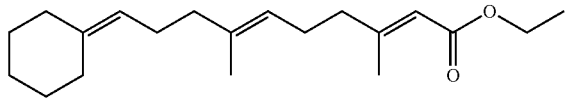 [SMILES: CCOC(=O)/C=C(\C)CC/C=C(\C)CCC=C1CCCCC1] |
| 134 | 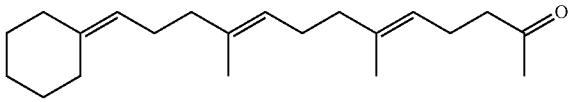 [SMILES: CC(=O)CC/C=C(\C)CC/C=C(\C)CCC=C1CCCCC1] |
| 135 | 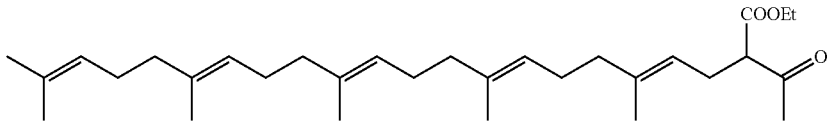 [SMILES: CCOC(=O)C(C/C=C(\C)CC/C=C(\C)CC/C=C(\C)CC/C=C(\C)CCC=C(C)C)C(C)=O] |
| 136 | 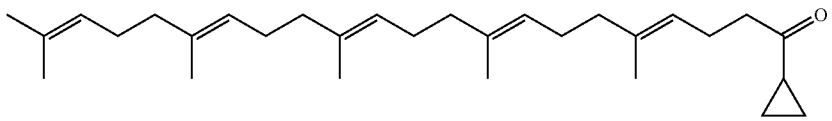 [SMILES: CC(C)=CCC/C(C)=C/CC/C(C)=C/CC/C(C)=C/CC/C(C)=C/CCC(=O)C1CC1] |
| 137 | 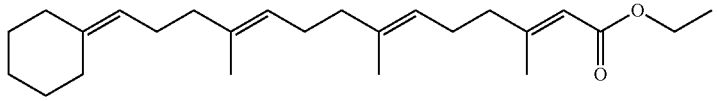 [SMILES: CCOC(=O)/C=C(\C)CC/C=C(\C)CC/C=C(\C)CCC=C1CCCCC1] |
| 138 | 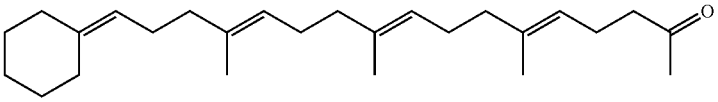 [SMILES: CC(=O)CC/C=C(\C)CC/C=C(\C)CC/C=C(\C)CCC=C1CCCCC1] |
| 139 | 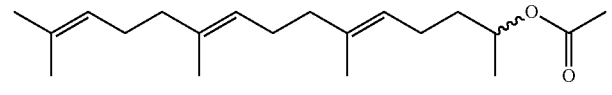 [SMILES: CC(=O)OC(C)CC/C=C(\C)CC/C=C(\C)CCC=C(C)C] |
| 140 | 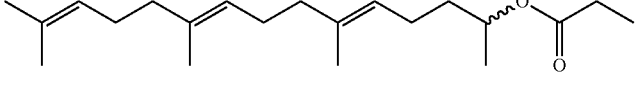 |
| 141 | 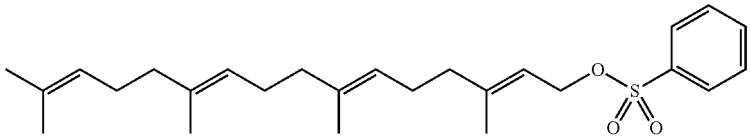 [SMILES: CC(C)=CCC/C(C)=C/CC/C(C)=C/CC/C(C)=C/COS(=O)(=O)c1ccccc1] |
| 142 | 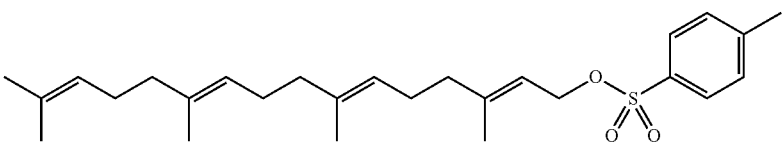 [SMILES: CC(C)=CCC/C(C)=C/CC/C(C)=C/CC/C(C)=C/COS(=O)(=O)c1ccc(C)cc1] |

TABLE 2-continued

| Compound ID | Chemical Structure |
|---|---|
| 143 | (structure: GGA-derived chain with ester linkage to 3,5-dinitrobenzoate) |
| 144 | (structure: GGA-derived chain with methanesulfonate ester) |
| 145 | (structure: GGA-derived chain with carbamate linkage to adamantyl group) |
| 146 | (structure: GGA-derived chain with ketone and terminal vinyl group) |
| 147 | (structure: GGA-derived chain attached to cycloheptanone) |

3. PHARMACEUTICAL COMPOSITIONS

In another aspect, this invention is also directed to pharmaceutical compositions comprising at least one pharmaceutically acceptable excipient and an effective amount of the trans-isomer compound of GGA according to this invention.

Pharmaceutical compositions can be formulated for different routes of administration. Although compositions suitable for oral delivery will probably be used most frequently, other routes that may be used include intravenous, intraarterial, pulmonary, rectal, nasal, vaginal, lingual, intramuscular, intraperitoneal, intracutaneous, transdermal, intracranial, and subcutaneous routes. Other dosage forms include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, $16^{th}$ ed., A. Oslo editor, Easton Pa. 1980).

The compositions are comprised of in general, GGA or a trans-isomer compound of GGA or a mixture thereof in combination with at least one pharmaceutically acceptable excipient. Acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc.

The concentration of the excipient is one that can readily be determined to be effective by those skilled in the art, and can vary depending on the particular excipient used. The total concentration of the excipients in the solution can be from about 0.001% to about 90% or from about 0.001% to about 10%.

In certain embodiments of this invention, there is provided a pharmaceutical composition comprising the compound of formula I and α-tocopherol. A related embodiment provides for a pharmaceutical composition comprising the compound of formula I, α-tocopherol, and hydroxypropyl cellulose. In another embodiment, there is provided a pharmaceutical composition comprising the compound of formula I, α-tocopherol, and gum arabic. In a further embodiment, there is a pharmaceutical composition comprising the compound of formula I, and gum arabic. In a related embodiment, there is provided the compound of formula I, gum arabic and hydroxypropyl cellulose.

When α-tocopherol is used alone or in combination with other excipients, the concentration by weight can be from about 0.001% to about 1% or from about 0.001% to about 0.005%, or from about 0.005% to about 0.01%, or from about 0.01% to about 0.015%, or from about 0.015% to about 0.03%, or from about 0.03% to about 0.05%, or from about 0.05% to about 0.07%, or from about 0.07% to about 0.1%, or from about 0.1% to about 0.15%, or from about 0.15% to about 0.3%, or from about 0.3% to about 0.5%, or from about 0.5% to about 1% by weight. In some embodiments, the concentration of α-tocopherol is about 0.001% by weight, or alternatively about 0.005%, or about 0.008%, or about 0.01%, or about 0.02%, or about 0.03%, or about 0.04%, or about 0.05% by weight.

When hydroxypropyl cellulose is used alone or in combination with other excipients, the concentration by weight can be from about 0.1% to about 30% or from about 1% to about 20%, or from about 1% to about 5%, or from about 1% to about 10%, or from about 2% to about 4%, or from about 5% to about 10%, or from about 10% to about 15%, or from about 15% to about 20%, or from about 20% to about 25%, or from about 25% to about 30% by weight. In some embodiments, the concentration of hydroxypropyl cellulose is about 1% by weight, or alternatively about 2%, or about 3%, or about 4%, or about 5%, or about 6%, or about 7%, or about 8%, or about 10%, or about 15% by weight.

When gum arabic is used alone or in combination with other excipients, the concentration by weight can be from about 0.5% to about 50% or from about 1% to about 20%, or from about 1% to about 10%, or from about 3% to about 6%, or from about 5% to about 10%, or from about 4% to about 6% by weight. In some embodiments, the concentration of hydroxypropyl cellulose is about 1% by weight, or alternatively about 2%, or about 3%, or about 4%, or about 5%, or about 6%, or about 7%, or about 8%, or about 10%, or about 15% by weight.

The concentration of GGA, or the trans-geranylgeranyl acetone isomer can be from about 1 to about 99% by weight in the pharmaceutical compositions provided herein. In other embodiments, the concentration of the trans-geranylgeranyl acetone isomer can be from about 1 to about 75%, or alternatively, from about 1 to about 40%, or alternatively, from about 1 to about 30%, or alternatively, from about 1 to about 25%, or alternatively, from about 1 to about 20%, or alternatively, from about 2 to about 20%, or alternatively, from about 1 to about 10%, or alternatively, from about 10 to about 20%, or alternatively from about 10 to about 15% by weight in the pharmaceutical composition. In certain embodiments, the concentration of geranylgeranyl acetone in the pharmaceutical composition is about 5% by weight, or alternatively, about 10%, or about 20%, or about 1%, or about 2%, or about 3%, or about 4%, or about 6%, or about 7%, or about 8%, or about 9%, or about 11%, or about 12%, or about 14%, or about 16%, or about 18%, or about 22%, or about 25%, or about 26%, or about 28%, or about 30%, or about 32%, or about 34%, or about 36%, or about 38%, or about 40%, or about 42%, or about 44%, or about 46%, or about 48%, or about 50%, or about 52%, or about 54%, or about 56%, or about 58%, or about 60%, or about 64%, or about 68%, or about 72%, or about 76%, or about 80% by weight.

In one embodiment, this invention provides sustained release formulations such as drug depots or patches comprising an effective amount of GGA. In another embodiment, the patch further comprises gum Arabic or hydroxypropyl cellulose separately or in combination, in the presence of alpha-tocopherol. Preferably, the hydroxypropyl cellulose has an average MW of from 10,000 to 100,000. In a more preferred embodiment, the hydroxypropyl cellulose has an average MW of from 5,000 to 50,000. The patch contains, in various embodiments, an amount of GGA, preferably the 5E, 9E, 13E isomer of it, which is sufficient to maintain a therapeutically effective amount GGA in the plasma for about 12 hours. In one embodiment, the GGA comprises at least 80%, at least 85%, at least 90%, at least 95%, or at least 99% of the 5E, 9E, 13E isomer of GGA.

Compounds and pharmaceutical compositions of this invention may be used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

In some embodiments, a compound of this invention can be used as an adjunct to conventional drug therapy.

4. TREATMENT METHODS

This invention provides methods for using GGA, preferably trans-GGA, still more preferably synthetic trans-GGA, or an isomer of each thereof for inhibiting neural death and increasing neural activity. For example, and without limitation, the invention provides methods for impeding the progression of neurodegenerative diseases or injury using the compound geranylgeranyl acetone (GGA). The pharmaceutical compositions and/or compounds described above are useful in the methods described herein.

In one aspect, there are methods for increasing the axon growth of neurons by contacting said neurons with an effective amount of GGA. Neural diseases can result in an impairment of signaling between neurons. This can in part be due to a reduction in the growth of axonal projections. Contacting neurons with GGA enhances axonal growth. It is contemplated that GGA will restore axonal grown in neurons afflicted with a neural disease. In a related embodiment, the pre-contacted neurons exhibit a reduction in the axon growth ability. In yet another embodiment, the GGA is the 5-trans isomer of GGA.

Methods include the use of GGA and the 5-trans isomer of GGA. In certain aspects, the 5-trans isomer of GGA has been shown to be more efficacious than the mixture of GGA, which contains both the 5-trans and 5-cis isomeric forms of GGA. Without being limited to a particular theory, it is believed that the 5-cis isomer of GGA has inhibitory properties. These inhibitory properties of the 5-cis isomer of GGA result in an attenuation of the effects exerted by the isomeric mixture and compositions of 5-trans GGA.

One embodiment of this invention is directed to a method for inhibiting the cell death of neurons susceptible to neuronal cell death, which method comprises contacting said neurons with an effective amount of GGA. Neurons susceptible to neuronal cell death include those that have the characteristics of a neurodegenerative disease and/or those that have undergone injury or toxic stress. One method of creating toxic stress to a cell is by mixing dopamine with neurons such as neuroblastoma cells. Another source of toxic stress is oxidative stress. Oxidative stress can occur from neuronal disease or injury. It is contemplated that contacting neurons with GGA will inhibit their death as measured by a MTT assay or other techniques commonly known to one skilled in the art.

In another aspect, there are methods for increasing the neurite growth of neurons by contacting said neurons with an effective amount of GGA. The term "neurite" refers to both axons and dendrites. Neural diseases can result in an impairment of signaling between neurons. This can in part be due to a reduction in the growth of axonal and/or dendritic projections. It is contemplated that contacting neurons with GGA will enhance neurite growth.

It is further contemplated that GGA will restore neurite grown in neurons afflicted with a neural disease. In a related embodiment, the pre-contacted neurons exhibit a reduction in the neurite growth ability. In yet another embodiment, the GGA is the 5-trans isomer of GGA.

One embodiment of this invention is directed to a method for increasing the expression and/or release of one or more neurotransmitters from a neuron by contacting said neurons with an effective amount of GGA. It is contemplated that contacting neurons with an effective amount of GGA will increase the expression level of one or more neurotransmitters. It is also contemplated that contacting neurons with GGA will increase the release of one or more neurotransmitters from neurons. The release of one or more neurotransmitters refers to the exocytotic process by which secretory vesicles containing one or more neurotransmitters are fused to cell membrane, which directs the neurotransmitters out of the neuron. It is contemplated that the increase in the expression and/or release of neurotransmitters will lead to enhanced signaling in neurons, in which levels of expression or release of neurotransmitters are otherwise reduced due to the disease. The increase in their expression and release can be measured by molecular techniques commonly known to one skilled in the art.

One embodiment of this invention is directed to a method for inducing synapse formation of a neuron by contacting said neurons with an effective amount of GGA. A synapse is a junction between two neurons. Synapses are essential to neural function and permit transmission of signals from one neuron to the next. Thus, an increase in the neural synapses will lead to an increase in the signaling between two or more neurons. It is contemplated that contacting the neurons with an effective amount of GGA will increase synapse formation in neurons that otherwise experience reduced synapse formation as a result of neural disease.

Another embodiment of this invention is directed to a method for increasing electrical excitability of a neuron by contacting said neurons with an effective amount of GGA. Electrical excitation is one mode of communication among two or more neurons. It is contemplated that contacting neurons with an effective amount of GGA will increase the electrical excitability of neurons in which electrical excitability and other modes of neural communication are otherwise impaired due to neural disease. Electrical excitability can be measured by electrophysiological methods commonly known to one skilled in the art.

In each of the three previous paragraphs above, the administration of GGA enhances communication between neurons and accordingly provides for a method of inhibiting the loss of cognitive abilities in a mammal that is at risk of dementia or suffering from incipient or partial dementia while retaining some cognitive skills. Incipient or partial dementia in a mammal is one in which the mammal still exhibits some cognitive skills, but the skills are being lost and/or diminished over time. Method comprises administering an effective amount of GGA to said patient.

In another embodiment, this invention is directed to a method for inhibiting the death of neurons due to formation of or further formation of pathogenic protein aggregates between, outside or inside neurons, wherein said method comprises contacting said neurons at risk of developing said pathogenic protein aggregates with an amount of GGA inhibitory to protein aggregate formation, provided that said pathogenic protein aggregates are not related to SBMA. In one embodiment of this invention, the pathogenic protein aggregates form between or outside of the neurons. In another embodiment of this invention, the pathogenic protein aggregates form inside said neurons. In one embodiment of this invention, the pathogenic protein aggregates are a result of toxic stress to the cell. One method of creating toxic stress to a cell is by mixing dopamine with neurons such as neuroblastoma cells. It is contemplated that contacting neurons with GGA will inhibit their death as measured by a MTT assay or other techniques commonly known to one skilled in the art.

Another embodiment of the invention is directed to a method for protecting neurons from pathogenic extracellular protein aggregates which method comprises contacting said neurons and/or said pathogenic protein aggregates with an amount of GGA that inhibits further pathogenic protein aggregation. In one embodiment of this invention, contacting said neurons and/or said pathogenic protein aggregates with an effective amount of GGA alters the pathogenic protein aggregates into a non-pathogenic form. Without being limited to any theory, it is contemplated that contacting the neurons and/or the pathogenic protein aggregates with GGA will solubilize at least a portion of the pathogenic protein aggregates residing between, outside, or inside of the cells. It is further contemplated that contacting the neurons and/or the pathogenic protein aggregates with GGA will alter the pathogenic protein aggregates in such a way that they are non-pathogenic. A non-pathogenic form of the protein aggregate is one that does not contribute to the death or loss of functionality of the neuron. There are many assays known to one skilled in the art for measuring the protection of neurons either in cell culture or in a mammal. One example is a measure of increased cell viability by a MTT assay. Another example is by immunostaining neurons in vitro or in vivo for cell death-indicating molecules such as, for example, caspases or propidium iodide.

In yet another embodiment of the invention is directed to a method for protecting neurons from pathogenic intracellular protein aggregates which method comprises contacting said neurons with an amount of GGA which will inhibit further pathogenic protein aggregation provided that said protein aggregation is not related to SBMA. This method is not intended to inhibit or reduce, negative effects of neural diseases in which the pathogenic protein aggregates are intranuclear or diseases in which the protein aggregation is related to SBMA. SBMA is a disease caused by pathogenic androgen receptor protein accumulation. It is distinct from the neural diseases mentioned in this application since the pathogenic protein aggregates of SBMA contain polyglutamines and are formed intranuclearly. It is also distinct from the neural diseases described in this application because the protein aggregates are formed from androgen receptor protein accumulation. It is contemplated that contacting neurons with an effective amount of GGA will alter the pathogenic protein aggregate into a non-pathogenic form.

One embodiment of the invention is directed to a method of modulating the activity of G proteins in neurons which method comprises contacting said neurons with an effective amount of GGA. It is contemplated that contacting neurons with GGA will alter the sub-cellular localization, thus changing the activities of the G protein in the cell. In one embodiment of the invention, contacting neurons with GGA will enhance the activity of G proteins in neurons. It is contemplated that contacting GGA with neurons will increase the expression level of G proteins. It is also contemplated that contacting GGA with neurons will enhance the activity of G proteins by changing their sub-cellular localization to the cell membranes where they must be to exert their biological activities.

One embodiment of the invention is directed to a method of modulating or enhancing the activity of G proteins in neurons at risk of death which method comprises contacting said neurons with an effective amount of GGA. Neurons may be at risk of death as a result of genetic changes related to ALS. One such genetic mutation is a depletion of the TDP-43 protein. It is contemplated that neurons with depleted TDP-43 or other genetic mutations associated with ALS will have an increase or change in the activity of G proteins after being contacted with GGA. It is further contemplated that GGA will result in an increase in the activity of G proteins in these cells by changing their sub-cellular localization to the cell membranes where they must be to exert their biological activities.

Another embodiment of the invention is directed to a method for inhibiting the neurotoxicity of β-amyloid peptide by contacting the β-amyloid peptide with an effective amount of GGA. In one embodiment of the invention the β-amyloid peptide is between or outside of neurons. In yet another embodiment of the invention, the β-amyloid peptide is part of the β-amyloid plaque. It is contemplated that contacting neurons with GGA will result in solubilizing at least a portion of the β-amyloid peptide, thus decreasing its neurotoxicity. It is further contemplated that GGA will decrease the toxicity of the β-amyloid peptide by altering it in such a way that it is no longer toxic to the cell. It is also believed that GGA will induce the expression of heat shock proteins (HSPs) in the neurons. It is also contemplated that HSPs will be induced in support cells such as glial cells. The induced heat shock proteins in the neurons or glial cells may be transmitted extracellularly and act to dissolve extracellular protein aggregates. Cell viability can be measured by standard assays known to those skilled in the art. One such example of an assay to measure cell viability is a MTT assay. Another example is a MTS assay. The modulation of protein aggregation can be visualized by immunostaining or histological staining techniques commonly known to one skilled in the art.

One embodiment of the invention is directed to a method for inhibiting neural death and increasing neural activity in a mammal suffering from neural diseases, wherein the etiology of said neural diseases comprises formation of protein aggregates which are pathogenic to neurons, and which method comprises administering to said mammal an amount of GGA which will inhibit further pathogenic protein aggregation. This method is not intended to inhibit neural death and increase neural activity in neural diseases in which the pathogenic protein aggregates are intranuclear or diseases in which the protein aggregation is related to SBMA.

Neural diseases such as AD and ALS disease have the common characteristic of protein aggregates either inside neural cells in cytoplasm or in the extracellular space between two or more neural cells. This invention relates to a method for using the compound GGA to inhibit the formation of the protein aggregates or alter the pathogenic protein aggregates into a non-pathogenic form. It is contemplated that this will attenuate some of the symptoms associated with these neural diseases.

In one embodiment the mammal is a human afflicted with a neural disease. In one embodiment of this invention, the negative effect of the neural disease being inhibited or reduced is ALS. ALS is characterized by a loss of functionality of motor neurons. This results in the inability to control muscle movements. ALS is a neurodegenerative disease that does not typically show intranuclear protein aggregates. It is contemplated that GGA will prevent or inhibit the formation of extracellular or intracellular protein aggregates that are cytoplasm, not intranuclear and not related to SBMA. It is also contemplated that GGA will alter the pathogenic protein aggregates into a form that is non-pathogenic. Methods for diagnosing ALS are commonly known to those skilled in the art. Additionally, there are numerous patents that describe methods for diagnosing ALS. These include U.S. Pat. No. 5,851,783 and U.S. Pat. No. 7,356,521 both of which are incorporated herein by reference in their entirety.

In one embodiment of the invention the negative effect of the neural disease being inhibited or reduced is AD. AD is a neurodegenerative disease that does not typically show intranuclear protein aggregates. It is contemplated that GGA will prevent or inhibit the formation of extracellular or intracellular protein aggregates. It is also contemplated that GGA will alter the pathogenic protein aggregates into a form that is non-pathogenic. Methods for diagnosing AD are commonly known to those skilled in the art. Additionally, there are numerous patents that describe methods for diagnosing AD. These include U.S. Pat. No. 6,130,048 and U.S. Pat. No. 6,391,553 both of which are incorporated herein by reference in their entirety.

In another embodiment, the mammal is a laboratory research mammal such as a mouse. In one embodiment of this invention, the neural disease is ALS. One such mouse model for ALS is a transgenic mouse with a Sod1 mutant gene. It is contemplated that GGA will enhance the motor skills and body weights when administered to a mouse with a mutant Sod1 gene. It is further contemplated that administering GGA to this mouse will increase the survival rate of Sod1 mutant mice. Motor skills can be measured by standard techniques known to one skilled in the art. Sod1 mutant mice provide an accepted mouse model for modeling ALS in humans. Accordingly, method aspects of this disclosure relate to a method for prolonging the survival or reducing mortality of a subject with ALS, comprising administering a therapeutically effective amount of GGA. In one embodiment, the GGA is a 5-trans isomer of GGA.

In yet another embodiment of this invention, the neural disease is AD. One example of a transgenic mouse model for AD is a mouse that overexpresses the APP (Amyloid beta Precursor Protein). It is contemplated that administering GGA to a transgenic AD mouse will improve the learning and memory skills of said mouse. It is further contemplated that GGA will decrease the amount and/or size of β-amyloid peptide and/or plaque found inside, between, or outside of neurons. The β-amyloid peptide or plaque can be visualized in histology sections by immunostaining or other staining techniques.

In one embodiment of the invention administering GGA to a mammal alters the pathogenic protein aggregate present into a non-pathogenic form. In another embodiment of the invention, administering GGA to a mammal will prevent pathogenic protein aggregates from forming.

Another aspect of this invention relates to a method for reducing seizures in a mammal in need thereof, which method comprises administering a therapeutically effective amount of GGA, thereby reducing seizures. The reduction of seizures refers to reducing the occurrence and/or severity of seizures. In one embodiment, the seizure is epileptic seizure. In another embodiment, the methods of this invention prevent neural death during epileptic seizures. The severity of the seizure can be measured by one skilled in the art.

In methods described herein, the GGA refers to the compounds and/or pharmaceutical compositions described previously of the cis isomer, the trans isomer or the mixture of GGA. In such methods, it is contemplated that the trans isomer may exhibit a more efficacious result compared to the mixture or the cis isomer. It is also contemplated that the inhibitory effects of the cis isomer allow it to be used to attenuate the effects of the mixture or the trans isomer in the above-described methods. Therefore, in one embodiment of each method, the GGA used is the trans isomer of GGA. In another embodiment, the GGA used is the cis isomer of GGA. In yet another embodiment, the method comprises contacting the neuron with an effective amount of the 5-cis isomer to attenuate the effect of the mixture or 5-trans isomer.

In certain aspects, the methods described herein relate to administering GGA or the isomeric compounds or compositions of GGA in vitro. In other aspects the administration is in vivo. In yet other aspects, the in vivo administration is to a mammal. Mammals include but are not limited to humans and common laboratory research animals such as, for example, mice, rats, dogs, pigs, cats, and rabbits.

5. SYNTHETIC METHODS

This invention provides a synthetic method comprising one or more of the following steps:

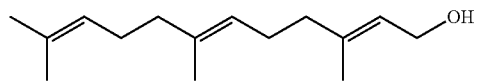
VIII (i) reacting a compound of formula III under halogenation conditions to provide a compound of formula IX;

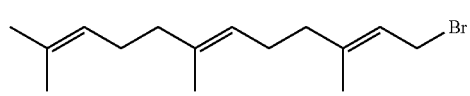
IX (ii) reacting the compound of formula IX with alkyl acetoacetate under alkylation conditions to provide a compound of formula X, where the stereochemistry at sterogenic center can be a racemic, R or S configuration:

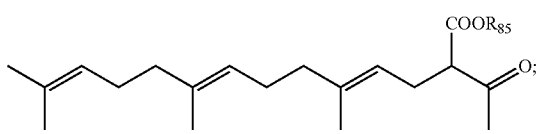
X (iii) reacting the compound of formula V under hydrolysis and decarboxylation conditions to provide a compound of formula XI:

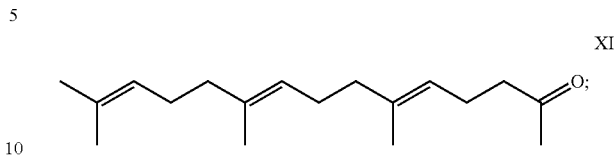
XI (iv) reacting the compound of formula XI with a compound of formula XII:

XII wherein $R_{74}$, $R_{75}$, $R_{85}$ and each $R_{86}$ independently are alkyl or substituted or unsubstituted aryl, under olefination conditions to selectively provide a compound of formula XIII:

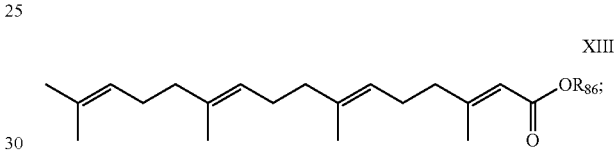
XIII (v) reacting the compound of formula XIII under reduction conditions to provide a compound of formula XIV

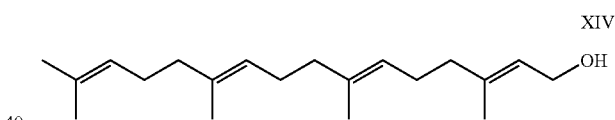
XIV

Compound VIII is combined with at least an equimolar amount of a halogenating agent typically in an inert solvent. As used in this application, an "inert solvent" is a solvent that does not react under the reaction conditions in which it is employed as a solvent. The reaction is typically run at a temperature of about 0° C. to 20° C. for a period of time sufficient to effect substantial completion of the reaction. Suitable solvents include, by way of example only, diethyl ether, acetonitrile, and the like. Suitable halogenating agents include $PBr_3$ or $PPh_3/CBr_4$. After reaction completion, the resulting product, compound IX, can be recovered under conventional conditions such as extraction, precipitation, filtration, chromatography, and the like or, alternatively, used in the next step of the reaction without purification and/or isolation.

Compound IX is combined with at least an equimolar amount of an alkyl acetoacetate, in the presence of a base and an inert solvent. The reaction is typically run initially at 0° C., and then warmed up to room temperature for a period of time sufficient to effect substantial completion of the reaction. Suitable solvents include, by way of example only, various alcohols, such as ethanol, dioxane, and mixtures thereof. Suitable bases include, by way of example only, alkali metal alkoxides, such as sodium ethoxide.

Compound X is reacted with at least an equimolar amount, preferably, an excess of aqueous alkali. The reaction is typically run at about 40 to 80° C. and preferably about 80° C. for a period of time sufficient to effect substantial completion of the reaction. Suitable solvents include, by way of examples only, alcohols, such as methanol, ethanol, and the like.

Compound XI is combined with at least an equimolar amount, preferably, an excess of a compound of formula XII, and at least an equimolar amount, preferably, an excess of base, in an inert solvent. The reaction is typically run, initially at about −30° C. for about 1-2 hours, and at room temperature for a period of time sufficient to effect substantial completion of the reaction. Suitable solvents include, by way of examples only tetrahydrofuran, dioxane, and the like. Suitable bases include, by way of example only, alkali metal hydrides, such as sodium hydride, or potassium hexamethyldisilazide (KH-MDS), or potassium tertiary butoxide ($^t$BuOK).

Compound XIII is combined with a reducing agent in an inert solvent. The reaction is typically run at about 0° C. for about 15 minutes, and at room temperature for a period of time sufficient to effect substantial completion of the reaction. Suitable reducing agents include, without limitation, LiAlH$_4$. Suitable solvents include, by way of examples only diethyl ether, tetrahydrofuran, dioxane, and the like.

As will be apparent to the skilled artisan, after reaction completion, the resulting product, can be recovered under conventional conditions such as precipitation, filtration, chromatography, and the like or, alternatively, used in the next step of the reaction without purification and/or isolation.

In some embodiments, the method further comprises repeating steps (i), (ii), and (iii) sequentially with compound of formula XIII to provide the compound of formula VI-B, wherein m is 2.

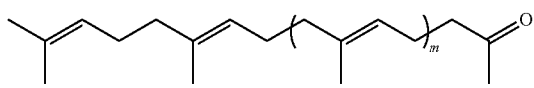

VI-B

In another embodiment, the method or procedure further comprises repeating steps (i), (ii), (iii), (iv), and (v), sequentially, 1-3 times.

In another of its synthetic method aspects, there is provided a method comprising one or more of the following steps:
(i) reacting a compound of formula VIII-B:

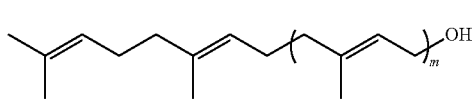

VIII-B wherein m is 1-3, under halogenation conditions to provide a compound of formula IXB:

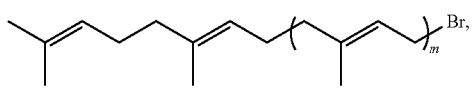

IX-B (ii) reacting the compound of formula IX-B with alkyl acetoacetates, under alkylating conditions to provide a compound of formula X-B, where the stereochemistry at sterogenic center can be a racemic, R or S configuration:

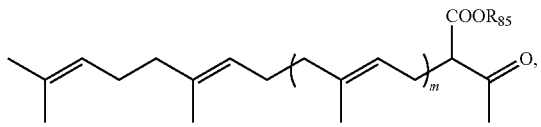

XB wherein R$^{31}$ alkyl is substituted or unsubstituted alkyl
(iii) reacting a compound of formula X-B under hydrolysis and decarboxylation conditions to provide a compound of formula XI-B:

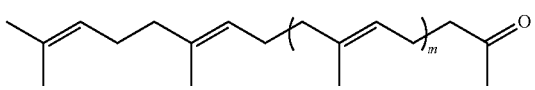

XIB

In another of its synthetic method aspects, this invention provides a method comprising step (i) or step (ii) or steps (i)+(ii):
(i) reacting a compound of formula XV-C:

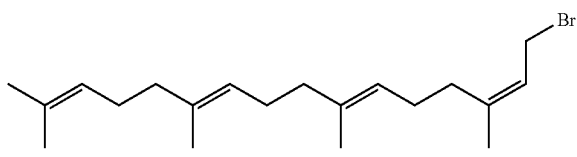

XV-C with alkyl acetoacetate under alkylating conditions to provide a compound of formula XVI-C, where the stereochemistry at sterogenic center can be a racemic, R or S configuration:

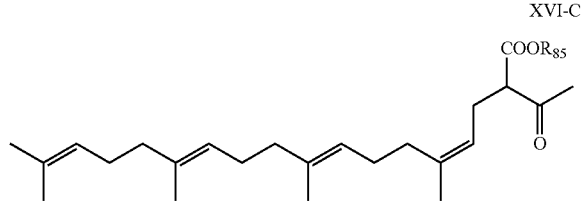

XVI-C wherein R$_{31}$ is as defined herein, and
(ii) reacting the compound XVI-C obtained under hydrolysis and decarboxylation conditions to provide a compound of formula II:

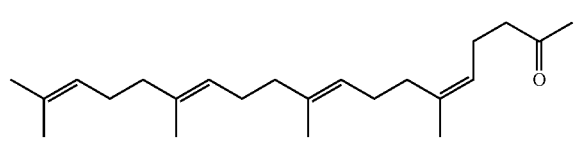

VII

As will be apparent to the skilled artisan, the various reaction steps leading to compound XI-B or to the 5Z isomer are performed in the manner described hereinabove.

In another of its synthetic method aspects, this invention provides a method comprising reacting a ketal compound of formula XVII:

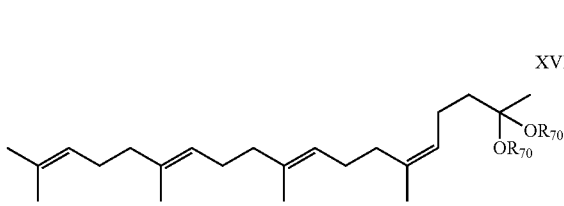

wherein each $R_{70}$ independently is $C_1$-$C_6$ alkyl, or two $R_{70}$ groups together with the oxygen atoms they are attached to form a 5 or 6 membered ring, which ring is optionally substituted with 1-3, preferably 1-2, $C_1$-$C_6$ alkyl groups, under hydrolysis conditions to provide a compound of formula II.

The ketal is combined with at least a catalytic amount, such as, 1-20 mole % of an aqueous acid, preferably, an aqueous mineral acid in an inert solvent. The reaction is typically run about 25° C. to about 80° C., for a period of time sufficient to effect substantial completion of the reaction. Suitable acids include, without limitation, HCl, $H_2SO_4$, and the like. Suitable solvents include alcohols, such as methanol, ethanol, tetrahydrofuran, and the like.

In another embodiment, this invention provides a method comprising reacting a compound of formula XVI:

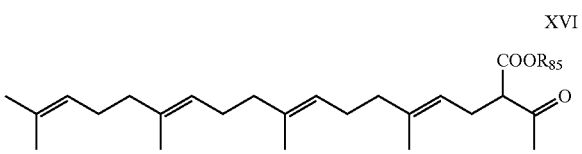

under hydrolysis and subsequently decarboxylation conditions to form a compound of formula I:

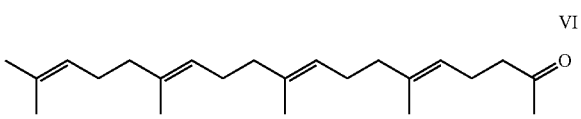 [SMILES: CC(=O)CC/C=C(\C)CC/C=C(\C)CC/C=C(\C)CCC=C(C)C]

Alternatively, reacting compound of formula XII with XV followed by in situ hydrolysis and decarboxylation of compound with formula XVI can afford the compound of formula VI.

In another embodiment, this invention provides a method comprising reacting a compound of formula XVI-C:

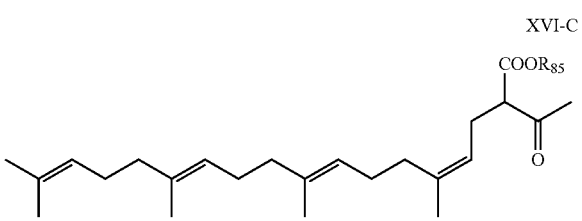

under hydrolysis and subsequent decarboxylation conditions to form the compound of formula VII

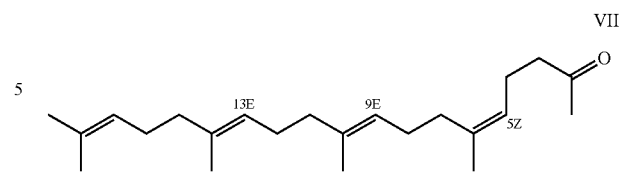

Hydrolysis and decarboxylation conditions useful in these methods will be apparent to the skilled artisan upon reading this disclosure.

It will also be apparent to the skilled artisan that the methods further employ routine steps of separation or purification to isolate the compounds, following methods such as chromatography, distillation, or crystallization.

Synthesis of GGA Derivatives

Certain methods for making GGA or certain GGA derivatives provided and/or utilized herein are described in PCT publication no. WO 2012/031028 and PCT application no. PCT/US2012/027147, each of which are incorporated herein by reference in its entirety. Other GGA derivatives can be prepared by appropriate substitution of reagents and starting materials, as will be well known to the skilled artisan upon reading this disclosure.

The reactions are preferably carried out in a suitable inert solvent that will be apparent to the skilled artisan upon reading this disclosure, for a sufficient period of time to ensure substantial completion of the reaction as observed by thin layer chromatography, $^1$H-NMR, etc. If needed to speed up the reaction, the reaction mixture can be heated, as is well known to the skilled artisan. The final and the intermediate compounds are purified, if necessary, by various art known methods such as crystallization, precipitation, column chromatography, and the likes, as will be apparent to the skilled artisan upon reading this disclosure.

The compounds provided and/or utilized in this invention are synthesized, e.g., from a compound of formula (III-A):

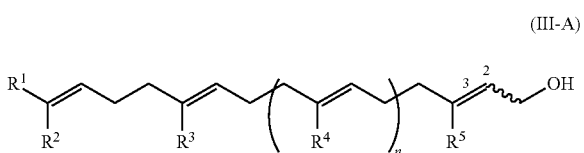

wherein n, $R^1$-$R^5$ and ⌇ are defined as in Formula (I) above, following various well known methods upon substitution of reactants and/or altering reaction conditions as will be apparent to the skilled artisan upon reading this disclosure. The compound of Formula (III-A) is itself prepared by methods well known to a skilled artisan, for example, and without limitation, those described in PCT Pat. App. Pub. No. WO 2012/031028 and PCT Pat. App. No. PCT/US2012/027147 (each supra). An illustrative and non-limiting method for synthesizing a compound of Formula (III-A), where n is 1, is schematically shown below.

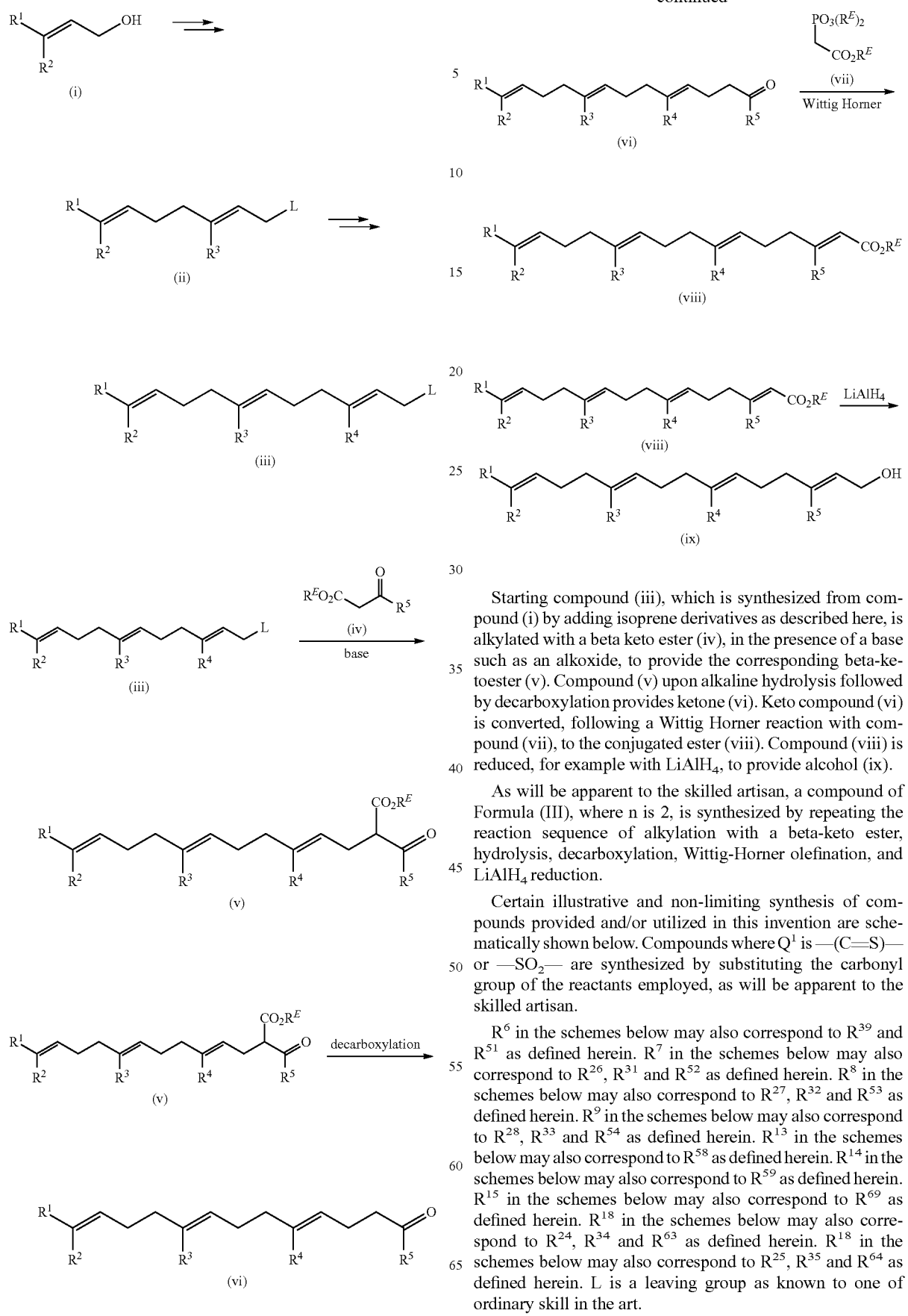

Starting compound (iii), which is synthesized from compound (i) by adding isoprene derivatives as described here, is alkylated with a beta keto ester (iv), in the presence of a base such as an alkoxide, to provide the corresponding beta-ketoester (v). Compound (v) upon alkaline hydrolysis followed by decarboxylation provides ketone (vi). Keto compound (vi) is converted, following a Wittig Horner reaction with compound (vii), to the conjugated ester (viii). Compound (viii) is reduced, for example with LiAlH$_4$, to provide alcohol (ix).

As will be apparent to the skilled artisan, a compound of Formula (III), where n is 2, is synthesized by repeating the reaction sequence of alkylation with a beta-keto ester, hydrolysis, decarboxylation, Wittig-Horner olefination, and LiAlH$_4$ reduction.

Certain illustrative and non-limiting synthesis of compounds provided and/or utilized in this invention are schematically shown below. Compounds where Q$^1$ is —(C=S)— or —SO$_2$— are synthesized by substituting the carbonyl group of the reactants employed, as will be apparent to the skilled artisan.

R$^6$ in the schemes below may also correspond to R$^{39}$ and R$^{51}$ as defined herein. R$^7$ in the schemes below may also correspond to R$^{26}$, R$^{31}$ and R$^{52}$ as defined herein. R$^8$ in the schemes below may also correspond to R$^{27}$, R$^{32}$ and R$^{53}$ as defined herein. R$^9$ in the schemes below may also correspond to R$^{28}$, R$^{33}$ and R$^{54}$ as defined herein. R$^{13}$ in the schemes below may also correspond to R$^{58}$ as defined herein. R$^{14}$ in the schemes below may also correspond to R$^{59}$ as defined herein. R$^{15}$ in the schemes below may also correspond to R$^{69}$ as defined herein. R$^{18}$ in the schemes below may also correspond to R$^{24}$, R$^{34}$ and R$^{63}$ as defined herein. R$^{18}$ in the schemes below may also correspond to R$^{25}$, R$^{35}$ and R$^{64}$ as defined herein. L is a leaving group as known to one of ordinary skill in the art.

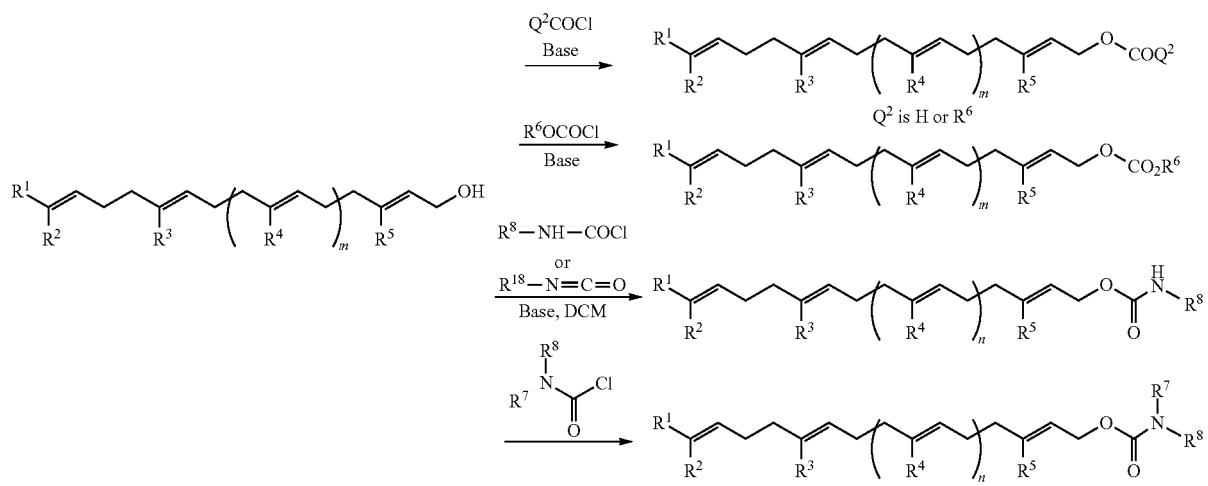
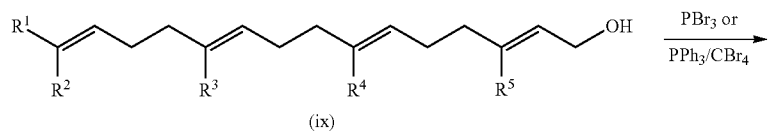
(ix)
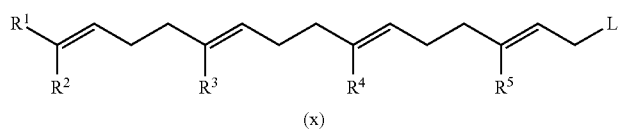
(x)
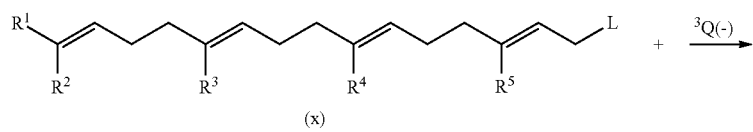
(x)
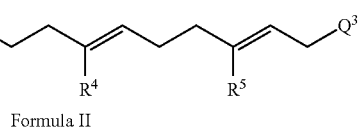
Formula II As shown above, $R^E$ is alkyl.

Compound (ix) with alcohol functionality is an intermediate useful for preparing the compounds provided and/or utilized in this invention. Compound (x), where L is an $R^sSO_2$— group is made by reacting compound (ix) with $R^sSO_2Cl$ in the presence of a base. The transformation of compound (iii) to compound (x) illustrates methods of adding isoprene derivatives to a compound, which methods are suitable to make compound (iii) from compound (i). Intermediate (ix) containing various $R^1$-$R^5$ substituents are prepared according to this scheme as exemplified herein below. The transformation of compound (iii) to compound (x) illustrates methods of adding isoprene derivatives to a compound, which methods are suitable to make compound (iii) from compound (i).

The intermediates prepared above are converted to the compounds provided and/or utilized in this invention as schematically illustrated below:

ing to the scheme herein above, is converted to amino intermediate (ixb) via the corresponding bromide. Intermediates (ixa) and (ixb) are converted to the compounds provided and/or utilized in this invention by reacting with suitable isocyanates or carbamoyl chlorides, which are prepared by art known methods. The thiocarbamates and thioureas of this invention are prepared according to the methods described above and replacing the isocyanates or the carbamoyl chlorides with isothiocyanates ($R^{18}$—N=C=S) or thiocarbamoyl chlorides ($R^{18}$—NH—C(=S)Cl or $R^{18}R^{19}N$—C(=S)Cl). These and other compounds provided and/or utilized in this invention are also prepared by art known methods, which may require optional modifications as will be apparent to the skilled artisan upon reading this disclosure. Intermediates for synthesizing compounds provided and/or utilized in this invention containing various $R^1$-$R^5$ substituents are illustrated in the examples section and/or are well known to the skilled artisan.

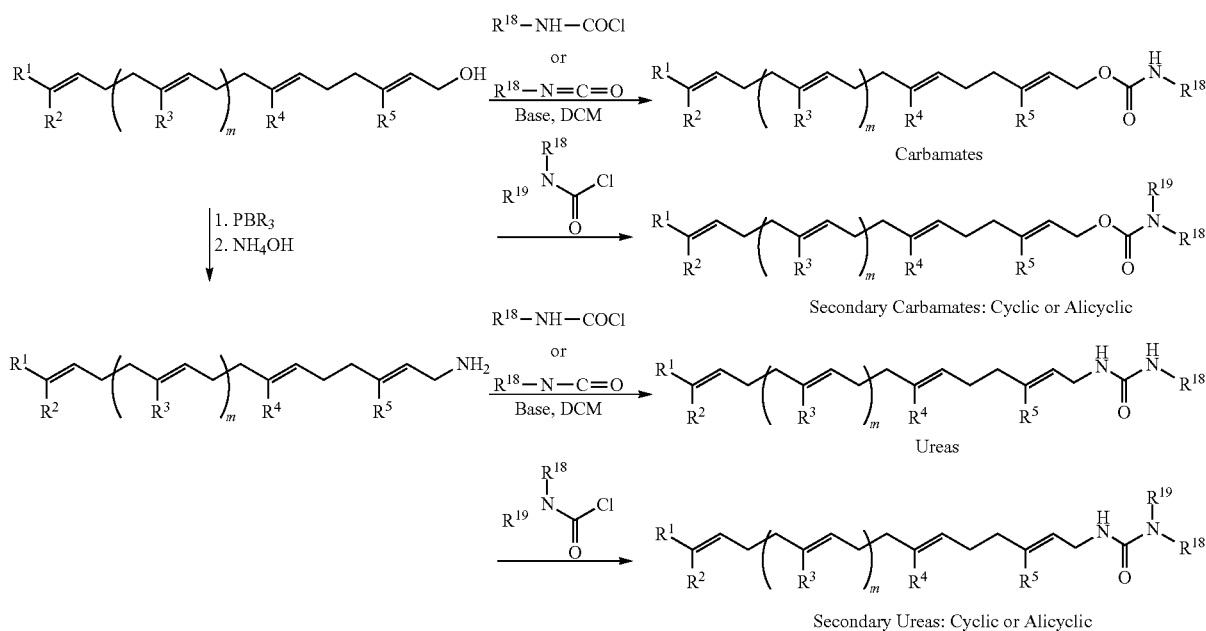

As used herein, for example, and without limitation, m is 0 or 1 and $R^1$-$R^5$ are as defined herein, and are preferably alkyl, or more preferably methyl. Intermediate (ixa), prepared accord- Certain GGA derivatives provided and/or utilized herein are synthesized as schematically shown below.

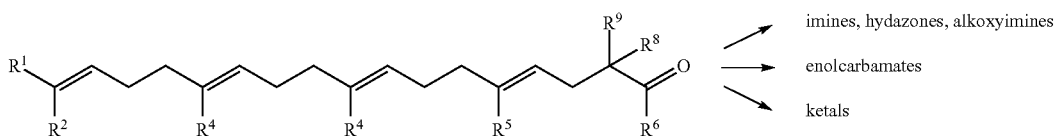

Certain compounds provided and/or utilized herein are obtained by reacting compound (x) with the anion Q(−), which can be generated by reacting the compound QH with a base. Suitable nonlimiting examples of bases include hydroxide, hydride, amides, alkoxides, and the like. Various compounds provided and/or utilized in this invention, wherein the carbonyl group is converted to an imine, a hydrazone, an alkoxyimine, an enolcarbamate, a ketal, and the like, are prepared following well known methods.

Other methods for making the compounds provided and/or utilized in this invention are schematically illustrated below:

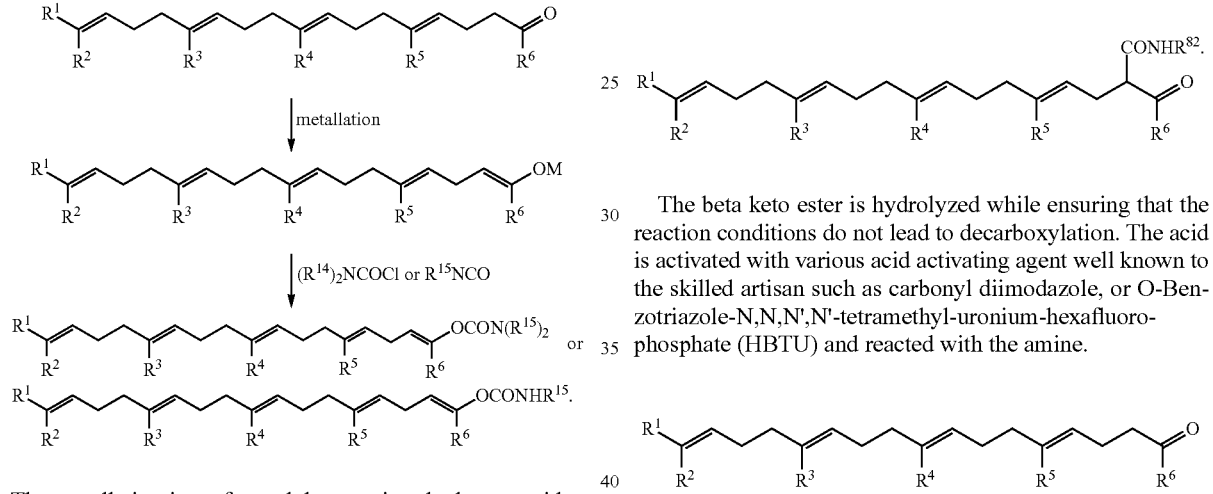

The metallation is performed, by reacting the ketone with a base such as dimsyl anion, a hindered amide base such as diisopropylamide, or hexamethyldisilazide, along with the corresponding metal cation, M. The amino carbonyl chloride or the isocyanate is prepared, for example, by reacting the amine $(R^{14})_2NH$ with phosgene or an equivalent reagent well known to the skilled artisan.

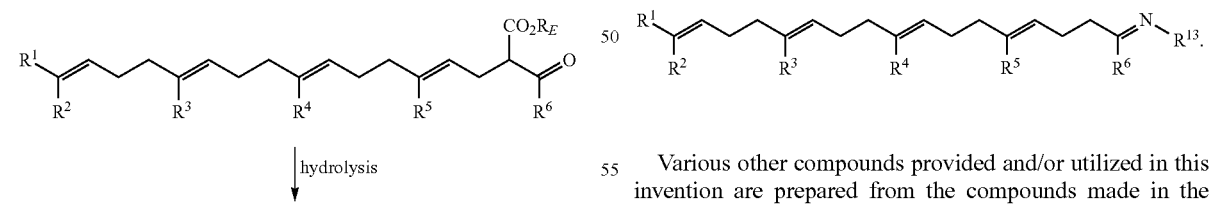

The beta keto ester is hydrolyzed while ensuring that the reaction conditions do not lead to decarboxylation. The acid is activated with various acid activating agent well known to the skilled artisan such as carbonyl diimodazole, or O-Benzotriazole-N,N,N',N'-tetramethyl-uronium-hexafluoro-phosphate (HBTU) and reacted with the amine.

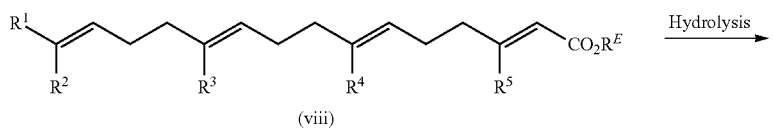

Various other compounds provided and/or utilized in this invention are prepared from the compounds made in the scheme above based on art known methods.

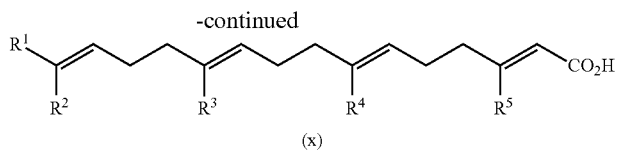
(x)
As shown above, $R^E$ is alkyl.
The intermediates prepared above are converted to the compounds provided and/or utilized in this invention as schematically illustrated below:
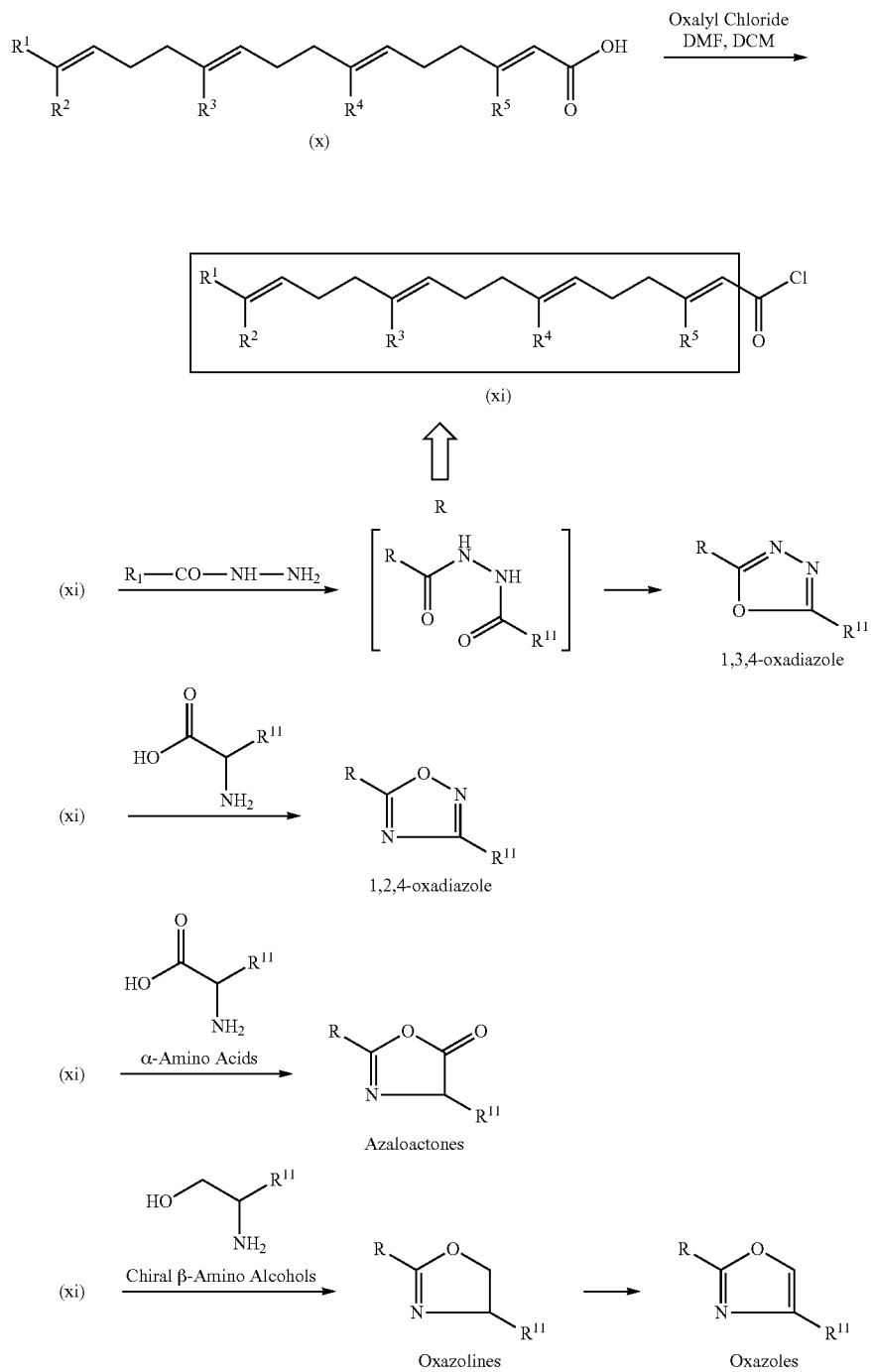

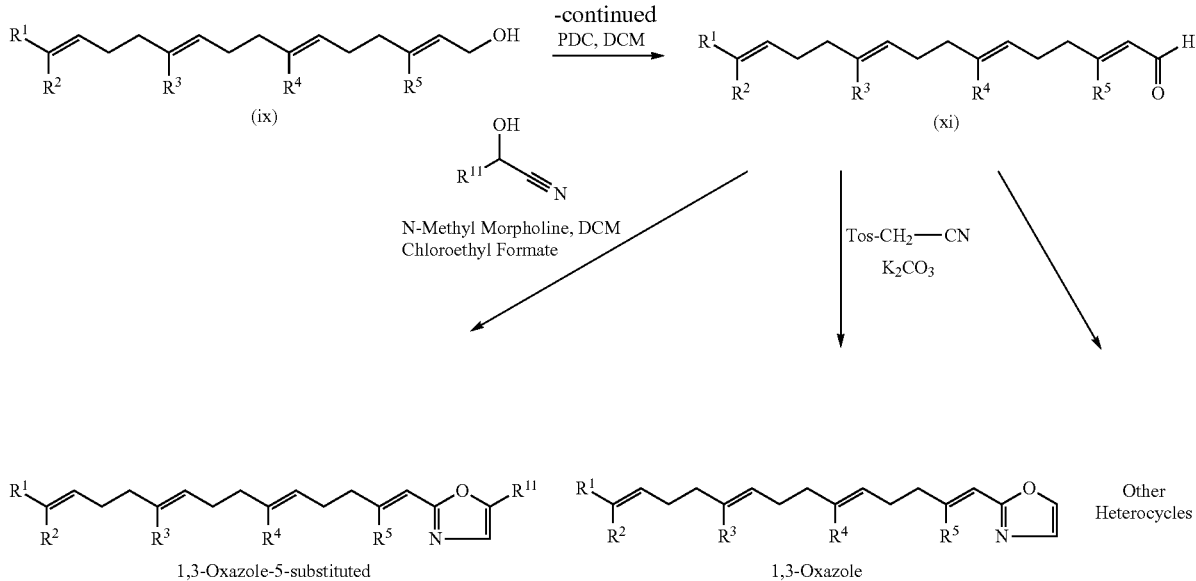

Compound (viii) is hydrolyzed to the carboxylic acid (x), which is then converted to the acid chloride (xi). Compound (xi) is reacted with a suitable nucleophile such as a hydrazide, a hydroxylamine, an amino alcohol, or an amino acid, and the intermediate dehydrated to provide a compound of Formula (IV). Alternatively, the allylic alcohol (ix) is oxidized to the aldehyde (xi), which is then reacted with a cyanohydrin or cyanotosylmethane to provide further compounds provided and/or utilized in this invention.

GGA derivatives provided and/or utilized in this invention can also be synthesized employing art known methods and those disclosed here by alkene-aryl, alkene-heteroaryl, or alkene-akene couplings such as Heck, Stille, or Suzuki coupling. Such methods can use (vi) to prepare intermediate (xii) that can undergo Heck, Stille, or Suzuki coupling under conditions well known to the skilled artisan to provide compounds provided and/or utilized in this invention.

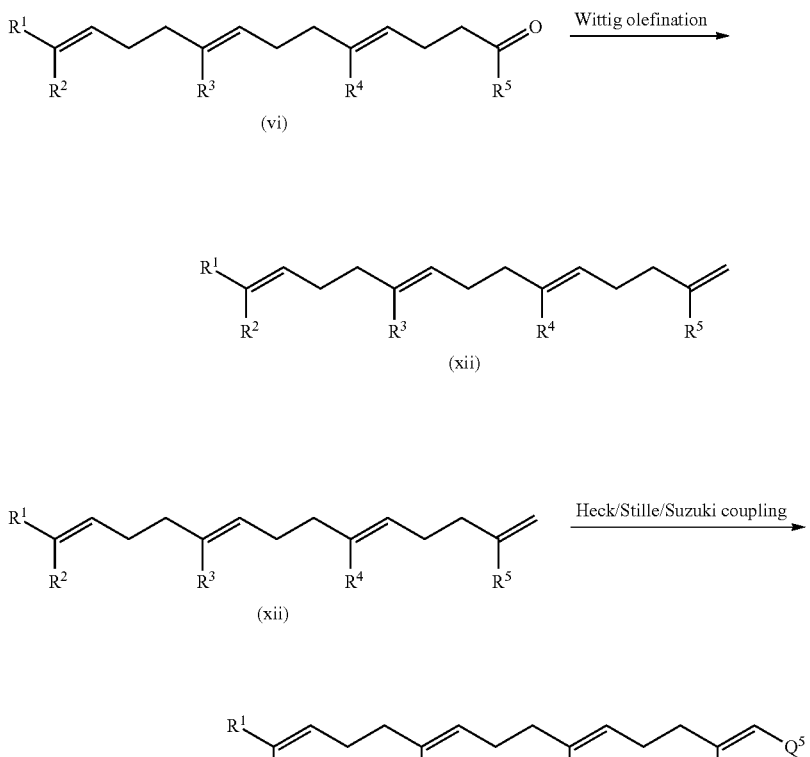

Higher and lower isoprenyl homologs of intermediates (x), (xi), and (xii), which are prepared following the methods disclosed here, can be similarly employed to prepare other compounds provided and/or utilized in this invention.

Compounds provided and/or utilized in this invention are also prepared as shown below

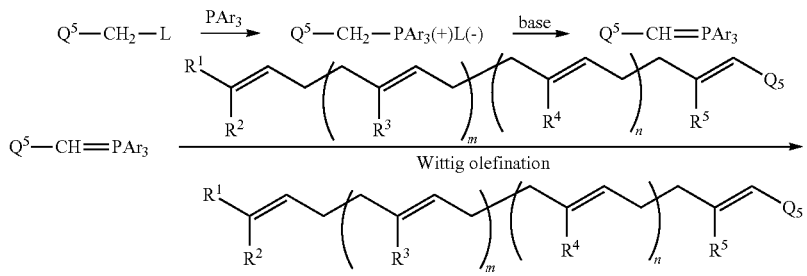

L is a leaving group and $Q_5$ are as defined herein, Ar is a preferably an aryl group such as phenyl, the base employed is an alkoxide such as tertiarybutoxide, a hydride, or an alkyl lithium such as n-butyl lithium. Methods of carrying out the steps shown above are well known to the skilled artisan, as are conditions, reagents, solvents, and/or additives useful for performing the reactions and obtaining the compound of Formula (IV) in the desired stereochemistry.

Other methods for making the compounds provided and/or utilized in this invention are schematically illustrated below:

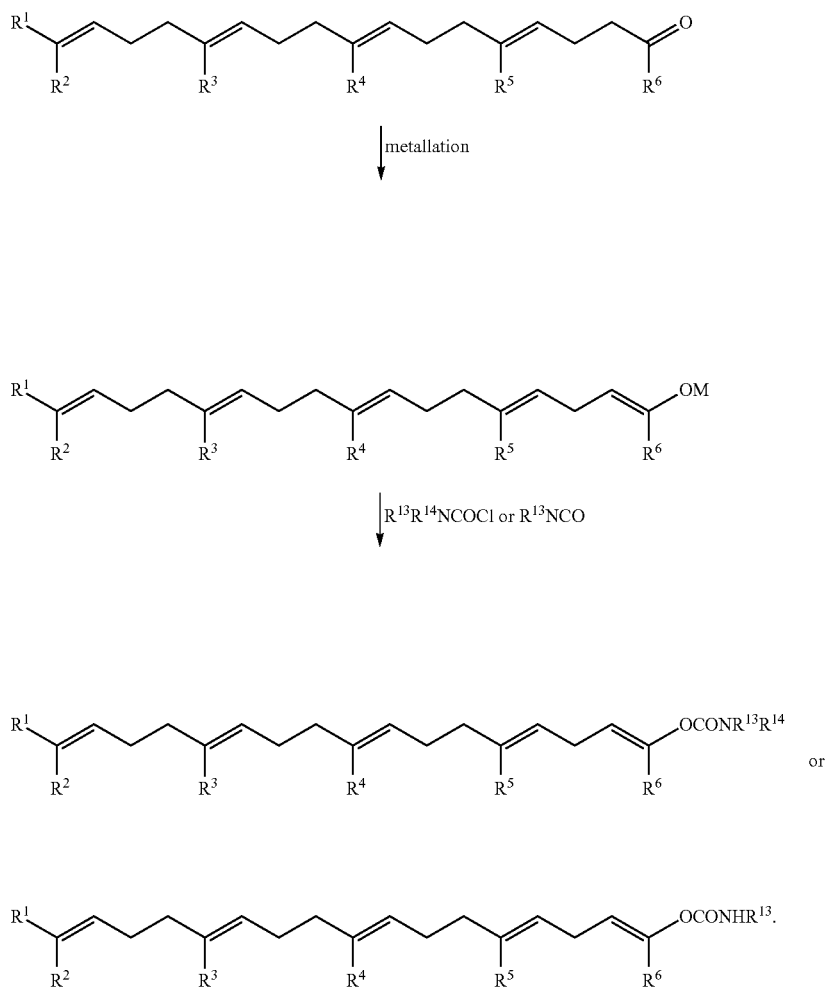

The metallation is performed, by reacting the ketone with a base such as dimsyl anion, a hindered amide base such as diisopropylamide, or hexamethyldisilazide, along with the corresponding metal cation, M. The amino carbonyl chloride or the isocyanate is prepared, for example, by reacting the amine $R^{13}R^{14}NH$ with phosgene or an equivalent reagent well known to the skilled artisan.

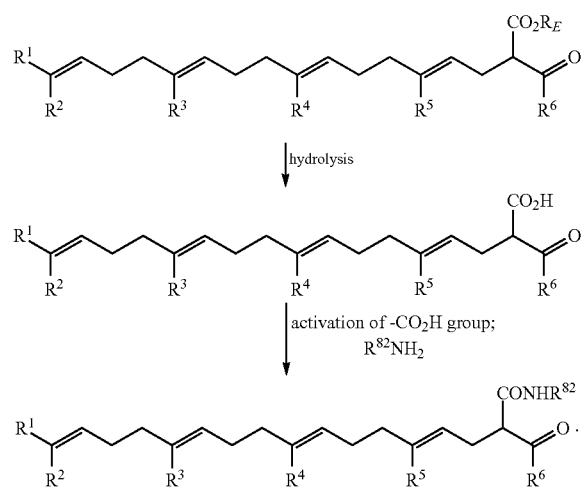

The beta keto ester is hydrolyzed while ensuring that the reaction conditions do not lead to decarboxylation. The acid is activated with various acid activating agent well known to the skilled artisan such as carbonyl diimodazole, or O-Benzotriazole-N,N,N',N'-tetramethyl-uronium-hexafluorophosphate (HBTU) and reacted with the amine. Certain other methods of preparing the conjugates are shown below.

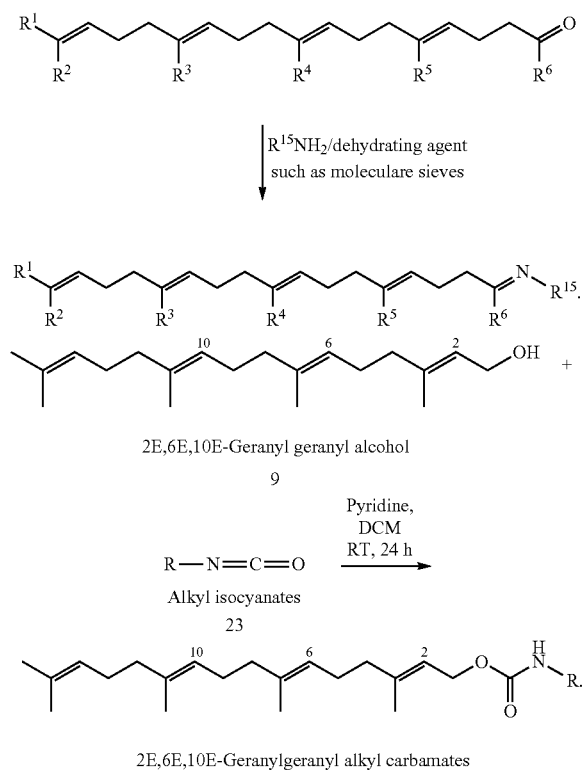

As shown above, R is a memantine or a riluzole residue.

6. UTILITY

GGA is a known anti-ulcer drug used commercially and in clinical situations. GGA has also been shown to exert cytoprotective effects on a variety of organs, such as the eye, brain, and heart (See for example Ishii Y., et al., Invest Ophthalmol Vis Sci 2003; 44:1982-92; Tanito M, et al., J Neurosci 2005; 25:2396-404; Fujiki M, et al., J Neurotrauma 2006; 23:1164-78; Yasuda H, et al., Brain Res 2005; 1032:176-82; Ooie T, et al., Circulation 2001; 104:1837-43; and Suzuki S, et al., Kidney Int 2005; 67:2210-20).

In certain situations, the concentration of GGA required to exert a cytoprotective effect is an excessive amount of more than 600 mg per kg per day (Katsuno et al., Proc. Natl. Acad. Sci. USA 2003, 100, 2409-2414). The trans-isomer of GGA has been shown to be more efficacious at lower concentrations than a composition containing from 1:2 to 1:3 cis:trans mixture of GGA, and a composition of the cis-isomer of GGA alone. Therefore, the trans-isomer of GGA is useful for exerting cytoprotective effects on cells at a lower concentration than the cis-isomer or the 1:2 to 1:3 mixture of cis and trans isomers. Surprisingly, increasing amounts of the cis-isomer was found to antagonize the activity of the trans-isomer, as exemplified below.

It is contemplated that the isomeric mixture of GGA and/or compositions containing the 5-trans isomer of GGA can be used to inhibit neural death and increase neural activity in a mammal suffering from a neural disease, wherein the etiology of said neural disease comprises formation of protein aggregates which are pathogenic to neurons which method comprises administering to said mammal an amount of GGA which will inhibit neural death and increase neural activity, or impede the progression of the neural disease. As it relates to the isomeric mixture of GGA, this method is not intended to inhibit or reduce the negative effect of a neural disease in which the pathogenic protein aggregates are intranuclear or diseases in which the protein aggregation is related to SBMA.

Negative effects of neural diseases that are inhibited or reduced by GGA and the 5-trans isomer of GGA according to this invention include but are not limited to Alzheimer's disease, Parkinson's disease, multiple sclerosis, prion diseases such as Kuru, Creutzfeltdt-Jakob disease, Fatal familial insomnia, and Gerstmann-Straussler-Scheinker syndrome, amyotrophic lateral sclerosis, or damage to the spinal cord. GGA and the 5-trans isomer of GGA are also contemplated to prevent neural death during epileptic seizure.

As will be apparent upon reading this disclosure, certain GGA derivatives provided herein are useful as synthetic intermediates in the synthetsis and/or manufacture of other GGA derivatives.

7. ASSAYS

The isolated cis- and trans-compounds described herein are also useful in assays which access a compound having putative cytoprotective effects. In particular, in such assays, the cis-isomer of GGA will behave as baseline or negative control and the trans-isomer as a positive control. The putative compound is tested in the assay described variously herein and its activity correlated against the cis- and trans-isomers. Compounds exhibiting activity similar to or exceeding that of the trans-isomer would be considered to be active compounds. Compounds providing activity similar to the cis-isomer would be considered to be inactive compounds.

Accordingly, the cis-isomer finds utility as a negative control in the assay.

8. EXAMPLES OF THE INVENTION

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

In the examples below as well as throughout the application, the following abbreviations have the following meanings. If not defined, the terms have their generally accepted meanings.

° C.=degrees Celsius
$PBr_3$=phosphorus tribromide
EE=ethyl ether
EtOH=Ethanol
NaOEt=sodium ethoxide
Oet=Ethoxide
N=Normal
KOH=potassium hydroxide
aq=aqueous
h=hour(s)
RT=Room temperature
LAH=lithium aluminum hydride
THF=Tetrahydrofuran
min=minute(s)
Et=Ethyl
MeOH=Methanol
NaH=sodium hydride
ON=Overnight
E or (E)=Trans
Z or (Z)=Cis
TLC=thin layer chromatography
GGA=geranylgeranyl acetone
μL=Microliter
mL=Milliliter
PK=negative logarithm of the dissociation constant K
HPC=hydroxypropyl cellulose
DI=Deionized
Mn=number average molar mass
Av=Average
p-TsOH=p-toluenesulfonic acid
$Ph_3P$=Triphenylphosphine
Br-=bromide ion
$CBr_4$=Tetrabromomethane
LC-MS=Liquid chromatography-mass spectrometry
Rf=retardation factor
PEG-200 polyethylene glycol
KHMDA=potassium hexamethylenediamine
ACN=Acetonitrile
TBDMS=tert-butyldimethyl silyl Kp=Ratio of $AUC_{brain}$ to $AUC_{plasma}$
AUC=Area Under the curve LC-MS Parameters for Analysis System: Agilent 1100 LC-MSD
Parameters:
Sample Concentration: 7.2 mg in 1.44 mL DMSO (5 mg/mL). Dilute 10 uL to 0.5 mL acetonitrile (100 ug/mL)
HPLC Column: Xterra MS, C18, 50×2.1, 3.5 micron
Column Temperature: 40° C.
Mobile Phase A: 0.1% formic acid in water
Mobile Phase B: 0.1% formic acid in acetonitrile
Flow Rate: 0.3 mL/min
Injection Volume: 5 uL
Gradient LC-MS:

| time (min) | B (%) |
| --- | --- |
| 0 | 5 |
| 15 | 100 |
| 25 | 100 |
| 25.1 | 5 |
| 30 | 5 |

MS Parameters:
Ion Source: Electrospray
Polarity: Positive
Mass Range: 100-1000 amu
Fragmentor: 80
Dry Gas: 10 l/min
Dry Gas temp: 350° C.
Vcap: 4000
Nebulizer Pressure: 35
Gain: 5

The starting materials for the reactions described below are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1 15 (John Wiley and Sons, 1991), Rodd's Chemistry of Carbon Compounds, Volumes 1 5 and Supplementals (Elsevier Science Publishers, 1989), Organic Reactions, Volumes 1 40 (John Wiley and Sons, 1991), March's Advanced Organic Chemistry, (John Wiley and Sons, 4.sup.th Edition), and Larock's Comprehensive Organic Transformations (VCH Publishers Inc., 1989).

Example 1

5E,9E,13E-Geranylgeranyl Acetone Synthesis

Synthesis of 5-trans-Isomer: 5E,9E,13E-Geranylgeranyl acetone 1: The synthesis of 5-trans isomer: 5E,9E,13E-geranylgeranyl acetone 1 can be achieved as per outlined in the scheme-1.

Scheme 1
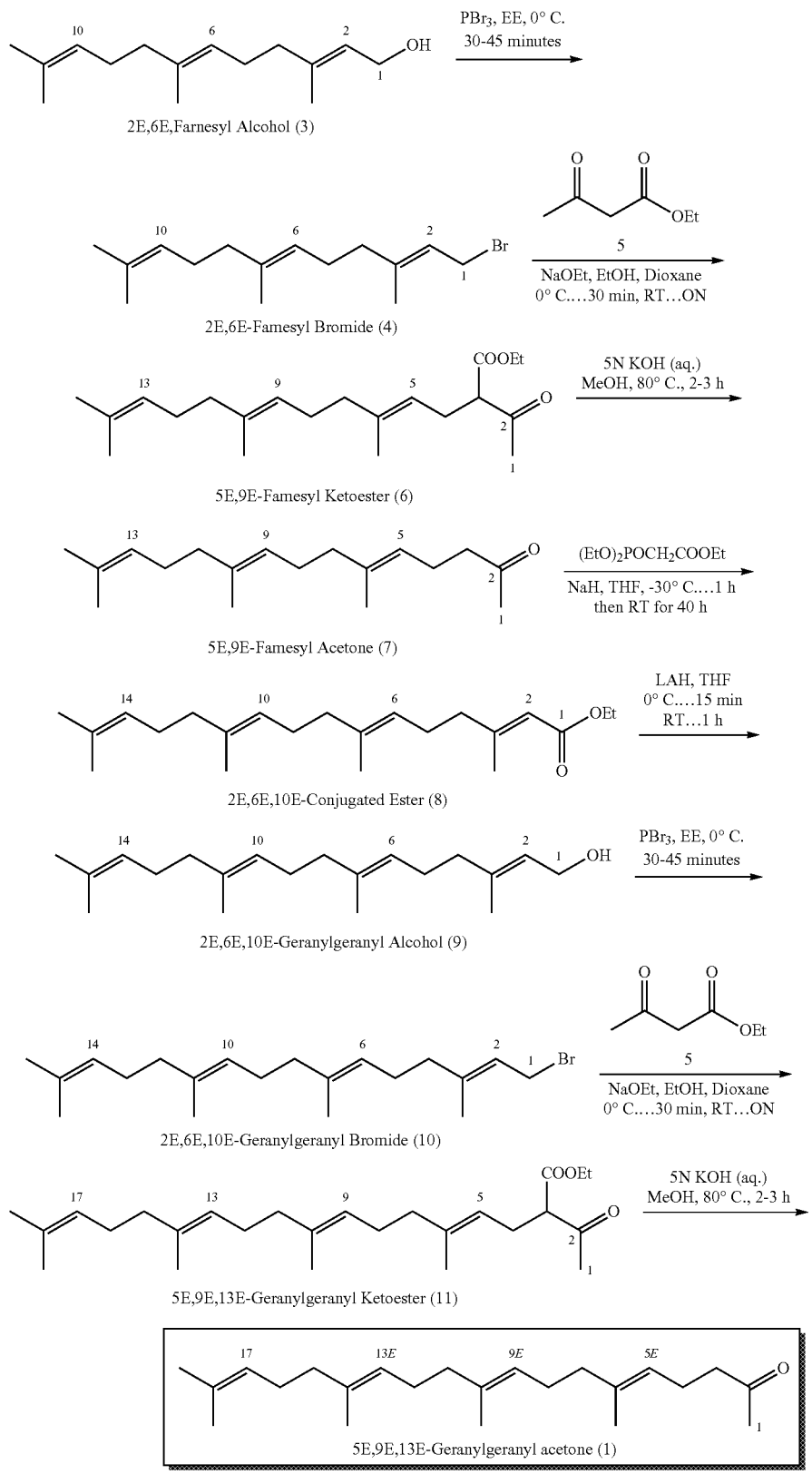

The 2E,6E-farnesyl alcohol 3 (where the geometry at C2 and C6 positions is already fixed as trans- or E) was designed and used as a commercially available starting material for the synthesis of 5E,9E,13E-geranylgeranyl acetone 1. The alcohol function of 2E, 6E-farnesyl alcohol 3 was converted to the corresponding bromide 4 by the treatment of phosphorus tribromide ($PBr_3$) in ethyl ether (EE) or with $Ph_3P$ and $CBr_4$ in acetonitrile (ACN) at 0° C. The resulting bromide was then reacted with carbanion (derived from the reaction of ethyl acetoacetate 5 and sodium ethoxide) to yield the desired 5E,9E-farnesyl ketoester 6. The homologated ketoester 6 after hydrolysis and decarboxylation using aqueous 5N KOH yielded the expected 5E,9E-farnesyl acetone 7. A one pot conversion of bromide 4 to the corresponding farnesyl acetone 7 can be possible without isolating intermediate ketoester 6.

In order to generate the trans-orientation of olefin at C2 of conjugated olefin 8 in a key step, the reaction of 5E,9E-farnesyl acetone 7 with carbanion [derived from the reaction of $(EtO)_2PO—CH_2—COOEt$ and sodium hydride (NaH)] at −30° C. was conducted to obtain the desired 2E,6E,10E-conjugated ester 8. The formation of the product 8 with the exclusive trans (E) geometry was observed when the reaction was conducted at −30° C. or temperature below −30° C., where all the three olefins are set in a trans (E) orientation (Ref.: Kato et al., J. Org. Chem. 1980, 45, 1126-1130 and Wiemer et al., Organic Letters, 2005, 7(22), 4803-4806). The minor cis-(Z)-isomer was eliminated/separated from the trans-(E)-isomer 8 by a careful silica gel column chromatographic purification. However, it was also noted that the formation the corresponding cis-isomer (Z) was increased when the reaction was conducted at 0° C. or at higher temperature. It was also noted that the mixture of cis (2Z)- and trans (2E)-isomer of 8 can be separated by a very careful column chromatographic separation.

The resulting 2E-conjugated ester 8 was reduced to the corresponding 2E-alcohol 9 by means of a lithium aluminum hydride (LAH) treatment, which was then converted into the corresponding 2E,6E,10E-geranylgeranyl bromide 10 by means of phosphorus tribromide ($PBr_3$) treatment in ethyl ether (EE) or with $Ph_3P$ and $CBr_4$ in acetonitrile (ACN) at 0° C. Furthermore, the interaction of carbanion (derived from ethyl acetoacetate 5 and sodium ethoxide) with the bromide 10 at 0° C. afforded the desired 2E,6E,10E-geranylgeranyl ketoester 11, a precursor needed for 5E,9E,13E-geranylgeranyl acetone 1. The subsequent ester hydrolysis and decarboxylation of ketoester 11 using aq. 5N KOH at 80° C. yielded the requisite 5E,9E,13E-geranylgeranyl acetone 1. TLC Rf: 0.28 (5% Ethyl Acetate in Hexanes); LC Retention time: 16.68 min; MS (m/e): 313 [M−18+H]+, 331 [MH]+, 353 [M+K].

Example 2

5-Z,9E,13E-Geranylgeranyl Acetone Synthesis

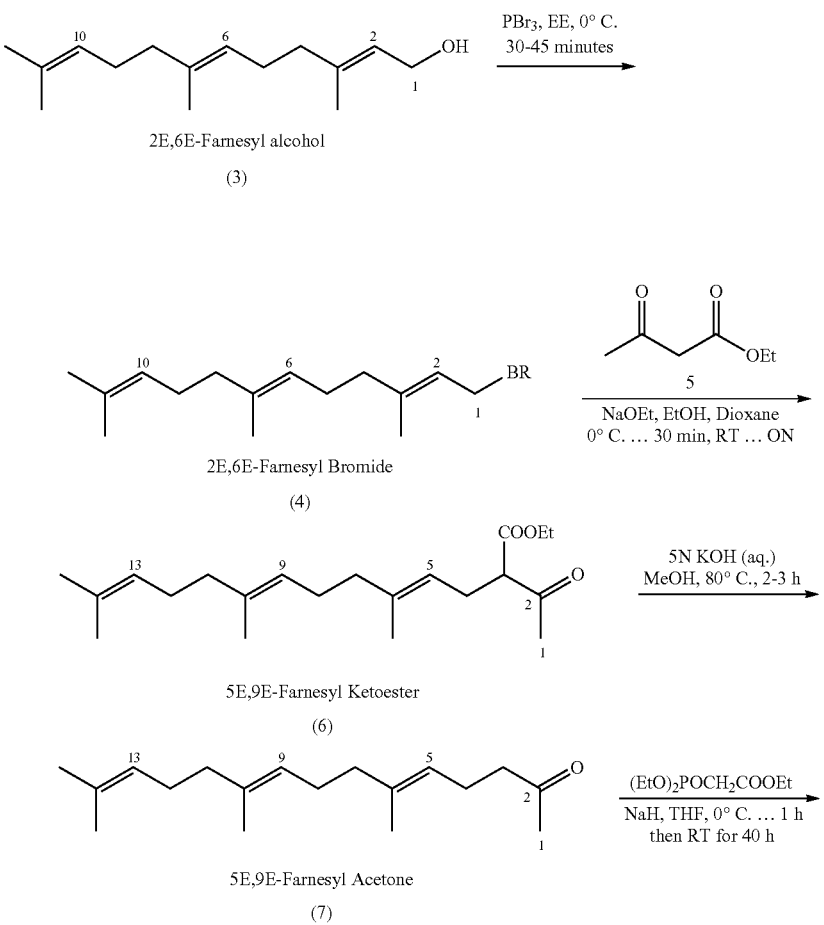

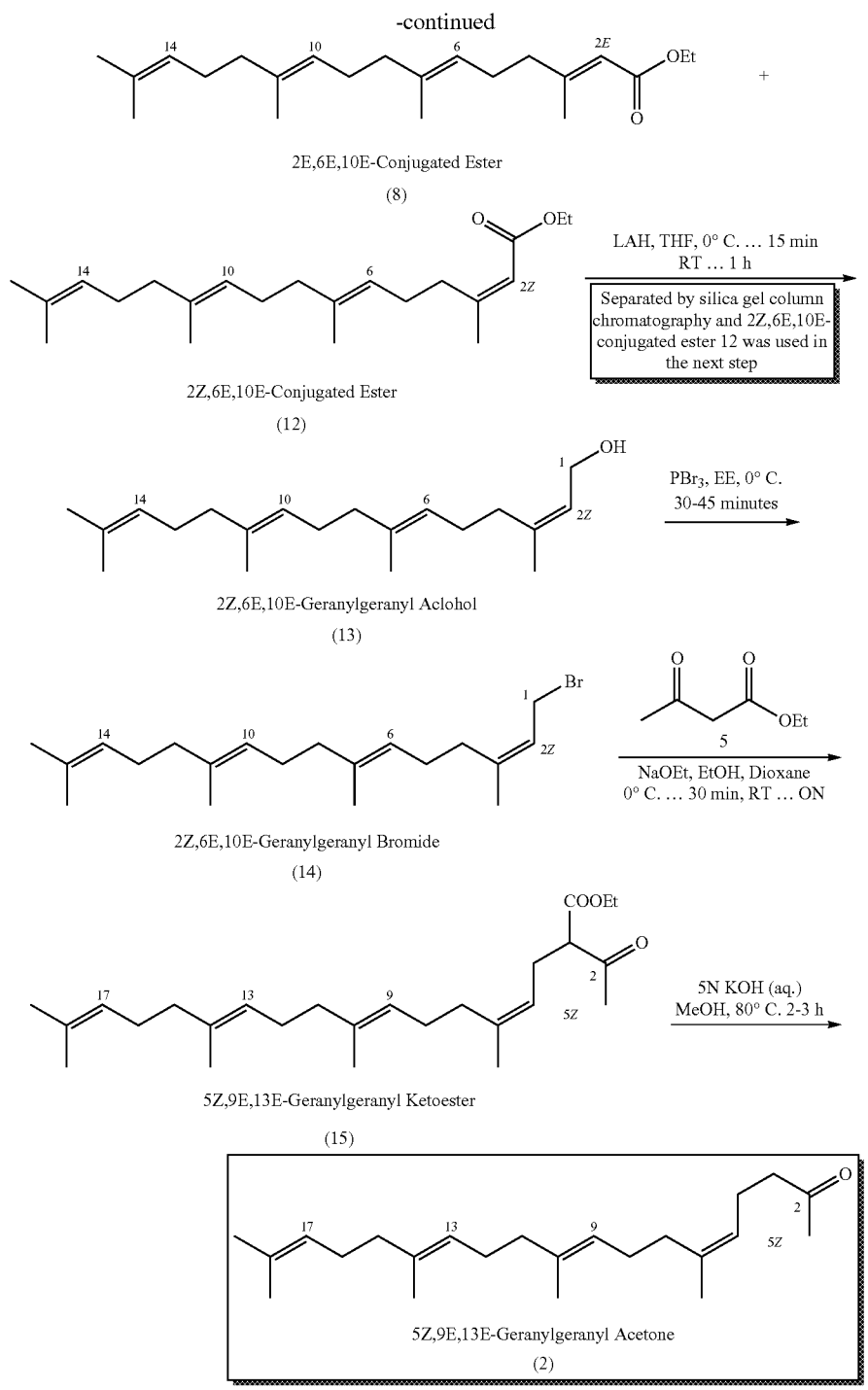

The 2E,6E-farnesyl alcohol 3 (where the geometry at C2 and C6 positions is already fixed as trans- or E) was used as a commercially available starting material for the synthesis of 5Z,9E,13E-geranylgeranyl acetone 2. The reaction of farnesyl alcohol 3 with phosphorus tribromide (PBr₃) in ethyl ether (EE) or with Ph₃P and CBr₄ in acetonitrile (ACN) at 0° C. afforded the requisite bromide 4, which was then reacted with carbanion (derived from the reaction of ethyl acetoacetate 5 and sodium ethoxide) to yield the desired 5E,9E-farnesyl ketoester 6. The homologated ketoester 6 after hydrolysis and decarboxylation using aqueous 5N KOH yielded the expected 5E,9E-farnesyl acetone 7, one of the key intermediate for the synthesis of 5E,9E,13E-geranylgeranyl acetone 1 and 5Z,9E,13E-geranylgeranyl acetone 2.

With a view to obtain product with cis-geometry at C2 with the conjugated olefin 12, the reaction of 5E,9E-farnesyl acetone 7 with carbanion [derived from the reaction of (EtO)₂PO—CH₂—COOEt and sodium hydride (NaH)] at 0° C. was conducted. This reaction afforded a mixture of 2E,6E,10E-conjugated ester 8 and 2Z,6E,10E-conjugated ester 12, from which the C2-cis (Z)-isomer 12 was separated by a repeated and careful silica gel column chromatography (Ref. Kato et al., J. Org. Chem., 1980, 45, 1126-1130).

The resulting 2Z-conjugated ester 12 was converted into the corresponding 2Z-alcohol 13 by means of a lithium aluminum hydride (LAH) treatment. The 2Z-alcohol 13 was transformed into the corresponding 2Z,6E,10E-geranylgeranyl bromide 14 by using phosphorus tribromide (PBr$_3$) treatment in ethyl ether (EE) or with Ph$_3$P and CBr$_4$ acetonitrile (ACN) at 0° C., and then reacted with carbanion (derived from ethyl acetoacetate 5 and sodium ethoxide) at 0° C. afforded the desired 2Z,6E,10E-geranylgeranyl ketoester 15, a precursor needed for 5Z,9E,13E-geranylgeranyl acetone 2.

The subsequent ester hydrolysis and decarboxylation of ketoester 15 using aq. 5N KOH at 80° C. yielded the requisite 5Z,9E,13E-geranylgeranyl acetone 2.

Example 3

5Z,9E,13E-Geranylgeranyl Acetone Synthesis

Alternative synthesis of 5-cis Isomer: 5Z,9E,13E-Geranylgeranyl acetone 2: The alternative synthesis of 5Z,9E,13E-geranylgeranyl acetone 2 can be achieved as shown in the scheme-3.

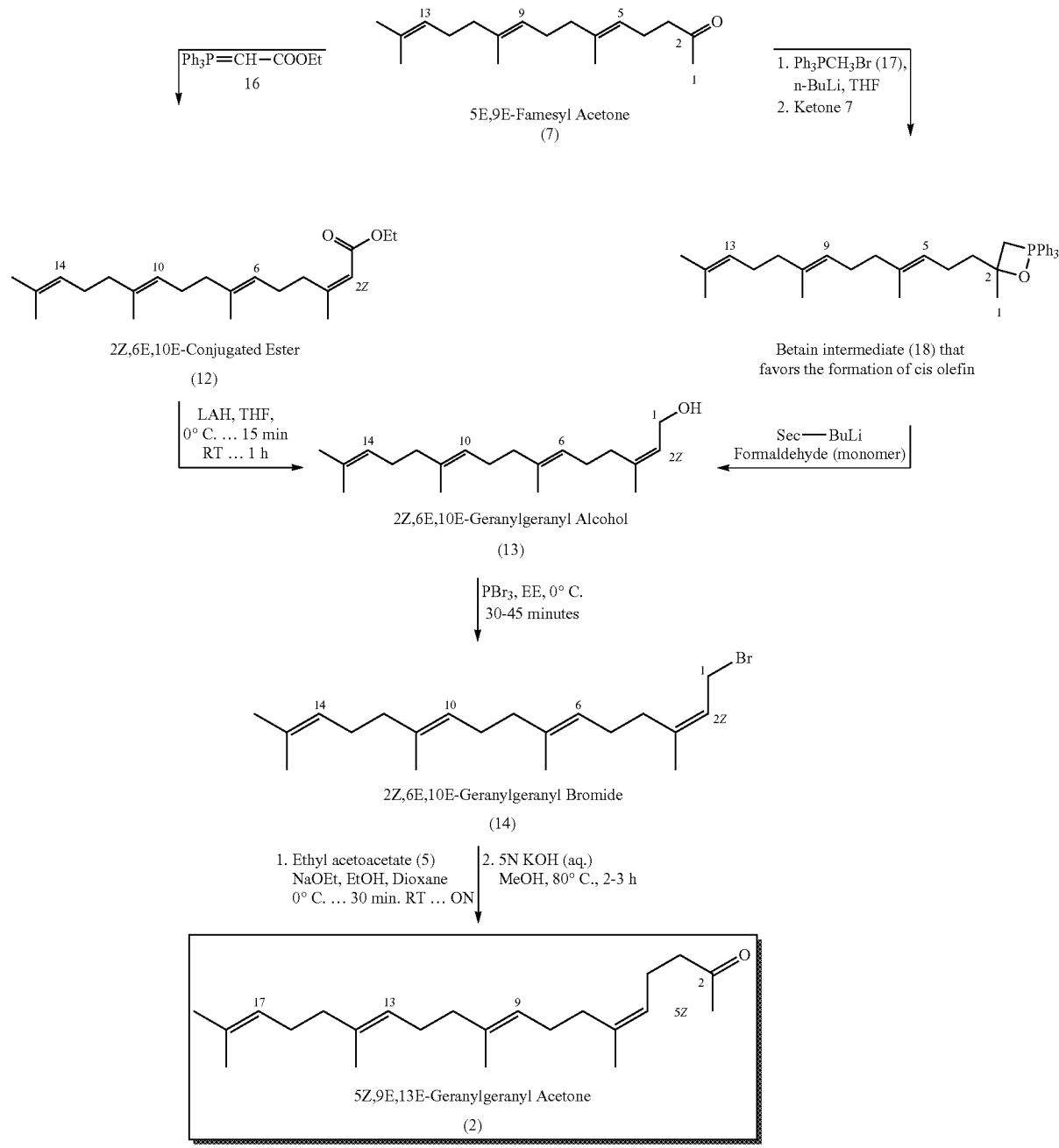

The use of 5E,9E-farnesyl acetone 7, as a key intermediate, can be used to generate additional double bond with cis-(Z)-orientation. In one approach, the reaction of 5E,9E-farnesyl acetone 7 with the witting reagent 16 can afford the conjugated ester 12 with cis-(Z)-geometry at C2 position. The subsequent reduction of ester 12 with lithium aluminum hydride (LAH) can generate the corresponding alcohol 13, which then can be converted into the corresponding bromide 14. The conversion of bromide 14 to the ketoester 15 followed by hydrolysis and decarboxylation can afford the desired 5-cis (Z) isomer; 5Z,9E,13E-geranygeranyl acetone (2).

In an alternative approach, the reaction of 5E,9E-farnesyl acetone 7 with triphenyl methylphosphonrane bromide 17 under a basic conditions followed by treatment with formaldehyde (monomeric) can afford the 2Z,6E10E-geranylgeranyl alcohol 13 with cis (Z)-orientation at C2 (Ref.: Wiemer et al., Organic Letters, 2005, 7(22), 4803-4806). The conversion of bromide 14 to the ketoester 15 followed by hydrolysis and decarboxylation can afford the desired 5-cis (Z)-isomer; 5Z,9E,13E-geranygeranyl acetone (2). TLC Rf: 0.32 (5% Ethyl Acetate in Hexanes); LC: Retention time: 17.18 min; MS (m/e): 313 [M−18+H]+, 331 [MH, very weak ionization]+, 339 [M−CH$_2$+Na], 353 [M+K].

All the intermediate products were purified by silica gel column chromatography and then used in the next step, except the bromides 4, 10 and 14. Due to the unstable nature of bromides 4, 10 and 14 towards silica gel column chromatography, these bromides were used in the next step without purification. Alternatively, all the intermediate products shown in the schemes 1, 2 and 3 are liquids and therefore can be separated and purified by a distillation process under appropriate levels of vacuum. All the intermediates and final products were characterized by LC-MS for mass along with the Thin Layer Chromatography (TLC) for Rf values.

Example 4

5-Z,9E,13E-Geranylgeranyl Acetone Synthesis

Alternative synthesis of 5-cis Isomer: 5Z,9E,13E-Geranylgeranyl acetone 2: The alternative synthesis of 5Z,9E,13E-geranylgeranyl acetone 2 can be achieved as shown in the scheme-4

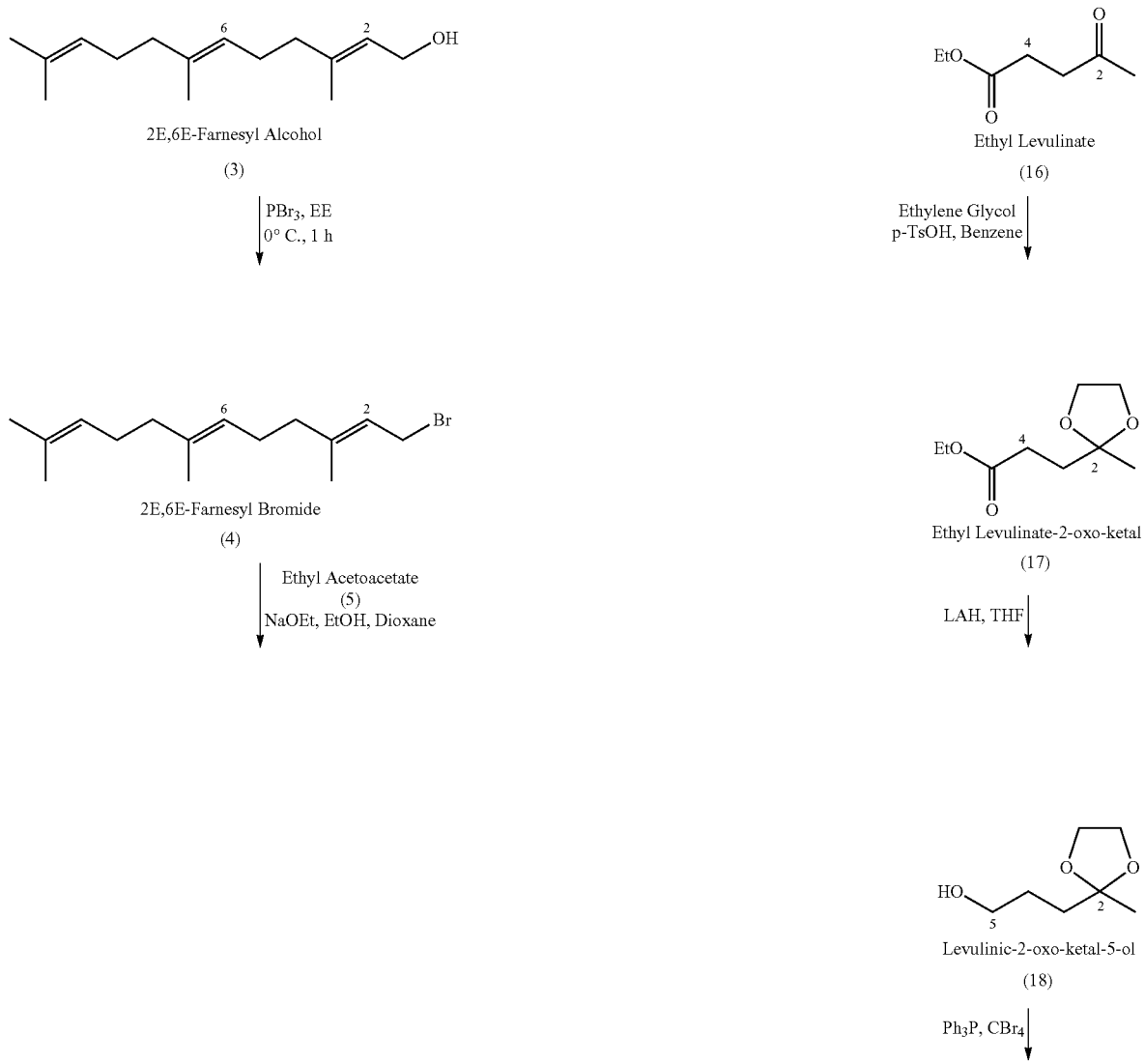

Scheme 4

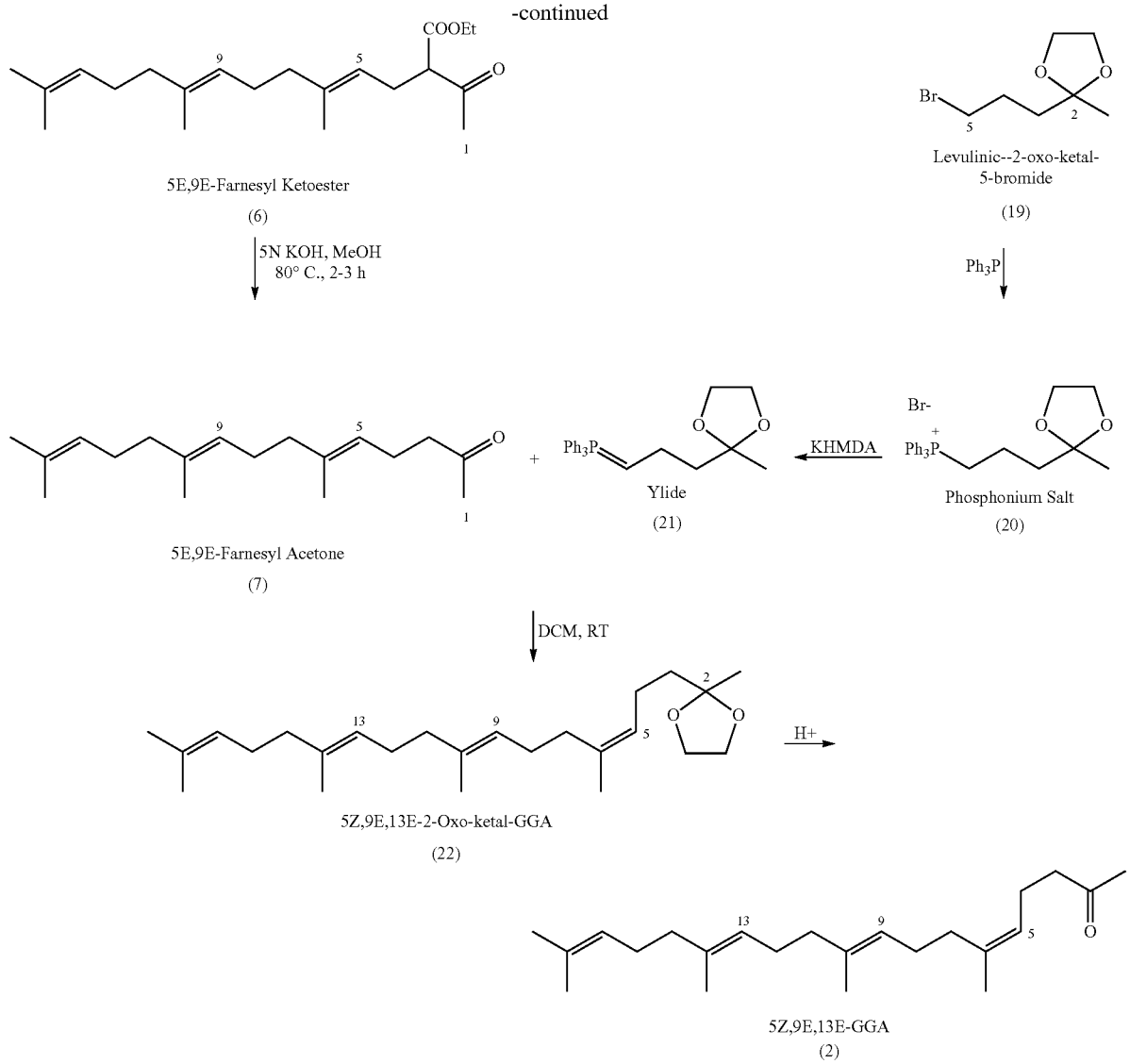

The convergent synthesis of 5Z,9E,13E-GGA 2 has been shown in the above scheme and is outlined as follows.

The 2E,6E-farnesyl alcohol 3 (where the geometry at C2 and C6 positions is already fixed as trans- or E) was used as a commercially available starting material for the synthesis of 5Z,9E,13E-geranylgeranyl acetone 2. The reaction of farnesyl alcohol 3 with phosphorus tribromide ($PBr_3$) in ethyl ether (EE) or with $Ph_3P$ and $CBr_4$ in acetonitrile (ACN) at 0° C. afforded the requisite bromide 4, which was then reacted with carbanion (derived from the reaction of ethyl acetoacetate 5 and sodium ethoxide) to yield the desired 5E,9E-farnesyl ketoester 6. The homologated ketoester 6 after hydrolysis and decarboxylation using aqueous 5N KOH yielded the expected 5E,9E-farnesyl acetone 7, one of the key intermediate for the synthesis of 5E,9E,13E-geranylgeranyl acetone 1 and 5Z,9E,13E-geranylgeranyl acetone 2.

The other synthon, namely the ylide 21 can be synthesized from a commercially available starting material, ethyl levulinate 16, a sugar industry by-product. The ketalization of ethyl levulinate 16 using conventional conditions (ethylene glycol, p-TsOH, azeotropic reflux) can yield the desired 2-oxo-ketal 17, which then can be reduced using LAH in THF at 0° C. to the corresponding alcohol 18. Furthermore, the alcohol 18 then can be treated with $Ph_3Br$ in diethyl ether at 0° C. to obtain the bromide 19, which then after treatment with $Ph_3P$ can yield the phosphonium bromide salt 20. The bromide salt 20 upon treatment with mild alkali (1N NaOH) can furnish the desired ylide 21, required to complete the synthesis of 5Z-GGA 2.

With a view to obtain product with cis-geometry, the reaction of 5E,9E-farnesyl acetone 7 with the ylide 21 in DCM at RT can afford the desired 5Z-oxoketal 22 (Ref.: Ernest et al, Tetrahedron Lett. 1982, 23(2), 167-170). The protected oxo-function from 22 can be removed by means of a mild acid treatment to yield the expected 5Z,9E,13E-GGA 2.

Example 5

5E,9E,13E-Geranylgeranyl Acetone Synthesis

Alternative synthesis of 5-trans Isomer: 5E,9E,13E-Geranylgeranyl acetone 1: The alternative synthesis of 5E,9E,13E-geranylgeranyl acetone 1 can be achieved as shown in the scheme-5.

Scheme 5:
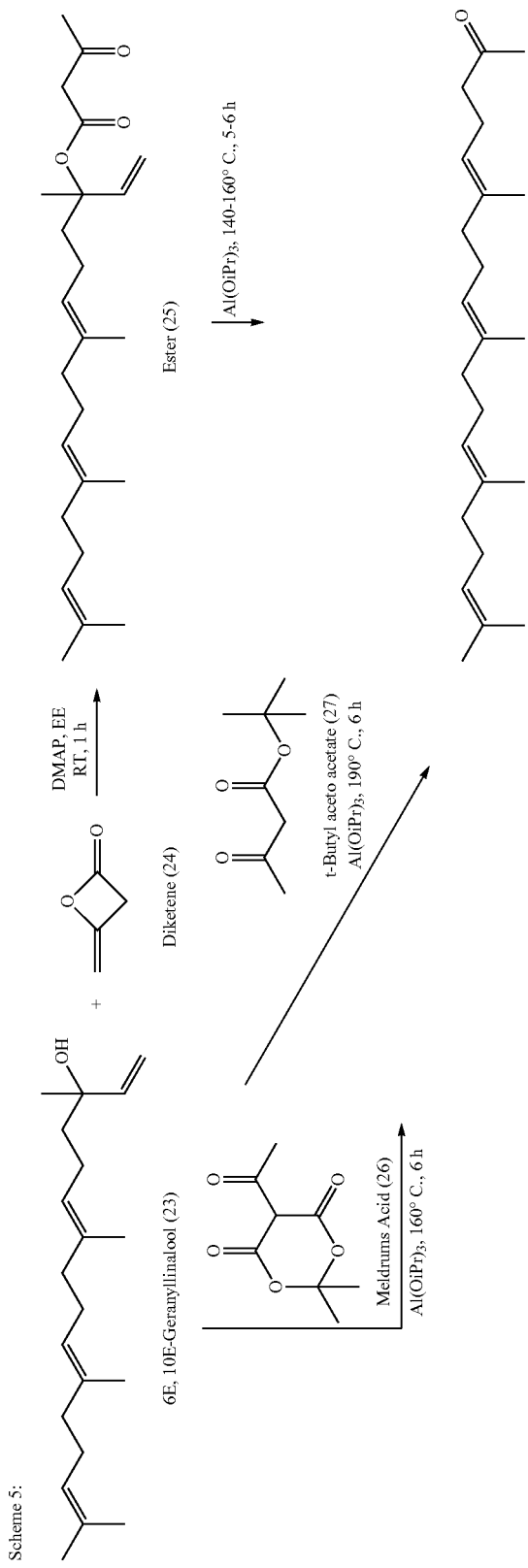

The 5E, 9E, 13E-geranyl geranyl acetone (1) can be prepared by reacting 6E-10E-geranyl linalool (23) with diketene (24) catalyzed by DMAP in ethyl ether to give the ester 25. The ester 25 in the Carroll rearrangement using Al(OiPr)$_3$ at elevated temperature can afford the desired 5E, 9E, 13E-geranyl geranyl acetone (1). In another approach, the GGA (1) can be prepared by treating geranyl linalool (23) with the Meldrum's acid 26 in the Carroll rearrangement using Al(OiPr)$_3$ at 160° C. Similarly, the use of tert-butyl acetoacetate (27) with geranyl linalool (23) in the Carroll rearrangement can also give the desired 5E, 9E, 13E-geranyl geranyl acetone (1).

Example 6

5-Z,9E,13E-Geranylgeranyl Acetone Synthesis

The alternative synthesis of 5Z,9E,13E-geranylgeranyl acetone 2 can be achieved as shown in the scheme-6.

Scheme 6:

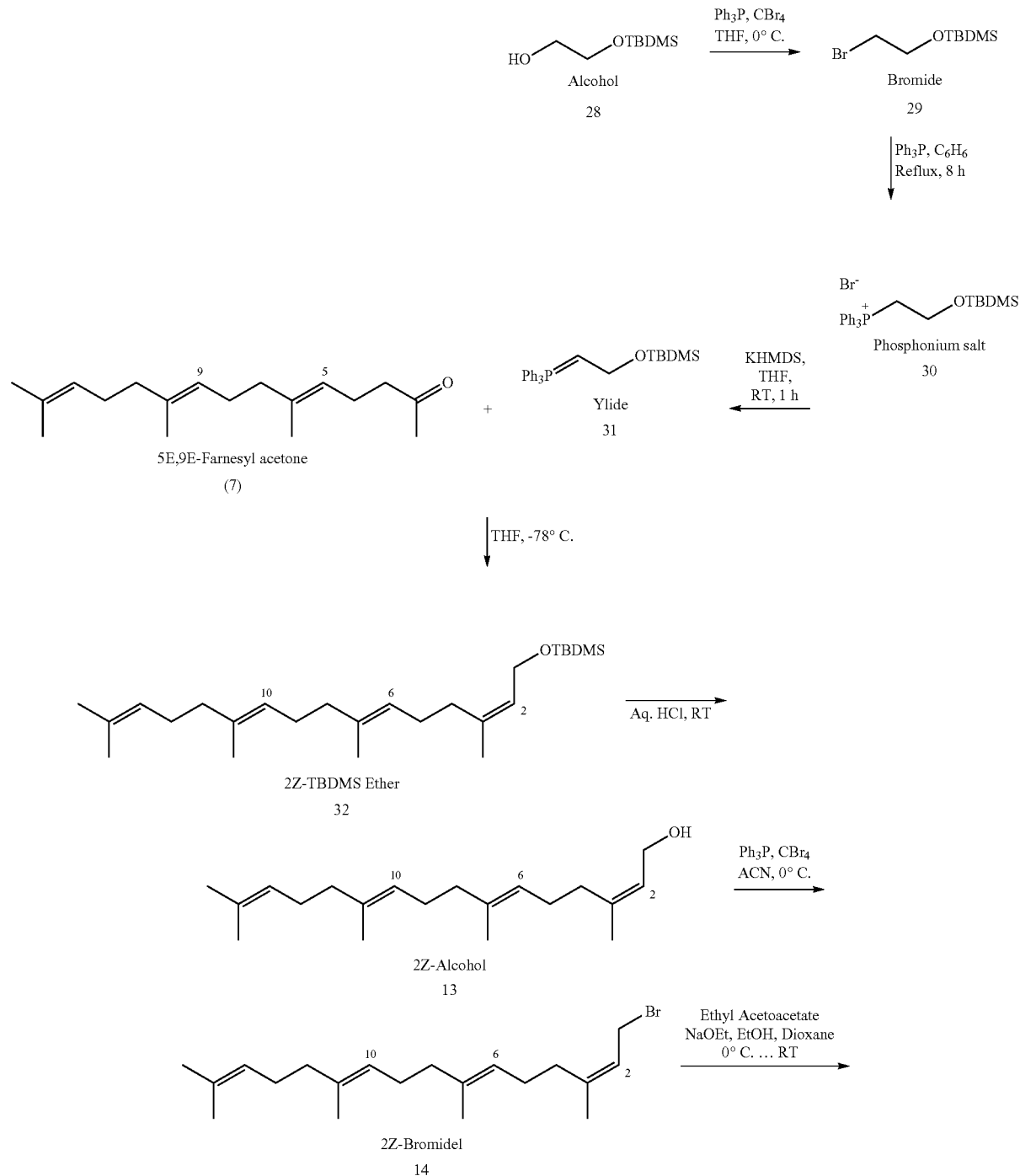

-continued

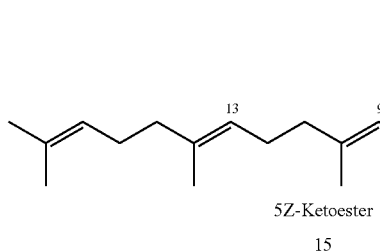
5Z-Ketoester
15

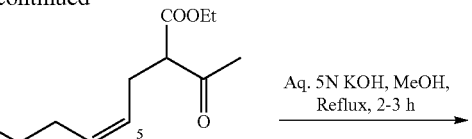
Aq. 5N KOH, MeOH,
Reflux, 2-3 h

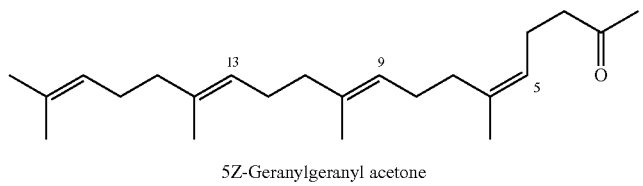
5Z-Geranylgeranyl acetone
2

Alternative synthesis of 5-cis Isomer: 5Z,9E,13E-Geranylgeranyl acetone 2: The 2E,6E-farnesyl alcohol 3 (where the geometry at C2 and C6 positions is already fixed as trans- or E) was used as a commercially available starting material for the synthesis of 5Z,9E,13E-geranylgeranyl acetone 2. The reaction of farnesyl alcohol 3 with phosphorus tribromide (PBr$_3$) in ethyl ether (EE) or with Ph$_3$P and CBr$_4$ in acetonitrile (ACN) at 0° C. afforded the requisite bromide 4, which was then reacted with carbanion (derived from the reaction of ethyl acetoacetate 5 and sodium ethoxide) to yield the desired 5E,9E-farnesyl ketoester 6. The homologated ketoester 6 after hydrolysis and decarboxylation using aqueous 5N KOH yielded the expected 5E,9E-farnesyl acetone 7, one of the key intermediate for the synthesis of 5E,9E,13E-geranylgeranyl acetone 1 and 5Z,9E,13E-geranylgeranyl acetone 2.

The ylide 31 synthesized from a commercially available mono-TBDMS protected ethylene glycol 28. The conversion of alcohol function of 28 by using Ph$_3$P and CBr$_4$ in acetonitrile can afford the corresponding bromide 29, which then can be used to make a phosphonium bromide salt 30 by treatment with Ph$_3$P at elevated temperature. The bromide salt 30 upon treatment with KHMDS in THF can afford the ylide 31, which then can be reacted in-situ with ketone 7 in a key step to establish cis geometry with the newly created double bond at C2 position and obtain the 2Z-TBDMS ether 32 (ref: Still et al, J. Org. Chem., 1980, 45, 4260-4262 and Donetti et al, Tetrahedron Lett. 1982, 23(21), 2219-2222). The deprotection of TBDMS with aqueous HCl to afford the corresponding alcohol 13 followed by conversion of alcohol to bromide using Ph$_3$P and CBr$_4$ can afford the desired bromide 14. The bromide 14 upon reaction with ethyl acetoacetate can give ketoester 15, which then upon hydrolysis followed by decarboxylation can yield the desired 5-Z-GGA (5-cis) 2.

Example 7

The Synthesis of Additional Compounds

Scheme 7:

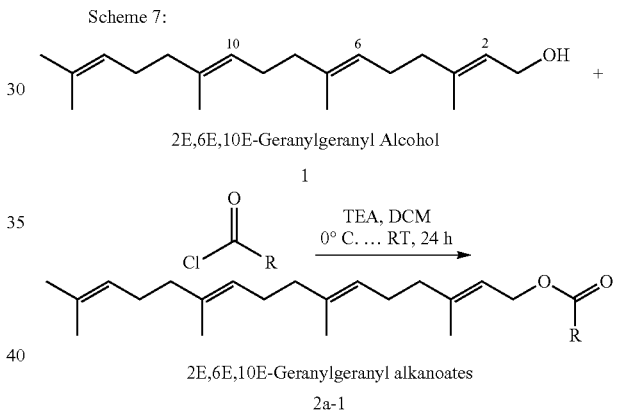

2E, 6E, 10E-Geranylgeranyl acetate (2a) (R=Methyl)

A dry reaction flask equipped with a stir bar and N$_2$ inlet was charged with Geranylgeranyl alcohol 1 (0.087 g, 0.3 mmol), triethyl amine (0.062 mL, 0.45 mmol) and dichloromethane, DCM (1 mL) and cooled to 0° C. To it was added acetyl chloride (1M solution in DCM, 0.42 mL, 0.042 mmol) drop-wise and the resulting reaction was stirred at room temperature for overnight, ~24 h. The reaction was quenched with aqueous NaHCO$_3$ solution, extracted with DCM (3×20 mL), the DCM extract was washed with water (20 mL), dried over anhydrous Na$_2$SO$_4$ and solvent was evaporated under a reduced pressure. The resulting oily residue was purified by a silica gel column chromatography using n-hexanes to 1-2% EtOAC in n-hexanes to afford a colorless liquid of ester 2a. Yield: 0.059 mg (60%); TLC Rf: 0.58 (10% EtOAc/n-Hexanes); LCMS: MS (m/z): 333.4 (M+H); Ret. Time: 14.13 minutes.

2E, 6E, 10E-Geranylgeranyl propionate (2b) (R=Ethyl)

Similar to the preparation of ester 2a, the reaction of alcohol 1 with n-propionyl chloride afforded the desired compound 2b in 63% yield (0.065 g) as colorless oil. TLC Rf: 0.57 (10% EtOAc/n-hexanes); LCMS: MS (m/z): 347 (M+H), ret. time: 14.60 min.

2E, 6E, 10E-Geranylgeranyl iso-butyrate (2c) (R=iso-Propyl)

Similar to the preparation of ester 2a, the reaction of alcohol 1 with iso-butyryl chloride afforded the desired compound 2c in 57% yield (0.061 g) as colorless oil. TLC Rf: 0.55 (10% EtOAc/n-hexanes); LCMS: MS (m/z): 361 (M+H), ret. time: 14.14 min.

2E, 6E, 10E-Geranylgeranyl cyclopropionate (2d) (R=Cyclopropyl)

Similar to the preparation of ester 2a, the reaction of alcohol 1 with cyclopropanecarbonyl chloride gave the desired compound 2d in 54% yield (0.057 g) as colorless oil. TLC Rf: 0.54 (10% EtOAc/n-hexanes); LCMS: MS (m/z): 359 (M+H), ret. time: 14.83 min.

2E, 6E, 10E-Geranylgeranyl cyclopentanoate (2e) (R=Cyclopentyl)

Similar to the preparation of ester 2a, the reaction of alcohol 1 with cyclopentanecarbonyl chloride gave the compound 2e in 61% yield (0.065 g) as colorless oil. TLC Rf: 0.53 (10% EtOAc/n-hexanes); LCMS: MS (m/z): 290 (M-Cyclopencarbonyl), ret. time: 14.60 min.

2E, 6E, 10E-Geranylgeranyl cyclohexanoate (2f) (R=Cyclohexyl)

Similar to the preparation of ester 2a, the reaction of alcohol 9 with cyclohexanecarbonyl chloride gave the compound 2f in 65% yield (0.078 g) as colorless oil. TLC Rf: 0.53 (10% EtOAc/n-hexanes); LCMS: MS (m/z): 401 (M+H), ret. time: 15.98 min.

The following Esters (2g-k) were prepared as a mixture of trans and cis isomers.

2E, 6E, 10E-Geranylgeranyl-3',5'-dinitrobenzoate (2g) (R=3',5'-Dinitrophenyl)

Similar to the preparation of ester 2a, the reaction of alcohol 9 with 3,5-dinitrobenzoyl chloride gave the desired compound 2g in 60% yield (0.145 g) as colorless oil. TLC Rf: 0.46 (7% EtOAc/n-hexanes); LCMS: MS (m/z): 484.30 (M+).

2E, 6E, 10E-Geranylgeranyl-3',4',5'-trimethoxybenzoate (2h) (R=3',4',5'-trimethoxyphenyl)

Similar to the preparation of ester 2a, the reaction of alcohol 1 (1.00 g, 3.44 mmol) with 3,4,5-trimethoxybenzoyl chloride (0.871 g, 5.16 mmol) gave the desired compound 2h in 77% yield (1.28 g) as colorless oil.; LCMS: MS (m/z) 471.0 (MH-CH3).

2E, 6E, 10E-Geranylgeranyl-3',5'-diethoxybenzoate (2i) (R=3',5'-diethoxyphenyl)

Similar to the preparation of ester 2a, the reaction of alcohol 1 (1.00 g, 3.44 mmol) with 3,5-diethoxybenzoyl chloride (0.861 g, 5.16 mmol) gave the desired compound 2i in 73% yield (1.28 g) as colorless oil.; LCMS: MS (m/z) 483.15 (M+H).

2E, 6E, 10E-Geranylgeranyl-2' ethoxybenzoate (2j) (R=2'-Ethoxyphenyl)

Similar to the preparation of ester 2a, the reaction of alcohol 1 (0.580 g, 2 mmol) with 2-ethoxybenzoyl chloride (0.340 mL, 3 mmol) gave the desired compound 2i in 78% yield (0.684 g) as colorless oil.; LCMS: MS (m/z) 461.30 (M+H).

2E, 6E, 10E-Geranylgeranyl-2',4'-dimethoxybenzoate (2k) (R=2',4'-Dimethoxyphenyl)

Similar to the preparation of ester 2a, the reaction of alcohol 1 (0.580 g, 2 mmol) with 2,4-dimethoxybenzoyl chloride (0.576 g, 3 mmol) gave the desired compound 2j in 81% yield (0.837 g) as colorless oil.; LCMS: MS (m/z) 477.25 (M+Na).

2E, 6E, 10E-Geranylgeranyl-2',4',6' trimethylbenzoate (2l) (R=2',4',6'-Trimethylphenyl)

Similar to the preparation of ester 2a, the reaction of alcohol 1 (0.580 g, 2 mmol) with 2,4,6-trimethylbenzoyl chloride (0.365 mL, 3 mmol) gave the desired compound 2k in 76% yield (0.664 g) as colorless oil.; LCMS: MS (m/z) 477.90 (M+acetonitrile).

Scheme 8:

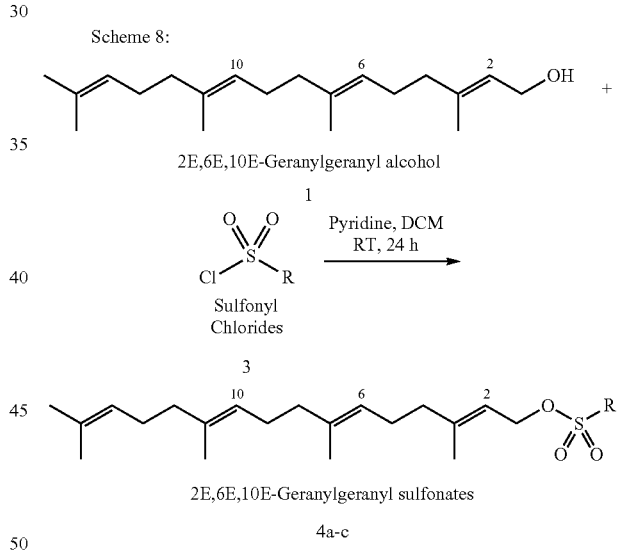

2E,6E,10E-Geranylgeranyl methanesulfonate (4a) (R=Methyl-)

A dry reaction flask equipped with a stir bar and $N_2$ inlet was charged with geranylgeranyl alcohol 1 (0.087 g, 0.3 mmol), pyridine (0.048 mL, 0.6 mmol) in DCM (2 mL). To it was added, methanesulfonyl chloride 3a (0.035 mL, 0.45 mmol) and stirred for 48 h at room temperature. The reaction was followed by TLC. After the completion of the reaction, it was quenched with water (10 mL), extracted with DCM (3×20 mL) and the combined DCM solution was washed with 2N NaOH solution (20 mL) followed by water (20 mL). The DCM layer upon drying over anhydrous $Na_2SO_4$ was evaporated and the residue was purified by silica gel column chromatography using n-hexanes the 1-2% EtOAc in n-hexanes to afford the desired sulfonate 4a. Yield: 0.066 g (66%); TLC Rf: 0.54 (10% EtOAc/n-Hexanes); LCMS: MS (m/z): 367.10 (M–H).

The following sulfonates 4b and 4c were prepared according to the procedure used to prepare sulfonate 4a.

2E, 6E, 10E-Geranylgeranyl benzenesulfonate (4b) (R=Phenyl)

The reaction of alcohol 1 with benzenesulfonyl chloride afforded the requisite sulfonate 4b. Yield: 0.087 g (68%); TLC Rf: 0.45 (10% EtOAc/n-Hexanes); LCMS: MS (m/z): 471.30 (M+Acetonitrile).

2E, 6E, 10E-Geranylgeranyl p-toluenesulfonate (4c) (R=p-Toluene)

The reaction of alcohol 1 with p-toluenesulfonyl chloride afforded the requisite sulfonate 4c. Yield: 0.072 g (54%); TLC Rf: 0.42 (10% EtOAc/n-Hexanes); LCMS: MS (m/z): 443.50 (M–H).

Scheme 9:

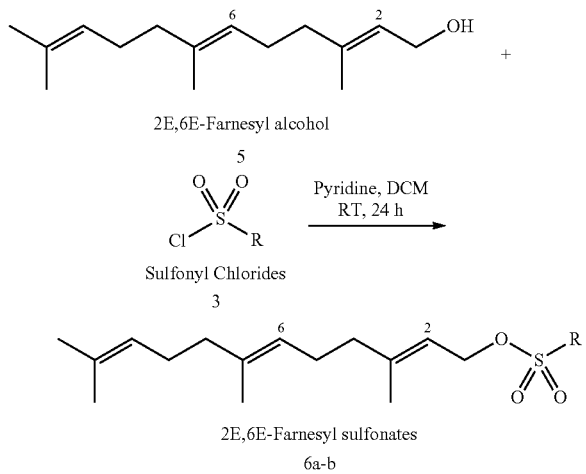

2E, 6E-Farnesyl alcohol
5

Sulfonyl Chlorides
3

2E,6E-Farnesyl sulfonates
6a-b

2E, 6E-Farnesyl benzenesulfonate (6a) (R=Phenyl)

A dry reaction flask equipped with a stir bar and $N_2$ inlet was charged with 2E,6E-Farnesyl alcohol 5 (0.165 g, 0.75 mmol), pyridine (0.120 mL, 1.5 mmol) in DCM (2 mL). To it was added, benzenesulfonyl chloride 3a (0.087 mL, 1.12 mmol) and stirred for 12 h at room temperature. The reaction was followed by TLC. After the completion of the reaction, it was quenched with water (10 mL), extracted with DCM (3×20 mL) and the combined DCM solution was washed with 2N NaOH solution (20 mL) followed by water (20 mL). The DCM layer upon drying over anhydrous $Na_2SO_4$ was evaporated and the residue was purified by silica gel column chromatography using n-hexanes the 1-2% EtOAc in n-hexanes to afford the desired sulfonate 6a. Yield: 0.119 g (44%).

2E, 6E-Farnesyl p-toluenesulfonate (6b) (R=p-Toluene)

Sulfonate 6b was prepared according to the procedure used to prepare sulfonate 6a. The reaction of alcohol 5 with p-toluenesulfonyl chloride afforded the requisite sulfonate 6b. Yield: 0.107 g (38%); LCMS: MS (m/z): 377.2 (M+H).

Scheme 10:

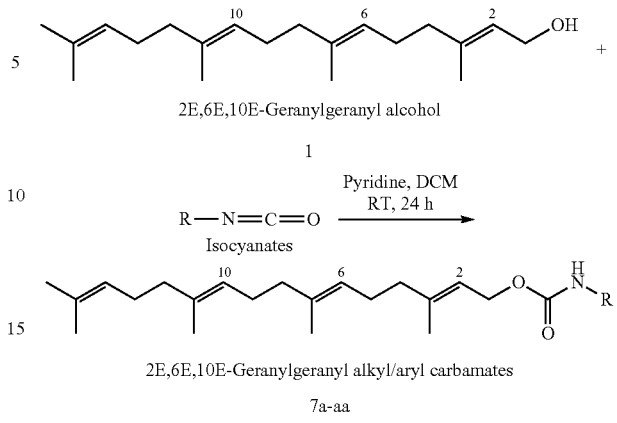

2E,6E,10E-Geranylgeranyl alcohol
1

Isocyanates 2E,6E,10E-Geranylgeranyl alkyl/aryl carbamates
7a-aa

Ethyl 2E,6E,10E-geranylgeranyl carbamate (7a) (R=Ethyl-)

A dry reaction flask equipped with a stir bar, $N_2$ inlet was charged with alcohol 1 (0.060 g, 0.2 mmol), pyridine (0.032 mL, 0.4 mmol) and DCM (2 mL). After cooling it to 0° C., ethyl isocyanate was added dropwise and the resulting reaction mixture was allowed to stir for 24 h. The reaction was monitored by TLC. After completion of the reaction, it was quenched with $H_2O$ (5 mL), acidified, extracted with n-hexanes (3×15 mL) and the combined n-hexanes were washed with $H_2O$ (10 mL). After drying the organic solution over anhydrous $Na_2SO_4$, the solvent was evaporated and the resulting residue was purified by silica gel column chromatography using 1-2% EtOAc in n-hexanes to afford the desired carbamate 7a. Yield: 0.039 g (54%); TLC Rf: 0.30 (10% EtOAc/n-Hexanes); LCMS: MS (m/z): 384 (M+Na); ret. time: 14.39 min.

The following carbamates 7b to 7z were prepared according to the procedure that was used to prepare carbamate 7a.

sec-Butyryl 2E,6E,10E-geranylgeranyl carbamate (7b) (R=sec-Butyryl-)

The reaction of alcohol 1 with sec-butyryl isocyanate afforded carbamate 7b. Yield: 0.039 g (54%); TLC Rf: 0.40 (10% EtOAc/n-Hexanes); LCMS: MS (m/z): 412 (M+Na); ret. time: 15.79 min.

iso-Propyl 2E,6E,10E-geranylgeranyl carbamate (7c) (R=iso-Propyl-)

The reaction of alcohol 1 with iso-propyl isocyanate gave the desired carbamate 7c. Yield: 0.039 g (52%); TLC Rf: 0.32 (10% EtOAc/n-Hexanes); LCMS: MS (m/z): 376.40 (M+H); ret. time: 14.34 min.

n-Pentyl 2E,6E,10E-geranylgeranyl carbamate (7d) (R=n-Pentyl)

The reaction of alcohol 1 with n-pentyl isocyanate gave the expected carbamate 7d. Yield: 0.054 g (67%); TLC Rf: 0.35 (10% EtOAc/n-Hexanes); LCMS: MS (m/z): 426 (M+H); ret. time: 16.40 min.

n-Hexyl 2E,6E,10E-geranylgeranyl carbamate (7e) (R=n-Hexyl-)

The reaction of alcohol 1 with n-hexyl isocyanate gave the carbamate 7e. Yield: 0.026 g (31%); TLC Rf: 0.29 (10% EtOAc/n-Hexanes); LCMS: MS (m/z): 418 (M+H); ret. time: 15.28 min.

Cyclopentyl 2E, 6E, 10E-geranylgeranyl carbamate (7f) (R=Cyclopentyl-)

The reaction of alcohol 1 with cyclopentyl isocyanate gave the desired carbamate 7f. Yield: 0.034 g (42%); TLC Rf: 0.32 (10% EtOAc/n-Hexanes); LCMS: MS (m/z): 402 (M+H).

Cyclohexyl 2E, 6E, 10E-geranylgeranyl carbamate (7g) (R=Cyclohexyl-)

The reaction of alcohol 1 with cyclohexyl isocyanate gave the desired carbamate 7g. Yield: 0.043 g (51%); TLC Rf: 0.29 (10% EtOAc/n-Hexanes); LCMS: MS (m/z): 416.30 (M+H).

Cyclohexylmethyl 2E, 6E, 10E-geranylgeranyl carbamate (7h) (R=Cyclohexylmethyl-)

The reaction of alcohol 1 with cyclohexylmethyl isocyanate afforded the expected carbamate 7h. Yield: 0.039 g (45%); TLC Rf: 0.23 (10% EtOAc/n-Hexanes); LCMS: MS (m/z): 430.40.

Cycloheptyl 2E, 6E, 10E-geranylgeranyl carbamate (7i) (R=Cycloheptyl-)

The interaction of alcohol 1 with cycloheptyl isocyanate afforded the carbamate 7i. Yield: 0.034 g (39%); TLC Rf: 0.61 (10% EtOAc/n-Hexanes); LCMS: MS (m/z): 430.40 (M+H).

Methyl 2-(S)-(−)-3-methylbutyrate 2E,6E,10E-geranylgeranyl Carbamate (7j) (R=2-methyl-(S)-(−)-3-methyl butyrate)

The reaction of alcohol 1 with methyl-(S)-(−)-3-methyl isobutyryl isocyanate gave the carbamate 7j. Yield: 0.032 g (42%); TLC Rf: 0.19 (10% EtOAc/n-Hexanes); LCMS: MS (m/z): 450.30 (M+2H).

Allyl 2E, 6E, 10E-geranylgeranyl carbamate (7k) (R=Allyl-)

The interaction of alcohol 1 (0.145 g, 0.5 mmol) with allyl isocyanate (0.131 mL, 0.75 mmol) afforded the carbamate 7lk. Yield: 0.091 g (41%); TLC Rf: 0.61 (10% EtOAc/n-Hexanes); LCMS: MS (m/z): 374.3 (M+H).

Benzyl 2E, 6E, 10E-geranylgeranyl carbamate (7l) (R=Benzyl-)

The interaction of alcohol 1 (0.145 g, 0.5 mmol) with benzyl isocyanate (0.185 mL, 0.75 mmol) afforded the carbamate 7l. Yield: 0.082 g (39%); LCMS: MS (m/z): 424.3 (M+H).

Ethoxycarbonyl ethyl 2E, 6E, 10E-geranylgeranyl carbamate (7m) (R=Ethoxycarbonyl ethyl-)

The interaction of alcohol 1 (0.145 g, 0.5 mmol) with ethoxycarbonyl ethyl isocyanate (0.197 mL, 0.75 mmol) afforded the carbamate 7m. Yield: 0.093 g (43%); LCMS: MS (m/z): 434.3 (M+H).

Phenyl 2E, 6E, 10E-geranylgeranyl carbamate (7n) (R=Phenyl-)

The interaction of alcohol 1 with phenyl isocyanate afforded the carbamate 7n. Yield: 0.087 g (56%); TLC Rf: 0.69 (10% EtOAchexanes); $^1$H NMR (300 MHz, CDCl$_3$): δ 7.40-7.25 (m, 5H), 6.60 (br s, 1H), 5.40 (t, 1H), 5.10 (m, 3H), 4.68 (d, 2H), 2.14-1.92 (m, 12H), 1.75 (s, 3H), 1.68 (s, 3H), 1.60 (s, 9H). LCMS: MS (m/z): 432.5 (M+Na).

P-Tolyl 2E, 6E, 10E-geranylgeranyl carbamate (7o) (R=p-Tolyl-)

The interaction of alcohol 1 (0.145 g, 0.5 mmol) with p-tolyl isocyanate (0.188 mL, 0.75 mmol) afforded the carbamate 7o. Yield: 0.095 g (45%); LCMS: MS (m/z): 424.3 (M+H).

Ethoxycarbonyl methyl 2E, 6E, 10E-geranylgeranyl carbamate (7p) (R=ethoxycarbonyl methyl-)

The interaction of alcohol 1 (0.145 g, 0.5 mmol) with ethoxycarbonyl methyl isocyanate (0.193 g, 0.75 mmol) afforded the carbamate 7p. Yield: 0.077 g (37%); LCMS: 436.3 (M+H)

p-Trifluoromethylphenyl 2E, 6E, 10E-geranylgeranyl carbamate (7q) (R=p-trifluoromethylphenyl-)

The interaction of alcohol 1 with p-trifluoromethylphenyl isocyanate afforded the carbamate 7q. Yield: 0.076 g (42%); TLC Rf: 0.69 (10% EtOAc/hexanes); $^1$H NMR (300 MHz, CDCl$_3$): δ 7.55 (d, 2H), 7.48 (d, 2H), 6.75 (br s, 1H), 5.39 (t, 1H), 5.10 (m, 3H), 4.70 (d, 2H), 2.14-1.98 (m, 12H), 1.75 (s, 3H), 1.68 (s, 3H), 1.60 (s, 9H). LCMS: MS (m/z): 476.1 (M−H).

The following carbamates (7s-y) were prepared as a mixture of 90:10 (trans:cis) isomers.

1'-Naphthyl 2E, 6E, 10E-geranylgeranyl carbamate (7r) (R=1'-Naphthyl-)

The interaction of alcohol 1 (0.725 g, 2.5 mmol) with 1-naphthyl isocyanate (0.430 mL, 3.00 mmol) afforded the carbamate 7r. Yield: 0.906 g (79%); LCMS: MS (m/z): 482.20 (M+Na).

2'-Naphthyl 2E, 6E, 10E-geranylgeranyl carbamate (7s) (R=2'-Naphthyl-)

The interaction of alcohol 1 (0.725 g, 2.5 mmol) with 2-naphthyl isocyanate (0.430 mL, 3.00 mmol) afforded the carbamate 7s. Yield: 0.946 g (93%); LCMS: MS (m/z): 482.30 (M+Na).

3',4'-Dimethoxyphenyl 2E, 6E, 10E-geranylgeranyl carbamate (7t) (R=3',4'-Dimethoxyphenyl-)

The interaction of alcohol 1 (0.725 g, 2.5 mmol) with 3,4-dimethoxyphenyl isocyanate (0.446 mL, 3.00 mmol) afforded the carbamate 7t. Yield: 0.914 g (78%); LCMS: MS (m/z): 492.30 (M+Na).

p-Benzoyl phenyl 2E, 6E, 10E-geranylgeranyl carbamate (7u) (R=p-Benzoyl phenyl-)

The interaction of alcohol 1 (0.725 g, 2.5 mmol) with p-benzoylphenyl isocyanate (0.669 g, 3.00 mmol) afforded the carbamate 7u. Yield: 0.872 g (68%); LCMS: MS (m/z): 514.3 (M+H).

3',4',5'-Trimethoxyphenyl 2E, 6E, 10E-geranylgeranyl carbamate (7v) (R=3',4',5'-Trimethoxyphenyl-)

The interaction of alcohol 1 (0.725 g, 2.5 mmol) with 3,4,5-trimethoxyphenyl isocyanate (0.537 mL, 3.00 mmol) afforded the carbamate 7v. Yield: 1.08 g (87%); MS (m/z): LCMS: MS (m/z): 522.40 (M+Na).

2',4'-Dimethoxyphenyl 2E, 6E, 10E-geranylgeranyl carbamate (7w) (R=2',4'-Dimethoxyphenyl-)

The interaction of alcohol 1 (0.725 g, 2.5 mmol) with 2,4-dimethoxyphenyl isocyanate (0.537 g, 3.00 mmol) afforded the carbamate 7w. Yield: 0.996 g (85%); LCMS: MS (m/z): 492.30 (M+Na).

9'H-Fluoren-2'-yl isocyanate 2E, 6E, 10E-geranylgeranyl carbamate (7x) (R=9'H-Fluoren-2'-yl isocyanate-)

The interaction of alcohol 1 (0.725 g, 2.5 mmol) with 9H-fluoren-2-yl isocyanate (0.621 mL, 3.00 mmol) afforded the carbamate 7x. Yield: 0.968 g (78%); LCMS: MS (m/z): 520.30 (M+Na).

3',4',5'-Trichlorophenyl 2E, 6E, 10E-geranylgeranyl carbamate (7y) (R=3',4',5'-Trichlorophenyl-)

The interaction of alcohol 1 (0.725 g, 2.5 mmol) with 3,4,5-trichlorophenyl isocyanate (0.666 g, 3.00 mmol) afforded the carbamate 7y. Yield: 0.932 g (73%); LCMS: MS (m/z): 534.10 (M+Na).

3'-Pyridyl 2E, 6E,10E-geranylgeranyl carbamate (7z)

The reaction of alcohol 1 with 3-pyridyl isocyanate afforded carbamate 7z. Yield: 0.112 g (48%); TLC Rf: 0.6 (5% MeOH/CH$_2$Cl$_2$); LCMS: MS (m/z): 411 (M+H).

2'-Furanyl methyl 2E, 6E, 10E]-geranylgeranyl carbamate (7aa)

The reaction of alcohol 1 with 2-furanylmethyl isocyanate afforded carbamate 7aa. Yield: 0.111 g (45%). LCMS: MS (m/z): 436.2 (M+Na).

2E,6E,10E-Geranylgeranyl Memantinyl Carbamate 41 (R=Memantinyl)

The reaction of alcohol 9 with memantine N-carbamoyl chloride gave the carbamate 41. Yield: 0.038 g (38%); TLC Rf: 0.47 (10% EtOAc/n-hexanes).

Scheme 11:

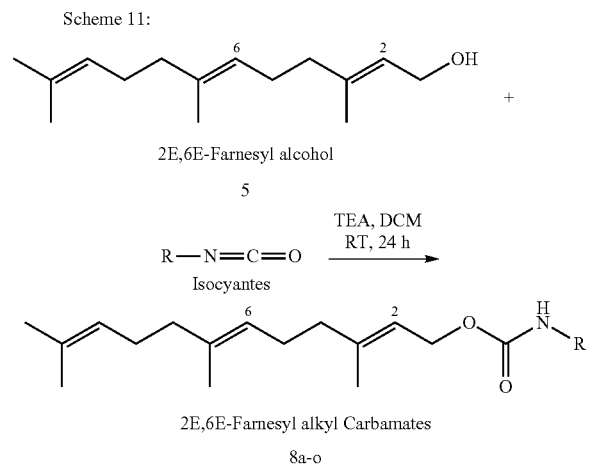

2E,6E-Farnesyl alcohol
5

Isocyantes 2E,6E-Farnesyl alkyl Carbamates
8a-o iso-Propyl 2E,6E-farnesyl carbamate (8a) (R=isoPropyl-)

A dry reaction flask equipped with a stir bar, N$_2$ inlet was charged with alcohol 5 (0.165 g, 0.75 mmol), TEA (0.2 mL, 1.4 mmol) and DCM (2 mL). After cooling it to 0° C., iso-propyl isocyanate (0.137 mL, 1.4 mmol) was added dropwise and the resulting reaction mixture was allowed to stir for 24 h. The reaction was monitored by TLC. After completion of the reaction, it was quenched with H$_2$O (5 mL), acidified, extracted with n-hexanes (3×15 mL) and the combined n-hexanes were washed with H$_2$O (10 mL). After drying the organic solution over anhydrous Na$_2$SO$_4$, the solvent was evaporated and the resulting residue was purified by silica gel column chromatography using 1-2% EtOAc in n-hexanes to afford the desired carbamate 8a. Yield: 0.103 g (45%); LCMS: MS (m/z): 330.25 (M+Na).

The following carbamates 8b to 8o were prepared according to the procedure that was used to prepare carbamate 8a.

n-Pentyl 2E, 6E-farnesyl carbamate (8b) (R=n-Pentyl-)

The reaction of alcohol 5 (0.165 g, 0.75 mmol) with n-pentyl isocyanate (0.180 g, 1.4 mmol) afforded the carbamate 8b. Yield: 0.080 g (32%); LCMS: MS (m/z): 358.25 (M+Na).

Cyclopentyl 2E, 6E-farnesyl carbamate (8c) (R=Cyclopentyl-)

The reaction of alcohol 5 (0.165 g, 0.75 mmol) with cyclopentyl isocyanate (0.158 mL, 1.4 mmol) afforded the carbamate 8c. Yield: 0.094 g (38%); LCMS: MS (m/z): 356.25 (M+Na).

Cycloheptyl 2E, 6E-farnesyl carbamate (8d) (R=Cycloheptyl-)

The reaction of alcohol 5 (0.165 g, 0.75 mmol) with cycloheptyl isocyanate (0.185 mL, 1.4 mmol) afforded the carbamate 8d. Yield: 0.105 g (39%); LCMS: MS (m/z): 384.3 (M+Na).

Adamantyl 2E, 6E-farnesyl carbamate (8e)
(R=Adamentyl-)

The reaction of alcohol 5 (0.165 g, 0.75 mmol) with adamantyl isocyanate (0.248 g, 1.4 mmol) afforded the carbamate 8e. Yield: 0.094 g (38%); LCMS: MS (m/z): 400.65 (M+H).

Cyclohexyl 2E, 6E-farnesyl carbamate (8f)
(R=Cyclohexyl-)

The reaction of alcohol 5 (0.165 g, 0.75 mmol) with cyclohexyl isocyanate (0.179 mL, 1.4 mmol) afforded the carbamate 8f. Yield: 0.109 g (42%); LCMS: MS (m/z): 370.20 (M+Na).

Sec-Butyl 2E, 6E-farnesyl carbamate (8g)
(R=sec-Butyl-)

The reaction of alcohol 5 (0.165 g, 0.75 mmol) with sec-butyl isocyanate (0.160 mL, 1.4 mmol) afforded the carbamate 8g. Yield: 0.052 g (29%); LCMS: MS (m/z): 344.30 (M+Na).

Ethyl 2E, 6E-farnesyl carbamate (8h) (R=Ethyl-)

The reaction of alcohol 5 (0.165 g, 0.75 mmol) with ethyl isocyanate (0.111 mL, 1.4 mmol) afforded the carbamate 8h. Yield: 0.094 g (44%); LCMS: MS (m/z): 316.25 (M+Na).

Hexyl 2E, 6E-farnesyl carbamate (8i) (R=Hexyl-)

The reaction of alcohol 5 (0.165 g, 0.75 mmol) with hexyl isocyanate (0.203 mL, 1.4 mmol) afforded the carbamate 8i. Yield: 0.063 g (34%); LCMS: MS (m/z): 372.3 (M+Na).

Allyl 2E, 6E-farnesyl carbamate (8j) (R=Allyl-)

The reaction of alcohol 5 (0.165 g, 0.75 mmol) with allyl isocyanate (0.124 mL, 1.4 mmol) afforded the carbamate 8j. Yield: 0.071 g (31%); LCMS: MS (m/z): 328.2 (M+Na).

Carboethoxymethyl 2E, 6E-farnesyl carbamate (8k)
(R=Carboethoxymethyl-)

The reaction of alcohol 5 (0.165 g, 0.75 mmol) with carboethoxymethyl isocyanate (0.157 mL, 1.4 mmol) afforded the carbamate 8k. Yield: 0.105 g (40%); LCMS: MS (m/z): 374.2 (M+Na).

p-Tolyl 2E, 6E-farnesyl carbamate (8l) (R=p-Tolyl-)

The reaction of alcohol 5 (0.165 g, 0.75 mmol) with p-tolyl isocyanate (0.158 mL, 1.4 mmol) afforded the carbamate 8l. Yield: 0.119 g (33%); LCMS: MS (m/z): 378.20 (M+Na).

Carboethoxy-2'-ethyl 2E, 6E-farnesyl carbamate (8m) (R=Carboethoxy-2'-ethyl-)

The reaction of alcohol 5 (0.165 g, 0.75 mmol) with carboethoxy-2-ethyl isocyanate (0.180 mL, 1.4 mmol) afforded the carbamate 8m. Yield: 0.112 g (35%); LCMS: MS (m/z): 388.20 (M+Na).

p-Trifluoromethylphenyl 2E, 6E-farnesyl carbamate (8n) (R=p-trifluoromethylphenyl-)

The reaction of alcohol 5 (0.165 g, 0.75 mmol) with p-trifluoromethylphenyl isocyanate (0.158 mL, 1.4 mmol) afforded the carbamate 8n. Yield: 0.128 g (31%); LCMS: MS (m/z): 432.2 (M+Na).

Phenyl 2E, 6E-farnesyl carbamate (8o) (R=Phenyl-)

The reaction of alcohol 5 (0.165 g, 0.75 mmol) with phenyl isocyanate (0.150 mL, 1.4 mmol) afforded the carbamate 8o. Yield: 0.066 g (26%); LCMS: MS (m/z): 364.20 (M+Na).

Scheme 12:

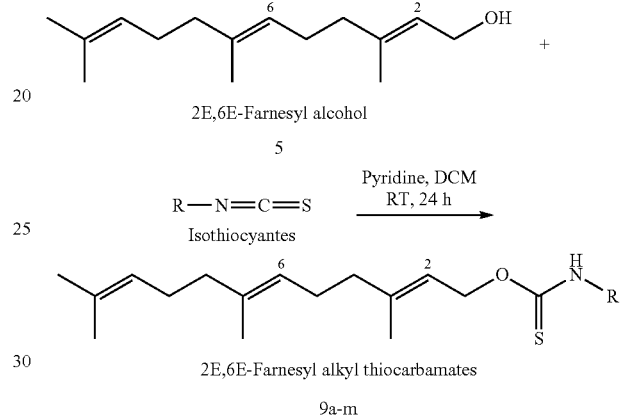

Ethyl 2E, 6E-farnesyl thiocarbamate (9a) (R=Ethyl-)

A dry reaction flask equipped with a stir bar, $N_2$ inlet was charged with alcohol 5 (0.111 g, 0.5 mmol), pyridine (0.08 mL, 1.0 mmol) and DCM (1 mL). After cooling it to 0° C., ethyl thioisocyanate (0.065 g, 1.0 mmol) was added dropwise and the resulting reaction mixture was allowed to stir for 24 h. The reaction was monitored by TLC. After completion of the reaction, it was quenched with $H_2O$ (5 mL), acidified, extracted with n-hexanes (3×15 mL) and the combined n-hexanes were washed with $H_2O$ (10 mL). After drying the organic solution over anhydrous $Na_2SO_4$, the solvent was evaporated and the resulting residue was purified by silica gel column chromatography using 1-2% EtOAc in n-hexanes to afford the desired thiocarbamate 9a.: 0.044 g (29%); LCMS: 310.2 (M+H).

The following carbamates 9b to 9k were prepared according to the procedure that was used to prepare carbamate 9a.

sec-Butyl 2E, 6E-farnesyl thiocarbamate (9b)
(R=sec-butyryl-)

The reaction of alcohol 5 (0.111 g, 0.5 mmol) with sec-butyl thioisocyanate (0.086 g, 1.0 mmol) afforded the thiocarbamate 9b. Yield: 0.045 g (27%); LCMS: MS (m/z): 338.2 (M+H).

n-Butyl 2E, 6E-farnesyl thiocarbamate (9c)
(R=n-Butyl-)

The reaction of alcohol 5 (0.111 g, 0.5 mmol) with n-butyl thioisocyanate (0.090 g, 1.0 mmol) afforded the thiocarbamate 9c. Yield: 0.053 g (32%); LCMS: MS (m/z): 338.20 (M+H).

Cyclopropyl 2E, 6E-farnesyl thiocarbamate (9d) (R=Cyclopropyl-)

The reaction of alcohol 5 (0.111 g, 0.5 mmol) with cyclopropyl thioisocyanate (0.070 g, 1.0 mmol) afforded the thiocarbamate 9d. Yield: 0.062 g (39%); LCMS: MS (m/z): 322.25 (M+H).

n-Hexyl 2E, 6E-farnesyl thiocarbamate (9e) (R=n-Hexyl-)

The reaction of alcohol 5 (0.111 g, 0.5 mmol) with n-hexyl thioisocyanate (0.115 g, 1.0 mmol) afforded the thiocarbamate 9e. Yield: 0.069 g (38%); LCMS: MS (m/z): 366.20 (M+H).

Methoxy-2-ethyl 2E, 6E-farnesyl thiocarbamate (9f) (R=Methoxy-2'-ethyl-)

The reaction of alcohol 5 (0.111 g, 0.5 mmol) with methoxy-2-ethyl thioisocyanate (0.087 g, 1.0 mmol) afforded the thiocarbamate 9f. Yield: 0.030 g (18%); LCMS: MS (m/z): 340.2 (M+H).

exo-Norbornyl 2E, 6E-farnesyl thiocarbamate (9g) (R=exo-Norbornyl-)

The reaction of alcohol 5 (0.111 g, 0.5 mmol) with exo-norbornyl thioisocyanate (0.114 g, 1.0 mmol) afforded the thiocarbamate 9g. Yield: 0.065 g (35%); LCMS: MS (m/z): 375.30 (M+H).

Phenyl 2E, 6E-farnesyl thiocarbamate (9h) (R=Phenyl-)

The reaction of alcohol 5 (0.111 g, 0.5 mmol) with Phenyl thioisocyanate (0.065 g, 1.0 mmol) afforded the thiocarbamate 9h. Yield: 0.073 g (41%); LCMS: MS (m/z): 358.20 (M+H).

Piperidinyl-2' ethyl 2E, 6E-farnesyl thiocarbamate (i) (R=Piperidinyl-2' ethyl-)

The reaction of alcohol 5 (0.111 g, 0.5 mmol) with piperidinyl-2-ethyl thioisocyanate (0.123 g, 1.0 mmol) afforded the thiocarbamate 9i. Yield: 0.054 g (28%); LCMS: MS (m/z): 393.30 (M+H).

Morpholinyl-N-2'-ethyl 2E, 6E-farnesyl thiocarbamate (9j) (R=Morpholinyl-N-2-ethyl-)

The reaction of alcohol 5 (0.111 g, 0.5 mmol) with morpholinyl-2-ethyl thioisocyanate (0.065 g, 1.0 mmol) afforded the thiocarbamate 9j. Yield: 0.061 g (31%); LCMS: MS (m/z): 395.25 (M+H).

Morpholinyl-N-3'-propyl 2E, 6E-farnesyl thiocarbamate (9k) (R=Morpholinyl-N-3'-propyl-)

The reaction of alcohol 5 (0.111 g, 0.5 mmol) with morpholinyl-N-3-propyl thioisocyanate (0.065 g, 1.0 mmol) afforded the thiocarbamate 9k. Yield: 0.055 g (27%); LCMS: MS (m/z): 395.3 (M+H).

Scheme 13:

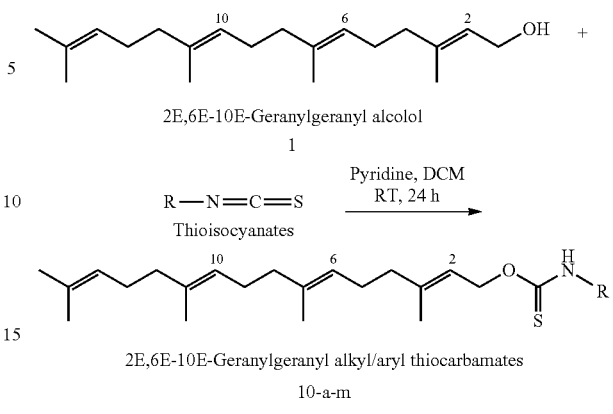

Methyl 2E,6E,10E-geranylgeranyl thiocarbamate (10a) (R=Methyl-)

A dry reaction flask equipped with a stir bar, $N_2$ inlet was charged with alcohol 1 (0.087 g, 0.3 mmol), pyridine (0.48 mL, 0.6 mmol) and DCM (1 mL). After cooling it to 0° C., methyl thioisocyanate (0.051 mL, 1.0 mmol) was added dropwise and the resulting reaction mixture was allowed to stir for 24 h. The reaction was monitored by TLC. After completion of the reaction, it was quenched with $H_2O$ (5 mL), acidified, extracted with n-hexanes (3×15 mL) and the combined n-hexanes were washed with $H_2O$ (10 mL). After drying the organic solution over anhydrous $Na_2SO_4$, the solvent was evaporated and the resulting residue was purified by silica gel column chromatography using 1-2% EtOAc in n-hexanes to afford the desired thiocarbamate 10a. Yield: 0.030 g (28%); LCMS: MS (m/z): 386.4 (M+Na).

The following carbamates 10b to 10m were prepared according to the procedure that was used to prepare carbamate 10a.

Ethyl 2E,6E,10E-geranylgeranyl thiocarbamate (10b) (R=Ethyl-)

The reaction of alcohol 1 (0.111 g, 0.5 mmol) with ethyl thioisocyanate (0.040 g, 0.6 mmol) afforded the thiocarbamate 10b. Yield: 0.034 g (30%); LCMS: MS (m/z): 378.35 (M+H).

sec-Butyryl 2E,6E,10E-geranylgeranyl thiocarbamate (10c) (R=sec-Butyryl-)

The reaction of alcohol 1 (0.111 g, 0.5 mmol) with sec-butyryl thioisocyanate (0.052 g, 0.6 mmol) afforded the thiocarbamate 10c. Yield: 0.038 g (32%); LCMS: MS (m/z): 406.3 (M+H).

Ethoxycarbonylmethyl 2E,6E,10E-geranylgeranyl thiocarbamate (10d) (R=Ethoxycarbonylmethyl-)

The reaction of alcohol 1 (0.111 g, 0.5 mmol) with ethoxycarbonylmethyl thioisocyanate (0.039 g, 0.6 mmol) afforded the thiocarbamate 10d. Yield: 0.027 g (21%); $^1$H NMR (300 MHz, $CDCl_3$): δ 6.71 (s, 1H), 5.44-5.39 (m, 1H), 5.13-5.08 (m, 3H), 4.98 (s, 1H), 4.95 (m, 1H), 4.33-4.21 (m, 3.6H), 4.04

(d, 0.4H), 2.09-1.97 (m, 12H), 1.73 (s, 3H), 1.68 (s, 3H), 1.60-1.57 (m, 9H), 1.33-1.28 (m, 3H). LCMS: MS (m/z): 436.3 (M+H).

n-Butyl 2E,6E,10E-geranylgeranyl thiocarbamate (10e) (R=n-Butyl-)

The reaction of alcohol 1 (0.111 g, 0.5 mmol) with butyl thioisocyanate (0.054 mL, 0.6 mmol) afforded the thiocarbamate 10e. Yield: 0.043 g (27%); TLC Rf: 0.7 (10% EtOAc:hexanes); $^1$H NMR (300 MHz, CDCl$_3$): δ 6.46 (br s, 0.4H), 6.20 (br s, 0.6H), 5.40 (t, 1H), 5.08 (m, 3H), 5.00 (d, 0.8H), 4.93 (s, 1.2H), 3.25 (d, 1.2H), 3.24 (m, 0.8H), 2.12-1.97 (m, 12H), 1.66 (s, 3H), 1.62 (s, 3H), 1.60 (s, 9H), 1.50-1.33 (m, 4H), 0.93 (m, 3H). LCMS: MS (m/z): 406 (M+H).

Cyclopropyl 2E,6E,10E-geranylgeranyl thiocarbamate (10f) (R=Cyclopropyl-)

The reaction of alcohol 1 (0.111 g, 0.5 mmol) with cyclopropyl thioisocyanate (0.042 mL, 0.6 mmol) afforded the thiocarbamate 10f. Yield: 0.036 g (31%); LCMS: MS (m/z): 390.3 (M+H).

Acetyl 2E,6E,10E-geranylgeranyl thiocarbamate (10g) (R=Acetyl-)

The reaction of alcohol 1 (0.111 g, 0.5 mmol) with acetyl thioisocyanate (0.039 mL, 0.6 mmol) afforded the thiocarbamate 10g. Yield: 0.019 g (16%); LCMS: MS (m/z): 414.30 (M+Na).

n-Hexyl 2E,6E,10E-geranylgeranyl thiocarbamate (10h) (R=n-Hexyl-)

The reaction of alcohol 1 (0.111 g, 0.5 mmol) with n-hexyl thioisocyanate (0.069 mL, 0.6 mmol) afforded the thiocarbamate 10h. Yield: 0.053 g (41%); LCMS: MS (m/z): 434.3 (M+H).

Methoxy-2'-ethyl 2E,6E,10E-geranylgeranyl thiocarbamate (10i) (R=Methoxy-2' ethyl-)

The reaction of alcohol 1 (0.111 g, 0.5 mmol) with methoxy-2-ethyl thioisocyanate (0.048 mL, 0.6 mmol) afforded the thiocarbamate 10i. Yield: 0.023 g (19%); $^1$H NMR (300 MHz, CDCl$_3$): δ 6.84 and 6.59 (m, 1H total), 5.43-5.38 (m 1H), 5.13-5.10 (m, 3H), 5.03-4.94 (m, 2H), 3.77-3.73 (m, 1H), 3.56-3.52 (m, 1H), 3.45 (s, 1H), 3.36 (s, 3H), 2.11-1.98 (m, 12H), 1.73 (s, 3H), 1.68 (s, 3H), 1.60-1.58 (m, 10H). LCMS: MS (m/z): 408.4 (M+H).

Exo-Norbornyl 2E,6E,10E-geranylgeranyl thiocarbamate (10j) (R=exo-Norbornyl-)

The reaction of alcohol 1 (0.111 g, 0.5 mmol) with exo-norbornyl thioisocyanate (0.061 mL, 0.6 mmol) afforded the thiocarbamate 10j. Yield: 0.038 g (29%); $^1$H NMR (300 MHz, CDCl$_3$): δ 6.46 and 6.11 (m, 1H total) 5.45-5.36 (m, 1H), 5.11-5.08 (m, 3H), 5.03-5.00 (m, 2H), 4.03-3.95 (m, 0.6H), 3.65-3.58 (m, 0.4H), 2.35-2.21 (m, 2H), 2.09-1.93 (m, 12H), 1.74-1.60 (m, 6H), 1.57-1.52 (m, 12H), 1.34-1.12 (m, 5H). LCMS: MS (m/z): 444.4 (M+H).

Phenyl 2E,6E,10E-geranylgeranyl thiocarbamate (10k) (R=n-Phenyl-)

The reaction of alcohol 1 (0.111 g, 0.5 mmol) with phenyl thioisocyanate (0.053 mL, 0.6 mmol) afforded the thiocarbamate 10k. Yield: 0.047 g (37%); LCMS: MS (m/z): 426.30 (M+H).

Piperidinyl-2'-ethyl 2E,6E,10E-geranylgeranyl thiocarbamate (10l) (R=Piperidinyl-2'-ethyl-)

The reaction of alcohol 1 (0.111 g, 0.5 mmol) with piperidinyl-2'-ethyl thioisocyanate (0.069 mL, 0.6 mmol) afforded the thiocarbamate 10l. Yield: 0.026 g (35%); $^1$H NMR (300 MHz, CDCl$_3$): δ 5.45-5.40 (m, 1H), 5.13-5.08 (m, 3H), 5.02-4.95 (m, 2H), 3.72-3.66 (m, 1.4H), 3.39-3.32 (m, 0.6H), 2.66-2.52 (m, 3H), 2.44-2.34 (m, 1H), 2.12-1.98 (m, 12H), 1.74-1.43 (m, 21H), 1.26 (m, 3H). LCMS: MS (m/z): 461.5 (M+H).

Morpholinyl-2'-ethyl 2E,6E,10E-geranylgeranyl thiocarbamate (10m) (R=Morpholinyl-2'-ethyl-)

The reaction of alcohol 1 (0.111 g, 0.5 mmol) with morpholinyl-2-ethyl thioisocyanate (0.063 mL, 0.6 mmol) afforded the thiocarbamate 10m. Yield: 0.040 g (29%); $^1$H NMR (300 MHz, CDCl$_3$): δ 7.26 and 6.83 (m, 1H total), 5.46-5.40 (m, 1H), 5.11-5.08 (m, 3H), 5.03-4.95 (m, 2H), 3.72-3.70 (m, 4H), 3.68-3.59 (m, 1H), 3.41-3.34 (m, 0.6H), 2.58-2.53 (m, 1H), 2.49-2.41 (m, 4.4H), 2.12-1.98 (m, 13H), 1.74 (s, 3H), 1.68 (s, 3H), 1.60 (s, 9H). LCMS: MS (m/z): 463.6 (M+H).

Scheme 14:

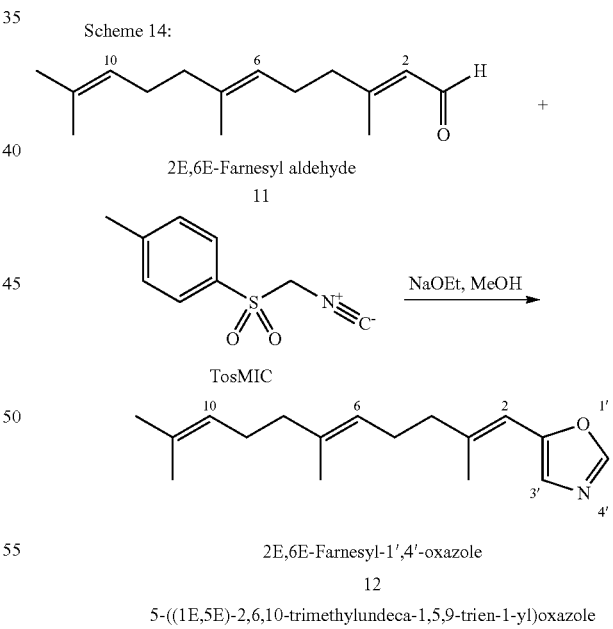

2E,6E-Farnesyl aldehyde
11

TosMIC 2E,6E-Farnesyl-1',4'-oxazole
12
5-((1E,5E)-2,6,10-trimethylundeca-1,5,9-trien-1-yl)oxazole

2E,6E-Farnesyl-1',4'-oxazole: 5-((1E,5E)-2,6,10-trimethylundeca-1,5,9-trien-1-yl)oxazole (12)

A dry reaction flask equipped with a stirring bar and N$_2$ inlet was charged with aldehyde 11 (0.110 g, 0.5 mmol) in 1 mL EtOH followed by NaOEt (21% solution in EtOH, 0.404 mL, 1.25 mmol). To this at 0° C. was added TosMIC (0.102 g, 0.525 mmol) and the resulting reaction was stirred at Room temperature for 24 h. The reaction mixture was quenched with 1N HCl (1 mL), H₂O (5 mL), and extracted with DCM (2×5 mL). After drying over anhydrous sodium sulfate, the solvent was removed under a reduced pressure and the residue was chromatographed over silica gel using n-hexane then 2% EtOAc in n-hexane to yield the desired oxazole 12. Yield: 0.040 g (30%). LCMS: MS (m/z): 260.2 (M+H).

Scheme-5:

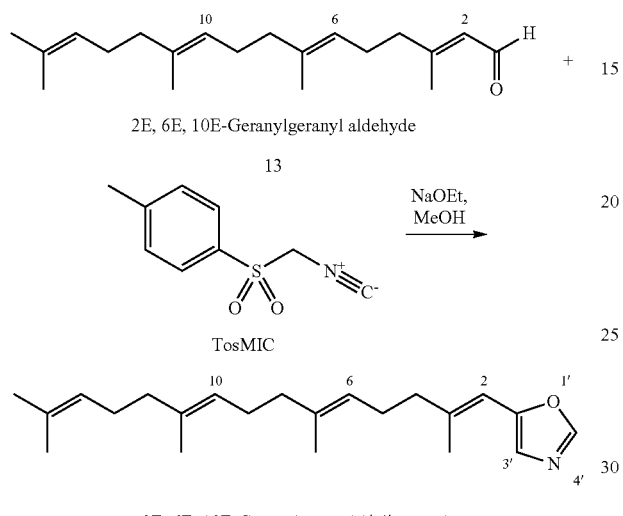

2E,6E,10E-Geranylgeranyl-1',4'-oxazole: 5-((1E,5E,9E)-2,6,10,14-tetramethylpentadeca-1,5,9,13-tetraen-1-yl)oxazole (14)

A dry reaction flask equipped with a stirring bar and N₂ inlet was charged with aldehyde 13 (0.057 g, 0.2 mmol) in 0.5 mL EtOH followed by NaOEt (21% solution in EtOH, 0.161 mL, 0.5 mmol). To this at 0° C. was added TosMIC (0.041 g, 0.21 mmol) and the resulting reaction was stirred at Room temperature for 24 h. The reaction mixture was quenched with 1N HCl (0.5 mL), extracted with DCM (2×3 mL). After drying over anhydrous sodium sulfate, the solvent was removed under a reduced pressure and the residue was chromatographed over silica gel using n-hexane then 2% EtOAc in n-hexane to yield the desired oxazole 14. Yield: 19 mg (28%). ¹H NMR (300 MHz, CDCl₃): δ 7.78 (s, 1H), 6.92 (s, 1H), 6.09 (s, 1H), 5.13-5.07 (m, 3H), 2.22-2.20 (m, 4H), 2.08-1.96 (m, 9H), 1.96 (s, 3H), 1.68-1.60 (m, 11H). LCMS: MS (m/z): 328.2 (M+H).

Scheme-16:

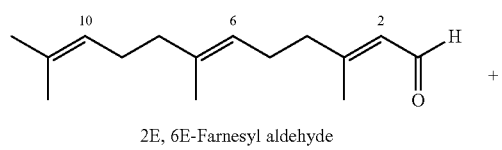

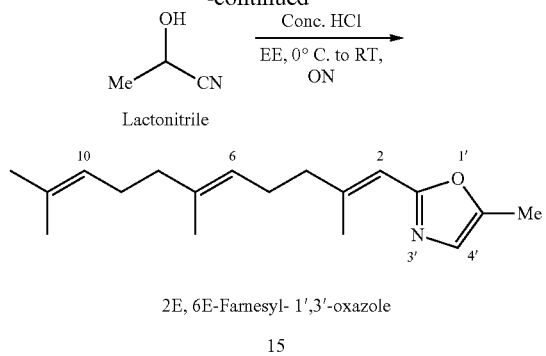

2E,6E-Farnesyl-5'-methyl-1',3'-oxazole: 5-methyl-2-((1E,5E)-2,6,10-trimethylundeca-1,5,9-trien-1-yl)oxazole (15)

A dry reaction flask equipped with a stirring bar and N₂ inlet at 0° C. was charged with aldehyde 11 (0.110 g, 0.5 mmol) diethyl ether (EE, 1 mL), lactonitrile (0.072 mL, 1 mmol) followed by conc. HCl (0.1 mL). The resulting reaction was stirred at room temperature for overnight (~16 h). The reaction mixture was quenched with H₂O (5 mL), and extracted with EE (2×5 mL). After drying over anhydrous sodium sulfate, the solvent was removed under a reduced pressure and the residue was chromatographed over silica gel using n-hexane then 2% EtOAc in n-hexane to yield the desired oxazole 15. Yield: 0.064 g (47%).

Scheme 17:

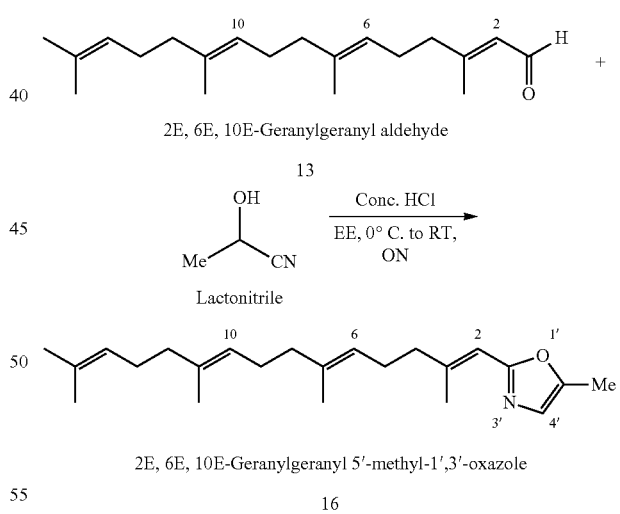

2E,6E,10E-Geranylgeranyl-5'-methyl-1',3'-oxazole: 5-methyl-2-((1E,5E,9E)-2,6,10,14-tetramethylpentadeca-1,5,9,13-tetraen-1-yl)oxazole (16)

A dry reaction flask equipped with a stirring bar and N₂ inlet at 0° C. was charged with aldehyde 13 (0.144 g, 0.5 mmol) diethyl ether (EE, 1 mL), lactonitrile (0.072 mL, 1 mmol) followed by conc. HCl (0.1 mL). The resulting reaction was stirred at room temperature for overnight (~16 h).

The reaction mixture was quenched with H$_2$O (5 mL), and extracted with EE (2×5 mL). After drying over anhydrous sodium sulfate, the solvent was removed under a reduced pressure and the residue was chromatographed over silica gel using n-hexane then 2% EtOAc in n-hexane to yield the desired oxazole 16. Yield: 0.075 g (44%). LCMS: MS (m/z): 364.30 (M+Na).

Scheme 18:

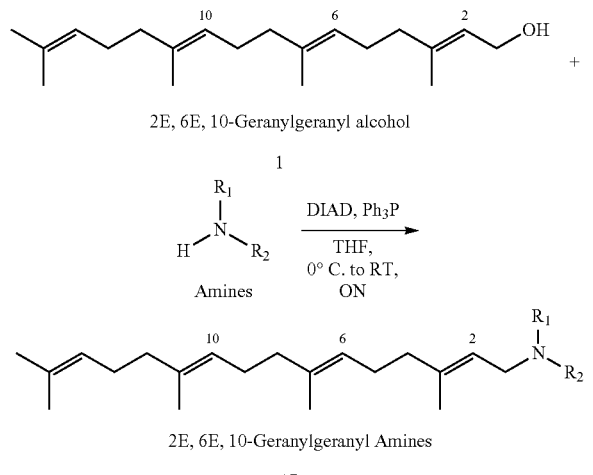

N-Cyclohexyl N-Methyl-2E,6E,10E-Geranylgeranyl amine (17a)

To a dry reaction flask equipped with stir bar, N$^2$ inlet was placed alcohol 1 (0.145 g, 0.5 mmol), triphenylphosphine (0.196 g, 0.75 mmol) and N-methylcyclohexylamine (0.065 mL, 0.5 mmol) in anhydrous THF (1 mL). The reaction was cooled to 0° C. and to it was added DIAD (0.151 g, 0.75 mmol) drop wise and the resulting reaction was stirred at room temperature for overnight (~16 h). After quenching it with H$_2$O (5 mL), it was extracted with DCM (2×10 mL), dried over anhydrous sodium sulfate and the solvent was removed under a reduced pressure. The resulting residue was chromatographed over silica gel using n-hexane and then 2-5% EtOAc in n-hexane to afford the desired amine 17a, yield: 0.072 g (38%). LCMS: MS (m/z): 408.4 (M+Na).

By employing the procedure that was used to prepare amine 17a, the following amines 17b-e have been prepared.

N-Methyl-N-n-pentyl-2E,6E,10E-Geranylgeranyl amine (17b)

The reaction of alcohol 1 with N-methyl-N-n-pentylamine (R$_1$=Me; R$_2$=n-pentyl) afforded the amine 17b. Yield: 0.076 g (41%); LCMS: MS (m/z): 374.50 (M+H).

N-Heptyl-N-Methyl-2E,6E,10E-Geranylgeranyl amine (17c)

The reaction of alcohol 1 with N-n-heptyl-N-methylamine (R$_1$=Me; R$_2$=n-heptyl) afforded the amine 17c. Yield: 0.072 g (36%); LCMS: MS (m/z): 402.4 (M+H).

N-(3'-iso-Propoxypropyl-2E,6E,10E-Geranylgeranyl amine (17d)

The reaction of alcohol 1 with 3-isopropoxypropylamine (R$_1$=H; R$_2$=3-isopropoxypropyl-) afforded the amine 17d. Yield: 0.056 g (29%); LCMS: MS (m/z):390 (M+H).

N-Adamantyl-2E,6E,10E-Geranylgeranyl amine (17e)

The reaction of alcohol 1 with adamentylamine (R1=H; R2=adamentyl) afforded the amine 17e. Yield: 0.071 g (31%); LCMS: MS (m/z): 424.4 (M+H).

Scheme 19:

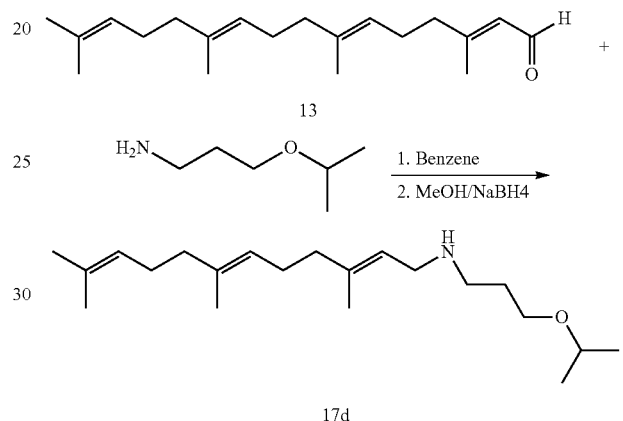

Alternative Synthesis of 17d:

To a solution of aldehyde 13 (150 mg, 0.523 mmol) in benzene (5 mL) was added 3-isopropoxypropylamine (61 mg, 0.523 mmol) and the reaction mixture was stirred at rt for 12 h. Solvent was removed and the residue was taken in MeOH (5 mL) and cooled to 0° C. Then NaBH$_4$ (40 mg, 1.05 mmol) was added and the reaction mixture was stirred at rt for 15 h. Saturated NaHCO$_3$ was added and the reaction mixture was extracted with EtOAc. Dried and solvent was evaporated to give a residue, which was purified by column chromatography (DCM/MeOH) to afford amine 17d in 65% (132 mg) yield. TLC Rf: 0.46 (10% MeH/DCM); $^1$H NMR (300 MHz, CDCl$_3$): δ 5.26 (m, 1H), 5.10 (m, 3H), 3.50 (m, 2H), 3.30 (t, 2H), 2.79 (m, 2H), 2.10-1.90 (m, 12H), 1.80 (m, 2H), 1.66 (s, 1H), 1.64 (s, 1H), 1.59 (s, 9H), 1.14 (d, 6H); LCMS: MS (m/z): 390 (M+H).

Scheme 20:

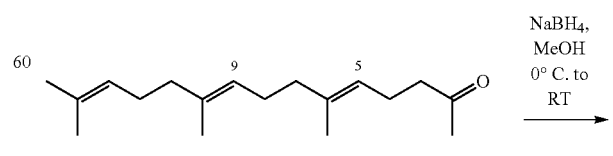

-continued

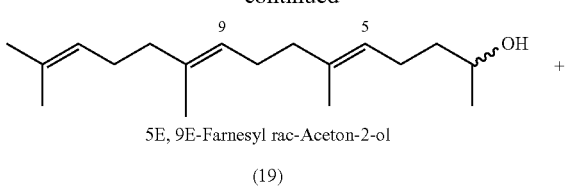

5E, 9E-Farnesyl rac-Aceton-2-ol (19)

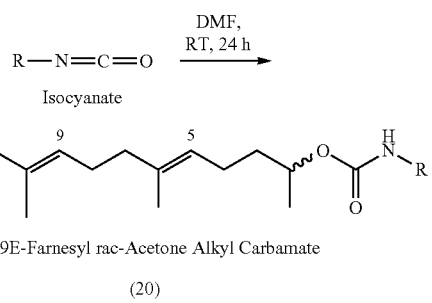

5E, 9E-Farnesyl rac-Acetone Alkyl Carbamate (20)

5E, 9E-Farnesyl 2-acetol (19)

A reaction flask with a stir bar and $N_2$ inlet was charged with ketone 18 (1.2 g, 5 mmol) and MeOH (10 mL). After cooling the reaction flask to 0° C., the addition of $NaBH_4$ (0.190 g, 5 mmol) was performed in portions over several minutes and the reaction was stirred for additional hour. The reaction was monitored by TLC. The reaction was quenched with $H_2O$ (40 mL) and the product was extracted with EtOAc (3×50 mL), dried over anhydrous $Na_2SO_4$ and solvent was removed under a reduced pressure to obtain the desired alcohol 19. Yield: 1.25 g (95%); TLC Rf: 0.24 (10% EtOAc/n-hexanes); LCMS: MS (m/z): 265 (M+H).

Ethyl 5E,9E-farnesyl prop-2-yl carbamate (20a) (R=Ethyl)

A dry reaction flask equipped with a stir bar, $N_2$ inlet was charged with alcohol 19 (0.052 g, 0.2 mmol), pyridine (0.032 mL, 0.4 mmol) and DCM (2 mL). After cooling it to 0° C., ethyl isocyanate was added dropwise and the resulting reaction mixture was allowed to stir for 24 h. The reaction was monitored by TLC. After completion of the reaction, it was quenched with $H_2O$ (5 mL), acidified, extracted with n-hexanes (3×15 mL) and the combined n-hexanes were washed with $H_2O$ (10 mL). After drying the organic solution over anhydrous $Na_2SO_4$, the solvent was evaporated and the resulting residue was purified by silica gel column chromatography using 1-2% EtOAc in n-hexanes to afford the desired carbamate 20a. Yield: 0.037 g (52%); TLC Rf: 0.23 (5% EtOAc/n-Hexanes); LCMS: MS (m/z): 336.40 (M+H).

The following carbamates 20b to 20j were prepared according to the procedure that was used to prepare carbamate 20a.

sec-Butyryl 5E, 9E-farnesyl prop-2-yl carbamate (20b) (R=iso-Butyryl)

The reaction of alcohol 19 with sec-butyryl isocyanate afforded the expected carbamate 20b. Yield: 0.038 g (50%); TLC Rf: 0.43 (10% EtOAc/n-Hexanes); LCMS: MS (m/z): 364 (M+H).

iso-Propyl 5E, 9E-farnesyl prop-2-yl carbamate (20c) (R=iso-Propyl-)

The reaction of alcohol 19 with iso-propyl isocyanate afforded the expected carbamate 20c. Yield: 0.036 g (48%); TLC Rf: 0.41 (10% EtOAc/n-Hexanes); LCMS: MS (m/z): 350.40 (M+H).

n-Pentyl 5E, 9E-farnesyl prop-2-yl carbamate (20d) (R=n-Pentyl)

The reaction of alcohol 19 with n-pentyl isocyanate afforded the expected carbamate 20d. Yield: 0.043 g (54%); TLC Rf: 0.40 (10% EtOAc/n-Hexanes); LCMS: MS (m/z): 378 (M+H).

n-Hexyl 5E, 9E-farnesyl prop-2-yl carbamate (20e) (R=n-Hexyl)

The reaction of alcohol 19 with n-hexyl isocyanate afforded the expected carbamate 20e. Yield: 0.040 g (49%); TLC Rf: 0.41 (10% EtOAc/n-Hexanes); LCMS: MS (m/z): 392 (M+H).

Cyclopentyl 5E, 9E-farnesyl prop-2-yl carbamate (20f) (R=Cyclopentyl)

The reaction of alcohol 19 with cyclopentyl isocyanate afforded the expected carbamate 20f. Yield: 0.035 g (45%); TLC Rf: 0.36 (10% EtOAc/n-Hexanes); LCMS: MS (m/z): 376.40 (M+H).

Cyclohexyl 5E, 9E-farnesyl prop-2-yl carbamate (20g) (R=Cyclohexyl)

The reaction of alcohol 19 with cyclohexyl isocyanate afforded the expected carbamate 20g. Yield: 0.040 g (54%); TLC Rf: 0.40 (10% EtOAc/n-Hexanes); LCMS: MS (m/z): 390.60 (M+H).

Cyclohexylmethyl 5E, 9E-farnesyl prop-2-yl carbamate (20h) (R=Cyclohexylmethyl)

The reaction of alcohol 19 with cyclohexylmethyl isocyanate afforded the expected carbamate 20h. Yield: 0.037 g (47%); TLC Rf: 0.40 (10% EtOAc/n-Hexanes); LCMS: MS (m/z): 404.60 (M+H).

Cycloheptyl 5E, 9E-farnesyl prop-2-yl carbamate (20i) (R=Cycloheptyl)

The reaction of alcohol 19 with cycloheptyl isocyanate afforded the expected carbamate 20i. Yield: 0.043 g (54%); TLC Rf: 0.54 (10% EtOAc/n-Hexanes); LCMS: MS (m/z): 404.60 (M+H).

5E,9E-farnesyl prop-2-yl Methyl 2-(S)-(−)-3-methylbutyrate Carbamate (20j) (R=Methyl-2-(S)-(−)-3-methylbutyrate)

The reaction of alcohol 19 with methyl 2-(S)-(−)-3-methylbutyryl isocyanate afforded the expected carbamate 20j. Yield: 0.41 g (49%); TLC Rf: 0.28 (10% EtOAc/n-Hexanes); LCMS: MS (m/z): 422.60 (M+H).

Scheme 21:

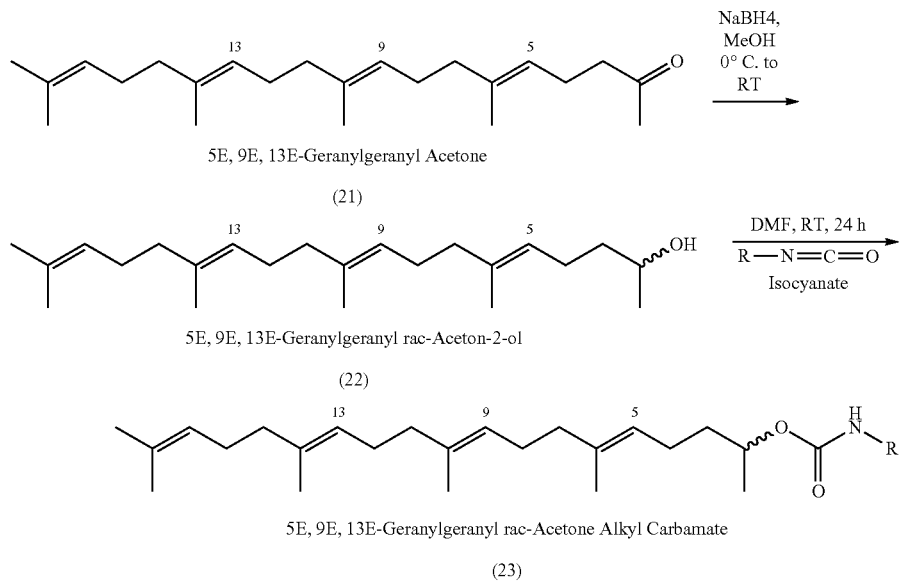

5E, 9E, 13E-Geranylgeranyl Acetone
(21)

5E, 9E, 13E-Geranylgeranyl rac-Aceton-2-ol
(22)

5E, 9E, 13E-Geranylgeranyl rac-Acetone Alkyl Carbamate
(23)

5E, 9E, 13E Geranylgeranyl aceton-2-ol (22)

A reaction flask with a stir bar and $N_2$ inlet was charged with ketone 21 (1.66 g, 5 mmol) and MeOH (10 mL). After cooling the reaction flask to 0° C., the addition of $NaBH_4$ (0.190 g, 5 mmol) was performed in portions over several minutes and the reaction was stirred for additional hour. The reaction was monitored by TLC. The reaction was quenched with $H_2O$ (40 mL) and the product was extracted with EtOAc (3×50 mL), dried over anhydrous $Na_2SO_4$ and solvent was removed under a reduced pressure to obtain the desired alcohol 22. Yield: 1.53 g (92%); TLC Rf: 0.23 (10% EtOAc/n-hexanes); LCMS: MS (m/z): 335 (M+H).

5E, 9E, 13E-Geranylgeranyl-rac-prop-2-yl iso-propyl carbamate (23a) (R=iso-Propyl)

A dry reaction flask equipped with a stir bar, $N_2$ inlet was charged with alcohol 22 (0.052 g, 0.2 mmol), pyridine (0.032 mL, 0.4 mmol) and DCM (2 mL). After cooling it to 0° C., iso-propyl isocyanate (0.49 mL, 0.5 mmol) was added dropwise and the resulting reaction mixture was allowed to stir for 24 h. The reaction was monitored by TLC. After completion of the reaction, it was quenched with $H_2O$ (5 mL), acidified, extracted with n-hexanes (3×15 mL) and the combined n-hexanes were washed with $H_2O$ (10 mL). After drying the organic solution over anhydrous $Na_2SO_4$, the solvent was evaporated and the resulting residue was purified by silica gel column chromatography using 1-2% EtOAc in n-hexanes to afford the desired carbamate 23a. Yield: 0.037 g (52%); TLC Rf: 0.23 (5% EtOAc/n-Hexanes); LCMS: MS (m/z): 418.40 (M+H), ret time 16.28 min.

The following carbamates 23b to 23g were prepared according to the procedure that was used to prepare carbamate 23a.

5E, 9E, 13E-Geranylgeranyl-rac-prop-2-yl n-pentyl carbamate (23b) (R=n-Pentyl)

The reaction of alcohol 22 with n-pentyl isocyanate afforded the desired carbamate 23b. Yield: 0.040 g (46%); TLC Rf: 0.33 (10% EtOAc/n-Hexanes); LCMS: MS (m/z): 446.60 (M+H).

Cyclopentyl 5E, 9E, 13E-geranylgeranyl-rac-prop-2-yl carbamate (23c) (R=cyclopentyl)

The reaction of alcohol 22 with cyclopentyl isocyanate afforded the desired carbamate 23c. Yield: 0.041 g (47%); TLC Rf: 0.39 (10% EtOAc/n-Hexanes); LCMS: MS (m/z): 444.60 (M+H).

Cyclohexylmethyl 5E, 9E, 13E-geranylgeranyl-rac-prop-2-yl carbamate (23d) (R=cyclohexylmethyl)

The reaction of alcohol 22 with n-cyclohexylmethyl isocyanate afforded the desired carbamate 23d. Yield: 0.045 g (48%); TLC Rf: 0.25 (10% EtOAc/n-Hexanes); LCMS: MS (m/z): 472.60 (M+H).

Cycloheptyl 5E, 9E, 13E-geranylgeranyl-rac-prop-2-yl carbamate (23e) (R=cycloheptyl)

The reaction of alcohol 22 with cycloheptyl isocyanate afforded the desired carbamate 23e. Yield: 0.048 g (51%); TLC Rf: 0.57 (10% EtOAc/n-Hexanes); LCMS: MS (m/z): 472.40 (M+H).

5E, 9E, 13E-Geranylgeranyl-rac-prop-2-yl n-hexyl carbamate (23f) (R=n-Hexyl)

The reaction of alcohol 22 with n-hexyl isocyanate afforded the desired carbamate 23f. Yield: 0.039 g (44%); TLC Rf: 0.36 (10% EtOAc/n-Hexanes); LCMS: MS (m/z): 460.5 (M+H).

5E, 9E, 13E-Geranylgeranyl-rac-prop-2-yl methyl 2-(S)-(−)-3-methylbutyryl carbamate (23g) (R=Methyl 2-(S)-(−)-3-methylbutyrate)

The reaction of alcohol 22 with methyl 2-(S)-(−)-3-methylbutyryl isocyanate afforded the desired carbamate 23g. Yield: 0.049 g (51%); TLC Rf: 0.37 (10% EtOAc/n-Hexanes); LCMS: MS (m/z): 490.60 (M+H).

Scheme 22:

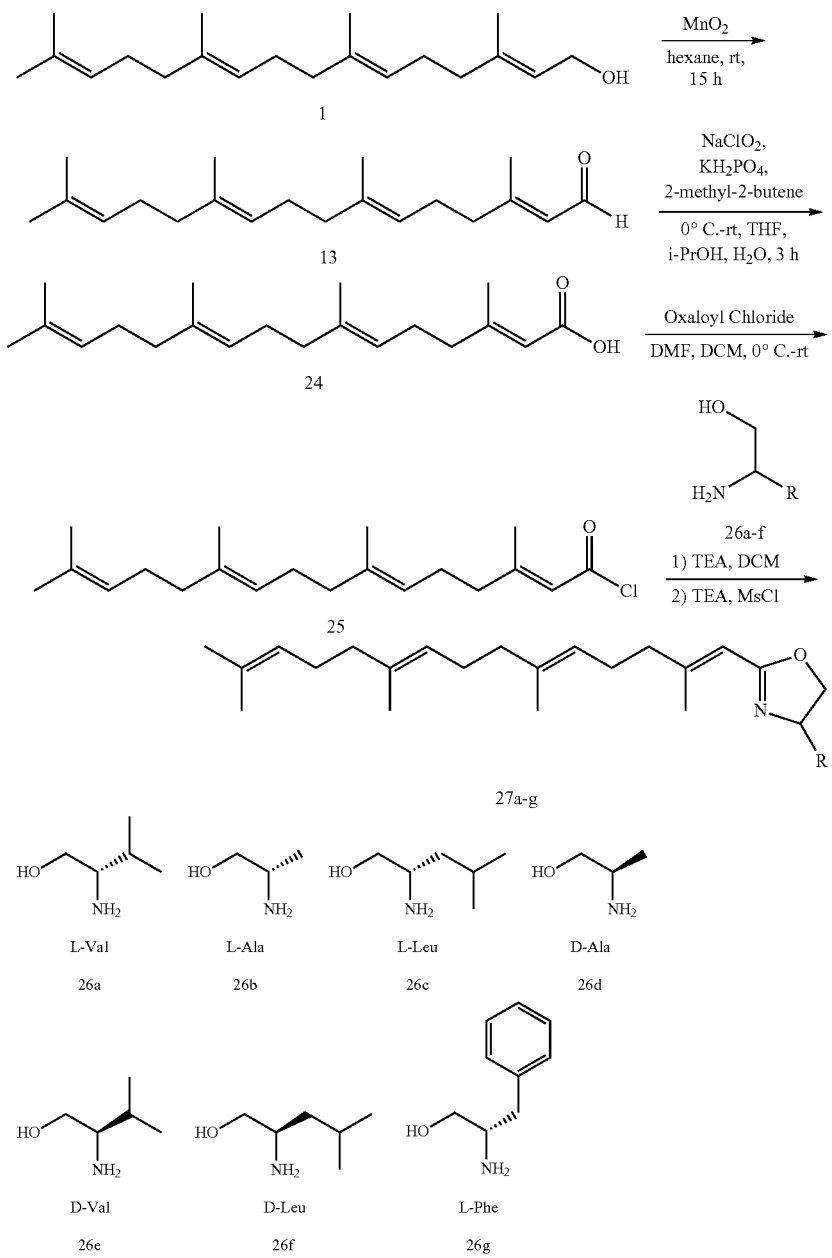

2E,6E,10E-geranylgeranyl aldehyde (13)

Alcohol 1 (5.0 g, 17.2 mmol) was stirred in hexane (85 mL) and MnO$_2$ (12.3 g, 13.6 mmol) was added, and the mixture was stirred at rt for 15 h. The mixture was filtered, concentrated and purified by a silica gel chromatography (Ethyl acetate: Petroleum ether=1: 60) to afford the product 13 (3.5 g, 67%); TLC Rf: 0.58 (3.3% Ethyl acetate/Petroleum ether).

2E,6E,10E-geranylgeranyl carboxylic acid (24)

To a solution of compound 13 (4.0 g, 13.9 mmol), KH$_2$PO$_4$ (18.9 g, 139 mmol) and 2-methyl-2-butene (9.73 g, 139 mmol) in THF—H$_2$O-t-butanol (50 mL-25 mL-25 mL) was added NaClO$_2$ (4.87 g, 69.5 mmol) at 0° C. portionwise. The mixture was stirred at 0° C. for 30 min and rt for 4 h. Saturated NaHSO$_3$ solution was added at 0° C. The mixture was extracted with DCM (100 mL). The organic layer was dried, concentrated and purified by a silica gel chromatography (Petroleum ether/Ethyl acetate=30:1) to get the product 24 (2.0 g, 47%).

2E,6E,10E)-geranylgeranyl carbonyl chloride (25)

To a solution of compound 24 (100 mg, 0.309 mmol) in DCM (3 mL) was added oxalyl chloride (43.3 mg, 0.340 mmol) at rt dropwise. DMF (1 drop) was added. The mixture was stirred at rt for 1 h. The mixture was concentrated to give 25, which was used directly for the next step.

(S)-4-isopropyl-2-((1E,5E,9E)-2,6,10,14-tetramethylpentadeca-1,5,9,13-tetraen-1-yl)-4,5-dihydrooxazole (27a)

To a solution of compound 26a (27.8 mg, 0.37 mmol) and triethylamine (91.8 mg, 0.91 mmol) in DCM (2 mL) was added acyl chloride 25 (0.309 mmol in 1 mL of DCM) dropwise. The mixture was stirred for 3 h. The mixture was quenched by water and washed by HCl (1N in water), MsCl (35 mg, 0309 mmol) was added to the residue and TEA (94 mg, 0.930 mmol) in DCM (2 mL). After stirring for 12 h, the result mixture was washed by water and extracted by DCM. The organic layer was dried and concentrated to give a residue, which was purified by prep-HPLC to afford the product 27a (20.0 mg, 17%); TLC Rf: 0.32 (20% EtOAc/petroleum ether); $^1$H NMR (400 MHz, CDCl$_3$): δ 6.11 (s, 1H), 5.02-4.99 (m, 3H), 4.86 (m, 1H), 4.60-4.58 (m, 1H), 4.22-4.20 (m, 1H), 2.29-2.25 (m, 2H), 2.12 (m, 5H), 1.98-1.66 (m, 8H), 1.59 (m, 5H), 1.51 (s, 9H), 0.95-0.88 (dd, 6H). LCMS: MS (m/z): 372.45 (M+H); ret. time: 6.77 min.

(S)-4-methyl-2-((1E,5E,9E)-2,6,10,14-tetramethylpentadeca-1,5,9,13-tetraen-1-yl)-4,5-dihydrooxazole (27b)

Similar to the preparation of 27a, the reaction of 25 with 26b afforded the desired compound 27b (12 mg, 11%) as oil. TLC Rf: 0.35 (20% EtOAc/petroleum ether); $^1$H NMR (400 MHz, CDCl$_3$): δ 5.11-5.08 (m, 2H), 4.33-4.31 (m, 1H), 3.76-3.77 (m, 1H), 2.14-1.94 (m, 12H), 1.72-1.41 (m, 16H), 1.28-1.19 (m, 5H). LCMS: MS (m/z): 344.30 (M+H); ret. time: 5.23 min.

(S)-4-isobutyl-2-((1E,5E,9E)-2,6,10,14-tetramethylpentadeca-1,5,9,13-tetraen-1-yl)-4,5-dihydrooxazole (27c)

Similar to the preparation of 17a, the reaction of 25 with 26c afforded the desired compound 27c (7.1 mg, 6%) as oil. TLC Rf: 0.30 (20% EtOAc/petroleum ether); $^1$H NMR (400 MHz, CDCl$_3$): δ 5.72 (m, 1H), 5.13-5.10 (m, 3H), 4.34-4.30 (m, 2H), 4.20-4.10 (m, 1H), 3.80 (m, 1H), 2.20-1.98 (m, 11H), 1.86 (s, 2H), 1.80-1.56 (m, 13H), 1.31-1.20 (m, 3H), 0.96-0.92 (m, 6H). LCMS: MS (m/z): 386.3 (M+H); ret. time: 9.07 min.

(R)-4-methyl-2-((1E,5E,9E)-2,6,10,14-tetramethylpentadeca-1,5,9,13-tetraen-1-yl)-4,5-dihydrooxazole (27d)

Similar to the preparation of 7a, the reaction of 25 with 26d afforded the desired compound 27d (5.0 mg, 4.7%) as oil. TLC Rf: 0.31 (20% EtOAc/petroleum ether); $^1$H NMR (400 MHz, CDCl$_3$): δ 5.09 (m, 2H), 4.34-4.32 (m, 1H), 3.79-3.75 (m, 1H), 2.14-1.93 (m, 12H), 1.72-1.41 (m, 16H), 1.28-1.19 (m, 5H). LCMS: MS (m/z): 344.35 (M+H); ret. time: 5.42 min.

(R)-4-isopropyl-2-((1E,5E,9E)-2,6,10,14-tetramethylpentadeca-1,5,9,13-tetraen-1-yl)-4,5-dihydrooxazole (27e)

Similar to the preparation of 27a, the reaction of 25 with 26e afforded the desired compound 27e (8.0 mg, 7%) as oil. TLC Rf: 0.35 (20% EtOAc/petroleum ether); $^1$H NMR (400 MHz, CDCl$_3$): δ 5.14-5.09 (m, 3H), 4.25-4.20 (m, 1H), 3.95-3.90 (m, 3H), 2.20-1.60 (m, 28H), 0.99-0.97 (m, 3H), 0.89-0.87 (m, 3H). LCMS: MS (m/z): 372.30 (M+H); ret. time: 6.31 min.

(R)-4-isobutyl-2-((1E,5E,9E)-2,6,10,14-tetramethylpentadeca-1,5,9,13-tetraen-1-yl)-4,5-dihydrooxazole (27f)

Similar to the preparation of 27a, the reaction of 25 with 26f afforded the desired compound 27f (7 mg, 5.9%) as oil. TLC Rf: 0.30 (20% EtOAc/petroleum ether); $^1$H NMR (400 MHz, CDCl$_3$): δ 5.14-5.09 (m, 3H), 4.35-4.30 (m, 2H), 4.17-4.15 (m, 1H), 3.82-3.78 (m, 1H), 2.15-1.60 (m, 28H), 1.31-1.26 (m, 2H), 0.96-0.92 (m, 6H). LCMS: MS (m/z): 386.3 (M+H); ret. time: 7.32 min.

(S)-4-benzyl-2-((1E,5E,9E)-2,6,10,14-tetramethylpentadeca-1,5,9,13-tetraen-1-yl)-4,5-dihydrooxazole (27g)

Similar to the preparation of 27b, the reaction of 25 with 26a afforded the desired compound 27g (15 mg, 11%) as oil. TLC Rf: 0.34 (20% EtOAc/petroleum ether); $^1$H NMR (400 MHz, CDCl$_3$): δ 7.35-7.20 (m, 5H), 6.23 (s, 1H), 5.30-5.02 (m, 3H), 5.09-5.04 (m, 2H), 3.28-3.24 (m, 1H), 2.97-2.94 (m, 1H), 2.34-2.30 (m, 2H), 2.22-2.16 (m, 2H), 2.13-1.94 (m, 12H), 1.70 (s, 3H), 1.59 (m, 9H). LCMS: MS (m/z): 420.50 (M+H); ret. time: 6.30 min.

Scheme 23:

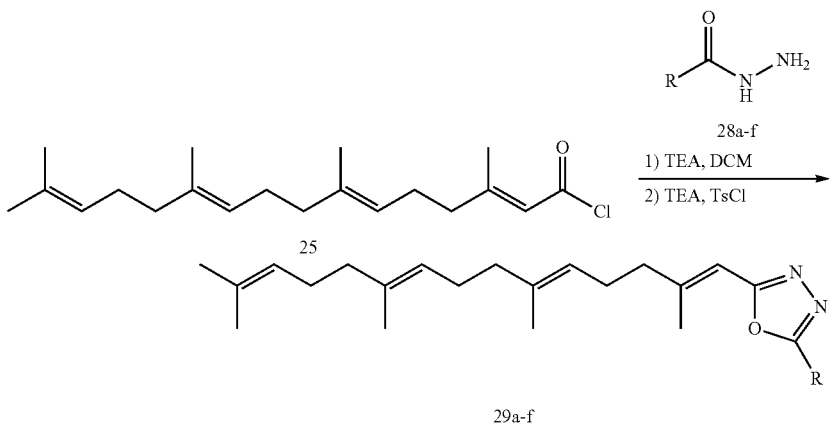

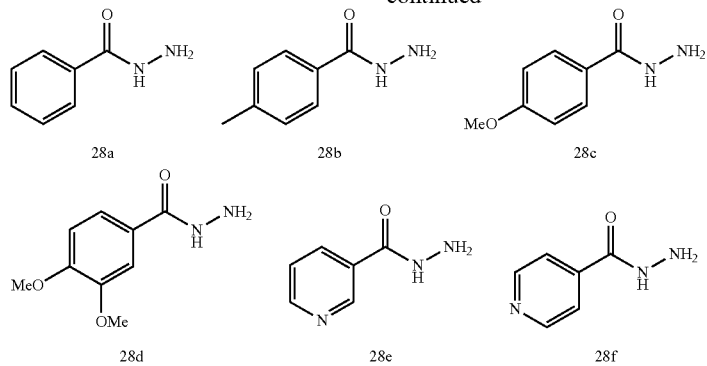

2-phenyl-5-((1E,5E,9E)-2,6,10,14-tetramethylpentadeca-1,5,9,13-tetraen-1-yl)-1,3,4-oxadiazole (29a)

To a solution of compound 28a (56 mg, 0.37 mmol) and triethylamine (91.8 mg, 0.91 mmol) in DCM (2 mL) was added acyl chloride 25 (0.309 mmol, in 1 mL of DCM) dropwise. The mixture was stirred for 3 h. The mixture was quenched with water and washed by HCl (1N in water), TsCl (71 mg, 0.370 mmol) was added to the residue and TEA (113 mg, 1.11 mmol) in DCM (2 mL). After stirring for 12 h, the result mixture was washed with water and extracted by DCM. The combined organic layers were dried and concentrated to get a residue, which was purified by prep-HPLC to give the product 29a (10.8 mg, 9%); TLC Rf: 0.42 (20% EtOAc/n-Hexanes); $^1$H NMR (400 MHz, CDCl$_3$): δ 8.03 (d, 2H), 7.51-7.49 (m, 3H), 5.11-5.09 (m, 3H), 4.98 (d, 2H), 3.67 (s, 2H), 2.19-2.17 (m, 4H), 2.07-2.04 (m, 4H), 1.99-1.96 (m, 4H), 1.67 (s, 3H), 1.61 (s, 3H), 1.59 (s, 3H), 1.58 (s, 3H). LCMS: MS (m/z): 405.40 (M+H); ret. time: 9.06 min.

2-((1E,5E,9E)-2,6,10,14-tetramethylpentadeca-1,5,9,13-tetraen-1-yl)-5-(p-tolyl)-1,3,4-oxadiazole (29b)

Similar to the preparation of 29a, the reaction of 25 with 28b afforded the desired compound 29b (20.8 mg, 16%) as oil. TLC Rf: 0.42 (20% EtOAc/petroleum ether); $^1$H NMR (400 MHz, CDCl$_3$): δ 7.92 (d, 2H), 7.29 (d, 2H) 5.11-5.09 (m, 3H), 4.98 (d, 2H), 3.65 (s, 2H), 2.42 (s, 3H), 2.18-2.16 (m, 4H), 2.07-2.04 (m, 4H), 1.99-1.96 (m, 4H), 1.67 (s, 3H), 1.60 (s, 3H), 1.59 (s, 3H), 1.58 (s, 3H). LCMS: MS (m/z): 419.40 (M+H); ret. time: 8.32 min.

2-(4-methoxyphenyl)-5-((1E,5E,9E-2,6,10,14-tetramethylpentadeca-1,5,9,13-tetraen-1-yl)-1,3,4-oxadiazole (29c)

Similar to the preparation of 29a, the reaction of 25 with 28c afforded the desired compound 29c (12.1 mg, 9%) as oil. TLC Rf: 0.42 (20% EtOAc/petroleum ether); $^1$H NMR (400 MHz, CDCl$_3$): δ 7.93 (d, 2H), 7.08 (d, 2H), 5.11-5.06 (m, 3H), 5.02 (s, 1H), 4.98 (s, 1H), 3.87 (s, 3H), 3.70 (s, 2H), 2.20-2.15 (m, 4H), 2.06-1.97 (m, 4H), 1.96-1.90 (m, 4H), 1.63 (s 3H), 1.60 (s, 3H), 1.56 (s, 3H), 1.55 (s, 3H). LCMS: MS (m/z): 435.5 (M+H); ret. time: 9.21 min.

2-(3,4-dimethoxyphenyl)-5-((1E,5E,9E-2,6,10,14-tetramethylpentadeca-1,5,9,13-tetraen-1-yl)-1,3,4-oxadiazole (29d)

Similar to the preparation of 29a, the reaction of 25 with 28d afforded the desired compound 29d (12.8 mg, 8.9%) as oil. TLC Rf: 0.45 (20% EtOAc/petroleum ether); $^1$H NMR (400 MHz, CDCl$_3$): δ 7.59-7.58 (m, 2H), 6.94 (d, 1H), 5.11-5.09 (m, 3H), 5.00 (s, 1H), 4.96 (s, 1H), 3.96 (s, 3H), 3.94 (s, 3H), 3.65 (s, 2H), 2.18-2.17 (m, 4H), 2.07-2.04 (m, 4H), 1.99-1.89 (m, 4H), 1.67 (s, 3H), 1.61-1.59 (s, 9H). LCMS: MS (m/z): 465.55 (M+H); ret. time: 6.44 min.

2-(pyridin-3-yl)-5-((1E,5E,9E-2,6,10,14-tetramethylpentadeca-1,5,9,13-tetraen-1-yl)-1,3,4-oxadiazole (29e)

Similar to the preparation of 29a, the reaction of 25 with 28e afforded the desired compound 29e (14 mg, 11%) as oil. TLC Rf: 0.36 (20% EtOAc/petroleum ether); $^1$H NMR (400 MHz, CDCl$_3$): δ 9.27 (s, 1H), 8.81 (s, 1H), 8.50 (d, 1H), 7.62-7.59 (m, 1H), 5.11-5.09 (m, 3H), 5.03 (s, 1H), 4.98 (s, 1H), 3.70 (s, 2H), 2.21-2.14 (m, 4H), 2.09-2.02 (m, 4H), 2.00-1.94 (m, 4H), 1.67 (s, 3H), 1.64 (s, 3H), 1.59-1.58 (m, 3H), 1.56 (m, 3H). LCMS: MS (m/z): 406.45 (M+H); ret. time: 8.59 min.

2-(pyridin-4-yl)-5-((1E,5E,9E-2,6,10,14-tetramethylpentadeca-1,5,9,13-tetraen-1-yl)-1,3,4-oxadiazole (29f)

Similar to the preparation of 29a, the reaction of 25 with 28f afforded the desired compound 29f (17 mg, 14%) as oil. TLC Rf: 0.36 (20% EtOAc/petroleum ether); $^1$H NMR (400 MHz, CDCl$_3$): δ 8.85 (m, 2H), 8.04-8.03 (m, 2H), 5.10-5.09 (m, 3H), 5.04 (m, 1H), 4.99 (s, 1H), 3.71 (s, 2H), 2.23-2.18 (m, 4H), 2.06-2.02 (m, 4H), 2.00-1.96 (m, 4H), 1.67 (s, 3H), 1.61-1.59 (m, 9H). LCMS: MS (m/z): 406.45 (M+H); ret. time: 9.09 min.

Scheme 24:

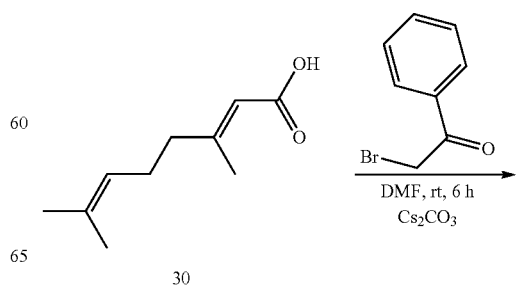

30

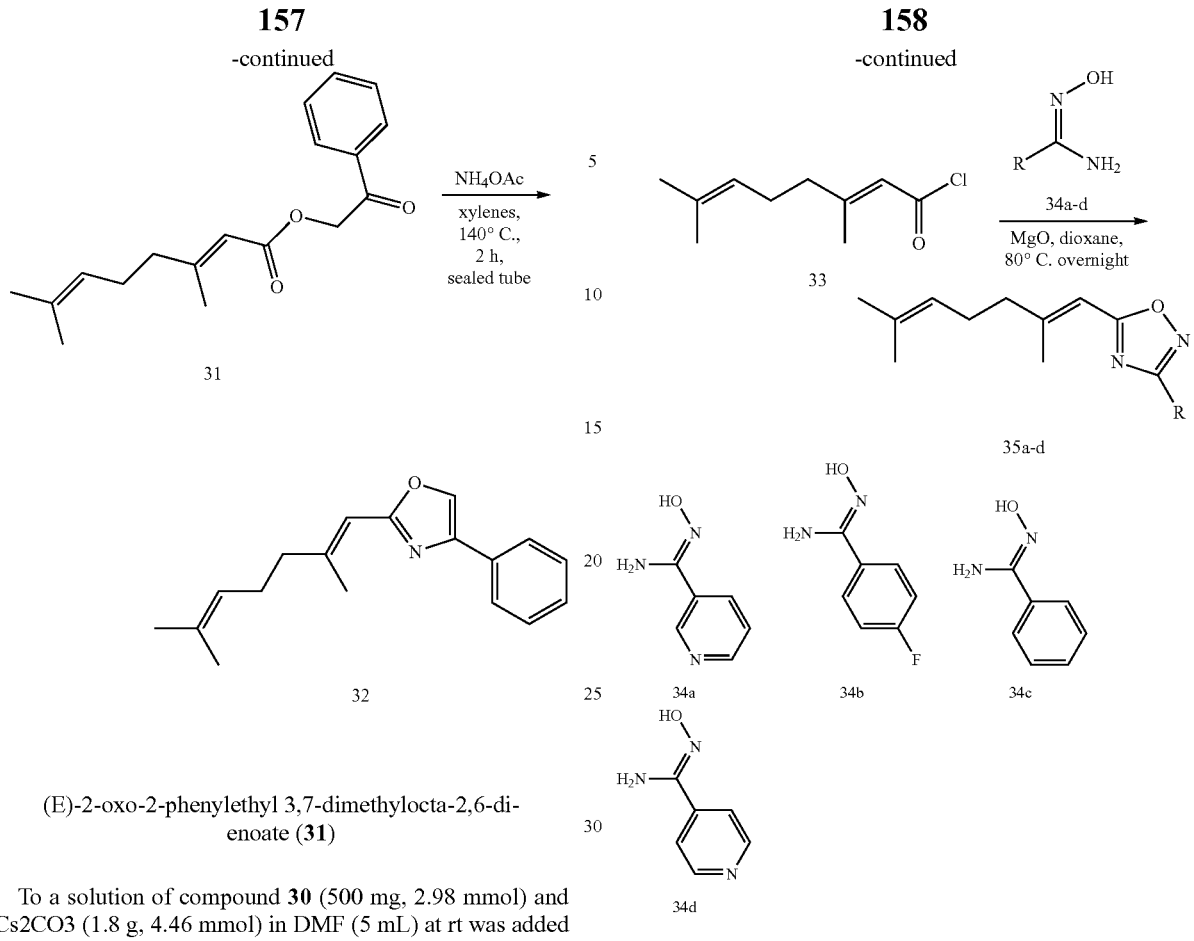

(E)-2-oxo-2-phenylethyl 3,7-dimethylocta-2,6-dienoate (31)

To a solution of compound 30 (500 mg, 2.98 mmol) and Cs2CO3 (1.8 g, 4.46 mmol) in DMF (5 mL) at rt was added 2-bromo-1-phenyl-ethanone (593 mg, 2.98 mmol) dropwise. After stirring for 7 h, the mixture was quenched with water and extracted with ether (100 mL). The organic layer was dried and concentrated to give a residue (350 mg, 41%). The residue was used directly for the next step. TLC Rf: 0.60 (20% EtOAc in petroleum ether).

(E)-2-(2,6-dimethylhepta-1,5-dien-1-yl)-4-phenyloxazole (32)

A solution of compound 31 (200 mg, 0.699 mmol) and NH4OAc (538 mg, 6.99 mmol) in xylenes (5 mL) in a sealed tube was stirred at 140° C. for 2.5 h. The mixture was diluted with water and extracted by ether (100 mL). The organic layer was dried and concentrated to give a residue, which was purified by prep-TLC to afford the desired product 32 (8 mg, 4%) as a mixture of isomers; TLC Rf: 0.60 (20% EtOAc/petroleum ether); $^1$H NMR (400 MHz, CDCl$_3$): δ 7.83-7.82 (m, 1H), 7.77-7.75 (m, 2H), 7.42-7.38 (m, 2H), 7.32-7.26 (m, 1H), 6.18-6.15 (m, 1H), 5.22 (m, 0.23H), 5.14 (m, 0.78H), 2.76-2.72 (m), 2.28-2.19 (m, 7H), 1.70-1.58 (m, 6H). LCMS: MS (m/z): 267.4 (M+H); ret. time: 9.48 min.

Scheme 25:

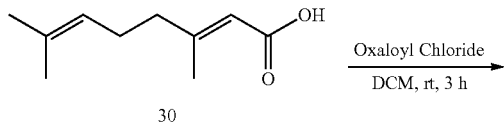

(E)-5-(2,6-dimethylhepta-1,5-dien-1-yl)-3-(pyridin-3-yl)-1,2,4-oxadiazole (35a)

A dry reaction flask equipped with a stir bar was charged with compound 30 (150 mg, 0.9 mmol), DCM (5 mL). To the solution was added oxalyl chloride (112 mg, 0.9 mmol) dropwise and the reaction was stirred at rt for 3 h. The mixture was concentrated to get crude compound 33, which was re-dissolved in dioxane (10 mL).

To above mixture were added compound 34a (123 mg, 0.9 mmol) and magnesium oxide (0.36 g, 9.0 mmol). The mixture was stirred at 80° C. overnight. The reaction was filtered and concentrated under reduced pressure, and the resulting oily residue was purified by silica gel column chromatography using (PE/EtOAc, 5/1) to afford a colorless liquid of compound 35a (50 mg, 21%) as a mixture of isomers; TLC Rf: 0.38 (20% EtOAc/n-Hexanes); $^1$H NMR (400 MHz, CDCl$_3$): δ 9.31 (m, 1H), 8.71-8.70 (m, 1H), 8.36-8.33 (m, 1H), 7.40-7.37 (m, 1H), 6.29 (s, 1H), 5.08 (m, 1H), 2.32-2.04 (m, 7H), 1.67-1.58 (m, 6H). LCMS: MS (m/z): 270.3 (M+H); ret. time: 3.98 min.

(E)-5-(2,6-dimethylhepta-1,5-dien-1-yl)-3-(4-fluorophenyl)-1,2,4-oxadiazole (35b)

Similar to the preparation of 35a, the reaction of 33 with 34b afforded the desired compound 35b (80 mg, 31%) as colorless oil. TLC Rf: 0.30 (20% EtOAc/PE); $^1$H NMR (400 MHz, CDCl$_3$): δ 8.12-8.08 (m, 2H), 7.18-7.13 (m, 2H), 6.29 (m, 1H), 5.11 (m, 1H), 2.34-2.24 (m, 7H), 1.70-1.61 (m, 6H). LCMS: MS (m/z): 287.40 (M+H); ret. time: 8.19 min.

(E)-5-(2,6-dimethylhepta-1,5-dien-1-yl)-3-phenyl-1,2,4-oxadiazole (35c)

Similar to the preparation of 35a, the reaction of 33 with 34c afforded the desired compound 35c (50 mg, 21%) as colorless oil. TLC Rf: 0.32 (20% EtOAc/PE); $^1$H NMR (400 MHz, CDCl$_3$): δ 8.13-8.10 (m, 2H), 7.49-7.46 (m, 3H), 6.30 (br s, 1H), 5.12 (m, 1H), 2.35-2.25 (m, 7H), 1.70-1.63 (m, 6H). LCMS: MS (m/z): 269.20 (M+H); ret. time: 8.04 min.

(E)-5-(2,6-dimethylhepta-1,5-dien-1-O-3-(pyridin-4-yl)-1,2,4-oxadiazole (35d)

Similar to the preparation of 35a, the reaction of 33 with 34d afforded the desired compound 35c (40 mg, 17%) as colorless oil. TLC Rf: 0.24 (20% EtOAc/PE); $^1$H NMR (400 MHz, CDCl$_3$): δ 8.77-8.75 (m, 2H), 7.97-7.95 (m, 2H), 6.31 (s, 1H), 5.10 (m, 1H), 2.35-2.06 (m, 7H), 1.69-1.62 (m, 6H). LCMS: MS (m/z): 270.05 (M+H); ret. time: 3.42 min.

reduced pressure. The resulting oily residue was purified by a silica gel column chromatography using (petroleum ether/EtOAc=5/1) to afford a colorless liquid of compound 37a (20 mg, 16%); TLC Rf: 0.68 (20% EtOAc/petroleum ether); $^1$H NMR (400 MHz, CDCl$_3$): δ 5.12-5.08 (m, 3H), 3.85-3.80 (m, 1H), 3.70-3.65 (m, 1H), 2.17-1.87 (m, 12H), 1.69-1.62 (m, 6H), 1.34-1.16 (m, 12H). LCMS: MS (m/z): 386.6 (M+H); ret. time: 8.11 min.

(S)-4-isopropyl-2-((1E,5E,9E)-2,6,10,14-tetramethylpentadeca-1,5,9,13-tetraen-1-yl)oxazol-5(4H)-one (37b)

Similar to the preparation of 37a, the reaction of 25 with 36b afforded the desired compound 37b (15 mg, 12%) as colorless oil. TLC Rf: 0.34 (20% EtOAc/n-Hexanes); $^1$H NMR (400 MHz, CDCl$_3$): δ 5.12-5.08 (m, 3H), 3.85-3.80 (m,

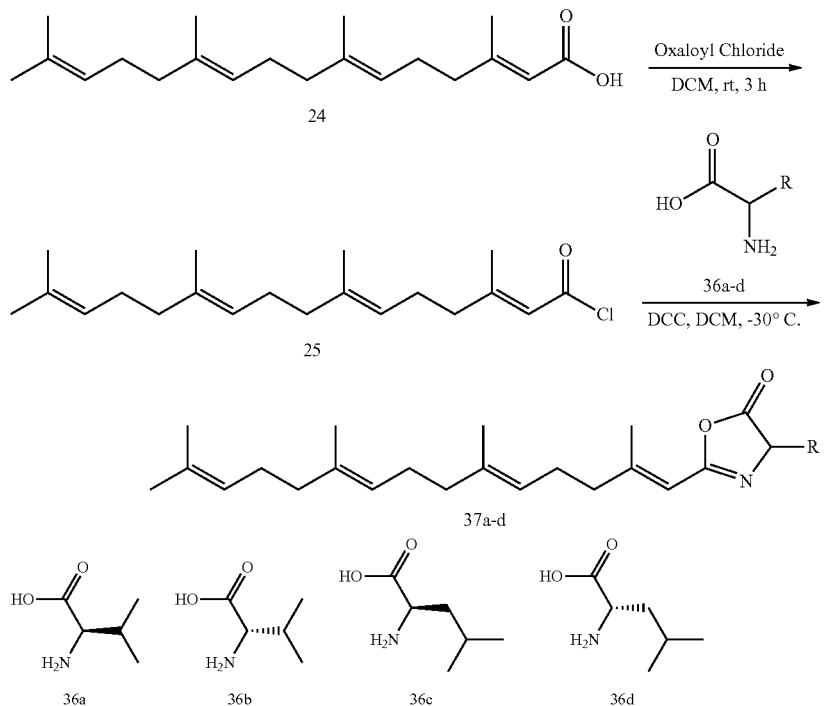

Scheme 26:

(R)-4-isopropyl-2-((1E,5E,9E)-2,6,10,14-tetramethylpentadeca-1,5,9,13-tetraen-1-yl)oxazol-5(4H)-one (37a)

A dry reaction flask equipped with a stir bar was charged with compound 24 (100 mg, 0.3 mmol), DCM (5 mL). Oxalyl chloride (37 mg, 0.3 mmol) was added dropwise and the resulting reaction was stirred at rt for 3 h. The mixture was concentrated to get compound 25, which was used directly for the next step. To the compound 25 in DCM (10 mL) at −30° C. were added compound 36a (44 mg, 0.3 mmol) and DCC (68 mg, 0.3 mmol) in DCM (2 mL) drop-wise. The mixture was stirred at −30° C. for 4 h and quenched with aqueous NaHCO$_3$ solution, extracted with DCM (3×10 mL). The DCM extract was washed with water (20 mL), dried over anhydrous Na$_2$SO$_4$ and solvent was evaporated under 1H), 3.70-3.65 (m, 1H), 2.17-1.87 (m, 12H), 1.69-1.62 (m, 6H), 1.34-1.16 (m, 12H). LCMS: MS (m/z): 386.35 (M+H); ret. time: 7.70 min.

(R)-4-isobutyl-2-((1E,5E,9E)-2,6,10,14-tetramethylpentadeca-1,5,9,13-tetraen-1-yl)oxazol-5(4H)-one (37c)

Similar to the preparation of 37a, the reaction of 25 with 36c afforded the desired compound 37c in 11% yield (0.015 g) as colorless oil. TLC Rf: 0.32 (20% EtOAc/n-Hexanes); $^1$H NMR (400 MHz, CDCl$_3$): δ 5.10-5.08 (m, 3H), 3.85-3.80 (m, 1H), 3.70-3.65 (m, 1H), 2.15-1.60 (m, 28H), 1.25-1.21 (m, 2H), 0.94-0.90 (m, 6H). LCMS: MS (m/z): 400.40 (M+H); ret. time: 4.22 min.

(S)-4-isobutyl-2-((1E,5E,9E)-2,6,10,14-tetramethyl-pentadeca-1,5,9,13-tetraen-1-yl)oxazol-5(4H)-one (37d)

Similar to the preparation of 37a, the reaction of 25 with 36d afforded the desired compound 37d (12 mg, 10%) as colorless oil. TLC Rf: 0.32 (20% EtOAc/n-Hexanes); $^1$H NMR (400 MHz, CDCl$_3$): δ 5.75-5.65 (m, 3H), 5.09-5.07 (m, 1H), 4.00-3.80 (m, 1H), 2.15-1.80 (m, 14H), 1.65-1.50 (m, 6H), 1.30-1.10 (m, 6H), 0.95-0.80 (m, 6H). LCMS: MS (m/z): 400.40 (M+H); ret. time: 4.98 min.

Scheme 27:

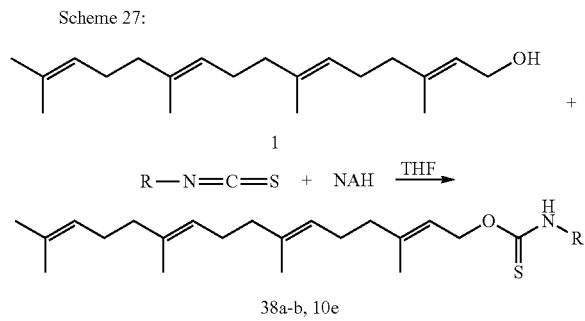

38a-b, 10e

O-((2E,6E,10E)-3,7,11,15-tetramethylhexadeca-2,6,10,14-tetraen-1-yl) pyridin-3-ylcarbamothioate (38a)

To a solution of NaH (60% dispersed in oil, 32 mg, 0.81 mmo) in THF (4 mL) at 0° C. was added alcohol 1 (180 mg, 0.62 mmol) in THF (1 mL) and the reaction mixture was stirred for 30 min at this temperature. Then 3-pyridyl isothiocyanate (169 mg, 124 mmol) in THF (1 mL) was added and stirred at rt. After stirring for 12 h, the reaction mixture was quenched water and extracted with EtOAc (3×). The organic layer was dried and concentrated to get a residue, which was purified by column chromatography (Hexane/EtOAc) to yield thiocarbamate 38a as a viscous liquid (179 mg, 70%). TLC Rf: 0.23 (20% EtOAc/hexanes); $^1$H NMR (300 MHz, CDCl$_3$): δ 8.55 (d, 1H), 8.40 (d, 1H), 7.95 (m, 1H), 7.30 (m, 2H), 5.49 (t, 1H), 5.11 (m, 3H), 4.70 (d, 2H), 2.16-1.19 (m, 12H), 1.76 (s, 3H), 1.68 (s, 3H), 1.60 (s, 9H); LCMS: MS (m/z): 427 (M+H).

O-((2E,6E,10E)-3,7,11,15-tetramethylhexadeca-2,6,10,14-tetraen-1-yl) (furan-2-ylmethyl)carbamothioate (38b)

Similar to the preparation of 38a, the reaction of alcohol 1 with 2-furanylmethyl isothiocyanate afforded the desired compound 38b in 23% yield (55 mg) as a viscous oil. Column (EtOAc/Hexane); TLC Rf: 0.65 (20% EtOAc/hexanes); $^1$H NMR (300 MHz, CDCl$_3$): δ 7.35 (s 1H), 6.35 (m, 1H), 5.15 (m, 3H), 5.04 (d, 0.4H), 4.95 (d, 0.6H), 4.75 (d, 0.6H), 4.42 (d 0.4H), 2.14-1.94 (m, 12H), 1.73 (s, 3H), 1.68 (s, 3H), 1.60 (s, 9H); LCMS: MS (m/z): 430.2 (M+H).

Alternative Synthesis of 10e

O-((2E,6E,10E)-3,7,11,15-tetramethylhexadeca-2,6,10,14-tetraen-1-yl) butylcarbamothioate (10e)

Similar to the preparation of 38a, the reaction of alcohol 1 with pentyl isothiocyanate afforded the desired compound 10e in 60% yield (135 mg) as a viscous oil. Column (EtOAc/Hexane); TLC Rf: 0.70 (10% EtOAc/hexanes); LCMS: MS (m/z): 406.1 (M+H).

Scheme 28:

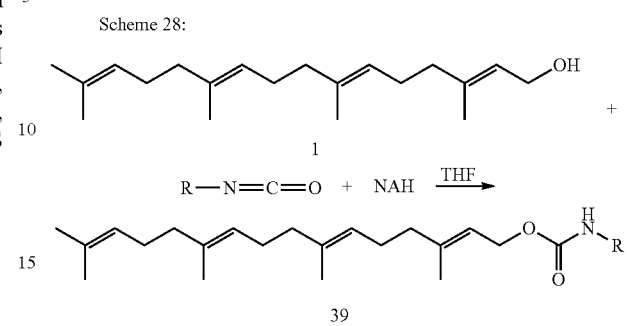

(2E,6E,10E)-3,7,11,15-tetramethylhexadeca-2,6,10,14-tetraen-1-yl pyridin-4-ylcarbamate (39)

Similar to the preparation of 38a, the reaction of alcohol 1 with 4-pyridyl isocyanate afforded the desired compound 39 in 3% yield (10 mg) as a viscous oil. Column (DCM/MeOH); TLC Rf: 0.34 (10% MeOH/DCM); LCMS: MS (m/z): 411 (M+H).

Scheme 29:

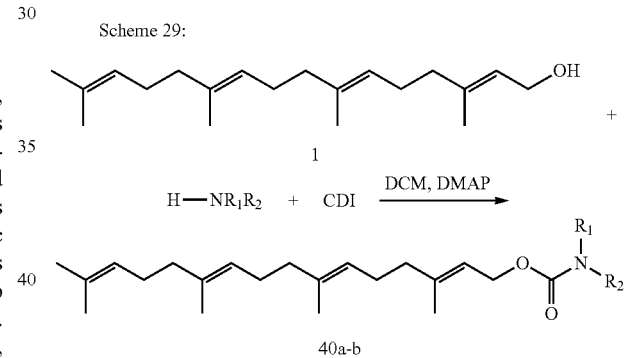

40a-b

2E,6E,10E)-3,7,11,15-tetramethylhexadeca-2,6,10,14-tetraen-1-yl 4-methylpiperazine-1-carboxylate (40a)

To a solution of alcohol 1 (160 mg, 55 mmol) in DCM (3 mL) at 0° C. was added carbonyldiimidazole (CDI) (107 mg, 0.66 mmol) and the reaction was stirred for 1 h. Then N-methylpiperazine (80 mg, 0.72 mmol) and DMAP (68 mg, 0.55 mmol) were added and stirred for 12 h. Solvent was removed and the residue was purified by column chromatography (DCM/MeOH) to give the carbamate 40a as a viscous oil in 88% yield (191 mg). TLC Rf: 0.54 (10% MeOH/DCM); $^1$H NMR (300 MHz, CDCl$_3$): δ 5.34 (t, 3H), 5.08 (m, 3H), 4.59 (d, 2H), 3.49 (m, 4H), 2.35 (m, 4H), 2.29 (s, 3H), 2.10-1.97 (m, 12H), 1.70 (s, 3H), 1.67 (s, 3H), 1.59 (s, 9H); LCMS: MS (m/z): 417 (M+H).

(2E,6E,10E)-3,7,11,15-tetramethylhexadeca-2,6,10,14-tetraen-1-ylpyridin-2-ylcarbamate (40b)

Similar to the preparation of 40a, the reaction of alcohol 1 with 2-aminopyridine and CDI afforded the desired compound 40b in 40% yield (30 mg) as a viscous solid. Column (DCM/MeOH); TLC Rf: 0.34 (10% MeOH/DCM); ¹H NMR (300 MHz, CDCl₃): δ 8.48 (s, 1H), 8.30 d, 1H), 7.95 (m, 1H), 6.65 (s, 1H), 5.40 (t, 1H), 5.11 (m, 3H), 4.70 (d, 2H), 2.16-1.94 (m, 12H), 1.76 (s, 3H), 1.69 (s, 3H), 1.61 (s, 9H); LCMS: MS (m/z): 411 (M+H).

(2E,6E,10E)-3,7,11,15-tetramethylhexadeca-2,6,10,14-tetraen-1-yl (3,5-dimethyladamantan-1-yl)carbamate (41)

Similar to the preparation of 40a, the reaction of alcohol 1 with memantine and CDI afforded the desired compound 41 as a viscous oil. Column (DCM/MeOH); TLC Rf: 0.70 (10% EtOAc/Hexanes).

O-((2E,6E)-3,7,11-trimethyldodeca-2,6,10-trien-1-yl) methylcarbamothioate (43)

Similar to the preparation of 38a, the reaction of alcohol 5 with methyl thioisocyanate afforded the desired compound 43 in 47% yield (316 mg) as a viscous oil as a mixture of isomers: TLC Rf: 38 (10% EtOAc/hexanes): ¹H NMR (300 MHz, CDCl₃): δ 6.5 (br s, 0.3H), 6.2 (br s, 0.7H), 5.40-5.39 (m, 1H), 5.09-5.08 (m, 2H), 5.03-5.01 (d, 0.7H), 4.97-4.94 (d, 1.3H), 3.09-3.08 (d, 2H), 2.88-2.86 (d, 1H), 2.12-1.96 (m, 8H), 1.73-1.72 (m, 3H), 1.68 (m, 3H), 1.60 (m, 6H). ¹³CNMR (75 MHz, CDCl₃): δ 143.1, 135.7, 131.6, 124.5, 123.8, 118.9, 118.2, 69.2, 67.6, 39.9, 39.8, 21.1, 30.0, 26.9, 26.4, 26.0, 18.0, 17.0, 16.9, 16.3.

Formulations and Pharmacokinetics (PK) Studies

With a view to administer the geranylgeranyl acetone (GGA) effectively to determine its PK and efficacy, preclinical research formulations, exemplified in Examples 8-12, 20, 21. 24-28, 31-39, 42 & 45, have been developed. The use of isomeric mixture of 5E- and 5Z-geranylgeranyl acetone (referred as GGA) was employed during the development of preclinical research formulations. It is contemplated that synthesized compositions of 5E- and/or 5Z-GGA can be used in such preclinical research formulations.

In the following examples, Plasma concentrations and PK parameters were obtained from CNS-101 IV dosing and oral formulation PK studies. PK Parameters were calculated from noncompartmental analysis (NCA) model using WinNonlin software and the linear/log trapezoidal method.

Definitions for PK Parameters:

Parameters that do not require 1z: $T_{max}$ (min): Time to reach $C_{max}$ (directly taken from analytical data).

Parameters that requires 1z: Terminal Half-Life $(t_{1/2})$=ln(2)/lz. Calculated using Lambda_z method to find best fit. If necessary, the concentration-time points were manually selected for use in the calculation. Bolded-italicized concentrations indicate points used for calculation.

Bioavailability $$F(\%) = \text{Bioavailability} = \frac{AUC(PO)/\text{Dose}(PO)}{AUC(PO)/\text{Dose}(PO)} \times 100$$

Example 8

GGA Formulation Using 5% Gum Arabic with 0.008% α-tocopherol

TABLE 3

| | Using 5% Gum Arabic with 0.008% α-tocopherol | | |
|---|---|---|---|
| Entry | Gum Arabic (μL) | GGA (μL) | GGA (%)* |
| 1. | 190 μL | 10 μL | 5% |
| 2. | 180 μL | 20 μL | 10% |
| 3. | 160 μL | 40 μL | 20% |
| 4. | 140 μL | 60 μL | 30% |

*The % ratios are based on volumes

Preparation of 5% Gum Arabic Solution 1.25 g of Gum Arabic was suspended in DI water (23.75 mL; until the total volume was 25 mL) and agitated using agitator until all Gum Arabic was miscible in DI water. To this solution was added α-tocopherol (2 μl, final concentration=0.008) and agitated to obtain a solution of 5% gum Arabic, which was then used as a stock solution to formulate GGA.

Preparation of GGA Suspension in 5% Gum Arabic Aqueous Solution

To a respective amount of 5% of Gum Arabic solution from the stock, the corresponding amount of GGA was added and the resulting mixture was agitated and sonicated to obtain an aqueous suspension formulation.

The in-vivo PK studies by using rat species with GGA in 5% Gum Arabic as an aqueous suspension formulation resulted in 37.3% oral bioavailability (% F) with t½=3.43 h and $T_{max}$=7.33 h. The in-vivo studies to obtain Kp, which is a ratio of $AUC_{brain}$ to $AUC_{plasma}$, was done in rat species at 4 h, 6 h, 8 h, and 10 h time points and found that the GGA has Kp from 0.08 to 0.11.

Example 9

GGA Formulation Using Hydroxypropyl Cellulose (HPC; Av. Mn=100,000; High Average Molecular Weight) with 0.008% α-tocopherol

TABLE 4

| | Hydroxypropyl Cellulose (HPC; Av. Mn = 100,000; High Average Molecular Weight) with 0.008% α-tocopherol | | |
|---|---|---|---|
| Entry | 3% HPC (μL) | GGA (μL) | GGA (%)* |
| 1. | 475 μL | 25 μL | 5% |
| 2. | 450 μL | 50 μL | 10% |
| 3. | 425 μL | 75 μL | 15% |
| 4. | 400 μL | 100 μL | 20% |

*The % ratios are based on volumes

Preparation of 3% Hydroxypropyl Cellulose Solution

To a mixture of 3 g of hydroxypropyl cellulose (Av. Mn=100,000) and α-tocopherol (8 μl, final concentration=0.008%) was added DI water (~97 mL) until the total volume reached 100 mL. The resulting mixture was agitated to obtain a stock solution to formulate the GGA.

Preparation of GGA suspension in 3% Hydroxypropyl Cellulose Aqueous Solution

To a respective amount of 3% of hydroxypropyl cellulose solution from the stock, the corresponding amount of GGA was added and the resulting mixture was agitated to obtain an aqueous suspension formulation.

The in-vivo PK studies by using rat species with GGA in 3% Hydroxypropyl Cellulose (HPC, Av, Mn=100,000) as an aqueous suspension formulation resulted in 41.8% oral bioavailability (% F) with t½=3.13 h and $T_{max}$=8.66 h.

Example 10

GGA Formulation Using Hydroxypropyl Cellulose (HPC; Av. Mn=10,262; Low Average Molecular Weight) with 0.008% α-tocopherol

TABLE 5

Hydroxypropyl Cellulose (HPC; Av. Mn = 10,262; Low Average Molecular Weight) with 0.008% α-tocopherol

| Entry | 3% HPC (μL) | GGA (μL) | GGA (%)* |
|---|---|---|---|
| 1. | 475 μL | 25 μL | 5% |
| 2. | 450 μL | 50 μL | 10% |
| 3. | 425 μL | 75 μL | 15% |
| 4. | 400 μL | 100 μL | 20% |

*The % ratios are based on volumes

Preparation of 3% Hydroxypropyl Cellulose Solution

To a mixture of 3 g of hydroxypropyl cellulose (Av. Mn=10,262) and α-tocopherol (8 μl, final concentration=0.008%) was added DI water (~97 mL) until the total volume reached 100 mL. The resulting mixture was agitated to obtain a stock solution to formulate the GGA.

Preparation of GGA Suspension/Solution in 3% Hydroxypropyl Cellulose Solution

To a respective amount of 3% of hydroxypropyl cellulose solution from the stock, the corresponding amount of GGA was added and the resulting mixture was agitated to obtain an aqueous suspension formulation.

The in-vivo PK studies by using rat species with GGA in 3% Hydroxypropyl Cellulose (HPC, Av, Mn=10,262) as an aqueous suspension formulation resulted in 35% oral bioavailability (% F) with t½=18.73 h and $T_{max}$=9.33 h.

Example 11

GGA Formulation Using 5% Gum Arabic+3% Hydroxypropyl Cellulose (HPC; Av. Mn=100,000; High Average Molecular Weight) and with 0.008% α-tocopherol

TABLE 6

5% Gum Arabic + 3% Hydroxypropyl Cellulose (HPC; Av. Mn = 100,000; High Average Molecular Weight) and with 0.008% α-tocopherol

| Entry | 5% Gum Arabic (0.008% α-tocopherol) (μL) | 3% HPC | GGA (μL) | GGA (%)* |
|---|---|---|---|---|
| 1. | 460 μL | 15 mg | 25 μL | 5% |
| 2. | 450 μL | 15 mg | 50 μL | 10% |
| 3. | 410 μL | 15 mg | 75 μL | 15% |
| 4. | 385 μL | 15 mg | 100 μL | 20% |

*The % ratios are based on volumes

A. Preparation of 5% Gum Arabic Solution 1.25 g of Gum Arabic was suspended in DI water (23.75 mL; until the total volume was 25 mL) and agitated using agitator until all gum Arabic was miscible in DI water. To this solution was added α-tocopherol (2 μL, 0.008%) and agitated for a minute to obtain 5% gum Arabic Preparation of GGA Suspension/Solution in 5% Gum Arabic+3% Hydroxypropyl Cellulose (Av. Mn=100,000)

To a respective amount of 5% of Gum Arabic solution from the stock, the corresponding amount of GGA and hydroxypropyl cellulose (Av. Mn=100,000) were added and the resulting mixture was agitated to obtain an aqueous suspension formulation.

The in-vivo PK studies by using rat species with GGA in 5% Gum Arabic+3% Hydroxypropyl Cellulose (Av. Mn=100,000) as an aqueous suspension formulation resulted in 58% oral bioavailability (% F) with t½=10.2 h and $T_{max}$=5.33 h.

Example 12

GGA Formulation Using 5% Gum Arabic+3% Hydroxypropyl Cellulose (HPC; Av. Mn=10,262; Low Av. Molecular Weight) and with 0.008% α-tocopherol

TABLE 7

5% Gum Arabic + 3% Hydroxypropyl Cellulose (HPC; Av. Mn = 10,262; Low Av. Molecular Weight) and with 0.008% α-tocopherol

| Entry | 5% Gum Arabic (0.008% α-tocopherol) (μL) | 3% HPC | GGA (μL) | GGA (%)* |
|---|---|---|---|---|
| 1. | 460 μL | 15 mg | 25 μL | 5% |
| 2. | 450 μL | 15 mg | 50 μL | 10% |

TABLE 7-continued

5% Gum Arabic + 3% Hydroxypropyl Cellulose (HPC; Av. Mn = 10,262; Low Av. Molecular Weight) and with 0.008% α-tocopherol

| Entry | 5% Gum Arabic (0.008% α-tocopherol) (µL) | 3% HPC | GGA (µL) | GGA (%)* |
|---|---|---|---|---|
| 3. | 410 µL | 15 mg | 75 µL | 15% |
| 4. | 385 µL | 15 mg | 100 µL | 20% |

*The % ratios are based on volumes

A. Preparation of 5% Gum Arabic Solution 1.25 g of Gum Arabic was suspended in DI water (23.75 mL; until the total volume was 25 mL) and agitated until all gum Arabic was miscible in DI water. To this solution was added α-tocopherol (2 µl, final concentration=0.008%) and agitated for a minute to obtain a solution of 5% gum Arabic, which was then used as a stock solution to formulate GGA.

Preparation of GGA Suspension/Solution in 5% Gum Arabic+3% Hydroxypropyl

Cellulose (Av. Mn=100,000): To a respective amount of 5% of Gum Arabic solution from the stock, the corresponding amount of GGA and hydroxypropyl cellulose (Av. Mn=10,262) were added and the resulting mixture was agitated to afford an aqueous suspension.

The in-vivo PK studies by using rat species with GGA in 5% Gum Arabic+3% Hydroxypropyl Cellulose (Av. Mn=10,262) as an aqueous suspension formulation resulted in 36.5% oral bioavailability (% F) with $t\frac{1}{2}$=6.73 h and $T_{max}$=13.3 h.

Example 13

Culturing of Primary Motor Neurons from Rats

Rat primary motor neurons were isolated from embryonic spinal cords in accordance with the method of Henderson et al.; J Cohen and G P Wilkin (ed.), Neural Cell Culture, (1995) p 69-81 which is herein incorporated by reference in its entirety. Briefly, spinal cords were dissected from day 15 embryo (E15) and incubated in a trypsin solution, and followed by DNase treatment to release spinal cord cells from tissue fragments. The cell suspension was centrifuged to remove tissue fragments. Then motor neurons were enriched by density gradient centrifugation.

Motor neurons were cultured in serum-free neurobasal medium containing insulin, forskolin, 3-isobutyl-1-methylxanthine, neurotrophic factors, Bovine serum albumin, selenium, transferrin, putrescine, progesterone and B27 supplement in tissue culture plate coated with poly-ornithine and laminin.

Example 14

5-trans Isomer of GGA (CNS-102) is More Efficacious In Vitro than the Isomer Mixture of GGA (CNS-101)

Rat primary motor neurons were prepared and cultured as described in Example 13. Various concentration of CNS-101, which is a mixture of 5-trans and 5-cis isomer (cis:trans ratio=1:2-1:3). CNS-102 (herein also referred to as 5-trans isomer of GGA), and CNS-103 (herein also referred to as 5-cis isomer of GGA) were added to the culture at the time of plating the cells. The cells extending axons were counted in five different fields for each treatment after 72 hrs. Percentage of positive cells relative to total cells in the same magnification field was calculated and the results were expressed as means +/– standard deviations, n=5. The $EC_{50}$ is a measure of the effectiveness of a compound, and corresponds to the concentration at which the drug exhibits half its maximum effect. These results are depicted in the table below:

| GGA | $EC_{50}$ |
|---|---|
| CNS-101 | 6.1 nM (4-7 nM)* |
| CNS-102 | 0.92 nM (0.5-2.0 nM)* |
| CNS-103 | 9.49 nM (8-12 nM)* |

*values in parenthesis indicate a reasonable range expected for the $EC_{50}$

Example 15

A Large Quantity of GGA Isomer Mixture (CNS-101) Inhibited Viability of Neuroblastoma Cells Human SH-SY5Y neuroblastoma cells were culture in DMEM/HAM F12 supplemented with 10% fetal bovine serum (FBS) for 24 hrs. The cells were treated with retinoic acid in DMEM/HAM F12 medium supplemented with 5% FBS for 48 hrs. Then the cells were treated with CNS-101 (100 micro molar (µM)) or vehicle, dimethyl sulfoxide for 48 hrs. Cell viability was determined using ATP detection assay (Promega). These results are depicted in the table below:

| GGA | Mean of cell viability (arbitrary units) | SE |
|---|---|---|
| 100 µM CNS-101 | 1181020 | 25815 |
| Vehicle | 1340600 | 23409 |
| P < 0.001 | | |

Example 16

A Large Quantity of GGA Isomer Mixture (CNS-101) and Cis-Isomer (CNS-103) Inhibited Viability of Neuroblastoma Cells Mouse Neuro2A neuroblastoma cells were cultured in DMEM supplemented with 10% FBS for 24 hrs. The cells were treated with various concentrations of CNS-101, CNS-102, and CNS-103 as indicated for 48 hrs. Then differentiation was induced by retinoic acid in DMEM supplemented with 2% FBS. The cell culture was incubated with a Geranylgeranyl Transferase inhibitor, GGTI-298. After 24 hrs incubation, cells with neurites were counted. A large quantity of GGA isomer mixture (CNS-101) and the cis-isomer (CNS-103) can inhibit viability of neuroblastoma cells. These results are depicted in the table below:

| GGA | Mean of cell numbers (Arbitrary units) | SE |
|---|---|---|
| CNS-101 (10 µM) | 0.551 | 0.1333 |
| CNS-102 (10 µM) | 0.738 | 0.0018 |
| CNS-103 (10 µM) | 0.195 | 0.0933 |
| P < 0.03 | | |

The data in examples 154 and 16 support the conclusion that the cis isomer, CNS-103, can have a deleterious effect on cell viability and that the trans isomer has a positive effect. The two examples taken together suggest that at higher concentrations, the cis isomer can have an inhibitory effect on the trans isomer.

Example 17

Effects of the GGA Isomer Mixture (CNS-101) on Cells Experiencing Oxidative Stress Human SH-SY5Y neuroblastoma cells were culture in DMEM/HAM F12 supplemented with 10% fetal bovine serum (FBS) for 2 days. The cells were treated with retinoic acid in DMEM/HAM F12 medium supplemented with 5% FBS for 48 hrs. Then the cells were treated with various concentrations of CNS101 for 48 hrs. Cells were exposed to hydrogen peroxide (75 micro M) or DMEM/HAM F12 (control) for 2 hrs, then cell viability was determined using ATP assay (Promega). These results are depicted in the table below:

| GGA | Mean of cell viability |
| --- | --- |
| CNS-101 (10 μM) | 6-10% |
| Vehicle | 3-5% |

100% of cell viability was evaluated in the absence of hydrogen peroxide and CNS-101.

Example 18

Effects of the GGA Isomer Mixture (CNS-101), the Trans-Isomer (CNS-102) and the Cis-Isomer (CNS-103), and an Inhibitor of a G-Protein (GGTI-298), on the Viability of Cells Neuro2A cells were cultured with CNS-101, CNS-102, or CNS-103 in the presence or absence of an inhibitor against a G-protein (GGTI-298). After differentiation was induced, cells that extended neurites were counted. These results are depicted in the table below:

| GGA | Mean of cell numbers (Arbitrary units) |
| --- | --- |
| CNS-101 (0.1-1 μM) | 0.45-0.65 |
| CNS-102 (0.1-1 μM) | 0.45-0.65 |
| CNS-103 (0.1-1 μM) | 0.20-0.45 |
| Vehicle | 0.0-0.20 |

Example 19

The GGA Isomer Mixture (CNS-101) Activated Neurite Outgrowth of Neuroblastoma Cells Human SH-SY5Y neuroblastoma cells were cultured in DMEM/HAM F12 supplemented with 10% fetal bovine serum (FBS) for 24 hrs. The cells were treated with retinoic acid in DMEM/HAM F12 medium supplemented with 5% FBS. Then the cells were treated with various concentrations of CNS-101. Total length of neurites for each treatment was measured. These results are depicted in the table below:

| GGA | Mean of neurite outgrowth |
| --- | --- |
| CNS-101 (0.1 μM) | 125% |
| CNS-101 (1 μM) | 166% |
| CNS-101 (10 μM) | 194% |
| Vehicle | 100% |

Data were spread in a range of +/−10% from each mean.

Example 20

The GGA Isomer Mixture (CNS-101) and the Trans-Isomer (CNS-102) Alleviated Neurodegeneration Induced by Kainic Acid CNS-101 or CNS-102 were orally dosed to Sprague-Dawley rats, and Kainic acid was injected. Seizure behaviors were observed and scored (Ref. R. J. Racine, Modification of seizure activity by electrical stimulation: II. Motor seizure, Electroencephalogr. Clin. Neurophysiol. 32 (1972) 281-294. Modifications were made for the methods). Brain tissues of rats were sectioned on histology slides, and neurons in hippocampus tissues were stained by Nissl. Neurons in dentate gyrus tissues damaged by Kainic acid were quantified. The Memantine composition used in comparison refers to a commercially available NMDA receptor agonist. These results are depicted in the tables below:

| GGA | Hippocampus dentate gyrus neurons damaged (Arbitrary units) |
| --- | --- |
| CNS-101 | 0.725 |
| Vehicle | 20.9 |
| Memantine | 3.53 |
| P-value to vehicle data | P < 0.05 |

| GGA | Seizure behaviors scores |
| --- | --- |
| CNS-102 | 18.8 |
| Vehicle | 34 |
| Memantine | 36.2 |
| P-value to vehicle data | P < 0.11 |

Example 21

Comparison of the Efficacy of CNS-101 and CNS-102 in Alleviating Neurodegeneration Induced by Kainic Acid CNS-101, CNS-102 or a vehicle only control were orally dosed to Sprague-Dawley rats, and Kainic ainic acid was injected. Seizure behaviors were observed and scored (Ref. R. J. Racine, Modification of seizure activity by electrical stimulation: II. Motor seizure, Electroencephalogr. Clin. Neurophysiol. 32 (1972) 281-294. Modifications were made for the methods). Brain tissues of rats were sectioned on histology slides, and neurons in hippocampus tissues were stained by Nissl. Neurons damaged by Kainic acid and behavior scores were quantified.

These results indicate that a lower concentration of the trans-isomer of GGA is more efficacious at protecting neurons from neuronal damage than a higher concentration of either the isomer mixture of the cis-isomer of GGA. Furthermore, it is contemplated that such effects of trans-GGA also renders it useful for protecting tissue damage during seizures, ischemic attacks, and neural impairment such as in glaucoma.

| GGA | Mean of Hippocampus CA3 neurons damaged (Arbitrary units) | Mean of Seizure behaviors scores |
|---|---|---|
| CNS-102 (3 mg/Kg rat) | 10.25 | 27.5 |
| CNS-102 (12 mg/Kg rat) | 10.16 | 22.5 |
| Vehicle | 37.67 | 50.5 |
| P value to vehicle data | $P < 0.085$ | $P < 0.165$ |

| GGA | Mean of Hippocampus CA3 neurons damaged (Arbitrary units) | Mean of Seizure behaviors scores |
|---|---|---|
| CNS-102 (25 mg/Kg rat) | 1.97 | 25.75 |
| Vehicle | 9.43 | 38 |
| P value to vehicle data | $P < 0.142$ | $P < 0.025$ |

| GGA | Mean of Hippocampus CA3 neurons damaged (Arbitrary units) | Mean of Seizure behaviors scores |
|---|---|---|
| CNS-101 (25 mg/Kg rat) | 37.38 | 33.83 |
| Vehicle | 38.77 | 28.5 |

| GGA | Mean of Hippocampus CA3 neurons damaged (Arbitrary units) |
|---|---|
| CNS-103 (12 mg/Kg rat) | 8.16 |
| CNS-103 (25 mg/Kg rat) | 10.64 |
| Vehicle | 10.71 |

Example 22

GGA's Effect on the Activity of G Proteins in a Neuron

Neuroblastoma cells can be obtained from the American Type Culture Collection (ATCC) and cultured according to the suggested culturing techniques of ATCC. The cultured cells will be contacted with an effective amount of GGA. The change in G protein activity will be monitored by a western blot of lysates obtained from subcellular fractionation of cells. Subcellular fractionation can be performed using commercially available kits (from Calbiochem for example) according to the manufacturer's protocol. The western analysis will be performed using subcellular fractions from the membrane and cytoplasmic compartments of cells. The western blot will be performed according to standard molecular biology techniques using antibodies directed to the different G proteins: RHOA, RAC1, CDC42, RASD2. It is contemplated that reacting the neuroblastoma cells with an effective amount of GGA will modulate the active, membrane-bound portion of RHOA, RAC1, CDC42, and/or RASD2. Interaction of those small G-proteins with gene products involved in protein aggregations will also be tested. Those gene products include Huntington gene product (Htt), sumoylation machinery, etc.

The same assay will be performed using neuroblastoma cells or other neurons that are depleted for the TDP-43 protein. TDP-43 depleted cells mimic the effects of neurodegeneration related to ALS. TDP-43 depletion can be accomplished using the siRNA and/or shRNA technologies. It is contemplated that neurons which are susceptible to neurodegeneration by TDP-43 depletion will have a change in the G protein activity after said neurons are contacted with an effective amount of GGA. It is further contemplated that reacting said neurons with an effective amount of GGA will increase the active membrane-bound portion of the G proteins.

The same assay will be performed using neuroblastoma cells or other neurons that are susceptible to neurodegeneration due to inhibition of geranylgeranylation of the G proteins. GGTI-298 is a specific inhibitor of geranylgeranylation and increases neuronal cell death through inhibiting the activation of G proteins by geranylgeranylation. Therefore, GGTI-298 and GGA will both be contacted with tissue cultures of neuroblastoma cells. It is contemplated that neurons which are susceptible to neurodegeneration by GGTI-298 will have a change in the G protein activity after said neurons are contacted with an effective amount of GGA. It is further contemplated that reacting said neurons with an effective amount of GGA will increase the active membrane-bound portion of the G proteins.

Example 23

GGA's Effect on the Pathogenicity of Protein Aggregates in Neurons Susceptible to Neurodegeneration Cultured neuroblastoma cells can be made susceptible to neurodegeneration by mixing the cells with dopamine. The addition of dopamine to the cells will cause pathogenic protein aggregates in the cytoplasm. To test the effect of GGA on neurons susceptible to neurodegeneration, an effective amount of dopamine will be first contacted with the neurons to induce pathogenic protein aggregate formation in the cells. Next, an effective amount of GGA will be contacted with said neurons. The change in the size and/or number of protein aggregates will then be measured using histological staining techniques and/or immunostaining techniques commonly known to one skilled in the art. It is contemplated that contacting GGA with neurons susceptible to neurodegeneration due to dopamine-induced protein aggregation will solubilize at least a portion of the protein aggregate, thus decrease the pathogenicity to the cell. It is further contemplated that contacting GGA with neurons susceptible to neurodegeneration due to dopamine-induced protein aggregation will alter the form of the pathogenic protein aggregate into a non-pathogenic form, thus decrease the pathogenicity to the cell.

Contacting neurons in vitro with β-amyloid peptide aggregates will recapitulate the toxic effects of AD due to β-amyloid peptide aggregates in vivo. To test if GGA reduces the pathogenicity of β-amyloid peptide aggregates in cultured neuroblastoma cells, the β-amyloid peptide aggregates will be added directly to the cell culture medium of the cultured cells. The β-amyloid peptide can be purchased commercially and aggregated in vitro. An effective amount of GGA will then be added to the cell culture to test for a modulation of the pathogenicity to the cells. It is contemplated that contacting GGA with neurons susceptible to neurodegeneration due to β-amyloid peptide aggregation will solubilize at least a portion of the protein aggregate, thus decrease the pathogenicity to the cell. It is further contemplated that contacting GGA with neurons susceptible to neurodegeneration due to β-amyloid peptide aggregation will alter the form of the pathogenic protein aggregate into a non-pathogenic form, thus decrease the pathogenicity. The change in the size and/or number of protein aggregates will then be measured using histological staining techniques and/or immunostaining techniques commonly known to one skilled in the art.

Example 24

GGA's Effect In Vivo in Mammals Susceptible to Neurodegeneration

Neurotoxins can be used to recapitulate the effect of AD in mice. To test the effects of administering GGA to a mammal that is susceptible to AD, neurotoxins will be administered systemically or by direct injection into the brain tissues of mice to induce the pathology associated with AD either before, simultaneously, or after the administration of GGA. The GGA may be administered to said mice mixed with a pharmaceutically acceptable excipient. These mice will then be monitored for survival rate, neuron and synaptic density in brain tissues, as well as learning, memory, anxiety-related behavior and motor skills. The learning, memory, anxiety-related behavior and motor skills measured by techniques commonly known to one skilled in the art. It is contemplated that treating the animal with an effective amount of GGA will attenuate symptoms associated with the injection of the neurotoxin.

There are a variety of mouse models available that are engineered to have the same pathology associated with different human diseases. One such mouse model over-expresses the human Amyloid beta Precursor Protein (hAPP) with familial Alzheimer's Disease (FAD)—associated mutations and exhibits a similar pathology to that of human AD. An effective amount of GGA will be administered to mice over-expressing mutant hAPP. The GGA may be administered to said mice mixed with a pharmaceutically acceptable excipient. These mice will then be monitored for body weight, plaque formation, soluble forms of β-amyloid, learning, memory, anxiety-related behavior and motor skills. Histology sections of these mice will also be analyzed by staining and immunohistochemical techniques to detect changes in the brain after GGA administration. It is contemplated that treating the animal with an effective amount of GGA will attenuate some of the symptoms associated with AD.

Mice expressing a Sod1 mutant protein exhibit similar pathology to humans with ALS. An effective amount of GGA will be administered to Sod1 mutant mice. The GGA may be administered to said mice mixed with a pharmaceutically acceptable excipient. These mice will then be monitored for survival rate, body weight, and motor skills. Histology sections of these mice will also be analyzed by histology staining and immunohistochemical techniques to detect changes in the brain, spinal cords, or muscles after GGA administration. It is contemplated that treating the Sod1 mutant mice with an effective amount of GGA will increase the survival rate, body weights, and enhance the motor skills of these mice.

Example 25

Effects of 5-trans Isomer of GGA on Neurological Function and Clinical Score in Sod1 Mutant Mice Wild type and Sod1 mutant mice (mice carrying multiple copies of the SOD1 mutant gene) were treated with 12 mg/kg of CNS-102 (5-trans GGA; N=16 Sod1 mutant mice and N=10 WT mice), 8 mg/kg of Riluzole (N=16 Sod1 mutant mice), or with vehicle alone (N=16 Sod1 mutant mice and N=10 WT mice). Drug or vehicle alone was administered once a day continuously for 62 days, from age 38 days to age 150 days. The percentage survival rate for each of the treated groups was calculated up to 150 days of age, and blood from animals in each group at P100 was analyzed for levels of alkaline phosphatase, alanine transaminase/serum glutamic pyruvic transaminase (ALT/SGPT); aspartate transaminase/ serum glutamic oxaloacetic transaminase (AST/SGOT), albumin, total protein, albumin, blood urea nitrate (BUN), creatinine cholesterol, and glucose, as well as the albumin/ globulin ratio.

Figure 2:
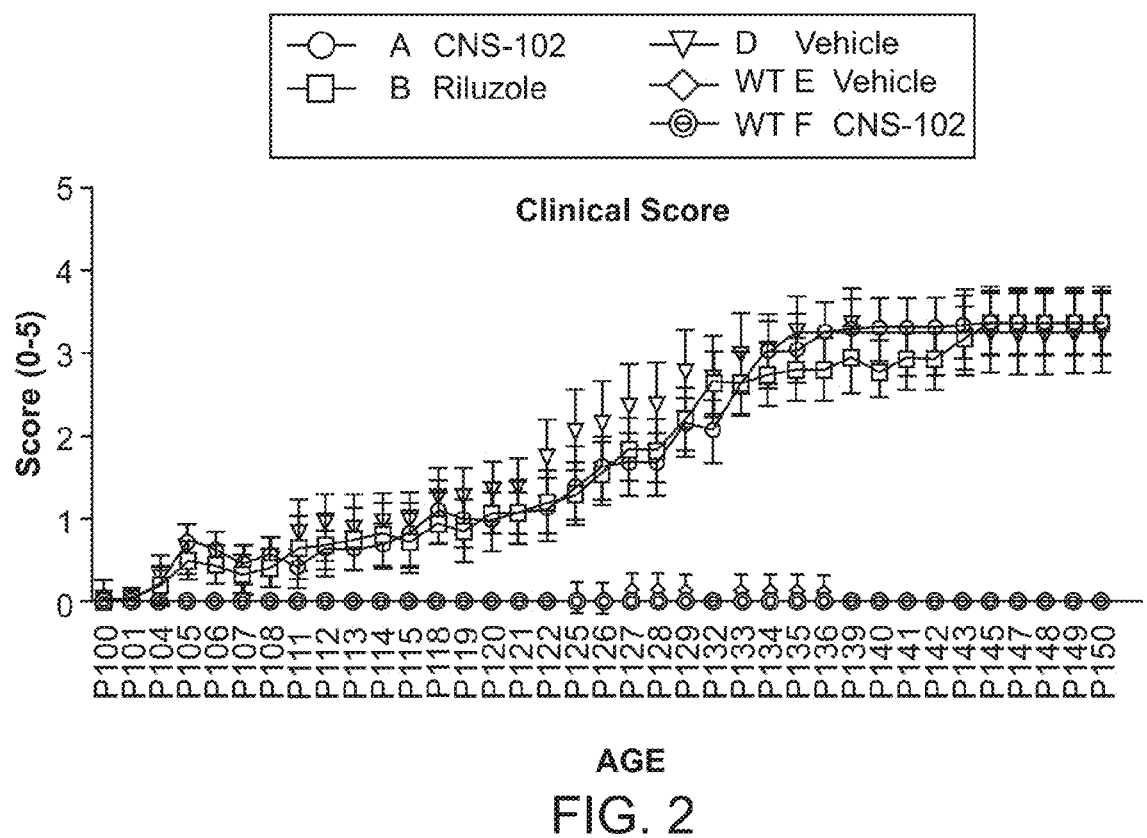
FIG. 2 shows imputed clinical scores of in vivo tests.
Figure 3:
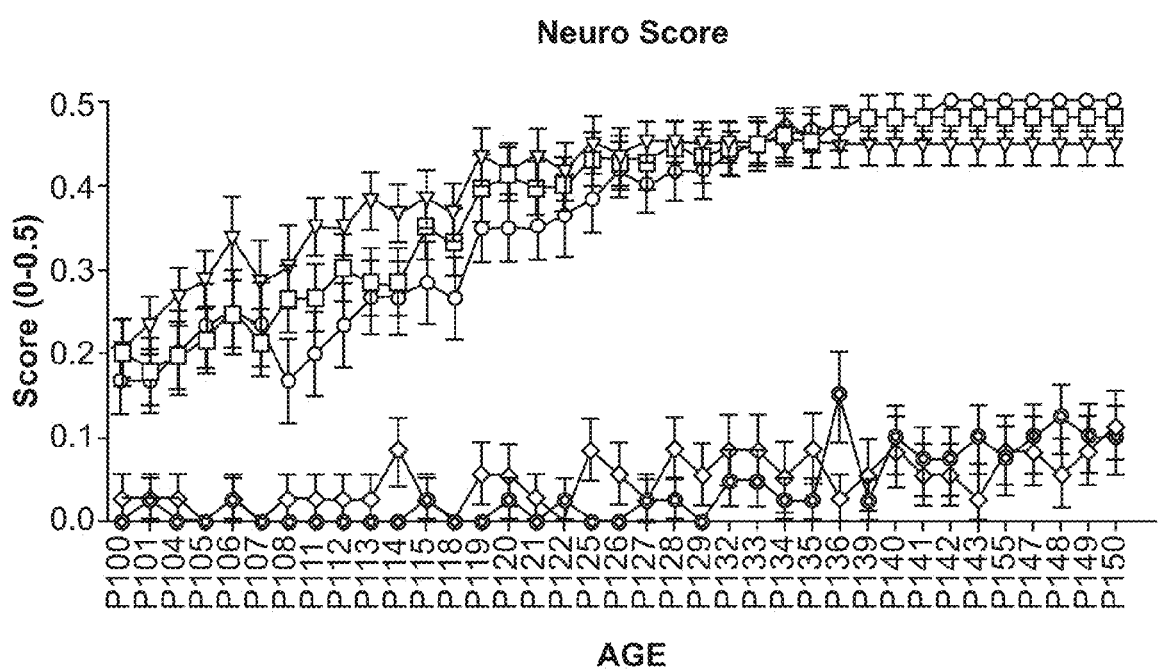
FIG. 3 shows imputed neuroscores of in vivo tests.

Effect of CNS-102 on Neurological Function and Clinical Score are described below. In clinical and neuroscore testing, shown in FIGS. 2 and 3, group A (CNS-102) and B (Riluzole) tended to outperform group D (vehicle). At several timepoints around and after P100, group A significantly outperforms group D in neuroscore testing, suggesting treatment with CNS-102 might be more effective in delaying onset or progression of symptoms. A similar trend was seen in clinical score testing.

Animals that did not survive until the terminal date (P150) were assigned their last score before death on subsequent testing days. No significant interaction ($p=0.9987$) in two-way repeated measure ANOVA analysis is found in the clinical scores test. Interaction between time and treatment is significant ($p=0.0012$) in neurological score performance. Group A and D differ significantly at timepoint P111 ($p<0.05$). Values represent means±SEMs.

Blood tests were performed on blood samples from animals in each group at P100 to evaluate the safety and efficacy of CNS-102. These results are tabulated below:

| TREATMENT/ GENOTYPE | ALKALINE PHOSPHATASE U/L | SGPT (ALT) U/L | SGOT (AST) U/L | ALBUMIN g/dL | TOTAL PROTEIN g/dL | GLOBULIN g/dL |
|---|---|---|---|---|---|---|
| CNS-102/SOD | 42 | 28.3 | 54.7 | 2.1 | 4.9 | 2.8 |
| Riluzole/SOD | 76.5 | 28.7 | 45.8 | 2.7 | 5.5 | 2.7 |
| Vehicle/SOD | 89.5 | 41 | 52.2 | 2.8 | 5.4 | 2.6 |
| Vehicle/WT | 70 | 56.4 | 70.5 | 2.6 | 5.7 | 2.7 |
| CNS-102/WT | 70.7 | 37.8 | 46.3 | 2.6 | 5.3 | 2.5 |

| TREATMENT/ GENOTYPE units | BUN mg/dL | CREATININE mg/dL | CHOLESTEROL mg/dL | GLUCOSE mg/dL | A/G RATIO N/A |
|---|---|---|---|---|---|
| CNS-102/SOD | 26.3 | <1 | 75 | 246 | 0.8 |
| Riluzole/SOD | 31.2 | <1 | 76.6 | 253.8 | 1 |
| Vehicle/SOD | 29 | <1 | 82 | 272 | 1.1 |
| Vehicle/WT | 28 | <1 | 85.7 | 223.8 | 1 |
| CNS-102/WT | 28.8 | <1 | 72.4 | 207.6 | 1 |

There were no abnormalities in blood and neurology examinations after more than two months of continuous once-daily oral dosing of 12 mg/kg CNS-102. Surprisingly, cholesterol levels were reduced after administration of CNS-102, suggesting that 5-trans GGA may provide benefits other than neuroprotection, such as the reduction of cholesterol levels.

Thus, the 5-trans-isomer of GGA administered to Sod1 mice increases their survival over mice treated with Riluzole and with vehicle alone and has been shown to be safe for continuous daily administration. In addition, these results suggest that daily administration of CNS-102 may reduce cholesterol levels in mice.

Example 26

Effects of 5-trans Isomer of GGA's on Survival, Behavior, and Pathology in Sod1 Mutant Mice A study was undertaken to examine the effect of treatment with CNS-102 (a 5-trans isomer of GGA) and/or Riluzole on survival, behavior, and pathology of Sod1 transgenic mice.

Materials and Methods

A total of 84 male mice (64 transgenic Sod1 mutant mice; 20 wild type mice) were included in the study. Dosing was administered daily beginning at postnatal day 38 (P38) via a single bolus oral gavage injection. Sod1 mutant mice were randomized into experimental groups and administered vehicle, CNS-102 (12 mg/kg), Riluzole (8 mg/kg). Wild type mice were randomized into two experimental groups and either administered vehicle alone or CNS-102 (12 mg/Kg).

Subjects were weighed and tested for Grip Strength, and assigned Clinical and Neurological scores three times a week beginning at P90 and five times a week beginning at P100. The table below summarizes the experimental design of the study.

| Group | Description | N | Age at Start | Grip Strength | Clinical & Neurology Scores |
|---|---|---|---|---|---|
| A | Sod1 (w/ CNS-102) | 16 | P36 | Baseline at P36, P37 Biweekly at P38-P90 Weekly at P90-P150 | 3 times per week at P90-P99 5 times per week at P100-P150 |
| B | Sod1 (w/ Riluzole) | 16 | P36 | | |
| D | Sod1 (w/ vehicle) | 16 | P36 | | |
| E | Wild type (w/ vehicle) | 10 | P36 | | |
| F | Wild type (w/ CNS-102) | 10 | P36 | | |

The grip strength test assesses motor function and control of the fore- and hindpaws. Mice were allowed to grab the bars on the Chatillon DFIS-10 digital force gauge (Largo, Fla.), while being gently pulled parallel away from the bars by the tail. The maximum force measured prior to release of the subject's paw from the bar was recorded.

Animals were scored clinically by allowing them to run in an exercise wheel and then scoring their gait using a scoring system adapted from Bruestle et al. (Neuromolecular Med. 2009; 11(2): 58-62). Animals were scored using the scoring system tabulated below.

| Score | Clinical Symptoms |
|---|---|
| 0 | Normal Gait |
| 0.5 | Slight dragging of knuckles (at least twice during circling of arena) |
| 1 | Dragging of feet or knuckles |
| 1.5 | Single limb extremely weak/limp (little to no use for walking) |
| 2 | Weakness/limpness in two limbs |
| 3 | Single limb paralysis |
| 4 | Paralysis in two limbs |
| 5 | Advanced paralysis or cannot right in 20 seconds |

Animals were scored neurologically using a scoring system adapted from Leitner et al. (Working with ALS mice; The Jackson Laboratories/Prize4Life, Appendix B, 2009). A score of 0 is given to mice that exhibit full extension of hind legs away from lateral midline when suspended by the tail. A score of 0.25 is given to mice that exhibit shaking or slight/partial collapse when suspended by the tail. A score of 0.5 is given to mice that exhibit collapse or partial collapse of leg extension towards the midline (weakness).

Results

Wildtype groups displayed a steady increase in weight throughout the study, with no noticeable differences between treatment groups E (vehicle) and F (CNS-102). See, FIG. 1. Body weight data for all transgenic groups showed a similar steady growth until P85. After a plateau, body weights begin dropping rapidly around P101. This rapid decline may be used as a marker for the onset of disease.

There was little to no difference observed between the transgenic groups. A similar pattern was seen in body condition scores. In grip strength testing, there was a rapid decline in strength in all of the transgenic groups between P93 and P107, also corresponding to the onset of disease.

Blood tests were performed on blood samples from animals in each group to evaluate the safety and efficacy of CNS-102. These results are tabulated below (X indicates incomplete test for analyte):

| GROUP | WBC (thousands) | RBC (Millions) | HGB (gram/dL) | HCT (%) | MCV (U³) | MCH (%) | MCHC (%) | NRBC (per 100 WBC) |
|---|---|---|---|---|---|---|---|---|
| Group A | 3.1 | 7.7 | 11.9 | 41.3 | 53.7 | 15.4 | 28.7 | 0.0 |
| Group B | 3.2 | 9.2 | 14.2 | 48.3 | 52.3 | 15.4 | 29.4 | 0.0 |
| Group D | 6.1 | 9.0 | 13.5 | 46.0 | 51.7 | 15.0 | 29.1 | 0.0 |
| Group E | 3.3 | 9.2 | 13.9 | 47.8 | 52.0 | 15.1 | 29.2 | 0.0 |
| Group F | 4.7 | 8.8 | 13.6 | 46.0 | 52.6 | 15.5 | 29.5 | 0.0 |

| GROUP | NEUTROPHIL SEG (%) | LYMPHOCYTE (%) | MONOCYTE (%) | EOSINOPHIL (%) | BASOPHIL (%) |
|---|---|---|---|---|---|
| Group A | 33.0 | 63.7 | 1.0 | 2.7 | 0.0 |
| Group B | 7.7 | 90.3 | 0.7 | 1.3 | 0.0 |
| Group D | 21.3 | 75.8 | 1.7 | 1.2 | 0.0 |
| Group E | 21.2 | 74.2 | 2.8 | 1.7 | 0.0 |
| Group F | 13.8 | 84.0 | 0.8 | 1.5 | 0.0 |

| GROUP | ABSOLUTE NEUTROPHIL SEG (per mm³) | ABSOLUTE LYMPHOCYTE (per mm³) | ABSOLUTE MONOCYTE (per mm³) | ABSOLUTE EOSINOPHIL (per mm³) | ABSOLUTE BASOPHIL (per mm³) |
|---|---|---|---|---|---|
| Group A | 1143.0 | 1864.7 | 31.0 | 78 | 0 |
| Group B | 241.8 | 2840.2 | 20.8 | 47.16666667 | 0 |
| Group D | 2123.8 | 3802.7 | 147.2 | 59.66666667 | 0 |
| Group E | 820.5 | 2318.0 | 138.3 | 42.25 | 0 |
| Group F | 659.6 | 3922.4 | 49.8 | 61.6 | 0 |

| GROUP | ALKALINE PHOSPHATASE (U/L) | SGPT (ALT) (U/L) | SGOT (AST) (U/L) | CPK (mg/dL) | ALBUMIN (mg/dL) | TOTAL PROTEIN (mg/dL) | GLOBULIN (mg/dL) |
|---|---|---|---|---|---|---|---|
| Group A | 42.0 | 28.3 | 54.7 | 291.0 | 2.1 | 4.9 | 2.8 |
| Group B | 76.5 | 28.7 | 45.8 | X | 2.7 | 5.5 | 2.7 |
| Group D | 89.5 | 41.0 | 52.2 | X | 2.8 | 5.4 | 2.6 |
| Group E | 70.0 | 56.4 | 70.5 | X | 2.6 | 5.7 | 2.7 |
| Group F | 70.7 | 37.8 | 46.3 | X | 2.6 | 5.3 | 2.5 |

| GROUP | TOTAL BILIRUBIN (mg/dL) | DIRECT BILIRUBIN (mg/dL) | BUN (mg/dL) | CREATININE (mg/dL) | CHOLESTEROL (mg/dL) | GLUCOSE (mg/dL) |
|---|---|---|---|---|---|---|
| Group A | 0.0 | 0.0 | 26.3 | <1 | 75.0 | 246.0 |
| Group B | X | X | 31.2 | <1 | 76.6 | 253.8 |
| Group D | 0.0 | 0.0 | 29.0 | <1 | 82.0 | 272.0 |
| Group E | X | X | 28.0 | <1 | 85.7 | 223.8 |
| Group F | X | X | 28.8 | <1 | 72.4 | 207.6 |

| GROUP | CALCIUM (mg/dL) | PHOSPHORUS (mg/dL) | BICARBONATE (mg/dL) | A/G RATIO | INDIRECT BILIRUBIN (mg/dL) | PLATELET COUNT (Thousands) |
|---|---|---|---|---|---|---|
| Group A | 7.7 | 5.7 | 5.0 | 0.8 | 0.0 | 1235.3 |
| Group B | X | X | X | 1.0 | X | 1169.2 |
| Group D | X | X | X | 1.1 | 0.0 | 1163.8 |
| Group E | X | X | X | 1.0 | X | 1232.5 |
| Group F | X | X | X | 1.0 | X | 1128.6 |

Example 27

Pharmacokinetics of 5-trans Isomer of GGA's in Rats

Rats were administered a single dose of CNS-102 either intravenously (12 mg/kg) or orally (24 mg/kg), and blood samples were taken to measure the average plasma concentrations of CNS-102 over time.

The formulation for this study includes the following:

| Formulations: (Dose: 24 mg/kg; Study Date: Apr. 16, 2012) | |
|---|---|
| Gum Arabic | 5% |
| Sodium Chloride | 1% |
| Alpha-tocopherol | 0.008% |
| CNS-102 | 0.27% |
| D.I. H2O | 93.72% |

The results for a 12 mg/kg IV dose of CNS-102 are tabulated below:

| | Plasma Concentration of CNS-102 (ng/mL) | | | | |
|---|---|---|---|---|---|
| Time (min) | Rat 1 | Rat 2 | Rat 3 | Average | SD |
| 5 | 1268.2 | 4087.5 | *1851.9* | 2402.5 | 1488.1 |
| 10 | 227.0 | 929.0 | *1452.8* | 869.6 | 615.1 |
| 20 | 0.00 | 652.7 | *903.9* | 518.9 | 466.6 |
| 30 | 0.00 | *376.6* | *627.5* | 334.7 | 315.9 |
| 60 | 0.00 | *334.4* | *643.1* | 325.8 | 321.6 |
| 120 | 0.00 | *174.3* | *276.3* | 150.2 | 139.7 |
| 240 | 0.00 | 0.00 | *627.1* | 209.0 | 362.1 |
| 480 | 0.00 | 0.00 | *232.2* | 77.4 | 134.0 |
| 720 | 0.00 | 0.00 | 0.00 | 0.0 | 0.0 |
| $C_0$ (ng/mL) | 7086.8 | 17984.5 | 2360.7 | 9144.0 | 8012.4 |
| $AUC_{(0-last)}$ (min*ng/ml) | 19934.3 | 95802.8 | 229701.4 | 115146 | 106212.9 |
| $t_{1/2}$ (min) | | 78.0 | 216.0 | 147.0 | |
| $AUC_{(0-inf)}$ (min*ng/ml) | | 115420.9 | 302035.6 | 208728 | |
| Vz (mL/kg) | | 11699.8 | 12378.5 | 12039 | |
| Vss (mL/kg) | | 6051.9 | 13539.6 | 9796 | |

BQL—Below the quantifiable limit < 250 ng/mL: substituted by zero for AUC calculation.
Bolded and italicized concentrations were used for calculation of z (1/min)

The results for a 24 mg/kg oral dose of CNS-102 are tabulated below:

| | Plasma Concentration of CNS-102 (ng/mL) | | | | |
|---|---|---|---|---|---|
| Time (min) | Rat 4 | Rat 5 | Rat 6 | Average | SD |
| Predose | 0.0 | 0.0 | 0.0 | 0.0 | |
| 10 | 0 | 0 | 0 | 0.0 | |
| 30 | 193.8 | 224.3 | 161.8 | 193.3 | 31.3 |
| 60 | 331.9 | *898.2* | 500.2 | 576.8 | 290.8 |
| 120 | 147.6 | *234.8* | *148* | 176.8 | 50.2 |
| 240 | 0 | *332.7* | *561.4* | 298.0 | 282.3 |
| 480 | *768* | *108.5* | *592.5* | 489.7 | 341.6 |
| 720 | *141.6* | 0 | 0 | 47.2 | 81.8 |
| 1440 | 0 | 0 | 0 | 0.0 | 0.0 |
| Cmax (ng/mL) | 768 | 898.2 | 592.5 | 752.9 | 153.4 |
| Tmax (min) | 480 | 60 | 480 | 340 | 242 |
| $AUC_{(0-last)}$ (min*ng/ml) | 214144 | 130474 | 222724 | 189114 | 50965 |

| | Plasma Concentration of CNS-102 (ng/mL) | | | | |
|---|---|---|---|---|---|
| Time (min) | Rat 4 | Rat 5 | Rat 6 | Average | SD |
| $F_{(0-last)}$ (%) | 93.0 | 56.7 | 96.7 | 82.1 | 22.1 |
| $t_{1/2}$ (min) (min) | 98.4 | 173.7 | 36.8 | 103 | 69 |
| $AUC_{(0-inf)}$ (min*ng/ml) | 234242 | 157666 | 222724 | 204878 | 41290 |
| $F_{(0-inf)}$ (%) | 56.1 | 37.8 | 53.4 | 49.1 | 9.9 |

BQL—Below the quantifiable limit < 250 ng/mL: substituted by zero for AUC calculation.
Bolded and italicized concentrations were used for calculation of z (1/min)

Example 28

Calculation of Total Brain to Total Plasma Concentration Ratio (Kp) of 5-Trans Isomer of GGA's in Rats The ratio of total brain concentration to total plasma concentration (Kp) for CNS-102 was calculated. First, the total plasma concentration of CNS-102 (in two different formulations) was calculated as described in Example 27. The total brain concentration of CNS-102 in ng/g for the same animals was also measured.

AUC(0-last) (min*ng/ml): area under the concentration-time curve from zero up to the last measurable time-point.

lz (1/min): the first order rate constant associated with the terminal (log-linear) portion of the curve, estimated by linear regression of time vs. log concentration.

Terminal Half-Life (t½)=ln(2)/lz: calculated using Lambda_z method to find best fit. If necessary, the concentration-time points were manually selected for use in the calculation. Bolded-italicized concentrations indicate points used for calculation.

AUC(0-inf) (min*ng/ml): Area under the concentration-time curve from zero up to infinity, based on the last observed concentration. Requires lz.

Ratio of Total Concentration of Drug in Brain relative to plasma (Kp):

$$Kp = \frac{AUCtot, \text{brain}}{AUCtot, \text{plasma}}$$

where AUCtot is the area under the concentration-time curve for total (bound and unbound) concentrations in brain or plasma.

The ratio data are summarized in the tabulations below (bolded concentrations indicate points used for calculations).

| | Formulation 1 | |
|---|---|---|
| | Average Conc | |
| Min | ng/g brain | ng/mL plasma |
| 240 | 270.7 | 3867.8 |
| 360 | *428.2* | *6469.1* |
| 480 | *338.9* | *5157.6* |
| 600 | *189.6* | *4061.3* |
| Terminal Half-Life (t1/2) (min): | 204.2 | 357.3 |
| AUC (0-last) (min*ng/ml): | 151090 | 2329500 |
| Kp (0-last): | 0.0649 | |

-continued

| Formulation 1 | | |
|---|---|---|
| | Average Conc | |
| Min | ng/g brain | ng/mL plasma |
| AUC (0-inf) (min*ng/ml): | 206924 | 4423305 |
| Kp (0-inf): | 0.0468 | |

| Formulation 2 | | |
|---|---|---|
| | Average Conc | |
| Min | ng/g brain | ng/mL plasma |
| 240 | *431.5* | *4983.0* |
| 360 | *333.2* | *3040.6* |
| 480 | *132.7* | *2131.0* |
| 600 | 0.0 | *317.4* |
| Terminal Half-Life (t1/2) (min): | 141.1 | 96.5 |
| AUC (0-last) (min*ng/ml): | 123533 | 1491186 |
| Kp (0-last): | 0.0828 | |
| AUC (0-inf) (min*ng/ml): | 150531 | 1535390 |
| Kp (0-inf): | 0.0980 | |

Formulation 1 and Formulation 2 refer to the following:

| Formulation #1 (Dose: 0.200 g/Kg) | |
|---|---|
| Gum Arabic | 5% |
| Sodium Chloride | 1% |
| Alpha-tocopherol | 0.008% |
| CNS-102 | 2.25% |
| D.I. H2O | 91.75% |

| Formulation #2 (Dose: 0.200 g/Kg) | |
|---|---|
| Gum Arabic: | 5% |
| Hydroxypropyl Cellulose (Mn = 100,000) | 3% |
| Sodium Chloride | 1% |
| Alpha-tocopherol | 0.008% |
| CNS-102 | 2.25% |
| D.I. H2O | 88.75% |

The amount of trans GGA used was to ensure that such GGA distributed to the brain is detected. It is contemplated that smaller amounts of GGA such as about 1 mg/kg/day to about 12 mg/kg/day will also be distributed to the brain in accordance with this invention.

Example 29

CNS-102 Induces Heat Shock Protein Expression In Vitro

Murine neuro2A neuroblastoma cells were treated with various concentrations of CNS-102 (all trans-GGA), CNS-101 (mixture of GGA isomers), and CNS-103 (all cis-GGA) for 48 hours. Differentiation was induced and cells incubated with geranylgeranyl transferase I inhibitor, GGTI-298. Cells were harvested and lysates were prepared and analyzed by western blot for HSP70 and HSP90. Western signals in the absence of the compounds were normalized as 1.00. The results are tabulated below.

| CNS-102-Induced HSP Expression in Neuro2A Cells | | | | | | |
|---|---|---|---|---|---|---|
| | HSP70 | | | HSP90 | | |
| Dose | 100 nM | 1 µM | 10 µM | 100 nM | 1 µM | 10 µM |
| CNS-102 | 1.38 | 2.05 | 2.14 | 3.29 | 1.74 | 1.21 |
| CNS-101 | 2.61 | 1.94 | 2.00 | nd | nd | nd |
| CNS-103 | 1.00 | 1.07 | 0.99 | nd | nd | nd | nd = not done

Both CNS-102 and CNS-101 induce expression of HSP70 at various concentrations, and the GGA cis isomer (CNS-103) failed to induce expression of HSP70.

Example 30

Effect of CNS-102 on Neurite Outgrowth

Murine neuro2A neuroblastoma cells were treated with various concentrations of CNS-101, CNS-102, or CNS-103 for 48 h. Differentiation was induced and cells incubated with geranylgeranyl transferase I inhibitor, GGTI-298. After 24 h digital images were taken and neurite outgrowth was quantified. The comparisons of the neuroprotective effect of these three compounds are shown below.

Performance of CNS-102 and Comparison to CNS-101

The estimated mean $\log_{10}$ counts, from five replicate wells for each treatment group were calculated by PROC GLM in SAS assuming a pooled estimate of variation. The anti-log values are given as the estimate of the median values and are tabulated below.

| Number of Cells with Neurite Outgrowth when Treated with CNS-101 or CNS-102 | | | | |
|---|---|---|---|---|
| Conc. nM | Treatment | Median Counts | Relative % | Protection % |
| | No Inhibition | 95.5 | 1 | |
| 0 | PBS | 21.5 | 0.225 | 0 |
| 10 | CNS-101 | 29.8 | 0.312 | 11.2 |
| | CNS-102 | 33.8 | 0.354 | 16.6 |
| 100 | CNS-101 | 38.7 | 0.405 | 23.2 |
| | CNS-102 | 43.4 | 0.454 | 29.6 |
| 1000 | CNS-101 | 41.6 | 0.436 | 27.2 |
| | CNS-102 | 51.0 | 0.534 | 39.9 |
| 10000 | CNS-101 | 27.7 | 0.290 | 8.4 |
| | CNS-102 | 38.2 | 0.400 | 22.6 |

Figure 4A:
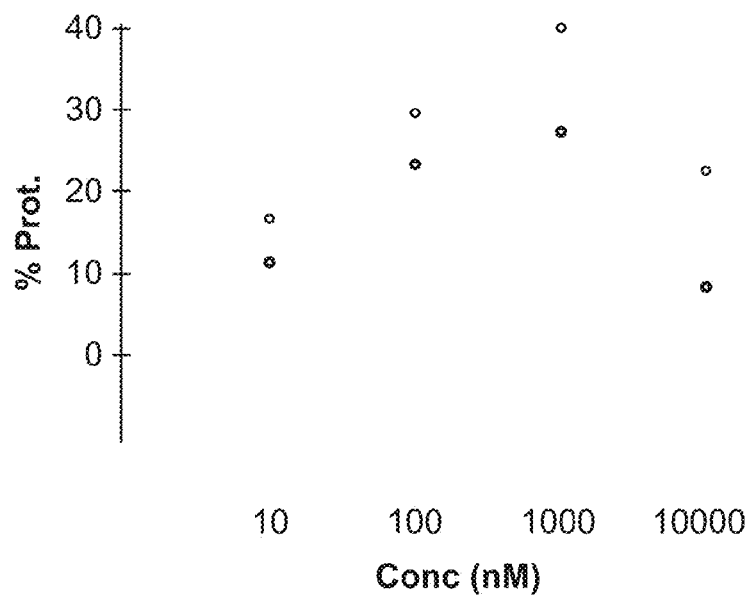
FIG. 4A illustrates the protection of cells by CNS-102 and CNS-101 in the presence of GGTI.

The median count is estimated to be 95.5 in the absence of inhibitor and 21.5 when cells are treated with inhibitor and PBS. This inhibited outcome is 0.225 of the uninhibited count (Relative Performance), and represents 0% protection from the adverse effects of the inhibitor (% Protection). The collected results are graphically plotted in FIG. 4A. Increasing concentrations of CNS-102 (light grey) and CNS-101 (dark grey) results in increases in median counts with a maximum protection of ~40% for CNS-102 and 27% for CNS-101.

The graph shows that both CNS-102 and the isomer mixture CNS-101, give protection in a range from 10 nM to 10000 nM. The CNS-102 treatment consistently provides more protection than does CNS-101, even at the highest dose, which has reduced counts over the maximum seen at 1000 nM.

Comparison of Performance of CNS-103 and CNS-102

The estimated mean log10 counts from five replicate wells for each treatment group were calculated by PROC GLM in SAS assuming a pooled estimate of variation. The anti-log values are given as the estimate of the median values and are tabulated below.

Number of Cells with Neurite Outgrowth when Treated with CNS-102 or CNS-103

| Conc. nM | Treatment | Median Counts | Relative % | Protection % |
|---|---|---|---|---|
|  | No Inhibition | 60.3 | 1 |  |
| 0 | PBS | 18.5 | 0.307 | 0 |
| 10 | CNS-103 | 26.7 | 0.443 | 19.6 |
| 100 | CNS-103 | 29.3 | 0.486 | 25.8 |
| 100 | CNS-102 | 33.5 | 0.556 | 35.9 |
| 1000 | CNS-103 | 28.7 | 0.476 | 24.4 |
| 1000 | CNS-102 | 23.8 | 0.395 | 12.7 |
| 10000 | CNS-103 | 16.3 | 0.270 | −5.3 |

Figure 4B:
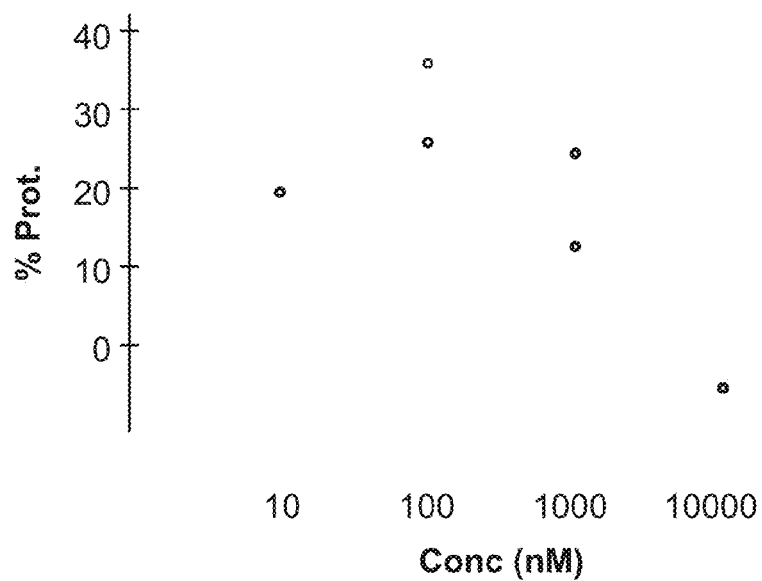
FIG. 4B illustrates the protection of cells by CNS-102 and CNS-103 in the presence of GGTI.

The median count is estimated to be 60.3 in the absence of inhibitor, and is 18.5 when cells are treated with inhibitor. This inhibited outcome is 0.307 of the uninhibited count (Relative Performance), and represents 0% protection from the adverse effects of the inhibitor (% Protection). The collected results are graphically plotted in FIG. 4B. The maximum protection is ~36% for CNS-102 (light grey) and ~26% for CNS-103 (dark grey).

The graph shows that both CNS-102 and the all-cis isomer, CNS-103, give protection in a range from 10 nM to 10000 nM, with the peak at about 100 nM, and CNS-102 providing greater protection at the optimal concentration of 100 nM Comparison of the Effect of GGA Isomers on Neurite Outgrowth Differences in mean log(counts) between treatments for each concentration were calculated using PROC GLM in SAS. The p-value given is for the comparison of the estimated difference to zero, the expected difference value for no treatment effect. The anti-log of the differences represent the estimated ratio of counts (relative effect on inhibition) and are tabulated below along with the lower and upper 95% confidence intervals.

Comparison of Ratio of Neurite Outgrowth

| Comparison | Conc. nM | LCL % | Ratio % | UCL % | p-value |
|---|---|---|---|---|---|
| CNS-102-CNS-101 | 10 | 90.4 | 113.6 | 142.7 | 0.266 |
| CNS-102-CNS-101 | 100 | 89.2 | 112.1 | 140.9 | 0.3173 |
| CNS-102-CNS-101 | 1000 | 97.6 | 122.7 | 154.2 | 0.0778 |
| CNS-102-CNS-101 | 10000 | 109.6 | 137.8 | 173.1 | 0.0073 |
| CNS-102-CNS-103 | 100 | 91.0 | 114.3 | 143.6 | 0.2413 |
| CNS-102-CNS-103 | 1000 | 66.1 | 83.0 | 104.3 | 0.1059 |

Figure 4C:
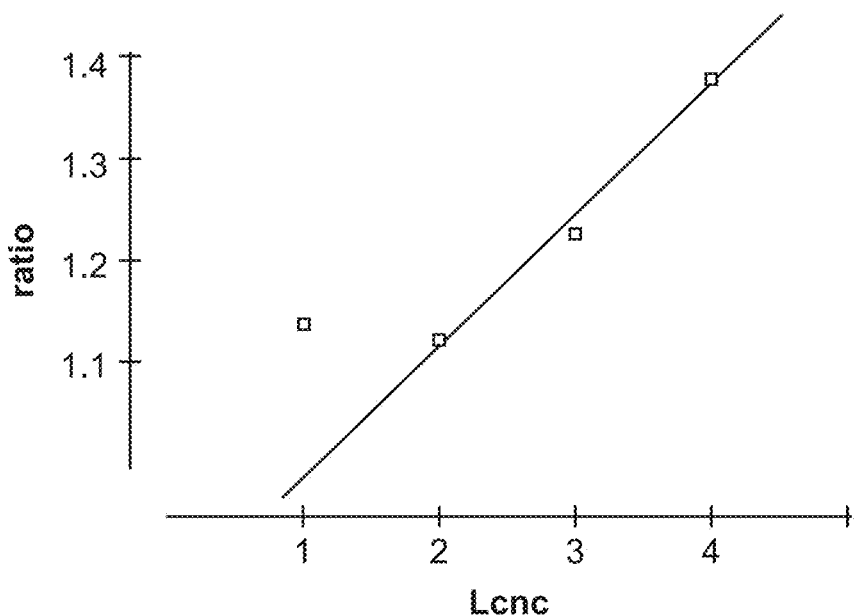
FIG. 4C illustrates neurite outgrowth ratio for CNS-102/CNS-101 versus $\text{Log}_{10}$ concentration.

There is insufficient difference between the treatments at all but one concentration for statistical significance at the 0.05 level. There exists, for CNS-102 and CNS-101, a concentration dependent trend in the ratio estimate above a threshold concentration (100 nM, p=0.06) as graphically shown in FIG. 4.C, Rescue Ratio for CNS-102/CNS-101 versus Log10 Concentration. It is notable that the ratio continues the trend at 4.0 log concentration even in the face of significant depression of the total number of cells exhibiting neurite outgrowth at this highest concentration, shown in the previous graphs in FIGS. 4A and 4B.

From this it can be concluded that CNS-102 is more effective at protecting neurite outgrowth than is either the GGA mixture or cis GGA.

Example 31

Time Course of CNS-102 Induced HSP70 Expression In Vivo

The time course of protein expression, as measured by western blot for HSP70, was determined in triplicate for hippocampus, and cortex tissue samples taken from each of 5 animals per group at each of four time points (24, 48, 72, and 96 h) after treatment with either PBS or 12 mg/kg CNS-102, administered orally. The average expression for each treatment group is calculated at each time point for each tissue using PROC MIXED in SAS and are tabulated, along with the difference (delta) between treatment averages and a p-value comparing the difference to zero, below.

HSP70 Expression Following Administration of CNS-102 vs PBS

| CNS-PBS | Treatment; Statistic | Cortex | Hippocampus |
|---|---|---|---|
| 24 hours | CNS | −0.016 | −0.159 |
|  | PBS | −0.256 | −0.072 |
|  | delta | 0.24 | −0.088 |
|  | p-value | 0.002 | 0.16 |
| 48 hours | CNS | −0.45 | 0.02 |
|  | PBS | −0.56 | −0.18 |
|  | delta | 0.11 | 0.2 |
|  | p-value | 0.15 | 0.14 |
| 72 hours | CNS | 0.14 | −0.06 |
|  | PBS | 0.01 | −0.2 |
|  | delta | 0.13 | 0.14 |
|  | p-value | 0.13 | 0.032 |
| 96 hours | CNS | 0.04 | −0.32 |
|  | PBS | −0.15 | −0.49 |
|  | delta | 0.19 | 0.17 |
|  | p-value | 0.09 | 0.07 |

Expression of HSP70 was observed after CNS-102 administration and the difference between CNS-102 and PBS induced expression (delta, in the table) in both the cortex at 24 h and the hippocampus at 72 h was statistically significant (bolded in the table).

These results demonstrate that CNS-102 induces expression of HSP70 as measured in the cortex 24 h after administration while in the hippocampus the level of HSP70 was not significant until 72 h after administration. No significant levels of HSP70 were found in the cortex after 24 h, however since no time points before 24 h were taken, it may be that HSP70 is expressed earlier. In the hippocampus the expression appears to peak after 48 h with significant levels measured at 72 hours.

HSP70 expression as measured by Western Blot in rat eyes following a single dose of 12 mg/kg CNS-102 is shown in the following table.

| Time (hr) | HSP70 Expression (Fold change vs vehicle control) mean ± SD |
|---|---|
| 24 | 1.47 ± 0.36 |
| 48 | 1.33 ± 0.10 |
| 72 | 1.40 ± 0.11 |

CNS-102 at 12 mg/kg or PBS was administered orally to Sprague-Dawley rats and the time course of HSP70 protein expression in tissues, was measured by ELISA. HSP70 protein expression was determined for lung, testicle, spleen, liver, kidney, blood plasma, skin, peripheral blood monocytes, heart, eye, muscle, intestine, and stomach at each of three time points (8 h, 17 h, 24 h) and for cerebral cortex at 24 h 48 h and 72 h.

Example 32

CNS-102 Induces Expression of Selected Heat Shock Proteins In Vivo

CNS-102 was administered orally to Sprague-Dawley rats at 12 mg/kg and brain tissue was extracted at 12, 24, 48, and 96 h after dosing. Expression of selected HSPs was detected using qRT-PCR with expression of the GAPDH gene used as the control. Results are shown in the table below. To represent the effect of CNS-102 on HSP expression, mean fold change is calculated as CNS-102 treated/PBS treated for each HSP at each time point.

|  | 24 h mean ± SD | 48 h mean ± SD | 72 h mean ± SD | 96 h mean ± SD |
| --- | --- | --- | --- | --- |
| HSP90 | 1.32 ± 0.95 | 1.16 ± 0.55 | 2.59 ± 1.27 | 1.68 ± 0.72 |
| HSP70 | 1.18 ± 0.01 | 1.48 ± 0.02 | 1.81 ± 0.01 | 1.58 ± 0.03 |
| HSP60 | 1.26 ± 0.07 | 0.89 ± 0.08 | 1.72 ± 0.07 | 1.57 ± 0.16 |

Gene expression of HSP60 (chaperonin), HSP70, and HSP90 was increased in CNS-102 treated animals compared to PBS treated animals for up to 96 h post dose with peak effects generally after 48 h post dose.

Example 33

Determination of Time Course of Neuroprotection by CNS-102 in the Kainic Acid Model CNS-102 was administered orally to Sprague Dawley rats at 12 mg/kg. After dosing, KA was stereotactically injected into the hippocampus at 24, 48, 72, 96 and 168 hours to induce neuron damage. After 24 h, hippocampus tissue was collected, stained, and imaged. The scans were analyzed by Image J to calculate the fraction of cells having KA-induced damage. Average fraction damaged in the hippocampus from ten animals for each treatment (PBS vs. 12 mg/kg CNS-102) by time (24, 48, 72, 96 and 168 hours) combination was estimated with PROC MIXED in SAS. Comparisons of the CNS-102 treatment groups to the pooled PBS treatment at the different times can be made, giving the results tabulated below.

| Time Course of Neuroprotection by CNS-102 | | | |
| --- | --- | --- | --- |
| Treatment | Mean | Difference | p-value |
| CNS-102 @ 24 | 0.193 | 0.005 | 0.848 |
| CNS-102 @ 48 | 0.123 | −0.064 | 0.066 |
| CNS-102 @ 72 | 0.096 | −0.092 | 0.004 |
| CNS-102 @ 96 | 0.131 | −0.056 | 0.081 |
| CNS-102 @ 168 | 0.162 | −0.026 | 0.403 |
| PBS | 0.187 | — | — |

The results of this study demonstrated a statistically significant (p-value of 0.004) efficacy of neuron protection by a single dose of 12 mg/kg of CNS-102. The maximal protection effect by CNS-102 was achieved in this model at the 72 h timepoint. This time frame was incorporated into subsequent concentration dependence studies.

Example 34

Concentration Dependence of Neuroprotection by CNS-102 in the Kainic Acid Model

Figure 5:
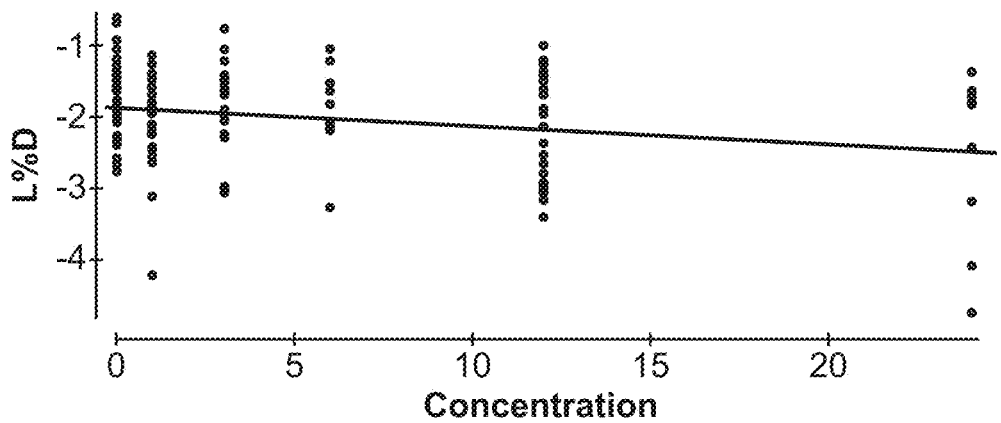
FIG. 5 illustrates concentration dependence of neuroprotection by CNS-102.

The fraction of cells damaged in the kainic acid model was determined on 130 rats, each receiving one dose of CNS-102 at either 0, 1, 3, 6, 12 or 24 mg/kg. PBS was used for dosing at 0 mg/kg. The linear model of the $\log_{10}$ percent damage versus concentration is graphically shown FIG. 5.

The ANOVA results for the model are tabulated below. The concentration dependence is statistically significant, with a p-value of 0.007.

| ANOVA Table for Concentration Dependence of Damage in Kainic Acid Rat Model Analysis of Variance For L % D No Selector 130 total cases of which 11 are missing | | | | | |
| --- | --- | --- | --- | --- | --- |
| Source | df | Sums of Squares | Mean Square | F-ratio | Prob |
| Const | 1 | 471.706 | 471.706 | 982.53 | ≤0.0001 |
| cnn | 1 | 3.58419 | 3.58419 | 7.4656 | 0.0073 |
| Error | 117 | 56.1708 | 0.480092 | | |
| Total | 118 | 59.7550 | | | |

These results demonstrate that neuroprotection by CNS-102 is concentration dependent with increasing protection up to at least 24 mg/kg. This study supports 12 mg/kg as the minimal effective dose.

Example 35

Effect of CNS-102 on Survival in the SOD1 Mouse Model of ALS

CNS-102 was administered daily by oral gavage to male SOD1 and wild type mice at 12 mg/kg beginning on postnatal day (P) 38. Groups of SOD1 mice were also administered 8 mg/kg riluzole.

Survival data showed no transgenic animals survived past age P153. Longer survival for subjects in group A (CNS-102) and B (Riluzole) was observed. In all testing, both wild type groups performed better than any transgenic group. There was negligible difference between wildtype animals dosed with vehicle versus CNS-102, suggesting that treatment with CNS-102 does not lead to obvious toxicity or behavioral abnormalities as tested and observed in the study.

Figure 6:
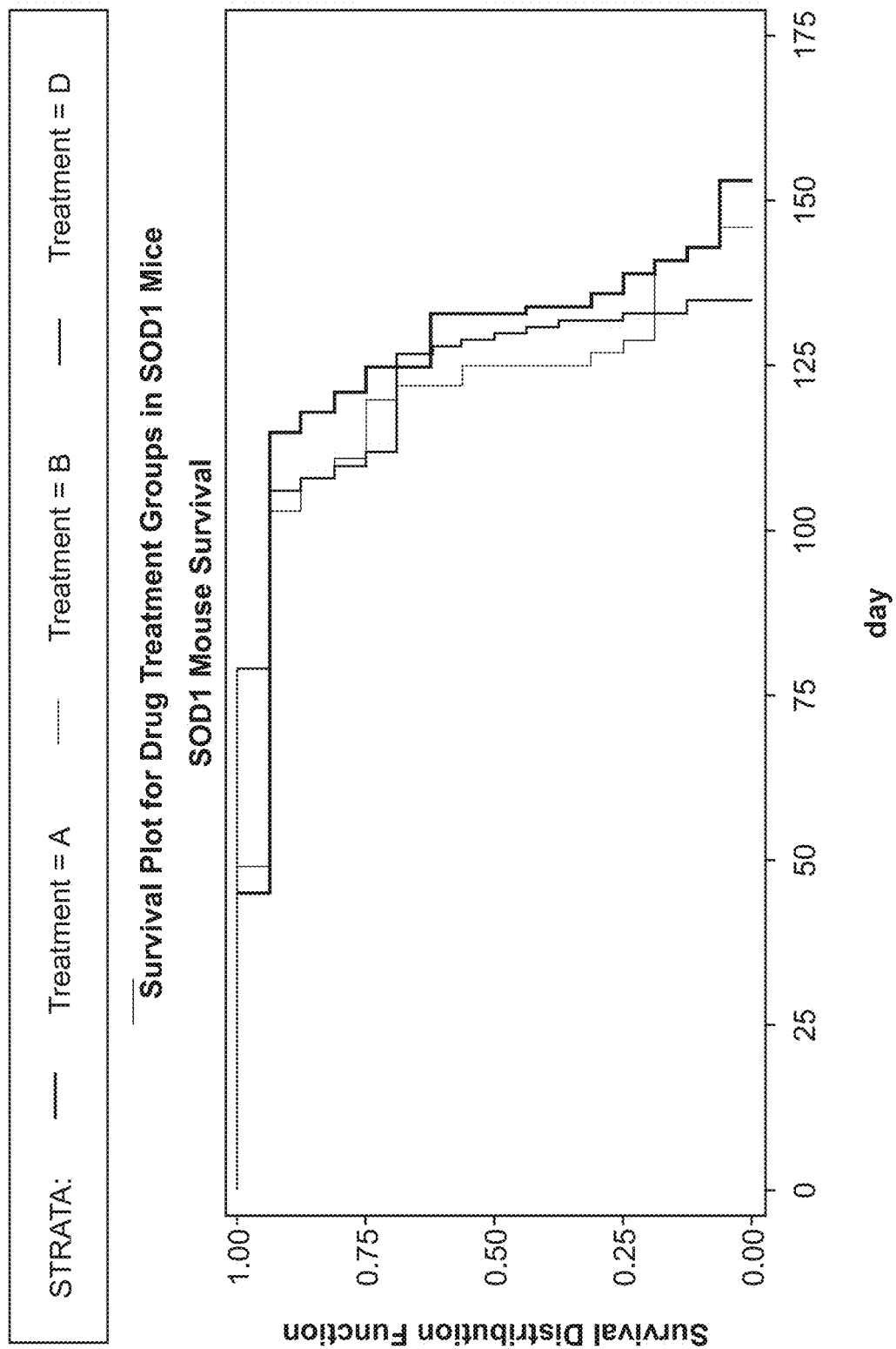
FIG. 6 illustrates survival plot for drug treatment groups in SOD1 mice.

The survival data was analyzed using PROC LIFETEST in SAS. The wild-type treatment groups were removed from the study since all of these animals, save one, survived to the end of the study. The remaining four groups were subjected to the standard survival analysis by the method of Kaplan-Meier, with median estimates tabulated below, and survival shown graphically in FIG. 6.

| Median Survival for Drug Treatment Groups in SOD1 Mice | |
| --- | --- |
| Treatment | Median Survival (days) |
| "A", CNS-102 | 133.0 |
| "B", Riluzole | 129.5 |
| "D", Vehicle | 125.0 |

A survival analysis comparison of the two drugs and the vehicle was conducted using PROC LIFETEST, yielding a p-value of 0.04. This outcome indicated that the data contains evidence of a significant difference between at least two of the three single compound treatment groups A, B, and D.

Parametric regression with PROC LIFEREG in SAS, using the gamma distribution as the model (p=0.0024), was conducted to further elucidate the nature of this difference. Separately comparing each of the two drug treatment groups A and B with the vehicle D, finds that there is significant evidence of differences for both groups. The magnitude of change in median time to death is +9% for the CNS-102 treatment group and +6% for the Riluzole treatment group, respectively, compared to that of the vehicle group as tabulated below.

| p-Values for Treatment Group Comparisons to Vehicle Group | | |
| --- | --- | --- |
| Group | % Increase | p-value |
| CNS-102 | 9.5 | 0.0007 |
| Riluzole | 6.3 | 0.0149 |

Example 36

Effect of CNS-102 on Gait Analysis in CatWalk

CatWalk results showed a severe change in gait during onset and progression of disease. Prior to onset, there was little to no difference between the transgenic and wildtype groups. Transgenic animals tended to rely more on front paws for movement as weakness and paralysis in the hind paws progressed. This began to show around timepoint P100, coinciding with the expected onset of disease. This impairment was seen through changes in front and hind paw step cycle, print area, mean intensity, and base of support.

Figure 7:
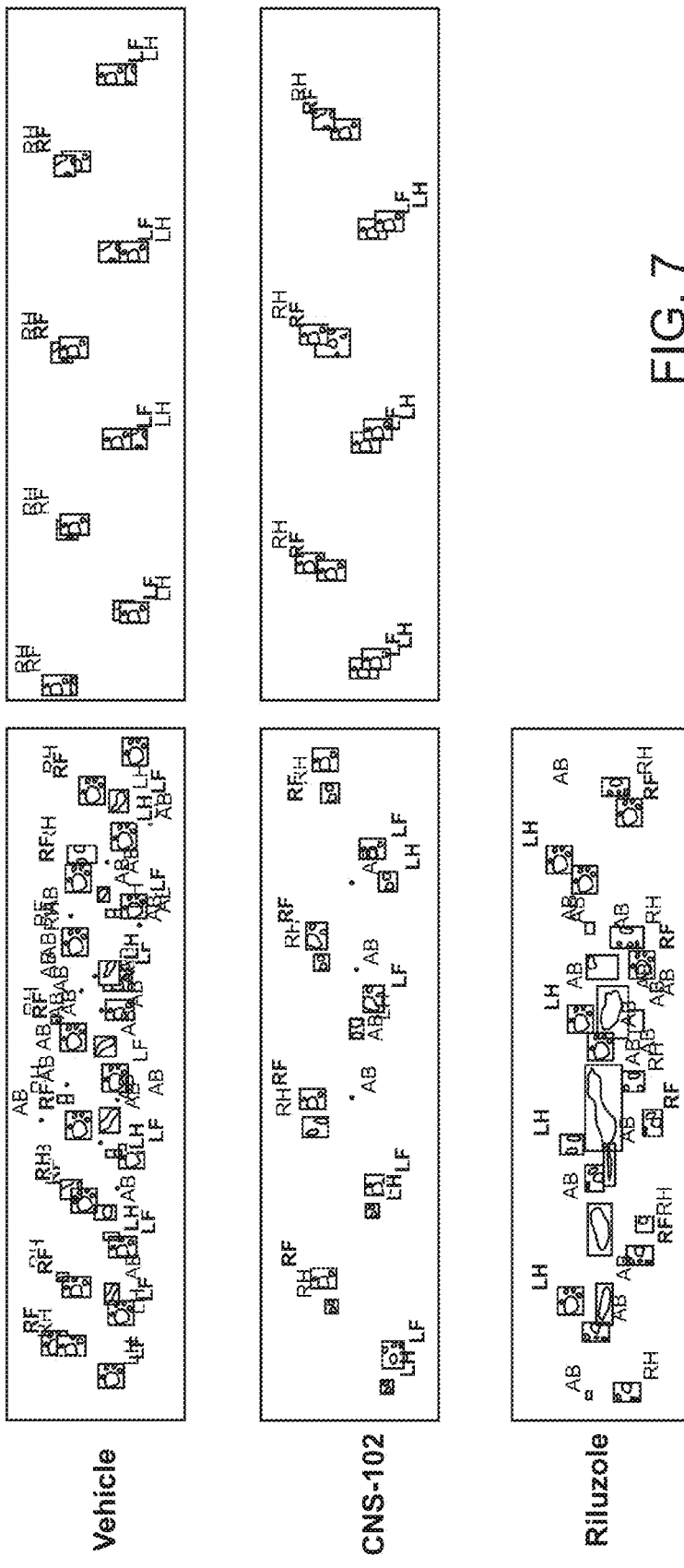
FIG. 7 illustrates comparative neurological motor function outcomes of SOD1 mice.

In general, group A (CNS-102 in transgenic mice) outperformed the Riluzole-transgenic treatment group in CatWalk. This was seen in multiple time points and through several metrics. Group A had a lower run duration, lower % body, and higher regulatory index, suggesting a less-impaired gait. There is very little difference between wildtype groups E (vehicle) and F (CNS-102). See, FIG. 7.

Three motor function outcomes (stride length, run duration, and swing speed) were compared for CNS-102 and vehicle by the Bootstrap method. Prior to P120, there were only small differences between treatment group averages. By P120, the progression of the disease had both increased the measured differences between CNS-102 and vehicle and removed significant but unequal fractions of each treatment group. The p-value for each difference in CNS-102-minus-vehicle averages is tabulated below.

| Bootstrap Comparison of Averages at P120 | | |
| --- | --- | --- |
| Metric | CNS-102 - vehicle | p-value |
| Stride Length | 1.46 | 0.031 |
| Run Duration | −1.68 | 0.034 |
| Swing Speed | 14.58 | 0.017 |

A minus-one jackknife procedure demonstrated that no single animal unduly influenced the construction of the reference distribution, thereby validating these p-values. Clearly, the fact that all three metrics show significantly better outcomes compared to PBS, indicates that CNS-102 not only prolongs survival but also slows the symptomatic progression of the disease.

| Run Duration | | WT/vehicle | SOD1/Vehicle | SOD1/CNS-102 | SOD1/Riluzole |
| --- | --- | --- | --- | --- | --- |
| P-42 | Mean/average | 1.594350194 | 1.484746201 | 1.684569504 | 1.650407384 |
| P-42 | SE | 0.09056 | 0.09987 | 0.10574 | 0.10639 |
| P-124 (+/−) 3 | Mean/average | 0.903035183 | 3.461605345 | 1.97609085 | 3.113141233 |
| P-124 (+/−) 3 | SE | 0.09056 | 0.35356 | 0.24074 | 0.58346 |

CNS-102-vehicle/P124(+/−)$_3$: P (bootstrap comparison method)=0.0077

| Hind stride length | | WT/vehicle | SOD1/Vehicle | SOD1/CNS-102 | SOD1/Riluzole |
| --- | --- | --- | --- | --- | --- |
| P-42 | Mean/average | 6.117764612 | 6.359471205 | 6.081819714 | 6.336835151 |
| P-42 | SE | 0.22497 | 0.13712 | 0.16008 | 0.1648 |
| P-124 (+/−) 3 | Mean/average | 7.477179217 | 3.607909383 | 5.475629249 | 4.243503725 |
| P-124 (+/−) 3 | SE | 0.41868 | 0.26801 | 0.32088 | 0.60992 |

CNS-102-vehicle/P124(+/−)$_3$: P (bootstrap comparison method)=0.0062.

| Swing speed | | WT/vehicle | SOD1/Vehicle | SOD1/CNS-102 | SOD1/Riluzole |
|---|---|---|---|---|---|
| P-42 | Mean/average | 44.67592914 | 45.8515272 | 41.17834654 | 43.07335875 |
| P-42 | SE | 0.22497 | 2.29897 | 1.94748 | 0.1648 |
| P-124 (+/−) 3 | Mean/average | 71.6358109 | 23.93413455 | 35.63032533 | 29.71423324 |
| P-124 (+/−) 3 | SE | 6.5373 | 0.80179 | 2.96443 | 3.87162 |

CNS-102-vehicle/P124(+/−)$_3$: P (bootstrap comparison method)=0.0206

Example 37

Effect of CNS-102 on Blood Chemistry and Hematology

Blood and serum samples from days P70 and P100 were collected on three animals from each of the six treatment groups. Hematology measures were white blood cell count, red blood cell count, hemoglobin, hematocrit, mean corpuscular volume, mean corpuscular hemoglobin, mean corpuscular hemoglobin concentration, and platelets. Chemistry values were alanine aminotransferase, aspartate aminotransferase, albumin, total protein, gamma globulin, blood urea nitrogen, cholesterol, and glucose. No analyses were conducted on any samples collected after P100.

Each outcome was fit to a linear discrete model with the age of the animal included as a covariate. None of these outcomes in either hematology or chemistry showed statistical significant differences between any of the 6 treatment groups, except for glucose. In this case, the observed difference resides in the mouse strain (SOD1 vs. wild type), not in the treatment groups A-D, or E-F.

In conclusion, there are no statistically significant treatment differences. There is a genotype difference in the glucose outcome. Time is a significant factor in several of the observed outcomes (red blood cell count, platelets, and hematocrit) across all treatments in the SOD1 animals, attributable to the progression of the disease state.

Example 38

Determination of Neuroprotection by CNS-102 in the Presence of GGA Cis-Isomer (CNS-103) in the Kainic Acid Model GGA trans isomer (CNS-102) was administered orally to Sprague Dawley rats at 24 mg/kg. In parallel experiments, a mixture of GGA cis- and trans isomer (10:90) was administered orally to Sprague Dawley rats at 26.66 mg/kg. An amount of GGA trans isomer that contained in the mixture was equivalent to 24 mg/Kg. After dosing, KA was stereotactically injected into the hippocampus at 72 hours to induce neuron damage. After 24 h, hippocampus tissue was collected, stained, and imaged. The scans were analyzed by Image J to calculate the fraction of cells having KA-induced damage.

| GGA | Mean of Hippocampus CA3 neurons damaged (Arbitrary units) | SE |
|---|---|---|
| CNS-102 (24 mg/Kg rat) | 19.8182 | 1.9756 |
| GGA cis- and trans mixture (10:90) | 23.2589 | 2.2362 |

In the presence of the GGA cis-isomer, neuroprotective effects of the GGA trans isomer were diminished demonstrating that the cis isomer inhibits the neuroprotective activity of trans isomer.

Example 39

Efficacy of Compounds in Alleviating Neurodegeneration Induced by Kainic Acid The indicated compounds or vehicle control were orally dosed to Sprague-Dawley rats, and Kainic acid was injected. After dosing, KA was stereotactically injected into the hippocampus at 72 hours to induce neuron damage. After 24 h, hippocampus tissue was collected, stained, and imaged. The scans were analyzed by Image J to calculate the fraction of cells having KA-induced damage. Neurons damaged by Kainic acid (mean of hippocampus CA3 neurons damaged) were quantified. These results are depicted in the following table:

Effect of GGA derivatives on kainic acid induced neurogeneration. Compound ID numbers in table refer to structures in Table 1 and Table 2.

| | Mean of Hippocampus CA3 Neurons Damaged | | | | | |
|---|---|---|---|---|---|---|
| Compound ID | Vehicle | 1 mg/kg | 2 mg/kg | 3 mg/kg | 12 mg/kg | 20 mg/kg |
| 7e | 22% | | | | 18% | |
| 7j | 21% | 13% | | | | |
| 8b | 23% | | | 20% | | |
| 10d | 15% | | 14% | | | |
| 10f | 18% | | | | | 16% |
| 10i | 26% | | 22% | | | |
| 10l | 17% | | | | | 14% |
| 14 | 14% | | 13% | | | |
| 27a | 14% | | 11% | | | |

Example 40

The Effect of CNS102 on Prenylation of Rap1 in Neuro2A Cells

Mouse neuroblastoma Neuro2A cells were cultured in DMEM supplemented with 10% FBS for 24 hrs. The cells were treated with 102GGA derivative compounds for 24 hrs first before GGTase inhibitor GGTI-298 was added to the culture medium for additional 24 hr incubation. At the end of 48 hr treatments, whole cell lysates were prepared from both controlcontrols (GGTI only) and the GGA compounds together with GGTI treated cell populations for western blotting analysis using antibodies specific for the un-prenylated or total level of Rap1. Both un-prenylated and total Rap1 protein bands were quantified using Image J and normalized to their respective loading control GAPDH. The results for control and each compound treatment were calculated as the ratio of normalized un-prenylated Rap1 to total Rap1, and averaged from two biological repeats of one experiment. The final results were presented as a percentage of the control treatments (GGTI only) from the same batch experiment. The data shown in the chart were averaged from two repeats of one experiment and presented as the ratio of normalized un-prenylated Rap1 to total Rap1. Compound ID numbers in table refer to structures in Table 1 and Table 2.

| | unprenylated/<br>total RAP1 (%)<br>100 nM |
|---|---|
| 2f | 65 |
| 2i | 92 |
| 7e | 64 |
| 7j | 63 |
| 7m | 54 |
| 7q | 48 |
| 7s | 89 |
| 7w | 77 |
| 7y | 68 |
| 8b | 55 |
| 8i | 59 |
| 10d | 62 |
| 10e | 56 |
| 10f | 40 |
| 10i | 83 |
| 10j | 91 |
| 10l | 164 |
| 10m | 100 |
| 14 | 96 |
| 20d | 67 |
| 20h | 58 |
| 20j | 59 |
| 27a | 96 |
| 27g | 129 |
| 29b | 49 |
| 37d | 128 |
| 52 | 71 |
| 84 | 72 |
| 105 | 64 |
| 127 | 77 |
| 128 | 67 |
| 131 | 61 |
| 132 | 103 |
| 135 | 50 |

| Compound<br>ID | unprenylated/total<br>RAP1 (%)<br>100 nM |
|---|---|
| CNS-102 | 59 |
| CNS-101 | 75 |
| CNS-103 | 96 |

Compared to control, CNS102 treatment at 100 nM appears to slightly increase the prenylation of Rap1 in Neuro2A cells (student's t-test, P=0.08).

Example 41

The Effect of CNS-102 on Activity of Rho GTPase in Neuro2A Cells

Mouse neuroblastoma Neuro2A cells were cultured in DMEM supplemented with 10% FBS for 24 hrs. The cells were then treated with GGA derivatives or the vehicle DMSO for 48 hrs before harvesting. Cell lysates were quantified and subjected either to active RhoA assay using G-LISA RhoA activation Assay Biochem Kit (Cytoskeleton Inc), or to total RhoA assay using Total RhoA ELISA Kit (Cytoskeleton Inc). The results were calculated as ratio of active RhoA to total RhoA and averaged from 3 biological repeats of one experiment with background subtraction. The data was presented as percentage of DMSO treatments.

Compound ID numbers in table refer to structures in Table 1 and Table 2.

| Compound<br>ID | % Relative<br>RhoGTPase Activity |
|---|---|
| 2i | 105.0 |
| 7q | 83.5 |
| 7s | 86.9 |
| 7w | 94.4 |
| 7y | 94.4 |
| 8b | 125.0 |
| 8f | 104.6 |
| 8g | 111.3 |
| 8j | 105.6 |
| 8m | 111.4 |
| 8o | 82.1 |
| 10b | 86.2 |
| 10e | 89.7 |
| 20j | 85.9 |
| 27b | 89.0 |
| 29b | 96.1 |
| 37a | 106.8 |
| 43 | 102.7 |
| 105 | 85.1 |
| 135 | 93.2 |

| CNS-102 | % Relative<br>RhoGTPase Activity |
|---|---|
| 10 nM | 103.6 |
| 100 nM | 120.1 |

Example 42

Stereotactic Injections of Kainic Acid into Rat Hippocampus Tissues LED to Increased Damages in Neurons Stereotactic injections of Kainic acid into rat hippocampus tissues led to increased damages in neurons. However, when GGA trans isomer (CNS-102) was dosed before the KA injection, neurons were protected. Under this condition, neurons and HSP70 expression was stained by immunohistochemistry techniques. HSP70 expression was induced in a very specific area only that KA was injected. The induced area was not stained by HSP70 antibody when KA was not injected, but CNS-102 was dosed. Therefore these data suggest that HSP70 induction by dosing CNS-102 which protects neurons really depends on neuron damages or stressors. Furthermore, interestingly, the induced area did not match with neurons.

Therefore, the data suggest that glial cells play an important role in the HSP70 induction, but not neurons.

Figure 8:
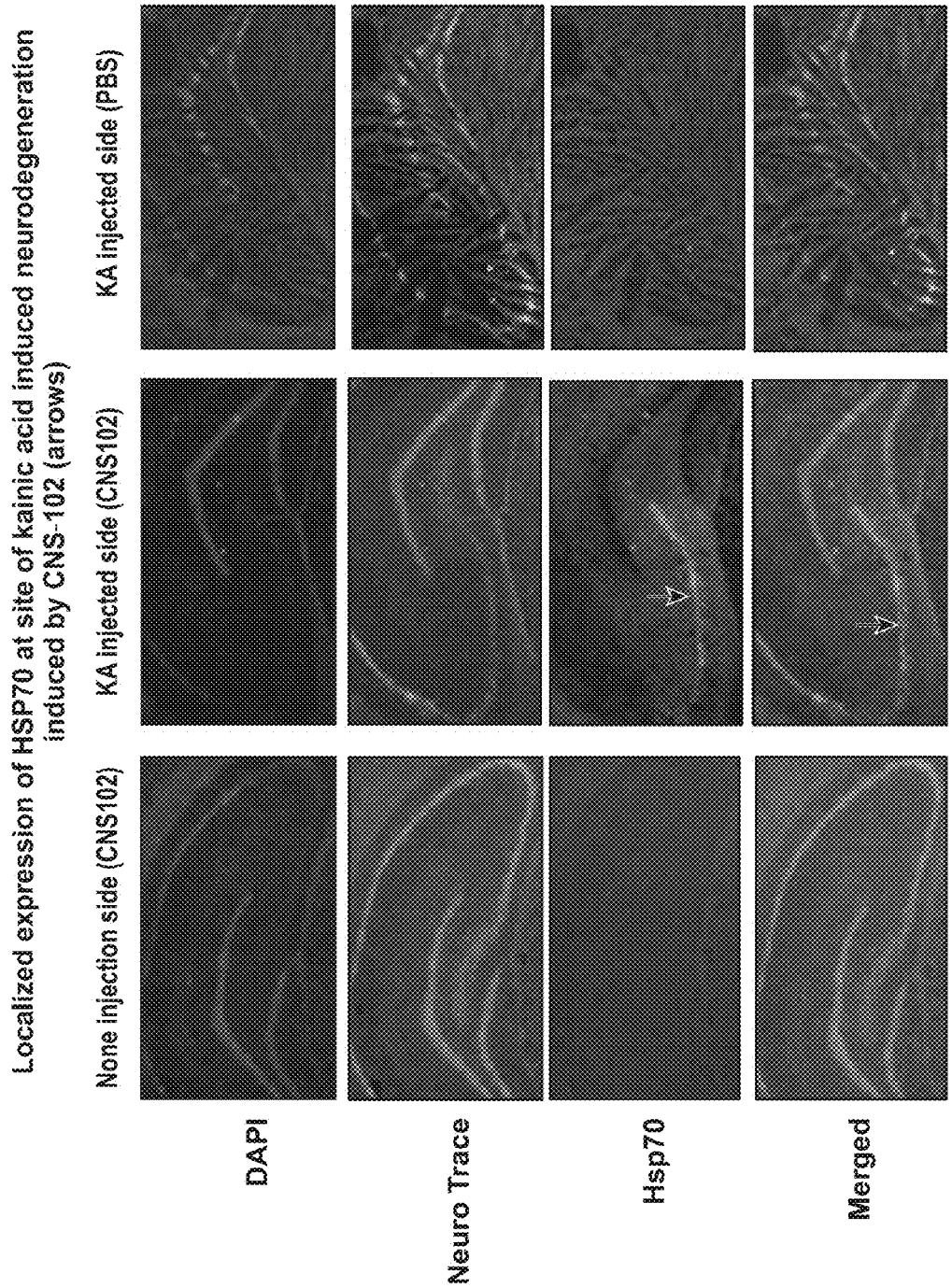
FIG. 8 illustrates localized expression of HSP 70 at site of kainic acid induced neurodegeneration induced by CNS-102 (arrows).

HSP70 induction by dosing CNS-102 in the absence of the KA injection was limited in western blot experiments using hippocampus lysates. 120% or 130% of HSP70 expression could be seen by comparing those of vehicle dosing control experiments. But by stereotactically injecting KA in hippocampus tissues, a strong induction of HSP70 was seen very clearly, and the induction was very localized in the injection site only. The results are shown in FIG. 8.

Without being limited to a particular theory, it is believed that one or more of the following may be occurring:
1. The stabilization will raise a minimal amount of HSP70 induction. But when a stressor or toxin that include SOD1 mutants of ALS, tau aggregations of Alzheimer disease, A-b aggregations, etc attacks neurons or glia cells, HSP70 is strongly induced in a specific area only.
2. CNS-102 will be a facilitator that optimally induces HSP70 in cells or neurons damaged by those stressors only.

Example 43

The Effect of GGA Derivatives on HSP70 Levels in Neuro 2A Cells as Measured by Enzyme Linked Immunosorbent Assay (ELISA)

Mouse neuroblastoma 2a cells were cultured in DMEM with 10% FBS for 24 hrs. Cells were treated with various concentrations of GGA derivatives for 48 hrs followed by incubation with geranylgeranyl transferase I inhibitor, GGTI-298. After 24 hrs cells were harvested and lysates were prepared and analyzed by ELISA for HSP70. ELISA signals in the absence of the compounds were normalized as 1.00 and are presented in the table below. Compound ID numbers in table refer to structures in Table 1 and Table 2.

| Compound ID | 10 nM | 100 nM | 10 uM |
|---|---|---|---|
| 2g |  |  | 0.91 |
| 2h |  |  | 0.94 |
| 2i |  | 1.08 |  |
| 2j |  |  | 0.95 |
| 2k |  |  | 0.88 |
| 2l |  |  | 1.05 |
| 6a |  |  | 1.11 |
| 6b |  |  | 1.18 |
| 7aa |  | 1.05 |  |
| 7k |  |  | 1.20 |
| 7l |  |  | 1.10 |
| 7m |  | 0.89 |  |
| 7n |  | 1.20 |  |
| 7o |  |  | 1.15 |
| 7p |  |  | 1.00 |
| 7q | 1.01 |  |  |
| 7r |  |  | 0.89 |
| 7s |  |  | 1.10 |
| 7t |  | 1.07 |  |
| 7u |  | 1.03 |  |
| 7v |  |  | 1.13 |
| 7w |  | 1.14 |  |
| 7x |  |  | 1.00 |
| 7y |  |  | 1.13 |
| 7z |  | 0.96 |  |
| 8a |  |  | 1.33 |
| 8b |  |  | 1.38 |
| 8c |  |  | 1.46 |
| 8d |  |  | 1.33 |
| 8e |  |  | 1.09 |
| 8f |  |  | 1.29 |
| 8g | 1.17 |  | 1.51 |
| 8h |  |  | 0.86 |
| 8i |  |  | 0.97 |
| 8j | 1.13 |  | 1.31 |
| 8k |  |  | 0.99 |
| 8l |  |  | 1.03 |
| 8m |  |  | 1.05 |
| 8n |  |  | 1.02 |
| 8o |  |  | 0.99 |
| 9a |  |  | 0.94 |
| 9b |  |  | 0.99 |
| 9c |  |  | 0.96 |
| 9d | 1.05 |  | 0.95 |
| 9k | 1.13 |  | 0.97 |
| 10a |  |  | 1.17 |
| 10b |  | 1.06 | 1.34 |
| 10c |  |  | 1.53 |
| 10d |  |  | 1.36 |
| 10e |  | 1.09 |  |
| 10f |  |  | 1.57 |
| 10g |  |  | 1.60 |
| 10h |  |  | 1.58 |
| 10i |  | 1.04 | 1.08 |
| 10j |  | 1.06 | 1.08 |
| 10k |  | 1.11 |  |
| 10l |  | 1.16 | 1.37 |
| 10m |  |  | 1.06 |
| 12 |  |  | 1.01 |
| 14 |  |  | 0.96 |
| 15 |  | 1.08 |  |
| 16 |  |  | 0.89 |
| 17a |  | 1.09 | 1.22 |
| 17b |  |  | 1.08 |
| 17c |  |  | 1.01 |
| 17d |  | 1.01 |  |
| 17e |  |  | 1.06 |
| 20a |  | 0.91 |  |
| 23a |  | 1.21 |  |
| 23b |  | 1.13 |  |
| 23c |  | 0.96 |  |
| 23e |  | 0.97 |  |
| 23f |  | 0.91 |  |
| 27a |  | 1.02 |  |
| 27b |  | 1.16 | 1.22 |
| 27c |  |  | 0.95 |
| 27d |  | 1.04 | 1.37 |
| 27e |  |  | 1.11 |
| 27f |  |  | 0.91 |
| 27g |  |  | 1.11 |
| 29a |  |  | 1.22 |
| 29b |  | 1.11 | 1.17 |
| 29c |  |  | 1.06 |
| 29d |  |  | 1.12 |
| 29e |  |  | 1.10 |
| 29f |  |  | 1.01 |
| 32 |  |  | 0.96 |
| 35a |  |  | 1.08 |
| 35b |  |  | 0.95 |
| 35c |  |  | 1.04 |
| 35d |  |  | 1.05 |
| 37a |  | 1.04 | 1.10 |
| 37b |  |  | 0.89 |
| 37c |  | 0.99 |  |
| 37d |  |  | 1.04 |
| 38a |  | 0.79 |  |
| 38b |  | 1.04 |  |
| 39 |  | 1.15 |  |
| 40a |  | 0.99 |  |
| 40b |  | 0.92 |  |
| 42 |  |  | 1.25 |
| 43 |  |  | 0.95 |
| 60 |  | 0.89 |  |
| 61 |  | 0.98 |  |
| 65 |  | 0.90 |  |
| 68 |  | 1.11 |  |
| 69 |  | 0.90 |  |
| 70 |  | 1.07 |  |
| 71 |  | 1.03 |  |

| Compound ID | 10 nM | 100 nM | 10 uM |
|---|---|---|---|
| 73 | | 0.99 | |
| 74 | | 1.08 | |
| 76 | | 0.75 | |
| 77 | | 1.03 | |
| 78 | | 1.00 | |
| 79 | | 0.98 | |
| 80 | | 1.02 | |
| 81 | | 1.12 | |
| 87 | | 0.95 | |
| 92 | | 0.92 | |
| 93 | | 0.87 | |
| 100 | | 1.14 | |
| 102 | | 1.04 | |
| 104 | | 0.90 | |
| 109 | | 1.12 | |
| 111 | | 1.10 | |
| 113 | | 1.01 | |
| 117 | | 1.08 | |
| 135 | | | 1.07 |
| 146 | | 1.13 | |
| 147 | | 0.94 | |

Example 44

Screening for GGA Derivative Compounds that can Rescue Amyloid-Beta Oligomer Induced Cytotoxicity in Neuro 2A Cells Preparation of amyloid-beta oligomer (A-beta (O)): Synthetic wild type A-beta (1-42) was purchased from American Peptide, and first dissolved with hexafluoroisopropanol (HFIP), then dried in the blowing tissue culture hood overnight to form a film in the eppendorf tube. The A-beta peptide film was first resuspended with DMSO to a concentration of 5 mM, further diluted with DMEM containing N2 supplement (Invitrogen) to achieve a concentration of 100 μM, and then sonicated in room temperature water bath for 10 minutes. The 100 μM peptide solution was then incubated at 4° C. for 24 hr and thoroughly vortexed before applied to cells.

Mouse neuroblastoma Neuro2A cells were plated in 96-well plates and cultured in DMEM supplemented with 10% FBS for 24 hr. Before treatment, cells were washed once with DMEM (containing N2 supplement), then treated with 24 hr-aged A-beta (O) only, or A-beta (O) together with GGA derivatives or with the vehicle DMSO for 48 hr. At the end of incubation, cells were harvested and subjected to viability assay using CellTiter-Glo Luminescent Cell Viability Assay Kit (Promega). The data for each treatment was calculated as average of 4 replicates and normalized to that of A-beta (O) treated only. Compound ID numbers in table refer to structures in Table 1 and Table 2.

| Compound ID | % viability vs. untreated |
|---|---|
| 2i | 89% |
| 7q | 103% |
| 7s | 95% |
| 7w | 111% |
| 7y | 110% |
| 8b | 100% |
| 8f | 86% |
| 8g | 107% |
| 8j | 102% |
| 8m | 99% |
| 8o | 106% |
| 10b | 93% |
| 10e | 100% |
| 20j | 88% |
| 27b | 92% |
| 29b | 106% |
| 37a | 98% |
| 43 | 103% |
| 105 | 88% |
| 135 | 91% |

| Compound 1 uM | Conformation | % viability vs. untreated |
|---|---|---|
| 101 | (cis/trans) | 126% |
| 102 | (all trans) | 140% |
| 103 | (all cis) | 128% |

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entirety.

What is claimed is:

1. A compound of Formula (I):

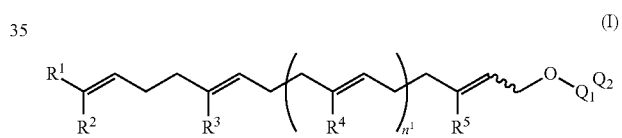

or pharmaceutically acceptable salt thereof, wherein
$n^1$ is 1 or 2;
$Q^1$ is —(C=O)—, —(C=S)—, or —S(O$_2$)—;
$Q_2$ is —NR$^7$R$^8$;
each R$^1$ and R$^2$ are independently C$_1$-C$_6$ alkyl, or R$^1$ and R$^2$ together with the carbon atom they are attached to form a C$_5$-C$_7$ cycloalkyl ring optionally substituted with 1-3 C$_1$-C$_6$ alkyl groups;
each of R$^3$, R$^4$, and R$^5$ independently are C$_1$-C$_6$ alkyl;
R$^6$ is:
C$_1$-C$_6$ alkyl, optionally substituted with —CO$_2$H or an ester thereof, C$_1$-C$_6$ alkoxy, oxo, —OH, —CR=CR$_2$, —C≡CR, C$_3$-C$_{10}$ cycloalkyl, C$_3$-C$_8$ heterocyclyl, C$_6$-C$_{10}$ aryl, C$_2$-C$_{10}$ heteroaryl, wherein each R independently is hydrogen or C$_1$-C$_6$ alkyl;
C$_3$-C$_{10}$ cycloalkyl;
C$_3$-C$_8$ heterocyclyl;
C$_6$-C$_{10}$ aryl; or
C$_2$-C$_{10}$ heteroaryl, provided that when $n^1$ is 2, and one of R$^7$ and R$^8$ is hydrogen, R$^6$ excludes C$_2$-C$_{10}$ heteroaryl
wherein each cycloalkyl, heterocyclyl, aryl, or heteroaryl is optionally substituted with 1-3 alkyl groups; —CF$_3$, 1-3 halo; 1-3 nitro groups; 1-3 C$_1$-C$_6$ alkoxy groups; —CO-phenyl; or —NR$^{18}$R$^{19}$;
each R$^7$ and R$^8$ are independently hydrogen or defined as R$^6$, provided that if $n^1$ is 1 and one of R$^7$ and R$^8$ is hydrogen, the other excludes hydrogen each $R^{18}$ and $R^{19}$ independently is hydrogen; $C_1$-$C_6$ alkyl, optionally substituted with —$CO_2H$ or an ester thereof, $C_1$-$C_6$ alkoxy, oxo, —CR=$CR_2$, —C≡CR, $C_3$-$C_{10}$ cycloalkyl, $C_3$-$C_8$ heterocyclyl, $C_6$-$C_{10}$ aryl, or $C_2$-$C_{10}$ heteroaryl, wherein each R independently is hydrogen or $C_1$-$C_6$ alkyl; $C_3$-$C_{10}$ cycloalkyl; $C_3$-$C_8$ heterocyclyl; $C_6$-$C_{10}$ aryl; or $C_2$-$C_{10}$ heteroaryl; wherein each cycloalkyl, heterocyclyl, aryl, or heteroaryl is optionally substituted with 1-3 alkyl groups, optionally substituted with 1-3 halo, or where $R^{18}$ and $R^{19}$ together with the nitrogen atom they are attached to form a 5-7 membered heterocycle.

2. The compound of claim 1, wherein the compound has a formula:

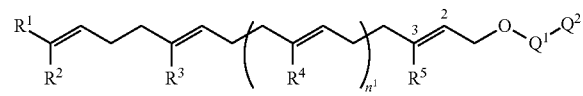

and wherein the variables are defined as in claim 1.

3. The compound of claim 1, wherein the compound has a formula:

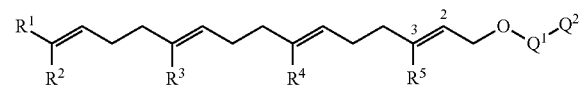

and wherein $n^1$ is 2.

4. The compound of claim 1, wherein the compound has a formula:

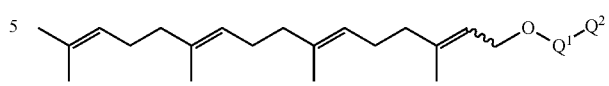

and wherein the variables are defined as in claim 1.

5. The compound of claim 1, wherein the compound has a formula selected from the group consisting of:

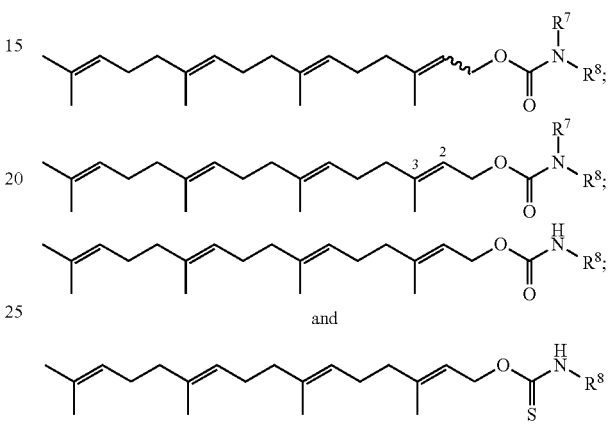

and wherein the variables are defined as in claim 1.

6. A compound selected from the group consisting of:

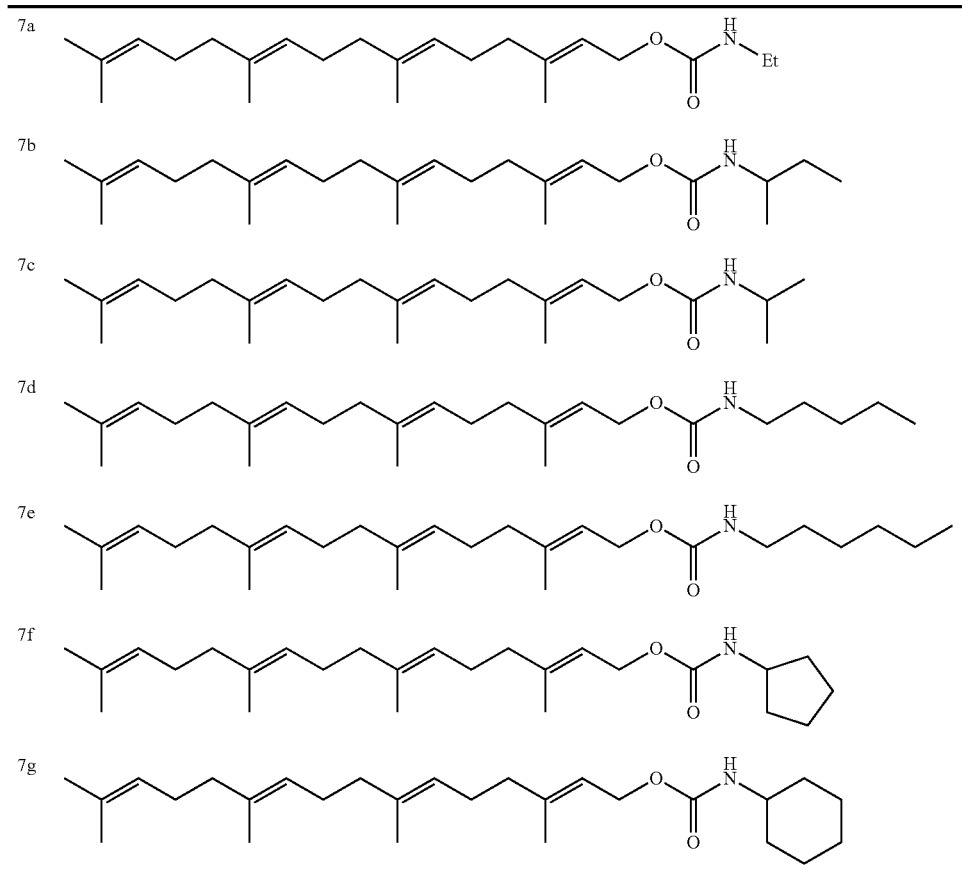

7h 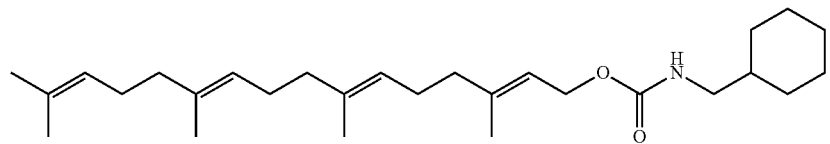 [SMILES: CC(C)=CCC/C(C)=C/CC/C(C)=C/CC/C(C)=C/COC(=O)NCC1CCCCC1]
7i 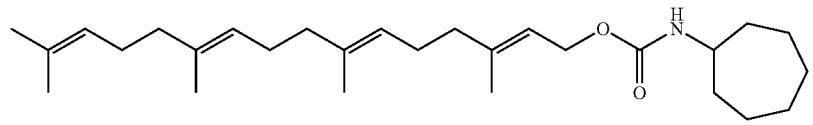 [SMILES: CC(C)=CCC/C(C)=C/CC/C(C)=C/CC/C(C)=C/COC(=O)NC1CCCCCC1]
7j 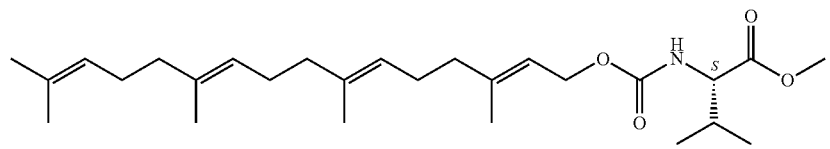
7k 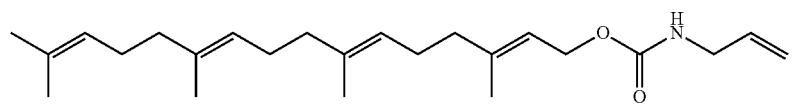 [SMILES: C=CCNC(=O)OC/C=C(\C)CC/C=C(\C)CC/C=C(\C)CCC=C(C)C]
7l 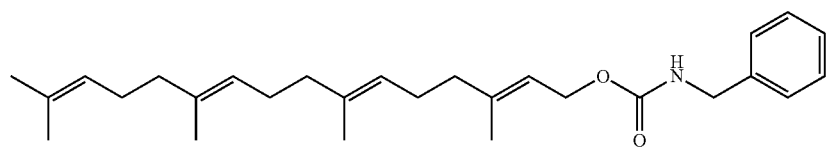 [SMILES: CC(C)=CCC/C(C)=C/CC/C(C)=C/CC/C(C)=C/COC(=O)NCc1ccccc1]
7m 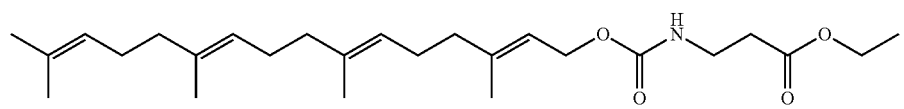 [SMILES: CCOC(=O)CCNC(=O)OC/C=C(\C)CC/C=C(\C)CC/C=C(\C)CCC=C(C)C]
7n 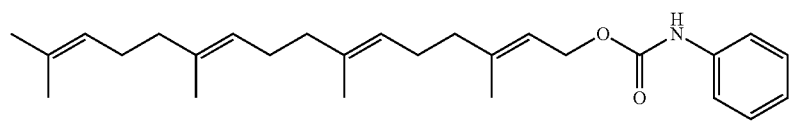
7o 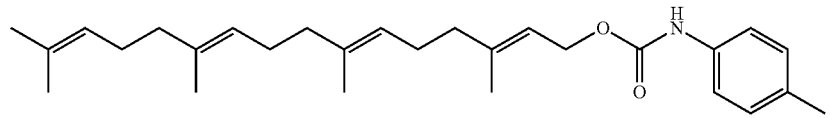 [SMILES: CC(C)=CCC/C(C)=C/CC/C(C)=C/CC/C(C)=C/COC(=O)Nc1ccc(C)cc1]
7p 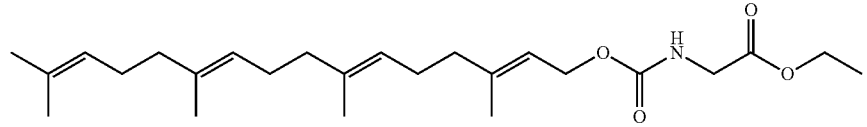 [SMILES: CCOC(=O)CNC(=O)OC/C=C(\C)CC/C=C(\C)CC/C=C(\C)CCC=C(C)C]
7q 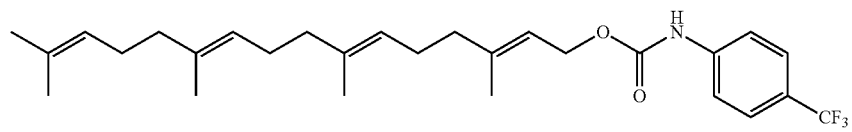 [SMILES: CC(C)=CCC/C(C)=C/CC/C(C)=C/CC/C(C)=C/COC(=O)Nc1ccc(C(F)(F)F)cc1]
7r 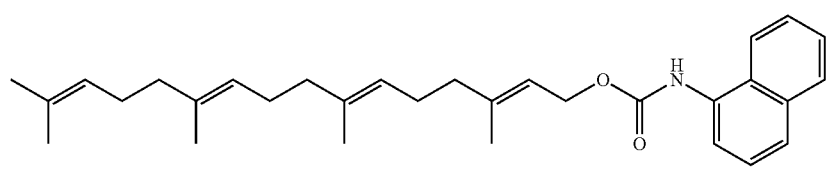 [SMILES: CC(C)=CCC/C(C)=C/CC/C(C)=C/CC/C(C)=C/COC(=O)Nc1cccc2ccccc12]

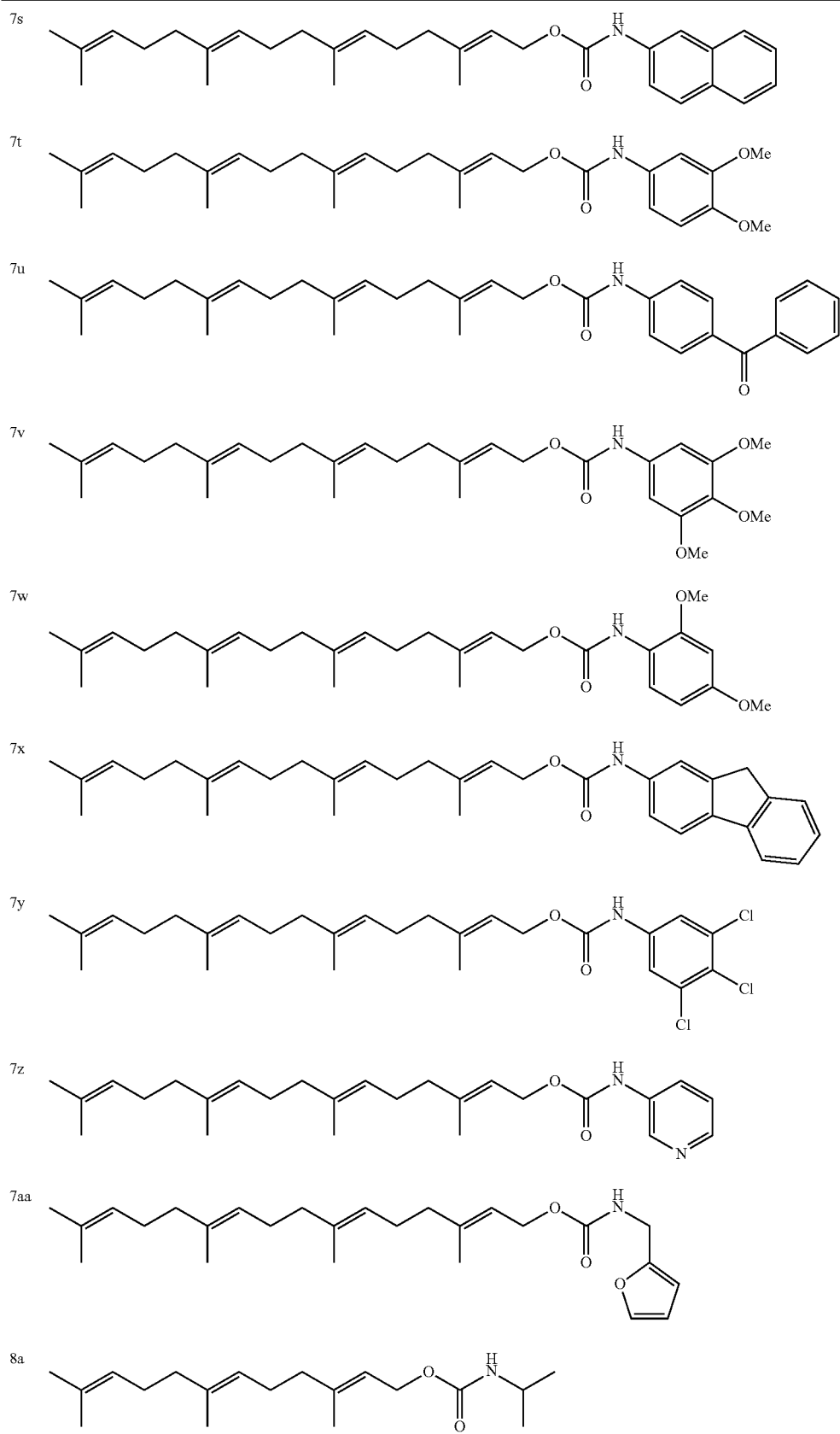

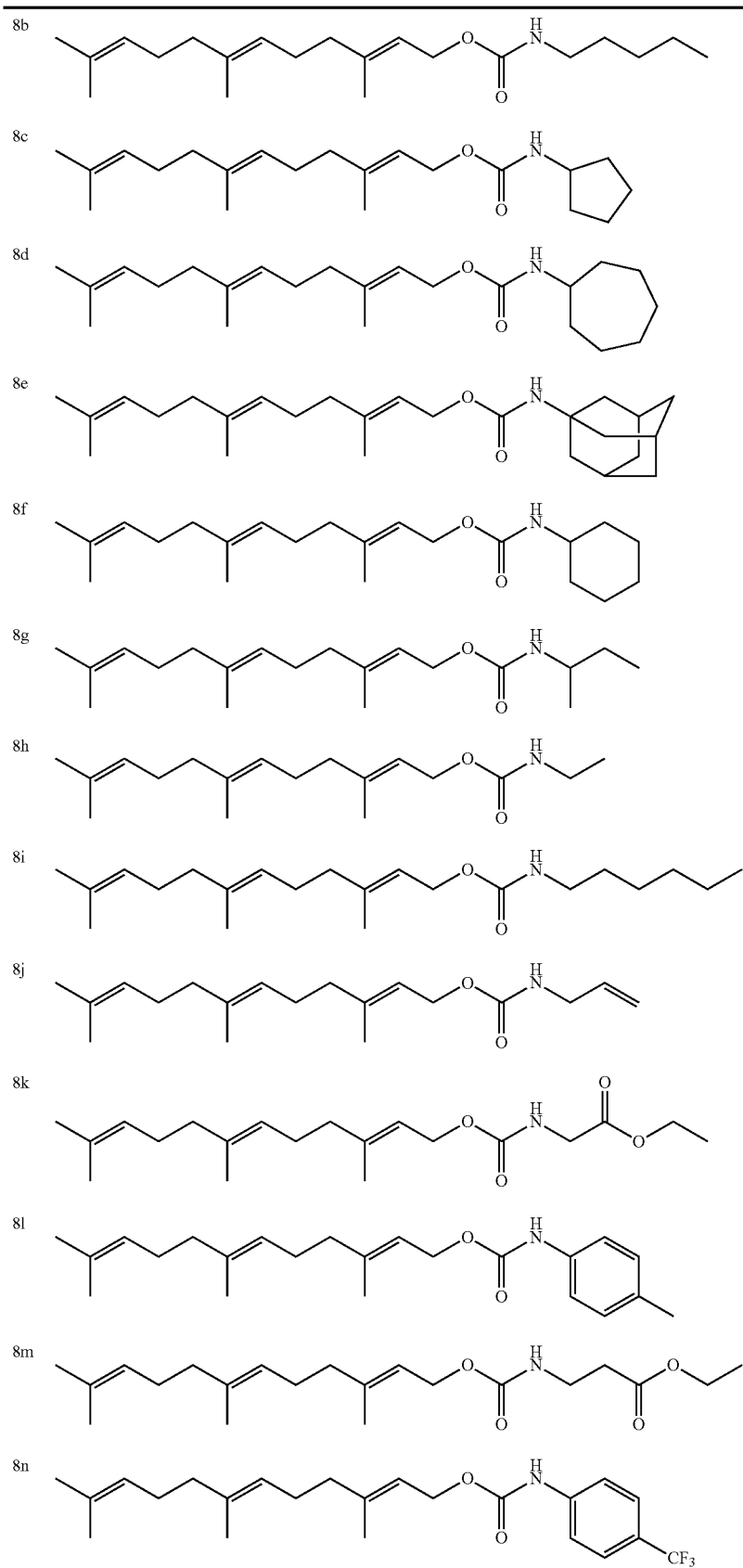

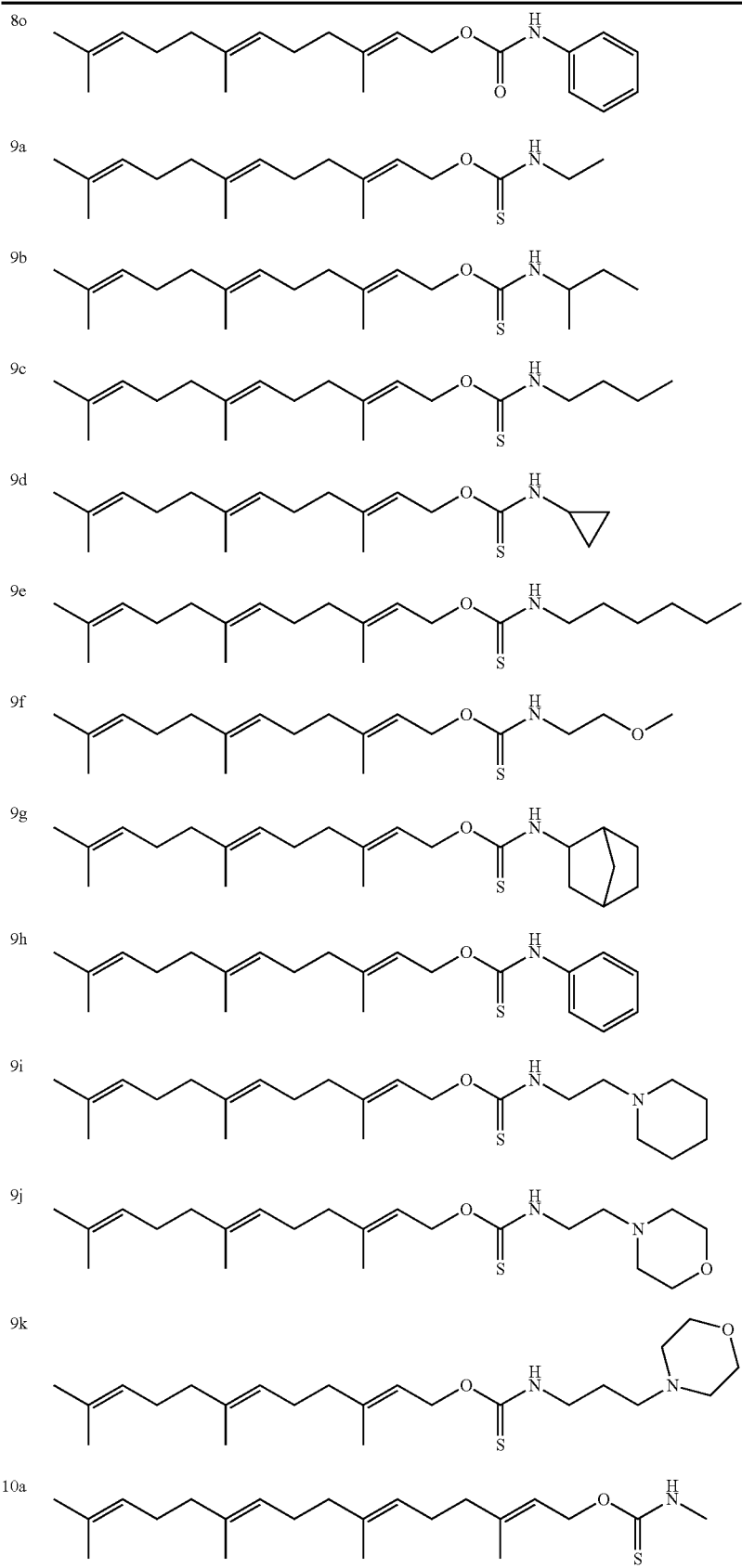

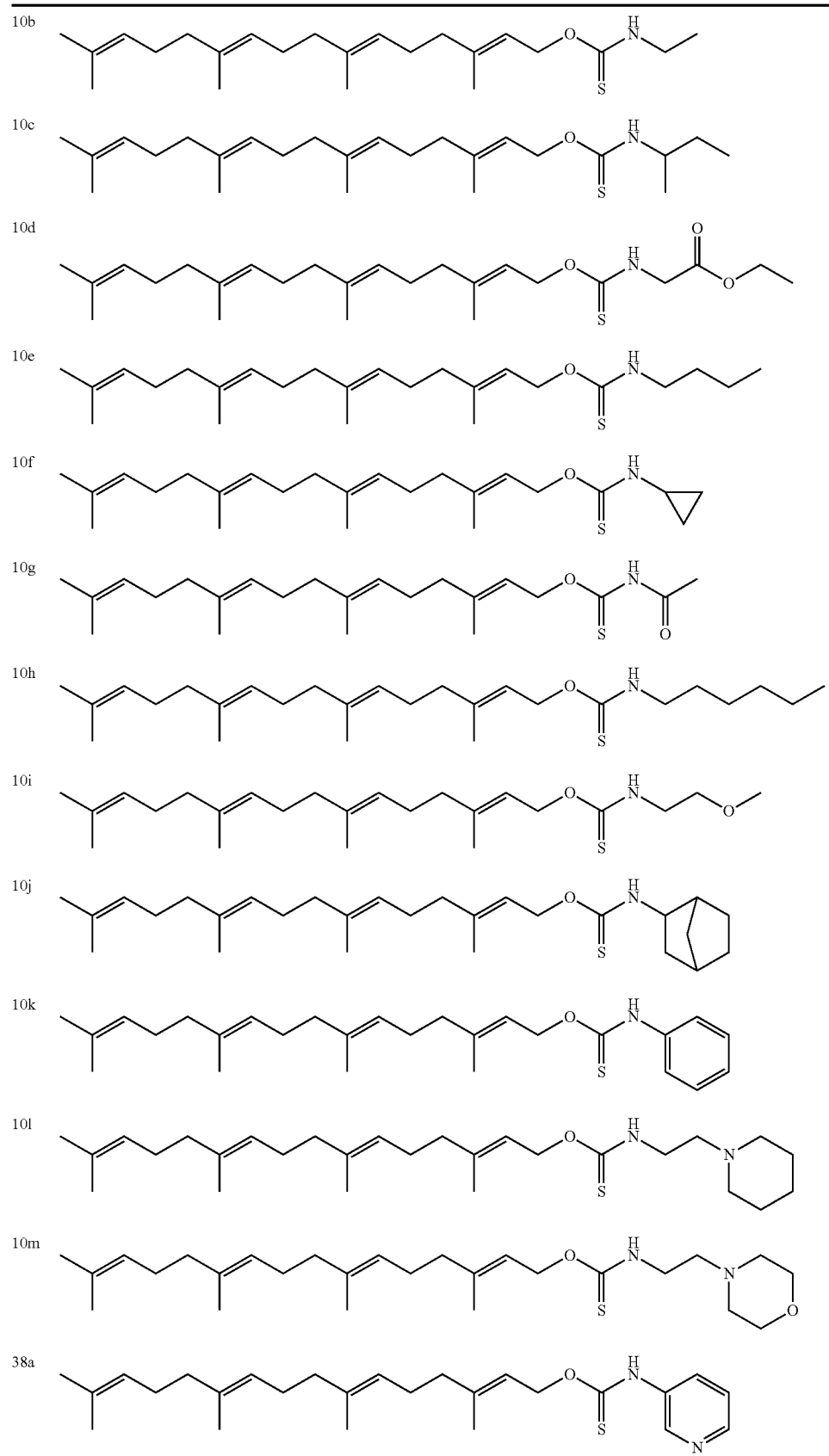

-continued
38b 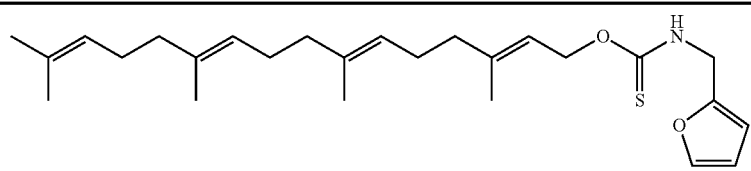
39 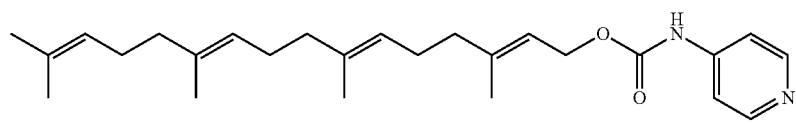 [SMILES: CC(C)=CCC/C(C)=C/CC/C(C)=C/CC/C(C)=C/COC(=O)Nc1ccncc1]
40a 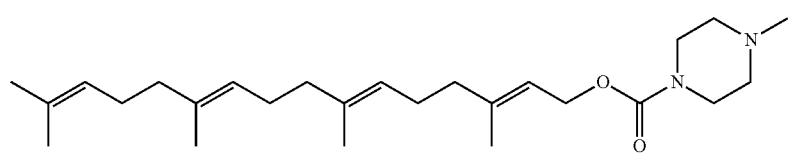 [SMILES: CC(C)=CCC/C(C)=C/CC/C(C)=C/CC/C(C)=C/COC(=O)N1CCN(C)CC1]
40b 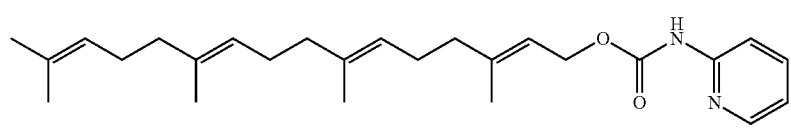
41 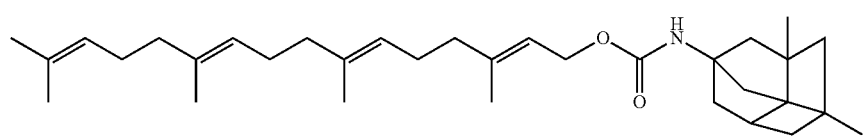 [SMILES: CC(C)=CCC/C(C)=C/CC/C(C)=C/CC/C(C)=C/COC(=O)NC12CC3CC4(C)CC(C)(C1)C34C2]
42 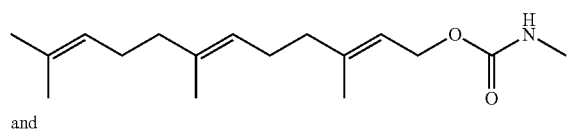
and
43 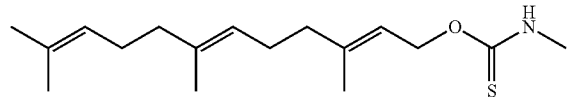 [SMILES: CNC(=S)OC/C=C(\C)CC/C=C(\C)CCC=C(C)C]
or a pharmaceutically acceptable salt thereof.
7. A pharmaceutical composition comprising a compound of claim 1 and a pharmaceutically acceptable excipient.
8. A pharmaceutical composition comprising a compound of claim 6 and a pharmaceutically acceptable excipient.
* * * * *